(12) United States Patent
Cecere et al.

(10) Patent No.: US 11,840,528 B2
(45) Date of Patent: Dec. 12, 2023

(54) ISOXAZOLYL ETHER DERIVATIVES AS GABA$_A$ α5 PAM

(71) Applicant: Hoffmann-La Roche Inc., Little Falls, NJ (US)

(72) Inventors: Giuseppe Cecere, Basel (CH); Katrin Groebke Zbinden, Oberwil BL (CH); Maria-Clemencia Hernandez, Delémont (CH); Henner Knust, Rheinfelden (DE); Andreas Koblet, Elsau ZH (CH); Andres Miguel Olivares Morales, Basel (CH); Angélique Patiny-Adam, Kembs (FR); Emmanuel Pinard, Linsdorf (FR); Valerie Runtz-Schmitt, Rixheim (FR); Sandra Steiner, Sursee (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 17/119,977

(22) Filed: Dec. 11, 2020

(65) Prior Publication Data
US 2021/0094945 A1 Apr. 1, 2021

Related U.S. Application Data

(63) Continuation of application No. PCT/EP2019/065129, filed on Jun. 11, 2019.

(30) Foreign Application Priority Data

Jun. 13, 2018 (EP) .................................... 18177522
Jun. 14, 2018 (EP) .................................... 18177825

(51) Int. Cl.
| | | |
|---|---|---|
| C07D 413/14 | (2006.01) | |
| C07D 487/04 | (2006.01) | |
| C07D 487/10 | (2006.01) | |
| C07D 491/08 | (2006.01) | |
| C07D 491/107 | (2006.01) | |
| C07D 498/04 | (2006.01) | |

(52) U.S. Cl.
CPC ......... *C07D 413/14* (2013.01); *C07D 487/04* (2013.01); *C07D 487/10* (2013.01); *C07D 491/08* (2013.01); *C07D 491/107* (2013.01); *C07D 498/04* (2013.01)

(58) Field of Classification Search
CPC .. C07D 413/14; C07D 498/22; C07D 493/10; A61K 31/506; A61K 31/501; A61K 9/5355; A61K 31/5386

USPC .............. 544/230, 238; 514/252.01, 252.02, 514/230.5, 236.5
See application file for complete search history.

(56) References Cited

U.S. PATENT DOCUMENTS

| | | |
|---|---|---|
| 2009/0143371 A1 | 4/2009 | Bucttelmann et al. |
| 2009/0143385 A1 | 6/2009 | Buettelmann et al. |

FOREIGN PATENT DOCUMENTS

| | | |
|---|---|---|
| WO | 2008/130314 A1 | 10/2008 |
| WO | 2009/071476 A1 | 6/2009 |
| WO | 2009/071477 A1 | 6/2009 |
| WO | 2010/127975 A1 | 11/2010 |
| WO | 2018/104419 A1 | 6/2018 |

OTHER PUBLICATIONS

"International Preliminary Report on Patentability—PCT/EP2019/065129" (dated Dec. 15, 2020; Capter I),:pp. 1-7 (Dec. 24, 2020).
"International Search Report—PCT/EP2019/065129" (w/Written Opinion),:pp. 1-11 (Aug. 7, 2019).

*Primary Examiner* — Jeffrey H Murray
(74) *Attorney, Agent, or Firm* — Bradley E. Davis

(57) ABSTRACT

The invention provides novel compounds having the general formula (I) or (II)

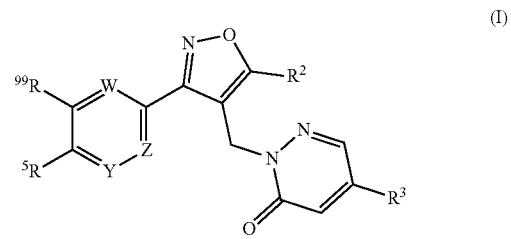

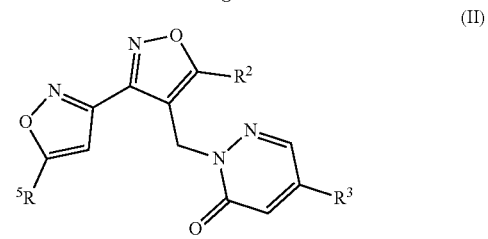

wherein $R^2$, $R^3$, $R^5$, $R^{99}$, W, Y and Z are as described herein, compositions including the compounds and methods of using the compounds.

15 Claims, No Drawings

ISOXAZOLYL ETHER DERIVATIVES AS GABA$_A$ α5 PAM

This application is a continuation of International Application No. PCT/EP2019/065129 having an International filing date of Jun. 11, 2019, which claims benefit of priority to European Patent Application No. 18177522.22, filed Jun. 13, 2018 and European Patent Application No. 18177825.9, filed Jun. 14, 2018, all of which are incorporated by reference in their entirety.

The present invention relates to organic compounds useful for therapy or prophylaxis in a mammal, and in particular to GABA$_A$ α5 receptor positive allosteric modulators (PAMs) for the treatment or prophylaxis of GABA$_A$ α5 receptor related diseases and diseases or conditions which can be treated by the modulation of GABA$_A$ α5 receptor activity, such Alzheimer's disease, mild cognitive impairment (MCI), age-related cognitive decline, negative and/or cognitive symptoms associated with schizophrenia, bipolar disorders, autism spectrum disorder (ASD), Angelman syndrome, Rett syndrome, Prader-Willi syndrome, epilepsy, post-traumatic stress disorder (PTSD), amyotrophic lateral sclerosis (ALS), fragile-X disorder.

The present invention provides a novel compound of formula (I) and (II)

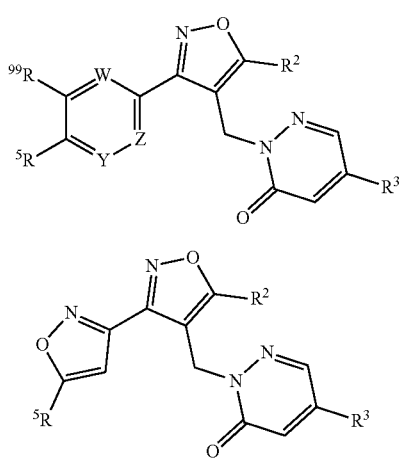

W is selected from
  i) N, and
  ii) CR$^4$;
Y is selected from
  i) N, and
  ii) CH;
Z is selected from
  i) N, and
  ii) CH;
R$^{99}$ is selected from
  i) C$_{1-6}$-alkyl,
  ii) C$_{1-6}$-alkoxy,
  iii) halo-C$_{1-6}$-alkoxy,
  iv) hydroxy-C$_{1-6}$-alkyl,
  v) C$_{3-8}$-cycloalkyl,
  vi) H, and
  vii) halogen;
R$^2$ is selected from
  i) H,
  ii) halogen,
  iii) C$_{1-6}$-alkyl,
  iv) C$_{3-8}$-cycloalkyl, and
  v) halo-C$_{1-6}$-alkyl;
R$^3$ is selected from
  i) heterocycloalkyl substituted with R$^6$, R$^7$ and R$^8$,
  ii) amino substituted on the nitrogen atom by one or two substituents independently selected from R$^9$ and R$^{10}$,
  iii) aryl substituted with R$^{11}$, R$^{12}$ and R$^{13}$, and
  iv) heteroaryl substituted with R$^{11}$, R$^{12}$ and R$^{13}$;
R$^4$ is selected from
  i) H,
  ii) C$_{1-6}$-alkyl,
  iii) halo-C$_{1-6}$-alkyl,
  iv) C$_{1-6}$-alkoxy,
  v) C$_{3-8}$-cycloalkyl, and
  vi) halogen;
R$^5$ is selected from
  i) H,
  ii) C$_{1-6}$-alkyl,
  iii) C$_{3-8}$-cycloalkyl,
  iv) halo-C$_{1-6}$-alkyl, and
  v) halogen;
R$^6$, R$^7$ and R$^8$ are independently selected from
  i) H,
  ii) C$_{1-6}$-alkyl,
  iii) C$_{1-6}$-alkoxy,
  iv) C$_{1-6}$-alkoxy-C$_{1-6}$-alkyl,
  v) C$_{1-6}$-alkoxycarbonyl,
  vi) cyano,
  vii) amino substituted on the nitrogen atom by one or two substituents independently selected from R$^{22}$ and R$^{23}$,
  viii) C$_{3-8}$-cycloalkyl, wherein the C$_{3-8}$-cycloalkyl is substituted with R$^{24}$, R$^{25}$ and R$^{26}$,
  ix) C$_{3-8}$-cycloalkoxy, wherein the C$_{3-8}$-cycloalkoxy is substituted with R$^{24}$, R$^{25}$ and R$^{26}$,
  x) C$_{3-8}$-cycloalkyl-C$_{1-6}$-alkoxy, wherein the C$_{3-8}$-cycloalkyl-C$_{1-6}$-alkoxy is substituted with R$^{24}$, R$^{25}$ and R$^{26}$
  xi) C$_{3-8}$-cycloalkylaminocarbonyl, wherein the C$_{3-8}$-cycloalkylaminocarbonyl is substituted with R$^{24}$, R$^{25}$ and R$^{26}$
  xii) C$_{3-8}$-cycloalkylcarbonyl, wherein the C$_{3-8}$-cycloalkylcarbonyl is substituted with R$^{24}$, R$^{25}$ and R$^{26}$
  xiii) C$_{3-8}$-cycloalkyl-C$_{1-6}$-alkoxycarbonyl, wherein the C$_{3-8}$-cycloalkyl-C$_{1-6}$-alkoxycarbonyl is substituted with R$^{24}$, R$^{25}$ and R$^{26}$
  xiv) aryloxy substituted with R$^{27}$, R$^{28}$ and R$^{29}$,
  xv) aryl substituted with R$^{27}$, R$^{28}$ and R$^{29}$,
  xvi) heteroaryl substituted with R$^{27}$, R$^{28}$ and R$^{29}$,
  xvii) heteroaryloxy substituted with R$^{27}$, R$^{28}$ and R$^{29}$,
  xviii) halo-C$_{1-6}$-alkoxy,
  xix) halo-C$_{1-6}$-alkyl,
  xx) halogen,
  xxi) hydroxy,
  xxii) hydroxy-C$_{1-6}$-alkyl, and
  xxiii) oxo;
R$^9$ and R$^{10}$ are independently selected from
  i) H,
  ii) halo-C$_{1-6}$-alkyl,
  iii) C$_{1-6}$-alkyl,
  iv) heterocycloalkyl substituted with R$^{30}$, R$^{31}$ and R$^{32}$,
  v) heterocycloalkyl-C$_{1-6}$-alkyl substituted with R$^{30}$, R$^{31}$ and R$^{32}$
  vi) hydroxy-C$_{1-6}$-alkyl,
  vii) C$_{1-6}$-alkoxy,
  viii) C$_{3-8}$-cycloalkyl, and ix) halogen;

R, $R^{12}$ and $R^{13}$ are independently selected from
i) H,
ii) hydroxy,
iii) hydroxy-$C_{1-6}$-alkyl,
iv) $C_{1-6}$-alkoxy,
v) $C_{1-6}$-alkyl,
vi) cyano,
vii) aryl,
viii) $C_{3-8}$-cycloalkyl,
ix) halo-$C_{1-6}$-alkyl,
x) halo-$C_{1-6}$-alkoxy,
xi) heteroaryl,
xii) amino substituted on the nitrogen atom by one or two substituents independently selected from $R^{14}$ and $R^{15}$,
xiii) $C_{3-8}$-cycloalkyl-$C_{1-6}$-alkyl,
xiv) heterocycloalkyl substituted with $R^{16}$, $R^{17}$ and $R^{18}$,
xv) heterocycloalkoxy substituted with $R^{16}$, $R^{17}$ and $R^{18}$,
xvi) heterocycloalkyl-$C_{1-6}$-alkyl substituted with $R^{16}$, $R^{17}$ and $R^{18}$, and
xvii) halogen;

$R^{14}$ and $R^{15}$ are independently selected from
i) H, and
ii) $C_{1-6}$-alkyl;

$R^{16}$, $R^{17}$ and $R^{18}$ are independently selected from
i) H,
ii) halogen,
iii) $C_{1-6}$-alkoxy,
iv) $C_{3-8}$-cycloalkyl,
v) $C_{1-6}$-alkyl;

$R^{22}$ and $R^{23}$ are independently selected from
i) H,
ii) $C_{1-6}$-alkyl, and
iii) $C_{1-6}$-alkylcarbonyl;

$R^{24}$, $R^{25}$ and $R^{26}$ are independently selected from
i) $C_{1-6}$-alkyl,
ii) H,
iii) $C_{1-6}$-alkoxy,
iv) $C_{3-8}$-cycloalkyl,
v) halo-$C_{1-6}$-alkyl,
vi) halo-$C_{1-6}$-alkoxy,
vii) halogen,
viii) hydroxy, and
ix) oxo;

$R^{27}$, $R^{28}$ and $R^{29}$ are independently selected from
i) H,
ii) $C_{1-6}$-alkoxy,
iii) $C_{1-6}$-alkyl,
iv) $C_{3-8}$-cycloalkyl, and
v) halogen;

$R^{30}$, $R^{31}$ and $R^{32}$ are independently selected from
i) H,
ii) halogen,
iii) $C_{1-6}$-alkoxy,
vi) $C_{3-8}$-cycloalkyl,
vii) $C_{1-6}$-alkyl;

or pharmaceutically acceptable salts.

Receptors for the major inhibitory neurotransmitter, gamma-aminobutyric acid (GABA), are divided into two main classes: (1) $GABA_A$ receptors, which are members of the ligand-gated ion channel superfamily and (2) $GABA_B$ receptors, which are members of the G-protein linked receptor family. The $GABA_A$ receptor complex which is a membrane-bound heteropentameric protein polymer is composed principally of α, β and γ subunits. $GABA_A$ receptors are ligand-gated chloride channels and the principal mediators of inhibitory neurotransmission in the human brain.

There are 19 genes encoding for $GABA_A$ receptor subunits that assemble as pentamers with the most common stoichiometry being two α, two β and one γ subunit. $GABA_A$ subunit combinations give rise to functional, circuit, and behavioral specificity (Sieghart, 2006; Vithlani et al., 2011). $GABA_A$ receptors containing the α5 subunit ($GABA_A$ α5) are of particular interest due to their restricted pattern of expression and unique physiological and pharmacological properties (Sur et al., 1999; Mohler, 2011). The $GABA_A$ α5 subunit-containing receptors are preferentially localized in the hippocampus, prefrontal cortex, nucleus accumbens and amygdala, which are key regions believed to be involved in the neuropathology and pathophysiology of a variety of CNS disorders.

Hippocampal hyperactivity as result of reduced $GABA_A$ α5 expression or GABAergic deficit or other conditions, is the common hallmark of a variety of CNS disorders characterized by cognitive decline (memory and executive functions). In such a disease state, a $GABA_A$ α5 positive allosteric modulator (PAM) and not a negative allosteric modulator (NAM) may be an effective treatment for the cognitive impairment associated with such diseases.

Multiple lines of evidence suggest that an imbalance between excitatory/inhibitory neurotransmission arising from dysfunction of GABAergic signaling system, the main inhibitory neurotransmitter system in the brain, to be at the core of the pathogenesis a variety of CNS disorders. Given the distribution of $GABA_A$ α5 receptors, they are very attractive targets for restoring levels of intracortical inhibition and consequently the (E/I) circuit balance in these conditions. Therefore compounds described herein and their pharmaceutically acceptable salts and esters can be used, alone or in combination with other drugs, as disease-modifying or as symptomatic agents for the treatment or prevention of acute neurological disorders, chronic neurological disorders, cognitive disorders, Alzheimer's disease, memory deficits, schizophrenia, positive, negative and/or cognitive symptoms associated with schizophrenia, bipolar disorders, autism, Angelman syndrome, Prader-Willi syndrome, Rett syndrome, Down syndrome, neurofibromatosis type I, sleep disorders, disorders of circadian rhythms, amyotrophic lateral sclerosis (ALS), fragile-X disorder, dementia caused by AIDS, age-associated memory impairment, psychotic disorders, substance-induced psychotic disorder, anxiety disorders, generalized anxiety disorder, panic disorder, delusional disorder, obsessive/compulsive disorders, acute stress disorder, post-traumatic stress disorder (PTSD), drug addictions, movement disorders, Parkinson's disease, restless leg syndrome, mild cognitive impairment (MCI), cognition deficiency disorders, age-related cognitive decline, multi-infarct dementia, mood disorders, depression, neuropsychiatric conditions, psychosis, attention-deficit/hyperactivity disorder, neuropathic pain, epilepsy, stroke and attentional disorders.

The most preferred indication in accordance with the present invention is autism spectrum disorder (ASD). ASD is a complex, heterogeneous neurodevelopmental disorder characterized by impairments in three core symptoms: social interactions, repetitive behaviors and cognitive deficits. The estimated prevalence of ASD in the United States is 1 in 68 children (CDC, 2014), and it is estimated that 1% of the world's population have ASD (WHO, 2013).

No approved pharmacological treatment exists for the core social communication and repetitive deficits of ASD Autism Spectrum Disorder, and this disorder continues to be an area of high unmet medical need. Current approved treatments for associated symptoms of ASD are limited to the antipsychotics (Risperidone and Aripiprazole) indicated for the treatment of irritability associated with ASD symptoms. Emerging evidence suggests that the GABAergic system, the main inhibitory neurotransmitter system in the brain, plays a key role in the pathophysiology of ASD (Dhossche et al., 2002; Pizzarelli and Cherubini, 2011; Robertson et al., 2016).

Both genetic and imaging studies using positron emission tomography study (PET) and magnetic resonance spectroscopy (MRS) suggest alterations in GABAergic signaling in ASD. $GABA_A$ receptor binding has been reported to be dramatically reduced in the superior and medial frontal cortex of patients with ASD using $[^{123}I]$-iomazenil PET (Mori et al., 2012). Also, a pilot $[^{11}C]$—RO154513 PET study found reduced binding of this tracer suggesting lower levels of $GABA_A$ α5 receptor in ASD (Mendez et al., 2012). MRS studies found altered GABA levels in ASD (Gaetz et al., 2014; Rojas et al., 2014) and in particular some recent studies showed reduced GABA and altered somatosensory function in children with ASD and (Puts et al., 2016; Robertson et al., 2016). In line with these observations, postmortem reduced expression of $GABA_A$ receptor subunits including GABRB3 (DeLorey, 2005; Abrahams and Geschwind, 2008) and the GABA synthesizing enzymes, glutamic acid decarboxylase (GAD) 65 and 67 were found in parietal and cerebellar cortices of patients with autism (Fatemi et al., 2002). Importantly, a reduction of GABAergic inhibitory activity has been proposed to result in hyperexcitability observed in ASD, including the high incidence of seizures and auditory-tactile hypersensitivity (Rubenstein and Merzenich, 2003; Frye et al., 2016). The altered GABAergic function may reduce the threshold for developing seizures as demonstrated by the high comorbidity of epilepsy in ASD, occurring in up to one-third of affected people. Finally, enhancement of $GABA_A$ receptor activity by non-selective BZDs have been shown to ameliorate behavioral deficits in mouse models of ASD, however very narrow therapeutic margins were observed due to sedation mediated by the $GABA_A$ α1 subtype (Han et al., 2012, 2014; Soto et al. 2013). These findings support the notion that rebalancing of GABAergic transmission via $GABA_A$ α5 receptors can improve symptoms in ASD without the side effects of non-selective benzodiazepines.

Objects of the present invention are compounds of formula (I) or (II) and their pharmaceutically acceptable salts and esters, the preparation of the above mentioned compounds, medicaments containing them and their manufacture as well as the use of the above mentioned compounds in the treatment or prevention of diseases related to $GABA_A$ α5 receptor related diseases and diseases or conditions which can be treated by the modulation of $GABA_A$ α5 receptor activity, such as Alzheimer's disease, mild cognitive impairment (MCI), age-related cognitive decline, negative and/or cognitive symptoms associated with schizophrenia, bipolar disorders, autism spectrum disorder (ASD), Angelman syndrome, Rett syndrome, Prader-Willi syndrome, epilepsy, post-traumatic stress disorder (PTSD), amyotrophic lateral sclerosis (ALS), fragile-X disorder. Compounds of the present invention are selective $GABA_A$ α5 receptor positive allosteric modulators (PAMs) as they enhance the function of α5-containing $GABA_A$ receptors by increasing GABAergic currents (influx of chloride) at a given $EC_{20}$ concentration of gamma amino butyric acid (GABA). The compounds of the present invention have higher PAM effect than the compounds of the state of the art. In a preferred embodiment the compounds of the invention are binding selective for the α5 subunit relative to the α1, α2 and α3 subunits. Compatible with the α5-subtype brain distribution, selective $GABA_A$ α5 PAMs will restore GABAergic signaling in key brain regions (e.g. hippocampus, amygdala, nucleus accumbens and preftrontal cortex) without the side-effects of non-selective $GABA_A$ modulators (e.g. benzodiazepines). In another preferred embodiment, the compounds of the present inventions have a increased chemical stability, particularly to low and high pH conditions.

The term "$C_{1-6}$-alkyl" denotes a monovalent linear or branched saturated hydrocarbon group of 1 to 6 carbon atoms. Examples of $C_{1-6}$-alkyl include methyl, ethyl, n-propyl, isopropyl, n-butyl, iso-butyl, sec-butyl, tert-butyl and pentyl. Particular $C_{1-6}$-alkyl groups are methyl, ethyl, isopropyl, iso-butyl and tert-butyl. More particular example is methyl.

The term "$C_{1-6}$-alkoxy" denotes a group of the formula —O—R', wherein R' is an $C_{1-6}$-alkyl group. Examples of $C_{1-6}$-alkoxy groups include methoxy, ethoxy, n-propoxy, isopropoxy, n-butoxy, isobutoxy and tert-butoxy. Particular examples are tert-butoxy, methoxy, ethoxy and isopropoxy. More particular examples are ethoxy, methoxy and tert-butoxy. Most particular example is tert-butoxy.

The term "halogen" and "halo" are used interchangeably herein and denote fluoro, chloro, bromo or iodo. Particular halogens include fluoro and chloro.

The term "halo-$C_{1-6}$-alkoxy" denotes an $C_{1-6}$-alkoxy group wherein at least one of the hydrogen atoms of the $C_{1-6}$-alkoxy group has been replaced by same or different halogen atoms. The term "perhalo-$C_{1-6}$-alkoxy" denotes an $C_{1-6}$-alkoxy group where all hydrogen atoms of the $C_{1-6}$-alkoxy group have been replaced by the same or different halogen atoms. Examples of halo-$C_{1-6}$-alkoxy include fluoromethoxy, difluoromethoxy, trifluoromethoxy, fluoroethoxy, difluoroethoxy, trifluoroethoxy, trifluoromethylethoxy, trifluorodimethylethoxy and pentafluoroethoxy. Particular halo-$C_{1-6}$-alkoxy groups include trifluoroethoxy, difluoromethoxy, difluoroethoxy, trifluoromethoxy, trifluoromethylethoxy and trifluorodimethylethoxy. More particular examples are trifluoroethoxy, difluoroethoxy and difluoromethoxy.

The term "halo-$C_{1-6}$-alkyl" denotes an $C_{1-6}$-alkyl group wherein at least one of the hydrogen atoms of the $C_{1-6}$-alkyl group has been replaced by the same or different halogen atoms. The term "perhalo-$C_{1-6}$-alkyl-$C_{1-6}$-alkyl" denotes an —$C_{1-6}$-alkyl-$C_{1-6}$-alkyl group where all hydrogen atoms of the alkyl group have been replaced by the same or different halogen atoms. Examples of halo-$C_{1-6}$-alkyl include fluoromethyl, difluoromethyl, trifluoromethyl, trifluoroethyl, trifluoromethylethyl and pentafluoroethyl. Particular halo-$C_{1-6}$-alkyl groups include difluoromethyl, trifluoromethyl, fluoromethyl, trifluoroethyl and difluoroethyl. More particular halo-$C_{1-6}$-alkyl groups include trifluoromethyl and difluoromethyl.

The term "hydroxy" denotes a —OH group.

The term "oxo" denotes a =O group.

The term "hydroxy-$C_{1-6}$-alkyl" denotes an $C_{1-6}$-alkyl group wherein one of the hydrogen atoms of the $C_{1-6}$-alkyl group has been replaced by a hydroxy group. Examples of hydroxy-$C_{1-6}$-alkyl include hydroxymethyl, hydroxyethyl, hydroxypropyl, hydroxymethylpropyl hydroxymethylethyl and hydroxybutyl. Particular examples include hydroxymethylpropyl and hydroxymethylethyl.

The term "amino" denotes a —$NH_2$ group.

The term "$C_{1-6}$-alkoxy-$C_{1-6}$-alkyl" denotes an $C_{1-6}$-alkyl group wherein at least one of the hydrogen atoms of the $C_{1-6}$-alkyl group has been replaced by an $C_{1-6}$-alkoxy group. Exemplary $C_{1-6}$-alkoxy-$C_{1-6}$-alkyl groups include methoxymethyl, ethoxymethyl, methoxymethyl, ethoxyethyl, methoxypropyl and ethoxypropyl.

The term "carbonyl" denotes a —C(O)— group.

The term "$C_{1-6}$-alkoxycarbonyl" denotes a group of the formula —C(O)—R', wherein R' is a $C_{1-6}$-alkoxy group. Examples of $C_{1-6}$-alkoxycarbonyl groups include groups wherein R' is methoxy, ethoxy, n-propoxy, isopropoxy, n-butoxy, isobutoxy or tert-butoxy. Particular examples of $C_{1-6}$-alkoxycarbonyl groups include wherein R' is ethoxy or tert-butoxy.

The term "$C_{1-6}$-alkylcarbonyl" of the formula —C(O)—R', wherein R' is an $C_{1-6}$-alkyl group. Examples of $C_{1-6}$-alkylcarbonyl groups include groups of the formula —C(O)—R', wherein R' is methyl or ethyl. Particular example of $C_{1-6}$-alkylcarbonyl groups include groups of the formula —C(O)—R', wherein R' is methyl.

The term "cyano" denotes a —C≡N group.

The term "$C_{3-8}$-cycloalkyl" denotes a monovalent saturated monocyclic or bicyclic hydrocarbon group of 3 to 8 ring carbon atoms. Bicyclic means a ring system consisting of two saturated carbocycles having one or two carbon atoms in common. Examples of monocyclic $C_3$-8-cycloalkyl are cyclopropyl, cyclobutanyl, cyclopentyl, cyclohexyl or cycloheptyl. Example of bicyclic $C_{3-8}$-cycloalkyl is spiro[3.3]heptanyl. Particular monocyclic $C_{3-8}$-cycloalkyl groups are cyclopropyl, cyclobutanyl. More particular monocyclic $C_{3-8}$-cycloalkyl groups include cyclopropyl.

The term "$C_{3-8}$-cycloalkoxy" denotes a group of the formula —O—R', wherein R' is a $C_{3-8}$-cycloalkyl group. Examples of cycloalkoxy group include cyclopropoxy, cyclobutoxy, cyclopentyloxy, cyclohexyloxy, cycloheptyloxy and cyclooctyloxy. Particular example is cyclopropoxy.

The term "$C_{3-8}$-cycloalkyl-$C_{1-6}$-alkoxy" denotes an $C_{1-6}$-alkoxy group wherein at least one of the hydrogen atoms of the $C_{1-6}$-alkoxy group is replaced by a $C_{3-8}$-cycloalkyl group. Examples of $C_{3-8}$-cycloalkyl-$C_{1-6}$-alkoxy include cyclopropylmethoxy, cyclobutylmethoxy, cyclopentylmethoxy, cyclohexylmethoxy, cyclopropylethoxy, cyclobutylethoxy, cyclopentylethoxy and cyclohexylethoxy. Particular examples include cyclopropylethoxy.

The term "$C_{3-8}$-cycloalkyl-$C_{1-6}$-alkyl" denotes an $C_{1-6}$-alkyl group wherein at least one of the hydrogen atoms of the $C_{1-6}$-alkyl group is replaced by a $C_{3-8}$-cycloalkyl group. Examples of $C_{3-8}$-cycloalkyl-$C_{1-6}$-alkyl include cyclopropylmethyl, cyclobutylmethyl, cyclopentylmethyl, cyclohexylmethyl, cyclopropylethyl, cyclobutylethyl, cyclopentylethyl and cyclohexylethyl. Particular example is cyclopropylethyl.

The term "$C_{3-8}$-cycloalkylcarbonyl" denotes a group of the formula —C(O)—R', wherein R' is a $C_{3-8}$-cycloalkyl group. Examples of $C_{3-8}$-cycloalkylcarbonyl groups include groups of the formula —C(O)—R', wherein R' is cyclopropyl. Particular examples include wherein R' is cyclopropyl.

The term "$C_{3-8}$-cycloalkyl-$C_{1-6}$-alkoxycarbonyl" denotes a group of the formula —C(O)—R', wherein R' is a $C_{3-8}$-cycloalkyl-$C_{1-6}$-alkoxy group. Examples of $C_{3-8}$-cycloalkyl-$C_{1-6}$-alkoxycarbonyl groups include groups wherein R' is cyclopropylmethoxy, cyclopropylethoxy, cyclobutylpropoxy or cyclopropylbutoxy.

The term "$C_{3-8}$-cycloalkylaminocarbonyl" denotes a group of the formula —C(O)NR'R", wherein R' is H and R" is an $C_{3-8}$-cycloalkyl group. Examples of $C_{3-8}$-cycloalkylaminocarbonyl groups include groups wherein R' is H and R" is cyclopropyl or cyclobutyl. Particular examples include wherein R' is H and R" is cyclopropyl, The term "$C_{1-6}$-alkyl-$C_{3-8}$-cycloalkyl-$C_{1-6}$-alkyl" denotes an $C_{1-6}$-alkyl group wherein at least one of the hydrogen atoms of the $C_{1-6}$-alkyl group is replaced by an $C_{1-6}$-alkyl-$C_{3-8}$-cycloalkyl group. Examples include methylcyclobutylmethyl, methylcyclopropylmethyl, methylcyclobutylethyl and methylcyclopropylethyl.

The term "$C_{1-6}$-alkyl-$C_{3-8}$-cycloalkylcarbonyl" denotes a group of the formula —C(O)—R', wherein R' is a $C_{1-6}$-alkyl-$C_{3-8}$-cycloalkyl group. Examples of $C_{1-6}$-alkyl-$C_{3-8}$-cycloalkylcarbonyl include methylcyclopropylcarbonyl and methylcyclobutylcarbonyl. Particular examples include methylcyclopropylcarbonyl.

The term "aryl" denotes a monovalent aromatic carbocyclic mono- or bicyclic ring system comprising 6 to 10 carbon ring atoms. Examples of aryl group include phenyl and naphthyl. Particular aryl groups include phenyl.

The term "aryloxy" denotes a group of the formula —O—R', wherein R' is an aryl. Particular aryloxy groups include phenoxy.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl and quinoxalinyl. Particular heteroaryl groups include pyridinyl, pyrazolyl, imidazolyl, pyrimidinyl, pyridazinyl, imidazo[1,2-a]pyridinyl, oxadiazolyl. More particular heteroaryl groups include pyrazolyl.

The term "heteroaryloxy" denotes a group of the formula —O—R', wherein R' is a heteroaryl. Particular examples for R' include pyridinyl, The term "heterocycloalkyl" denotes a monovalent saturated or partly unsaturated mono- or bicyclic ring system of 4 to 11 ring atoms, comprising 1, 2, or 3 ring heteroatoms selected from N, O and S, the remaining ring atoms being carbon. Bicyclic means consisting of two cycles having one or two ring atoms in common. Examples for monocyclic saturated heterocycloalkyl are 4,5-dihydro-oxazolyl, oxetanyl, azetidinyl, pyrrolidinyl, 2-oxo-pyrrolidin-3-yl, tetrahydrofuranyl, tetrahydrothiophenyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are oxabicyclo[2.2.1]heptanyl, oxaspiro[3.3]heptanyl, 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Particular heterocycloalkyl are pyrrolidinyl, piperidinyl, morpholinyl, piperazinyl, 2-oxa-6-azaspiro[3.3]heptanyl, 1,2,3,4,6,7,8,8a-octahydropyrrolo[1,2-a]pyrazinyl, 3,5,6,7,8,8a-hexahydro-1H-oxazolo[3,4-a]pyrazinyl, 2-oxa-7-azaspiro[3.5]nonanyl, 1-oxa-7-azaspiro[3.5]nonanyl, 3,3a,4,5,6,6a-hexahydro-1H-furo[3,4-c]pyrrolyl, 2,6-diazaspiro[3.3]heptanyl, 5-oxa-2-azaspiro[3.4]

octanyl, 7-oxa-2-azaspiro[3.5]nonanyl, 3-oxa-9-azaspiro[5.5]undecanyl, 5-oxa-2-azaspiro[3.5]nonanyl, 1-oxa-9-azaspiro[5.5]undecanyl, 5-oxa-2-azaspiro[3.6]decanyl, 2-azaspiro[3.3]heptanyl, 4,7-diazaspiro[2.5]octanyl, 2-azaspiro[3.5]nonanyl, 6-oxa-3-azabicyclo[3.1.1]heptanyl, 1-oxa-8-azaspiro[4.5]decanyl, 8-oxa-3-azabicyclo[3.2.1]octanyl, 3-oxa-6-azabicyclo[3.1.1]heptanyl, 3-oxa-8-azabicyclo[3.2.1]octanyl and azetidinyl. More particular examples include morpholinyl, piperazinyl, azetidinyl, 5-oxa-2-azaspiro[3.5]nonanyl, 2,6-diazaspiro[3.3]heptanyl, 5-oxa-2-azaspiro[3.4]octanyl, 2-azaspiro[3.3]heptanyl. Even more particular examples include morpholinyl, piperazinyl, azetidinyl, 5-oxa-2-azaspiro[3.5]nonanyl. Most particular examples include azetidinyl, 5-oxa-2-azaspiro[3.5]nonanyl.

The term "heterocycloalkyl-$C_{1-6}$-alkyl" denotes an $C_{1-6}$-alkyl group wherein one of the hydrogen atoms of the $C_{1-6}$-alkyl group has been replaced by a heterocycloalkyl group. Particular heterocycloalkyl-$C_{1-6}$-alkyl are methyloxetanyl and methyltetrahydropyranyl.

The term "heterocycloalkoxy" denotes a group of the formular —O—R', wherein R' is a heterocycloalkyl group. Particular heterocycloalkyloxy is tetrahydrofuranyloxy.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) or (II) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I) or (II), similar to the metabolically labile esters, which are capable of producing the parent compounds of general formula (I) or (II) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn) groups. Further particular protecting groups are the tert-butoxycarbonyl (Boc) and the fluorenylmethoxycarbonyl (Fmoc) groups. More particular protecting group is the tert-butoxycarbonyl (Boc) group.

The abbreviation uM means microMolar and is equivalent to the symbol µM.

The abbreviation uL means microliter and is equivalent to the symbol µL.

The abbreviation ug means microgram and is equivalent to the symbol µg.

The compounds of formula (I) or (II) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention is a compound according to formula (I) or (II) as described herein and pharmaceutically acceptable salts or esters thereof, in particular compounds according to formula (I) as described herein and pharmaceutically acceptable salts thereof, more particularly compounds according to formula (I) as described herein.

A particular embodiment of the present invention provides a compound according to formula (I) or (II) as described herein, wherein W is selected from
  i) N, and
  ii) $CR^4$;
Y is selected from
  i) N, and
  ii) CH;
Z is selected from
  i) N, and
  ii) CH;
$R^{99}$ is selected from
  i) H, and
  ii) halogen;
$R^2$ is selected from
  i) H,
  ii) $C_{1-6}$-alkyl,
  iii) $C_{3-8}$-cycloalkyl, and
  iv) halo-$C_{1-6}$-alkyl;
$R^3$ is selected from
  i) heterocycloalkyl substituted with $R^6$, $R^7$ and $R^8$, wherein the heterocycloalkyl is selected from
    a. pyrrolidinyl,
    b. piperidinyl,
    c. morpholinyl,
    d. piperazinyl,
    e. 2-oxa-6-azaspiro[3.3]heptanyl,
    f. 1,2,3,4,6,7,8,8a-octahydropyrrolo[1,2-a]pyrazinyl,
    g. 3,5,6,7,8,8a-hexahydro-1H-oxazolo[3,4-a]pyrazinyl,
    h. 2-oxa-7-azaspiro[3.5]nonanyl,
    i. 1-oxa-7-azaspiro[3.5]nonanyl,
    j. 3,3a,4,5,6,6a-hexahydro-1H-furo[3,4-c]pyrrolyl,
    k. 2,6-diazaspiro[3.3]heptanyl,
    l. 5-oxa-2-azaspiro[3.4]octanyl, m. 7-oxa-2-azaspiro[3.5]nonanyl,
n. 3-oxa-9-azaspiro[5.5]undecanyl,
o. 5-oxa-2-azaspiro[3.5]nonanyl,
p. 1-oxa-9-azaspiro[5.5]undecanyl,
q. 5-oxa-2-azaspiro[3.6]decanyl,
r. 2-azaspiro[3.3]heptanyl,
s. 4,7-diazaspiro[2.5]octanyl,
t. 2-azaspiro[3.5]nonanyl,
u. 6-oxa-3-azabicyclo[3.1.1]heptanyl,
v. 1-oxa-8-azaspiro[4.5]decanyl,
w. 8-oxa-3-azabicyclo[3.2.1]octanyl,
x. 3-oxa-6-azabicyclo[3.1.1]heptanyl,
y. 3-oxa-8-azabicyclo[3.2.1]octanyl, and
z. azetidinyl;
ii) amino substituted on the nitrogen atom by one or two substituents independently selected from $R^9$ and $R^{10}$,
iii) phenyl substituted with $R^{11}$, $R^{12}$ and $R^{13}$, wherein $R^{11}$, $R^{12}$ and $R^{13}$ are independently selected from
  a. H,
  b. $C_{1-6}$-alkoxy,
  c. halo-$C_{1-6}$-alkyl,
  d. halo-$C_{1-6}$-alkoxy, and
  e. halogen;
iv) heteroaryl substituted with $R^{11}$, $R^{12}$ and $R^{13}$, wherein $R^{11}$, $R^{12}$ and $R^{13}$ are independently selected from
  a. H,
  b. $C_{1-6}$-alkoxy,
  c. $C_{1-6}$-alkyl,
  d. cyano,
  e. $C_{3-8}$-cycloalkyl,
  f. halo-$C_{1-6}$-alkyl,
  g. halo-$C_{1-6}$-alkoxy,
  h. amino substituted on the nitrogen atom by one or two substituents independently selected from $R^{14}$ and R,
  i. $C_{3-8}$-cycloalkyl-$C_{1-6}$-alkyl,
  j. heterocycloalkyl substituted with $R^{16}$, $R^{17}$ and $R^{18}$, wherein $R^{16}$, $R^{17}$ and $R^{18}$ are H, and wherein the heterocycloalkyl is piperazinyl,
  k. heterocycloalkoxy, wherein the heterocycloalkoxy is substituted with $R^{16}$, $R^{17}$ and $R^{18}$, wherein $R^{16}$, $R^{17}$ and $R^{18}$ are H, and wherein the heterocycloalkoxy is tetrahydrofuranyloxy,
  l. heterocycloalkyl-$C_{1-6}$-alkyl, wherein the heterocycloalkyl-$C_{1-6}$-alkyl is substituted with $R^{16}$, $R^{17}$ and $R^{18}$, wherein $R^{16}$, $R^{17}$ and $R^{18}$ are independently selected from
    i. H, and
    ii. $C_{1-6}$-alkyl;
  and wherein the heterocycloalkyl-$C_{1-6}$-alkyl is oxetanyl-$C_{1-6}$-alkyl,
  m. halogen;
and wherein heteroaryl is selected from pyridinyl, imidazo[1,2-a]pyridinyl and pyrazolyl;
$R^4$ is selected from
  i) H, and
  ii) halogen;
$R^5$ is selected from
  i) $C_{1-6}$-alkyl,
  ii) $C_{3-8}$-cycloalkyl,
  iii) halo-$C_{1-6}$-alkyl, and
  iv) halogen;
$R^6$, $R^7$ and $R^8$ are independently selected from
  i) H,
  ii) $C_{1-6}$-alkyl,
  iii) $C_{1-6}$-alkoxy,
  iv) $C_{1-6}$-alkoxycarbonyl,
  v) cyano,
  vi) amino substituted on the nitrogen atom by one or two substituents independently selected from $R^{22}$ and $R^{23}$,
  vii) $C_{3-8}$-cycloalkyl-$C_{1-6}$-alkoxy, wherein the $C_{3-8}$-cycloalkyl is substituted with $R^{24}$, $R^{25}$ and $R^{26}$, wherein $R^{24}$, $R^{25}$ and $R^{26}$ are independently selected form H and $C_{1-6}$-alkyl;
  viii) $C_{3-8}$-cycloalkylaminocarbonyl, wherein the $C_{3-8}$-cycloalkyl is substituted with $R^{24}$, $R^{25}$ and $R^{26}$, wherein $R^{24}$, $R^{25}$ and $R^{26}$ are H;
  ix) $C_{3-8}$-cycloalkylcarbonyl, wherein the $C_{3-8}$-cycloalkyl is substituted with $R^{24}$, $R^{25}$ and $R^{26}$, wherein $R^{24}$, $R^{25}$ and $R^{26}$ are independently selected from H and $C_{1-6}$-alkyl;
  x) $C_{3-8}$-cycloalkyl substituted with $R^{24}$, $R^{25}$ and $R^{26}$, wherein $R^{24}$, $R^{25}$ and $R^{26}$ are independently selected from H and $C_{1-6}$-alkyl;
  xi) $C_{3-8}$-cycloalkoxy substituted with $R^{24}$, $R^{25}$ and $R^{26}$, wherein $R^{24}$, $R^{25}$ and $R^{26}$ are H;
  xii) aryloxy, wherein the aryl is substituted with $R^{27}$, $R^2$ and $R^{29}$, wherein $R^{27}$, $R^{28}$ and $R^{29}$ are independently selected from
    a. H, and
    b. halogen;
  and wherein the aryl is phenyl;
  xiii) aryl substituted with $R^{27}$, $R^{28}$ and $R^{29}$, wherein $R^{27}$, $R^{28}$ and $R^{29}$ are independently selected from
    a. H, and
    b. alkoxy;
  and wherein the aryl is phenyl;
  xiv) heteroaryl substituted with $R^{27}$, $R^{28}$ and $R^{29}$, wherein $R^{27}$, $R^{28}$ and $R^{29}$ are independently selected from
    a. H, and
    b. $C_{1-6}$-alkyl,
    and wherein the heteroaryl is selected from imidazolyl, triazolyl, pyrimidinyl, pyridazinyl, pyrazolyl, pyridinyl and oxadiazolyl;
  xv) heteroaryloxy, wherein the heteroaryl is substituted with $R^{27}$, $R^{28}$ and $R^{29}$, wherein $R^{27}$, $R^{28}$ and $R^{29}$ are independently selected from
    a. H,
    b. $C_{1-6}$-alkyl, and
    c. halogen;
    and wherein the heteroaryl is selected from
    a. pyridinyl, and
    b. pyridazinyl;
  xvi) halo-$C_{1-6}$-alkoxy,
  xvii) halo-$C_{1-6}$-alkyl,
  xviii) halogen,
  xix) oxo,
  xx) hydroxy, and
  xxi) hydroxy-$C_{1-6}$-alkyl;
$R^9$ and $R^{10}$ are independently selected from
  i) H,
  ii) $C_{1-6}$-alkyl,
  iii) heterocycloalkyl substituted with $R^{30}$, $R^{31}$ and $R^{32}$, wherein $R^{30}$, $R^{31}$ and $R^{32}$ are independently selected from
    i) H, and
    ii) $C_{3-8}$-cycloalkyl;
    and wherein heterocycloalkyl is selected from azetidinyl and oxetanyl, iv) heterocycloalkyl-$C_{1-6}$-alkyl, wherein the heterocycloalkyl-$C_{1-6}$-alkyl is substituted with $R^{30}$, $R^{31}$ and $R^{32}$, wherein $R^{30}$, $R^{31}$ and $R^{32}$ are H, and wherein heterocyclalkyl-$C_{1-6}$-alkyl is tetrahydropyranyl-$C_{1-6}$-alkyl,
v) hydroxy-$C_{1-6}$-alkyl, and
vi) $C_{3-8}$-cycloalkyl;

$R^{14}$ and $R^{15}$ are independently selected from
i) H, and
ii) $C_{1-6}$-alkyl;

$R^{22}$ and $R^{23}$ are independently selected from
i) $C_{1-6}$-alkyl, and
ii) $C_{1-6}$-alkylcarbonyl;

or pharmaceutically acceptable salts.

A more particular embodiment of the present invention provides a compound according to formula (I) as described herein,
W is $CR^4$;
Y is selected from
i) N, and
ii) CH;
Z is selected from
i) N, and
ii) CH;
$R^{99}$ is selected from
i) H, and
ii) halogen;
$R^2$ is selected from
i) H, and
ii) $C_{1-6}$-alkyl;
$R^3$ is selected from
i) heterocycloalkyl substituted with $R^6$, $R^7$ and $R^8$, and
ii) heteroaryl substituted with $R^{11}$, $R^{12}$ and $R^{13}$;
$R^4$ is H,
$R^5$ is selected from
i) $C_{1-6}$-alkyl,
ii) halo-$C_{1-6}$-alkyl, and
iii) halogen;
$R^6$, $R^7$ and $R^8$ are independently selected from
i) H,
ii) $C_{1-6}$-alkyl,
iii) $C_{1-6}$-alkoxy,
iv) $C_{3-8}$-cycloalkyl,
v) $C_{3-8}$-cycloalkoxy,
vi) halo-$C_{1-6}$-alkoxy,
vii) halo-$C_{1-6}$-alkyl,
viii) halogen;
$R^{11}$, $R^{12}$ and $R^{13}$ are independently selected from
i) $C_{1-6}$-alkyl,
ii) H,
iii) $C_{3-8}$-cycloalkyl, and
iv) halo-$C_{1-6}$-alkyl;
$R^{24}$, $R^{25}$ and $R^{26}$ are H;
or pharmaceutically acceptable salts.

An even more particular embodiment of the present invention provides a compound according to formula (I) as described herein,
W is $CR^4$;
Y is selected from
i) N, and
ii) CH;
Z is selected from
i) N, and
ii) CH;
$R^{99}$ is selected from H and halogen;
$R^2$ is selected from
i) H, and
ii) $C_{1-6}$-alkyl;

$R^3$ is selected from
i) heterocycloalkyl substituted with $R^6$, $R^7$ and $R^8$, wherein heterocycloalkyl is selected from piperazinyl, azetidinyl, 5-oxa-2-azaspiro[3.5]nonanyl, 5-oxa-2-azaspiro[3.4]octanyl, 2,6-diazaspiro[3.3]heptanyl, morpholinyl and 2-azaspiro[3.3]heptanyl, and
ii) pyrazolyl substituted with $R^{11}$, $R^{12}$ and $R^{13}$;
$R^4$ is H,
$R^5$ is selected from
i) $C_{1-6}$-alkyl,
ii) halo-$C_{1-6}$-alkyl, and
iii) halogen;
$R^6$, $R^7$ and $R^8$ are independently selected from
i) H,
ii) $C_{1-6}$-alkyl,
iii) $C_{1-6}$-alkoxy,
iv) $C_{3-8}$-cycloalkyl,
v) $C_{3-8}$-cycloalkoxy,
vi) halo-$C_{1-6}$-alkoxy,
vii) halo-$C_{1-6}$-alkyl,
viii) halogen;
$R^{11}$, $R^{12}$ and $R^{13}$ are independently selected from
i) $C_{1-6}$-alkyl,
ii) H,
iii) $C_{3-8}$-cycloalkyl, and
iv) halo-$C_{1-6}$-alkyl;
$R^{24}$, $R^{25}$ and $R^{26}$ are H;
or pharmaceutically acceptable salts.

A furthermore particular embodiment of the present invention provides a compound according to formula (I) as described herein,
W is $CR^4$;
Y is N;
Z is selected from
i) N, and
ii) CH;
$R^{99}$ is H;
$R^2$ is $C_{1-6}$-alkyl;
$R^3$ is heterocycloalkyl substituted with $R^6$, $R^7$ and $R^8$;
$R^4$ is H,
$R^5$ is selected from
i) $C_{1-6}$-alkyl, and
ii) halogen;
$R^6$, $R^7$ and $R^8$ are independently selected from
i) H,
ii) $C_{1-6}$-alkyl,
iii) $C_{1-6}$-alkoxy,
iv) $C_{3-8}$-cycloalkyl,
v) $C_{3-8}$-cycloalkoxy,
vi) halogen;
$R^{24}$, $R^{25}$ and $R^{26}$ are H;
or pharmaceutically acceptable salts.

A most particular embodiment of the present invention provides a compound according to formula (I) as described herein,
W is $CR^4$;
Y is N;
Z is selected from
i) N, and
ii) CH;
$R^{99}$ is H;
$R^2$ is methyl;

R³ is heterocycloalkyl substituted with R⁶, R⁷ and R⁸, wherein heterocycloalkyl is selected from piperazinyl, azetidinyl, 5-oxa-2-azaspiro[3.5]nonanyl and morpholinyl;
R⁴ is H,
R⁵ is selected from
   i) methyl, and
   ii) chloro;
R⁶, R⁷ and R⁸ are independently selected from
   i) H,
   ii) methyl,
   iii) tert-butoxy,
   iv) cyclopropyl,
   v) $C_{3-8}$-cycloalkoxy,
   vi) fluoro;
R²⁴, R²⁵ and R²⁶ are H;
or pharmaceutically acceptable salts.

An even most particular embodiment of the present invention provides a compound according to formula (I) as described herein,
   W is CR⁴;
   Y is N;
   Z is selected from
      i) N, and
      ii) CH;
   R⁹⁹ is H;
   R² is $C_{1-6}$-alkyl;
   R³ is heterocycloalkyl substituted with R⁶, R⁷ and R⁸;
   R⁴ is H,
   R⁵ is selected from
      i) $C_{1-6}$-alkyl, and
      ii) halogen;
   R⁶, R⁷ and R⁸ are independently selected from
      i) $C_{1-6}$-alkoxy,
      ii) H,
      iii) halogen;
or pharmaceutically acceptable salts.

An even most particular embodiment of the present invention provides a compound according to formula (I) as described herein,
   W is CR⁴;
   Y is N;
   Z is selected from
      i) N, and
      ii) CH;
   R⁹⁹ is H;
   R² is methyl;
   R³ is selected from
      i) azetidinyl substituted with R⁶, R⁷ and R¹, and
      ii) 5-oxa-2-azaspiro[3.5]nonanyl substituted with R⁶, R⁷ and R⁸;
   R⁴ is H,
   R⁵ is selected from
      i) methyl, and
      ii) fluoro;
   R⁶, R⁷ and R⁸ are independently selected from
      i) tert-butoxy,
      ii) H,
      iii) fluoro;
or pharmaceutically acceptable salts.

A particular embodiment of the present invention provides a compound as described herein, wherein the compound is a compound of formula (I).

A particular embodiment of the present invention provides a compound as described herein, wherein W is CR⁴.

A particular embodiment of the present invention provides a compound as described herein, wherein Y is N.

A particular embodiment of the present invention provides a compound as described herein, wherein R⁹⁹ is selected from H or halogen.

A more particular embodiment of the present invention provides a compound as described herein, wherein R⁹⁹ is H.

A particular embodiment of the present invention provides a compound as described herein, wherein R² is selected from H, $C_{1-6}$-alkyl, $C_{3-8}$-cycloalkyl, and halo-$C_{1-6}$-alkyl.

A more particular embodiment of the present invention provides a compound as described herein, wherein R² is $C_{1-6}$-alkyl.

A furthermore particular embodiment of the present invention provides a compound as described herein, wherein R² is methyl.

A particular embodiment of the present invention provides a compound as described herein, wherein R³ is selected from
   i) heterocycloalkyl substituted with R⁶, R⁷ and R⁸, and
   ii) heteroaryl substituted with R⁶, R⁷ and R.

A more particular embodiment of the present invention provides a compound as described herein, wherein R³ is selected from
   i) heterocycloalkyl substituted with R⁶, R⁷ and R⁸, wherein heterocycloalkyl is selected from
      a. pyrrolidinyl,
      b. piperidinyl,
      c. morpholinyl,
      d. piperazinyl,
      e. 2-oxa-6-azaspiro[3.3]heptanyl,
      f. 1,2,3,4,6,7,8,8a-octahydropyrrolo[1,2-a]pyrazinyl,
      g. 3,5,6,7,8,8a-hexahydro-1H-oxazolo[3,4-a]pyrazinyl,
      h. 2-oxa-7-azaspiro[3.5]nonanyl,
      i. 1-oxa-7-azaspiro[3.5]nonanyl,
      j. 3,3a,4,5,6,6a-hexahydro-1H-furo[3,4-c]pyrrolyl,
      k. 2,6-diazaspiro[3.3]heptanyl,
      l. 5-oxa-2-azaspiro[3.4]octanyl,
      m. 7-oxa-2-azaspiro[3.5]nonanyl,
      n. 3-oxa-9-azaspiro[5.5]undecanyl,
      o. 5-oxa-2-azaspiro[3.5]nonanyl,
      p. 1-oxa-9-azaspiro[5.5]undecanyl,
      q. 5-oxa-2-azaspiro[3.6]decanyl,
      r. 2-azaspiro[3.3]heptanyl,
      s. 4,7-diazaspiro[2.5]octanyl,
      t. 2-azaspiro[3.5]nonanyl,
      u. 6-oxa-3-azabicyclo[3.1.1]heptanyl,
      v. 1-oxa-8-azaspiro[4.5]decanyl,
      w. 8-oxa-3-azabicyclo[3.2.1]octanyl,
      x. 3-oxa-6-azabicyclo[3.1.1]heptanyl,
      y. 3-oxa-8-azabicyclo[3.2.1]octanyl, and
      z. azetidinyl; and
   ii) heteroaryl substituted with R⁶, R⁷ and R⁸, wherein heteroaryl is selected from
      a. pyridinyl,
      b. imidazo[1,2-a]pyridinyl, and
      c. pyrazolyl.

An even more particular embodiment of the present invention provides a compound as described herein, wherein R³ is heterocycloalkyl substituted with R⁶, R⁷ and R⁸, wherein heterocycloalkyl is selected from
   i) morpholinyl,
   ii) piperazinyl,
   iii) azetidinyl, and
   iv) 5-oxa-2-azaspiro[3.5]nonanyl.

A furthermore particular embodiment of the present invention provides a compound as described herein, wherein $R^3$ is heterocycloalkyl substituted with $R^6$, $R^7$ and $R^8$, wherein heterocycloalkyl is selected from
  i) azetidinyl, and
  ii) 5-oxa-2-azaspiro[3.5]nonanyl.

A particular embodiment of the present invention provides as described herein, wherein $R^4$ is H and halogen.

A more particular embodiment of the present invention provides as described herein, wherein $R^4$ is H.

A particular embodiment of the present invention provides a compound according to formula (I) as described herein, wherein $R^5$ is selected from $C_{1-6}$-alkyl, $C_{3-8}$-cycloalkyl, halo-$C_{1-6}$-alkyl, and halogen.

A more particular embodiment of the present invention provides a compound as described herein, wherein $R^5$ is $C_{1-6}$-alkyl or halogen.

A furthermore particular embodiment of the present invention provides a compound as described herein, $R^5$ is methyl or chloro.

A particular embodiment of the present invention provides a compound as described herein, wherein $R^6$, $R^7$ and R are independently selected from
  i) H,
  ii) $C_{1-6}$-alkyl,
  iii) $C_{1-6}$-alkoxy,
  iv) $C_{1-6}$-alkoxycarbonyl,
  v) cyano,
  vi) amino substituted on the nitrogen atom by one or two substituents independently selected from $R^{22}$ and $R^{23}$,
  vii) $C_{3-8}$-cycloalkyl-$C_{1-6}$-alkoxy, wherein the $C_{3-8}$-cycloalkyl is substituted with $R^{24}$, $R^{25}$ and $R^{26}$, wherein $R^{24}$, $R^{25}$ and $R^{26}$ are independently selected form H and $C_{1-6}$-alkyl;
  viii) $C_{3-8}$-cycloalkylaminocarbonyl, wherein the $C_{3-8}$-cycloalkyl is substituted with $R^{24}$, $R^{25}$ and $R^{26}$, wherein $R^{24}$, $R^{25}$ and $R^{26}$ are H;
  ix) $C_{3-8}$-cycloalkylcarbonyl, wherein the $C_{3-8}$-cycloalkyl is substituted with $R^{24}$, $R^{25}$ and $R^{26}$, wherein $R^{24}$, $R^{25}$ and $R^{26}$ are independently selected from H and $C_{1-6}$-alkyl;
  x) $C_{3-8}$-cycloalkyl substituted with $R^{24}$, $R^{25}$ and $R^{26}$, wherein $R^{24}$, $R^{25}$ and $R^{26}$ are independently selected from H and $C_{1-6}$-alkyl;
  xi) $C_{3-8}$-cycloalkoxy substituted with $R^{24}$, $R^{25}$ and $R^{26}$, wherein $R^{24}$, $R^{25}$ and $R^{26}$ are H;
  xii) aryloxy, wherein the aryl is substituted with $R^{27}$, $R^{28}$ and $R^{29}$, wherein $R^{27}$, $R^{28}$ and $R^{29}$ are independently selected from
    a. H, and
    b. halogen;
    and wherein the aryl is phenyl;
  xiii) aryl substituted with $R^{27}$, $R^{28}$ and $R^{29}$, wherein $R^{27}$, $R^{28}$ and $R^{29}$ are independently selected from
    a. H, and
    b. alkoxy;
    and wherein the aryl is phenyl;
  xiv) heteroaryl substituted with $R^{27}$, $R^{28}$ and $R^{29}$, wherein $R^{27}$, $R^{28}$ and $R^{29}$ are independently selected from
    a. H, and
    b. $C_{1-6}$-alkyl,
    and wherein the heteroaryl is selected from imidazolyl, triazolyl, pyrimidinyl, pyridazinyl, pyrazolyl, pyridinyl and oxadiazolyl;
  xv) heteroaryloxy, wherein the heteroaryl is substituted with $R^{27}$, $R^{28}$ and $R^{29}$, wherein $R^{27}$, $R^{28}$ and $R^{29}$ are independently selected from
    a. H,
    b. $C_{1-6}$-alkyl, and
    c. halogen;
    and wherein the heteroaryl is selected from
    a. pyridinyl, and
    b. pyridazinyl;
  xvi) halo-$C_{1-6}$-alkoxy,
  xvii) halo-$C_{1-6}$-alkyl,
  xviii) halogen,
  xix) oxo,
  xx) hydroxy, and
  xxi) hydroxy-$C_{1-6}$-alkyl A more particular embodiment of the present invention provides a compound as described herein, wherein $R^6$ is selected from
  i) H,
  ii) $C_{1-6}$-alkyl,
  iii) $C_{1-6}$-alkoxy,
  iv) $C_{3-8}$-cycloalkyl,
  v) $C_{3-8}$-cycloalkoxy, and
  vi) halogen.

A furthermore particular embodiment of the present invention provides a compound as described herein, wherein $R^6$ is selected from
  i) $C_{1-6}$-alkoxy, and
  ii) halogen.

A most particular embodiment of the present invention provides a compound as described herein, wherein $R^6$ is selected from
  i) tert-butoxy, and
  ii) fluoro.

A more particular embodiment of the present invention provides a compound as described herein, wherein $R^7$ is selected from
  i) H,
  ii) $C_{1-6}$-alkyl, and
  iii) halogen.

A furthermore particular embodiment of the present invention provides a compound as described herein, wherein $R^7$ is H.

A more particular embodiment of the present invention provides a compound as described herein, wherein $R^8$ is H.

A particular embodiment of the present invention provides as described herein, wherein $R^9$ and $R^1$ (are independently selected from
  i) H,
  ii) $C_{1-6}$-alkyl,
  iii) heterocycloalkyl substituted with $R^{30}$, $R^{31}$ and $R^{32}$, wherein $R^{30}$, $R^{31}$ and $R^{32}$ are independently selected from
    i) H, and
    ii) $C_{3-8}$-cycloalkyl;
    and wherein heterocycloalkyl is selected from azetidinyl and oxetanyl,
  iv) heterocycloalkyl-$C_{1-6}$-alkyl, wherein the heterocycloalkyl-$C_{1-6}$-alkyl is substituted with $R^{30}$, $R^{31}$ and $R^{32}$, wherein $R^{30}$, $R^{31}$ and $R^{32}$ are H, and wherein heterocyclalkyl-$C_{1-6}$-alkyl is tetrahydropyranyl-$C_{1-6}$-alkyl,
  v) hydroxy-$C_{1-6}$-alkyl, and
  vi) $C_{3-8}$-cycloalkyl.

A particular embodiment of the present invention provides as described herein, wherein $R^{14}$ and $R^{15}$ are independently selected from
  i) H, and
  ii) $C_{1-6}$-alkyl.

A particular embodiment of the present invention provides a compound as described herein, wherein $R^{22}$ and $R^{23}$ are independently selected from
i) $C_{1-6}$-alkyl, and
ii) $C_{1-6}$-alkylcarbonyl.

A particular embodiment of the present invention provides a compound as described herein, wherein $R^{24}$, $R^{25}$ and $R^{26}$ are independently selected from
i) H, and
ii) $C_{1-6}$-alkyl.

A particular embodiment of the present invention provides a compound as described herein, wherein $R^{24}$, $R^{25}$ and $R^{26}$ are H.

A particular embodiment of the present invention provides a compound as described herein, wherein $R^{27}$, $R^{28}$ and $R^{29}$ are independently selected form
i) H,
ii) $C_{1-6}$-alkyl,
iii) $C_{1-6}$-alkoxy, and
iv) halogen.

A particular embodiment of the present invention provides a compound as described herein, wherein $R^{30}$, $R^{31}$ and $R^{32}$ are independently selected from
i) H, and
ii) $C_{3-8}$-cycloalkyl.

Particular examples of a compound of formula (I) or (II) as described herein are selected from N-methyl-N-((3S)-1-(1-((5-methyl-3-(6-methylpyridin-3-yl)-1,2-oxazol-4-yl)methyl)-6-oxopyridazin-4-yl)pyrrolidin-3-yl)acetamide;

N-methyl-N-((3R)-1-(1-((5-methyl-3-(6-methylpyridin-3-yl)-1,2-oxazol-4-yl)methyl)-6-oxopyridazin-4-yl)pyrrolidin-3-yl)acetamide;

5-((3R)-3-hydroxypyrrolidin-1-yl)-2-((5-methyl-3-(6-methylpyridin-3-yl)-1,2-oxazol-4-yl)methyl)pyridazin-3-one;

5-((3S)-3-hydroxypyrrolidin-1-yl)-2-((5-methyl-3-(6-methylpyridin-3-yl)-1,2-oxazol-4-yl)methyl)pyridazin-3-one;

5-(4-hydroxypiperidin-1-yl)-2-((5-methyl-3-(6-methylpyridin-3-yl)-1,2-oxazol-4-yl)methyl)pyridazin-3-one;

5-(2,2-dimethylmorpholin-4-yl)-2-((5-methyl-3-(6-methylpyridin-3-yl)-1,2-oxazol-4-yl)methyl)pyridazin-3-one;

5-((2S,6R)-2,6-dimethylmorpholin-4-yl)-2-((5-methyl-3-(6-methylpyridin-3-yl)-1,2-oxazol-4-yl)methyl)pyridazin-3-one;

ethyl 1-(1-((5-methyl-3-(6-methylpyridin-3-yl)-1,2-oxazol-4-yl)methyl)-6-oxopyridazin-4-yl)piperidine-4-carboxylate;

5-(4-(cyclopropanecarbonyl)piperazin-1-yl)-2-((5-methyl-3-(6-methylpyridin-3-yl)isoxazol-4-yl)methyl)pyridazin-3(2H)-one;

2-((5-methyl-3-(6-methylpyridin-3-yl)isoxazol-4-yl)methyl)-5-(4-(1-methylcyclopropanecarbonyl)piperazin-1-yl)pyridazin-3(2H)-one;

2-((3-(4-Fluorophenyl)-5-methylisoxazol-4-yl)methyl)-5-morpholinopyridazin-3(2H)-one;

5-(cis-2,6-Dimethylmorpholino)-2-((3-(4-fluorophenyl)-5-methylisoxazol-4-yl)methyl)pyridazin-3(2H)-one;

2-((3-(5-Chloropyridin-2-yl)-5-methylisoxazol-4-yl)methyl)-5-(cis-2,6-dimethylmorpholino)pyridazin-3(2H)-one;

2-((3-(5-Chloropyridin-2-yl)-5-cyclopropylisoxazol-4-yl)methyl)-5-(cis-2,6-dimethylmorpholino)pyridazin-3(2H)-one;

2-((3-(4-Fluorophenyl)-5-methylisoxazol-4-yl)methyl)-5-(4-(1-methylcyclopropanecarbonyl)piperazin-1-yl)pyridazin-3(2H)-one;

2-((3-(5-Chloropyridin-2-yl)-5-methylisoxazol-4-yl)methyl)-5-(4-(1-methylcyclopropanecarbonyl)piperazin-1-yl)pyridazin-3(2H)-one;

2-((5-methyl-3-(6-methylpyridin-3-yl)isoxazol-4-yl)methyl)-5-(trifluoromethyl)pyridazin-3(2H)-one;

5-(tert-butyl)-2-((5-methyl-3-(6-methylpyridin-3-yl)isoxazol-4-yl)methyl)pyridazin-3(2H)-one;

5-isopropyl-2-((5-methyl-3-(6-methylpyridin-3-yl)isoxazol-4-yl)methyl)pyridazin-3(2H)-one;

5-ethyl-2-((5-methyl-3-(6-methylpyridin-3-yl)isoxazol-4-yl)methyl)pyridazin-3(2H)-one;

tert-Butyl 4-(1-((5-methyl-3-(6-methylpyridin-3-yl)isoxazol-4-yl)methyl)-6-oxo-1,6-dihydropyridazin-4-yl)-5,6-dihydropyridine-1(2H)-carboxylate;

2-((5-Methyl-3-(6-methylpyridin-3-yl)isoxazol-4-yl)methyl)-5-morpholinopyridazin-3(2H)-one;

5-(3,6-Dihydro-2H-pyran-4-yl)-2-((5-methyl-3-(6-methylpyridin-3-yl)isoxazol-4-yl)methyl)pyridazin-3(2H)-one;

2-((5-Methyl-3-(6-methylpyridin-3-yl)isoxazol-4-yl)methyl)-5-(4-(trifluoromethyl)piperidin-1-yl)pyridazin-3(2H)-one;

2-((3-(5-Chloropyridin-2-yl)-5-cyclopropylisoxazol-4-yl)methyl)-5-(4-(cyclopropanecarbonyl)piperazin-1-yl)pyridazin-3(2H)-one;

2-((3-(5-Chloropyridin-2-yl)-5-cyclopropylisoxazol-4-yl)methyl)-5-(4-(1-methylcyclopropanecarbonyl)piperazin-1-yl)pyridazin-3(2H)-one;

N-Cyclopropyl-1-(1-((5-methyl-3-(6-methylpyridin-3-yl)isoxazol-4-yl)methyl)-6-oxo-1,6-dihydropyridazin-4-yl)piperidine-4-carboxamide;

5-((1R,5S)-8-Oxa-3-azabicyclo[3.2.1]octan-3-yl)-2-((5-methyl-3-(6-methylpyridin-3-yl)isoxazol-4-yl)methyl)pyridazin-3(2H)-one;

5-((2S,6S)-2,6-Dimethylmorpholino)-2-((5-methyl-3-(6-methylpyridin-3-yl)isoxazol-4-yl)methyl)pyridazin-3(2H)-one;

5-((2R,6R)-2,6-Dimethylmorpholino)-2-((5-methyl-3-(6-methylpyridin-3-yl)isoxazol-4-yl)methyl)pyridazin-3(2H)-one;

2-((5-Methyl-3-(6-methylpyridin-3-yl)isoxazol-4-yl)methyl)-5-(4-(2,2,2-trifluoroethyl)piperazin-1-yl)pyridazin-3(2H)-one;

5-(cis-2,6-Dimethylmorpholino)-2-((3-(6-methylpyridin-3-yl)isoxazol-4-yl)methyl)pyridazin-3(2H)-one;

5-(3-Oxa-6-azabicyclo[3.1.1]heptan-6-yl)-2-((5-methyl-3-(6-methylpyridin-3-yl)isoxazol-4-yl)methyl)pyridazin-3(2H)-one;

1-(1-((5-Methyl-3-(6-methylpyridin-3-yl)isoxazol-4-yl)methyl)-6-oxo-1,6-dihydropyridazin-4-yl)piperidine-4-carbonitrile;

5-(3-Oxa-8-azabicyclo[3.2.1]octan-8-yl)-2-((5-methyl-3-(6-methylpyridin-3-yl)isoxazol-4-yl)methyl)pyridazin-3(2H)-one;

5-(4-Cyclopropylpiperazin-1-yl)-2-((5-methyl-3-(6-methylpyridin-3-yl)isoxazol-4-yl)methyl)pyridazin-3(2H)-one;

5-Cyclopropyl-2-((5-methyl-3-(6-methylpyridin-3-yl)isoxazol-4-yl)methyl)pyridazin-3(2H)-one;

2-((5-Methyl-3-(6-methylpyridin-3-yl)isoxazol-4-yl)methyl)-5-(2-oxa-6-azaspiro[3.3]heptan-6-yl)pyridazin-3(2H)-one;

5-(cis-2,6-Dimethylmorpholino)-2-((5-methyl-3-(6-(trifluoromethyl)pyridin-3-yl)isoxazol-4-yl)methyl)pyridazin-3(2H)-one;

2-((5-Methyl-3-(6-(trifluoromethyl)pyridin-3-yl)isoxazol-4-yl)methyl)-5-(4-(1-methylcyclopropanecarbonyl)piperazin-1-yl)pyridazin-3(2H)-one;

5-(cis-2,6-Dimethylmorpholino)-2-((3-(3-fluoropyridin-4-yl)-5-methylisoxazol-4-yl)methyl)pyridazin-3(2H)-one;

2-((3-(3-Fluoropyridin-4-yl)-5-methylisoxazol-4-yl)methyl)-5-(4-(1-methylcyclopropanecarbonyl)piperazin-1-yl)pyridazin-3(2H)-one;

2-(1-((5-methyl-3-(6-methylpyridin-3-yl)isoxazol-4-yl)methyl)-6-oxo-1,6-dihydropyridazin-4-yl)hexahydropyrrolo[1,2-a]pyrazin-6(2H)-one;

7-(1-((5-methyl-3-(6-methylpyridin-3-yl)isoxazol-4-yl)methyl)-6-oxo-1,6-dihydropyridazin-4-yl)tetrahydro-1H-oxazolo[3,4-a]pyrazin-3(5H)-one;

5-(dimethylamino)-2-((5-methyl-3-(6-methylpyridin-3-yl)isoxazol-4-yl)methyl)pyridazin-3(2H)-one;

2-((5-Methyl-3-(6-methylpyridin-3-yl)isoxazol-4-yl)methyl)-5-(2-oxa-7-azaspiro[3.5]nonan-7-yl)pyridazin-3(2H)-one;

(R)-7-(1-((5-methyl-3-(6-methylpyridin-3-yl)isoxazol-4-yl)methyl)-6-oxo-1,6-dihydropyridazin-4-yl)hexahydroimidazo[1,5-a]pyrazin-3(2H)-one;

(S)-7-(1-((5-methyl-3-(6-methylpyridin-3-yl)isoxazol-4-yl)methyl)-6-oxo-1,6-dihydropyridazin-4-yl)hexahydroimidazo[1,5-a]pyrazin-3(2H)-one;

2-((5-Methyl-3-(6-methylpyridin-3-yl)isoxazol-4-yl)methyl)-5-(((3aR,6aS)-tetrahydro-1H-furo[3,4-c]pyrrol-5(3H)-yl)pyridazin-3(2H)-one;

(R)-2-((5-Methyl-3-(6-methylpyridin-3-yl)isoxazol-4-yl)methyl)-5-(3-methylpiperazin-1-yl)pyridazin-3(2H)-one;

(S)-2-((5-Methyl-3-(6-methylpyridin-3-yl)isoxazol-4-yl)methyl)-5-(3-methylpiperazin-1-yl)pyridazin-3(2H)-one;

2-((3-(5-Chloro-3-fluoropyridin-2-yl)-5-methylisoxazol-4-yl)methyl)-5-(cis-2,6-dimethylmorpholino)pyridazin-3(2H)-one;

2-((3-(5-Chloro-3-fluoropyridin-2-yl)-5-methylisoxazol-4-yl)methyl)-5-(4-(1-methylcyclopropanecarbonyl)piperazin-1-yl)pyridazin-3(2H)-one;

5-(4-(3,5-Dimethyl-4H-1,2,4-triazol-4-yl)piperidin-1-yl)-2-((5-methyl-3-(6-methylpyridin-3-yl)isoxazol-4-yl)methyl)pyridazin-3(2H)-one;

5-(4-(3,5-Dimethyl-4H-1,2,4-triazol-4-yl)piperidin-1-yl)-2-((3-(4-fluorophenyl)-5-methylisoxazol-4-yl)methyl)pyridazin-3(2H)-one;

(R)—N-Cyclopropyl-1-(1-((5-methyl-3-(6-methylpyridin-3-yl)isoxazol-4-yl)methyl)-6-oxo-1,6-dihydropyridazin-4-yl)pyrrolidine-3-carboxamide;

(S)—N-Cyclopropyl-1-(1-((5-methyl-3-(6-methylpyridin-3-yl)isoxazol-4-yl)methyl)-6-oxo-1,6-dihydropyridazin-4-yl)pyrrolidine-3-carboxamide;

5-(6-Cyclopropyl-2,6-diazaspiro[3.3]heptan-2-yl)-2-((5-methyl-3-(6-methylpyridin-3-yl)isoxazol-4-yl)methyl)pyridazin-3(2H)-one;

(R)-5-(4-Cyclopropyl-3-methylpiperazin-1-yl)-2-((5-methyl-3-(6-methylpyridin-3-yl)isoxazol-4-yl)methyl)pyridazin-3(2H)-one;

(S)-5-(4-Cyclopropyl-3-methylpiperazin-1-yl)-2-((5-methyl-3-(6-methylpyridin-3-yl)isoxazol-4-yl)methyl)pyridazin-3(2H)-one;

5-(4-(2-methoxyphenyl)piperidin-1-yl)-2-((5-methyl-3-(6-methylpyridin-3-yl)isoxazol-4-yl)methyl)pyridazin-3(2H)-one;

2-((5,5'-Dimethyl-[3,3'-biisoxazol]-4-yl)methyl)-5-(cis-2,6-dimethylmorpholino)pyridazin-3(2H)-one;

5-(4-Cyclopropylpiperazin-1-yl)-2-((5,5'-dimethyl-[3,3'-biisoxazol]-4-yl)methyl)pyridazin-3(2H)-one;

5-(cyclopropyl(methyl)amino)-2-((5-methyl-3-(6-methylpyridin-3-yl)isoxazol-4-yl)methyl)pyridazin-3(2H)-one;

5-(methyl(oxetan-3-yl)amino)-2-((5-methyl-3-(6-methylpyridin-3-yl)isoxazol-4-yl)methyl)pyridazin-3(2H)-one;

5-(4-Cyclopropylpiperazin-1-yl)-2-((5-methyl-3-(6-(trifluoromethyl)pyridin-3-yl)isoxazol-4-yl)methyl)pyridazin-3(2H)-one;

2-((5-methyl-3-(6-methylpyridin-3-yl)isoxazol-4-yl)methyl)-5-phenylpyridazin-3(2H)-one;

5-(4-fluorophenyl)-2-[[5-methyl-3-(6-methylpyridin-3-yl)-1,2-oxazol-4-yl]methyl]pyridazin-3-one;

2-((5-Methyl-3-(6-methylpyridin-3-yl)isoxazol-4-yl)methyl)-5-(2-azaspiro[3.3]heptan-2-yl)pyridazin-3(2H)-one;

5-((2-hydroxy-2-methylpropyl)(methyl)amino)-2-((5-methyl-3-(6-methylpyridin-3-yl)isoxazol-4-yl)methyl)pyridazin-3(2H)-one;

5-(2-fluorophenyl)-2-[[5-methyl-3-(6-methylpyridin-3-yl)-1,2-oxazol-4-yl]methyl]pyridazin-3-one;

5-(cis-2,6-Dimethylmorpholino)-2-((3-(6-(trifluoromethyl)pyridin-3-yl)isoxazol-4-yl)methyl)pyridazin-3(2H)-one;

5-(2-methoxyphenyl)-2-((5-methyl-3-(6-methylpyridin-3-yl)-1,2-oxazol-4-yl)methyl)pyridazin-3-one;

2-((5-Methyl-3-(6-methylpyridin-3-yl)isoxazol-4-yl)methyl)-5-(4,7-diazaspiro[2.5]octan-7-yl)pyridazin-3(2H)-one;

2-((5-Methyl-3-(6-methylpyridin-3-yl)isoxazol-4-yl)methyl)-5-(piperazin-1-yl)pyridazin-3(2H)-one;

5-(4-methoxyphenyl)-2-[[5-methyl-3-(6-methylpyridin-3-yl)-1,2-oxazol-4-yl]methyl]pyridazin-3-one;

2-((5-Methyl-3-(6-methylpyridin-3-yl)isoxazol-4-yl)methyl)-5-(2,6-diazaspiro[3.3]heptan-2-yl)pyridazin-3(2H)-one;

2-((5-methyl-3-(6-methylpyridin-3-yl)isoxazol-4-yl)methyl)-5-(methylamino)pyridazin-3(2H)-one;

5-(4-ethoxyphenyl)-2-((5-methyl-3-(6-methylpyridin-3-yl)isoxazol-4-yl)methyl)pyridazin-3(2H)-one;

5-(3-fluoro-4-methoxyphenyl)-2-((5-methyl-3-(6-methylpyridin-3-yl)isoxazol-4-yl)methyl)pyridazin-3(2H)-one;

5-(6-methoxypyridin-3-yl)-2-((5-methyl-3-(6-methylpyridin-3-yl)isoxazol-4-yl)methyl)pyridazin-3(2H)-one;

2-((5-Methyl-3-(6-methylpyridin-3-yl)isoxazol-4-yl)methyl)-5-(6-methyl-2,6-diazaspiro[3.3]heptan-2-yl)pyridazin-3(2H)-one;

2-((5-methyl-3-(6-methylpyridin-3-yl)isoxazol-4-yl)methyl)-5-(4-(trifluoromethyl)phenyl)pyridazin-3(2H)-one;

5-(5-methoxypyridin-2-yl)-2-((5-methyl-3-(6-methylpyridin-3-yl)isoxazol-4-yl)methyl)pyridazin-3(2H)-one;

1-(1-((5-Methyl-3-(6-methylpyridin-3-yl)isoxazol-4-yl)methyl)-6-oxo-1,6-dihydropyridazin-4-yl)azetidine-3-carbonitrile;

2-((3-(5-Chloropyridin-2-yl)-5-methylisoxazol-4-yl)methyl)-5-(6-cyclopropyl-2,6-diazaspiro[3.3]heptan-2-yl)pyridazin-3(2H)-one;

5-(6-Cyclopropyl-2,6-diazaspiro[3.3]heptan-2-yl)-2-((5,5'-dimethyl-[3,3'-biisoxazol]-4-yl)methyl)pyridazin-3(2H)-one;

2-((5-methyl-3-(6-methylpyridin-3-yl)isoxazol-4-yl)methyl)-5-(((tetrahydro-2H-pyran-4-yl)methyl)amino)pyridazin-3(2H)-one;

(S)-2-((5-Methyl-3-(6-methylpyridin-3-yl)isoxazol-4-yl)methyl)-5-(2-methylmorpholino)pyridazin-3(2H)-one;

(R)-5-(3-(tert-Butoxy)pyrrolidin-1-yl)-2-((5-methyl-3-(6-methylpyridin-3-yl)isoxazol-4-yl)methyl)pyridazin-3(2H)-one;

(S)-5-(2-Methylmorpholino)-2-((3-(6-methylpyridin-3-yl)isoxazol-4-yl)methyl)pyridazin-3(2H)-one;

(R)-5-(2-Methylmorpholino)-2-((3-(6-methylpyridin-3-yl)isoxazol-4-yl)methyl)pyridazin-3(2H)-one;

5-((3S,5R)-3,5-dimethylpiperazin-1-yl)-2-((5-methyl-3-(6-methylpyridin-3-yl)isoxazol-4-yl)methyl)pyridazin-3(2H)-one;

2-((5-Methyl-3-(6-methylpyridin-3-yl)isoxazol-4-yl)methyl)-5-(3-phenoxyazetidin-1-yl)pyridazin-3(2H)-one;

2-((5-Methyl-3-(6-methylpyridin-3-yl)isoxazol-4-yl)methyl)-5-(5-oxa-2-azaspiro[3.4]octan-2-yl)pyridazin-3(2H)-one;

5-((1-cyclopropylazetidin-3-yl)amino)-2-((5-methyl-3-(6-methylpyridin-3-yl)isoxazol-4-yl)methyl)pyridazin-3(2H)-one;

5-(azetidin-1-yl)-2-((5-methyl-3-(6-methylpyridin-3-yl)isoxazol-4-yl)methyl)pyridazin-3(2H)-one;

5-(3-Hydroxy-3-methylazetidin-1-yl)-2-((5-methyl-3-(6-methylpyridin-3-yl)isoxazol-4-yl)methyl)pyridazin-3(2H)-one;

5-(3-ethoxyazetidin-1-yl)-2-((5-methyl-3-(6-methylpyridin-3-yl)isoxazol-4-yl)methyl)pyridazin-3(2H)-one;

5-(6-oxa-3-azabicyclo[3.1.1]heptan-3-yl)-2-((5-methyl-3-(6-methylpyridin-3-yl)isoxazol-4-yl)methyl)pyridazin-3(2H)-one;

5-(4-(2-Methoxypyridin-3-yl)piperazin-1-yl)-2-((5-methyl-3-(6-methylpyridin-3-yl)isoxazol-4-yl)methyl)pyridazin-3(2H)-one;

5-(dimethylamino)-2-[[3-(5-fluoro-6-methyl-3-pyridyl)-5-methyl-isoxazol-4-yl]methyl]pyridazin-3-one;

2-((5-methyl-3-(6-methyl-3-pyridyl)isoxazol-4-yl)methyl)-5-(1-methylpyrazol-4-yl)pyridazin-3-one;

5-(3-methoxyazetidin-1-yl)-2-((5-methyl-3-(6-methylpyridin-3-yl)isoxazol-4-yl)methyl)pyridazin-3(2H)-one;

5-(3-hydroxyazetidin-1-yl)-2-((5-methyl-3-(6-methylpyridin-3-yl)isoxazol-4-yl)methyl)pyridazin-3(2H)-one;

2-((5-methyl-3-(6-methylpyridin-3-yl)isoxazol-4-yl)methyl)-5-(2-methylpyridin-4-yl)pyridazin-3(2H)-one;

5-(2-methoxypyridin-4-yl)-2-((5-methyl-3-(6-methylpyridin-3-yl)isoxazol-4-yl)methyl)pyridazin-3(2H)-one;

2-((5-methyl-3-(6-methylpyridin-3-yl)isoxazol-4-yl)methyl)-5-(2-(trifluoromethyl)pyridin-4-yl)pyridazin-3(2H)-one;

5-(4-(2-Ethyl-1H-imidazol-1-yl)piperidin-1-yl)-2-((5-methyl-3-(6-methylpyridin-3-yl)isoxazol-4-yl)methyl)pyridazin-3(2H)-one;

5-(4-(2-Methyl-1H-imidazol-1-yl)piperidin-1-yl)-2-((5-methyl-3-(6-methylpyridin-3-yl)isoxazol-4-yl)methyl)pyridazin-3(2H)-one;

5-(3-(Cyclopropylmethoxy)azetidin-1-yl)-2-((5-methyl-3-(6-methylpyridin-3-yl)isoxazol-4-yl)methyl)pyridazin-3(2H)-one;

5-(3-Isopropoxyazetidin-1-yl)-2-((5-methyl-3-(6-methylpyridin-3-yl)isoxazol-4-yl)methyl)pyridazin-3(2H)-one;

5-(3,4-dimethoxyphenyl)-2-((5-methyl-3-(6-methyl-3-pyridyl)isoxazol-4-yl)methyl)pyridazin-3-one;

2-((5-methyl-3-(6-methyl-3-pyridyl)isoxazol-4-yl)methyl)-5-(4-(trifluoromethoxy)phenyl)pyridazin-3-one;

5-(4-isopropoxyphenyl)-2-((5-methyl-3-(6-methyl-3-pyridyl)isoxazol-4-yl)methyl)pyridazin-3-one;

5-[6-(dimethylamino)-3-pyridyl]-2-((5-methyl-3-(6-methyl-3-pyridyl)isoxazol-4-yl)methyl)pyridazin-3-one;

5-(3-hydroxy-3-(trifluoromethyl)azetidin-1-yl)-2-((5-methyl-3-(6-methylpyridin-3-yl)isoxazol-4-yl)methyl)pyridazin-3(2H)-one;

5-(3-hydroxy-3-methylpyrrolidin-1-yl)-2-((5-methyl-3-(6-methylpyridin-3-yl)isoxazol-4-yl)methyl)pyridazin-3(2H)-one;

5-(4-hydroxy-4-methylpiperidin-1-yl)-2-((5-methyl-3-(6-methylpyridin-3-yl)isoxazol-4-yl)methyl)pyridazin-3(2H)-one;

5-((3S)-3-(2-hydroxypropan-2-yl)pyrrolidin-1-yl)-2-((5-methyl-3-(6-methylpyridin-3-yl)-1,2-oxazol-4-yl)methyl)pyridazin-3-one;

2-ethyl-7-(1-((5-methyl-3-(6-methylpyridin-3-yl)isoxazol-4-yl)methyl)-6-oxo-1,6-dihydropyridazin-4-yl)hexahydroimidazo[1,5-a]pyrazin-3(2H)-one;

2-((5-methyl-3-(6-methylpyridin-3-yl)isoxazol-4-yl)methyl)-5-((3aS,6aS)-tetrahydro-2H-furo[3,2-b]pyrrol-4(5H)-yl)pyridazin-3(2H)-one;

5-(3-(4-Fluorophenoxy)azetidin-1-yl)-2-((5-methyl-3-(6-methylpyridin-3-yl)isoxazol-4-yl)methyl)pyridazin-3(2H)-one;

2-((5-Methyl-3-(6-methylpyridin-3-yl)isoxazol-4-yl)methyl)-5-(3-(pyridin-2-yloxy)azetidin-1-yl)pyridazin-3(2H)-one;

5-((3aR,6aS)-hexahydro-1H-furo[3,4-b]pyrrol-1-yl)-2-((5-methyl-3-(6-methylpyridin-3-yl)isoxazol-4-yl)methyl)pyridazin-3(2H)-one;

2-((5-Methyl-3-(6-methylpyridin-3-yl)isoxazol-4-yl)methyl)-5-(3-(pyridin-3-yloxy)azetidin-1-yl)pyridazin-3(2H)-one;

5-(3-(3-Fluorophenoxy)azetidin-1-yl)-2-((5-methyl-3-(6-methylpyridin-3-yl)isoxazol-4-yl)methyl)pyridazin-3(2H)-one;

5-(3-(2-Fluorophenoxy)azetidin-1-yl)-2-((5-methyl-3-(6-methylpyridin-3-yl)isoxazol-4-yl)methyl)pyridazin-3(2H)-one;

2-((5-Methyl-3-(6-methylpyridin-3-yl)isoxazol-4-yl)methyl)-5-(3-(pyridin-4-yloxy)azetidin-1-yl)pyridazin-3(2H)-one;

5-(3-((5-Chloropyridin-2-yl)oxy)azetidin-1-yl)-2-((5-methyl-3-(6-methylpyridin-3-yl)isoxazol-4-yl)methyl)pyridazin-3(2H)-one;

(S)-5-(7-Hydroxy-5-oxa-2-azaspiro[3.4]octan-2-yl)-2-((5-methyl-3-(6-methylpyridin-3-yl)isoxazol-4-yl)methyl)pyridazin-3(2H)-one;

(R)-5-(7-Hydroxy-5-oxa-2-azaspiro[3.4]octan-2-yl)-2-((5-methyl-3-(6-methylpyridin-3-yl)isoxazol-4-yl)methyl)pyridazin-3(2H)-one;

(S)-5-(7-Methoxy-5-oxa-2-azaspiro[3.4]octan-2-yl)-2-((5-methyl-3-(6-methylpyridin-3-yl)isoxazol-4-yl)methyl)pyridazin-3(2H)-one;

(R)-5-(7-Methoxy-5-oxa-2-azaspiro[3.4]octan-2-yl)-2-((5-methyl-3-(6-methylpyridin-3-yl)isoxazol-4-yl)methyl)pyridazin-3(2H)-one;

(R)-5-(7-Ethoxy-5-oxa-2-azaspiro[3.4]octan-2-yl)-2-((5-methyl-3-(6-methylpyridin-3-yl)isoxazol-4-yl)methyl)pyridazin-3(2H)-one;

5-(3-Cyclopropoxyazetidin-1-yl)-2-((5-methyl-3-(6-methylpyridin-3-yl)isoxazol-4-yl)methyl)pyridazin-3(2H)-one;

5-((1-cyclopropylazetidin-3-yl)(methyl)amino)-2-((5-methyl-3-(6-methylpyridin-3-yl)isoxazol-4-yl)methyl)pyridazin-3(2H)-one;

5-(3-((6-Chloropyridin-3-yl)oxy)azetidin-1-yl)-2-((5-methyl-3-(6-methylpyridin-3-yl)isoxazol-4-yl)methyl)pyridazin-3(2H)-one;

5-(4-Methoxypiperidin-1-yl)-2-((5-methyl-3-(6-methylpyridin-3-yl)isoxazol-4-yl)methyl)pyridazin-3(2H)-one;
2-((5,5'-Dimethyl-[3,3'-biisoxazol]-4-yl)methyl)-5-(3-methoxyazetidin-1-yl)pyridazin-3(2H)-one;
5-(3-(Cyclopropylmethoxy)azetidin-1-yl)-2-((5,5'-dimethyl-[3,3'-biisoxazol]-4-yl)methyl)pyridazin-3(2H)-one;
2-((5,5'-Dimethyl-[3,3'-biisoxazol]-4-yl)methyl)-5-(5-oxa-2-azaspiro[3.4]octan-2-yl)pyridazin-3(2H)-one;
2-((3-(5-Chloropyridin-2-yl)-5-methylisoxazol-4-yl)methyl)-5-(3-(cyclopropylmethoxy)azetidin-1-yl)pyridazin-3(2H)-one;
2-((3-(5-Chloropyridin-2-yl)-5-methylisoxazol-4-yl)methyl)-5-(5-oxa-2-azaspiro[3.4]octan-2-yl)pyridazin-3(2H)-one;
5-(6-methoxy-2-pyridyl)-2-((5-methyl-3-(6-methyl-3-pyridyl)isoxazol-4-yl)methyl)pyridazin-3-one;
2-((5-Methyl-3-(6-methylpyridin-3-yl)isoxazol-4-yl)methyl)-5-(7-methyl-5-oxa-2-azaspiro[3.4]octan-2-yl)pyridazin-3(2H)-one;
5-(3-((2-Chloropyridin-4-yl)oxy)azetidin-1-yl)-2-((5-methyl-3-(6-methylpyridin-3-yl)isoxazol-4-yl)methyl)pyridazin-3(2H)-one;
5-(5-chloro-3-pyridyl)-2-((5-methyl-3-(6-methyl-3-pyridyl)isoxazol-4-yl)methyl)pyridazin-3-one;
5-(6-(difluoromethoxy)pyridin-3-yl)-2-((5-methyl-3-(6-methylpyridin-3-yl)isoxazol-4-yl)methyl)pyridazin-3(2H)-one;
5-(3-(tert-Butoxy)azetidin-1-yl)-2-((5-methyl-3-(6-methylpyridin-3-yl)isoxazol-4-yl)methyl)pyridazin-3(2H)-one;
5-(6-ethoxypyridin-3-yl)-2-((5-methyl-3-(6-methylpyridin-3-yl)isoxazol-4-yl)methyl)pyridazin-3(2H)-one;
5-(1-cyclopropyl-1H-pyrazol-4-yl)-2-((5-methyl-3-(6-methylpyridin-3-yl)isoxazol-4-yl)methyl)pyridazin-3(2H)-one;
5-(1-(2,2-difluoroethyl)-1H-pyrazol-4-yl)-2-((5-methyl-3-(6-methylpyridin-3-yl)isoxazol-4-yl)methyl)pyridazin-3(2H)-one;
5-(1-(difluoromethyl)-1H-pyrazol-4-yl)-2-((5-methyl-3-(6-methylpyridin-3-yl)isoxazol-4-yl)methyl)pyridazin-3(2H)-one;
5-(1-ethyl-1H-pyrazol-4-yl)-2-((5-methyl-3-(6-methylpyridin-3-yl)isoxazol-4-yl)methyl)pyridazin-3(2H)-one;
5-(2-(dimethylamino)pyridin-4-yl)-2-((5-methyl-3-(6-methylpyridin-3-yl)isoxazol-4-yl)methyl)pyridazin-3(2H)-one;
5-(1-(cyclopropylmethyl)-1H-pyrazol-4-yl)-2-((5-methyl-3-(6-methylpyridin-3-yl)isoxazol-4-yl)methyl)pyridazin-3(2H)-one;
2-((5-Methyl-3-(6-methylpyridin-3-yl)isoxazol-4-yl)methyl)-5-(3-(2,2,2-trifluoroethoxy)azetidin-1-yl)pyridazin-3(2H)-one;
5-(4-(4-Methoxypyrimidin-5-yl)piperazin-1-yl)-2-((5-methyl-3-(6-methylpyridin-3-yl)isoxazol-4-yl)methyl)pyridazin-3(2H)-one;
2-((3-(4-chlorophenyl)-5-methylisoxazol-4-yl)methyl)-5-(3-methoxyazetidin-1-yl)pyridazin-3(2H)-one;
2-((3-(4-chlorophenyl)-5-methylisoxazol-4-yl)methyl)-5-(3-ethoxyazetidin-1-yl)pyridazin-3(2H)-one;
2-((3-(4-chlorophenyl)-5-methylisoxazol-4-yl)methyl)-5-(5-oxa-2-azaspiro[3.4]octan-2-yl)pyridazin-3(2H)-one;
2-((5-methyl-3-(6-methylpyridin-3-yl)isoxazol-4-yl)methyl)-5-(2-(piperazin-1-yl)pyridin-4-yl)pyridazin-3(2H)-one;
2-((5-methyl-3-(6-methylpyridin-3-yl)isoxazol-4-yl)methyl)-5-(1-phenyl-1H-pyrazol-4-yl)pyridazin-3(2H)-one;
5-(4-(3-Methoxypyridazin-4-yl)piperazin-1-yl)-2-((5-methyl-3-(6-methylpyridin-3-yl)isoxazol-4-yl)methyl)pyridazin-3(2H)-one;
5-(4-(1-methyl-1H-pyrazol-5-yl)piperidin-1-yl)-2-((5-methyl-3-(6-methylpyridin-3-yl)isoxazol-4-yl)methyl)pyridazin-3(2H)-one;
5-(4-(1-ethyl-1H-pyrazol-5-yl)piperidin-1-yl)-2-((5-methyl-3-(6-methylpyridin-3-yl)isoxazol-4-yl)methyl)pyridazin-3(2H)-one;
5-(3-(Difluoromethoxy)azetidin-1-yl)-2-((5-methyl-3-(6-methylpyridin-3-yl)isoxazol-4-yl)methyl)pyridazin-3(2H)-one;
5-(3-methoxyazetidin-1-yl)-2-((5-methyl-3-(6-methylpyridin-3-yl)isoxazol-4-yl)methyl)pyridazin-3(2H)-one;
5-(3-ethoxyazetidin-1-yl)-2-((5-methyl-3-(6-methylpyridin-3-yl)isoxazol-4-yl)methyl)pyridazin-3(2H)-one;
2-((5-methyl-3-(6-methylpyridazin-3-yl)isoxazol-4-yl)methyl)-5-(5-oxa-2-azaspiro[3.4]octan-2-yl)pyridazin-3(2H)-one;
5-(1-isobutylpyrazol-4-yl)-2-[[5-methyl-3-(6-methyl-3-pyridyl)isoxazol-4-yl]methyl]pyridazin-3-one;
5-(6-cyclopropyl-3-pyridyl)-2-[[5-methyl-3-(6-methyl-3-pyridyl)isoxazol-4-yl]methyl]pyridazin-3-one;
5-(6-(methylamino)-3-pyridyl)-2-((5-methyl-3-(6-methyl-3-pyridyl)isoxazol-4-yl)methyl)pyridazin-3-one;
5-(2-(difluoromethoxy)pyridin-4-yl)-2-((5-methyl-3-(6-methylpyridin-3-yl)isoxazol-4-yl)methyl)pyridazin-3(2H)-one;
2-((5-methyl-3-(6-methylpyridin-3-yl)isoxazol-4-yl)methyl)-5-(1-((3-methyloxetan-3-yl)methyl)-1H-pyrazol-4-yl)pyridazin-3(2H)-one;
2-((5-methyl-3-(6-methylpyridin-3-yl)isoxazol-4-yl)methyl)-5-(2-((tetrahydrofuran-3-yl)oxy)pyridin-4-yl)pyridazin-3(2H)-one;
(R)-2-((5-methyl-3-(6-methylpyridin-3-yl)isoxazol-4-yl)methyl)-5-(3-methylpyrrolidin-1-yl)pyridazin-3(2H)-one;
5-(5,6-dimethoxypyridin-3-yl)-2-((5-methyl-3-(6-methylpyridin-3-yl)isoxazol-4-yl)methyl)pyridazin-3(2H)-one;
5-(6-ethoxy-5-methylpyridin-3-yl)-2-((5-methyl-3-(6-methylpyridin-3-yl)isoxazol-4-yl)methyl)pyridazin-3(2H)-one;
5-(3-Fluoroazetidin-1-yl)-2-((5-methyl-3-(6-methylpyridin-3-yl)isoxazol-4-yl)methyl)pyridazin-3(2H)-one;
2-((5-(Difluoromethyl)-3-(6-methylpyridin-3-yl)isoxazol-4-yl)methyl)-5-((2S,6R)-2,6-dimethylmorpholino)pyridazin-3(2H)-one;
5-(5-fluoro-6-methoxypyridin-3-yl)-2-((5-methyl-3-(6-methylpyridin-3-yl)isoxazol-4-yl)methyl)pyridazin-3(2H)-one;
(S)-5-(4-isopropyl-3-methylpiperazin-1-yl)-2-((5-methyl-3-(6-methylpyridin-3-yl)isoxazol-4-yl)methyl)pyridazin-3(2H)-one;
5-(3-(cyclopropylmethoxy)azetidin-1-yl)-2-((5-methyl-3-(6-methylpyridazin-3-yl)isoxazol-4-yl)methyl)pyridazin-3(2H)-one;
2-((5-Methyl-3-(6-methylpyridin-3-yl)isoxazol-4-yl)methyl)-5-(3-((6-methylpyridazin-3-yl)oxy)azetidin-1-yl)pyridazin-3(2H)-one;
5-(2-(azetidin-1-yl)pyridin-4-yl)-2-((5-methyl-3-(6-methylpyridin-3-yl)isoxazol-4-yl)methyl)pyridazin-3(2H)-one;

5-(5-chloro-6-methoxypyridin-3-yl)-2-((5-methyl-3-(6-methylpyridin-3-yl)isoxazol-4-yl)methyl)pyridazin-3(2H)-one;

5-(2-chloro-5-fluoro-3-pyridyl)-2-((5-methyl-3-(6-methyl-3-pyridyl)isoxazol-4-yl)methyl)pyridazin-3-one;

5-(6-isopropoxy-3-pyridyl)-2-((5-methyl-3-(6-methyl-3-pyridyl)isoxazol-4-yl)methyl)pyridazin-3-one;

5-(5-fluoro-2-methoxypyridin-4-yl)-2-((5-methyl-3-(6-methylpyridin-3-yl)isoxazol-4-yl)methyl)pyridazin-3(2H)-one;

5-(2,6-dimethylpyridin-4-yl)-2-((5-methyl-3-(6-methylpyridin-3-yl)isoxazol-4-yl)methyl)pyridazin-3(2H)-one;

5-(7,7-Difluoro-5-oxa-2-azaspiro[3.4]octan-2-yl)-2-((5-methyl-3-(6-methylpyridin-3-yl)isoxazol-4-yl)methyl)pyridazin-3(2H)-one;

5-((2R,3R)-3-methoxy-2-methylazetidin-1-yl)-2-((5-methyl-3-(6-methylpyridin-3-yl)isoxazol-4-yl)methyl)pyridazin-3(2H)-one;

2-((5-methyl-3-(6-methylpyridin-3-yl)isoxazol-4-yl)methyl)-5-(2-azaspiro[3.5]nonan-2-yl)pyridazin-3(2H)-one;

5-(2-ethyl-4-pyridyl)-2-((5-methyl-3-(6-methyl-3-pyridyl)isoxazol-4-yl)methyl)pyridazin-3-one;

5-((2S,3S)-3-methoxy-2-methylazetidin-1-yl)-2-((5-methyl-3-(6-methylpyridin-3-yl)isoxazol-4-yl)methyl)pyridazin-3(2H)-one;

5-((2S,3S)-3-ethoxy-2-methylazetidin-1-yl)-2-((5-methyl-3-(6-methylpyridin-3-yl)isoxazol-4-yl)methyl)pyridazin-3(2H)-one;

2-((5-methyl-3-(6-methylpyridin-3-yl)isoxazol-4-yl)methyl)-5-(7-oxa-2-azaspiro[3.5]nonan-2-yl)pyridazin-3(2H)-one;

(R)-5-(7-Fluoro-5-oxa-2-azaspiro[3.4]octan-2-yl)-2-((5-methyl-3-(6-methylpyridin-3-yl)isoxazol-4-yl)methyl)pyridazin-3(2H)-one;

(S)-5-(7-Fluoro-5-oxa-2-azaspiro[3.4]octan-2-yl)-2-((5-methyl-3-(6-methylpyridin-3-yl)isoxazol-4-yl)methyl)pyridazin-3(2H)-one;

2-((5-methyl-3-(6-methylpyridin-3-yl)isoxazol-4-yl)methyl)-5-(2-(methylamino)pyridin-4-yl)pyridazin-3(2H)-one;

(R)-5-(7-(Difluoromethoxy)-5-oxa-2-azaspiro[3.4]octan-2-yl)-2-((5-methyl-3-(6-methylpyridin-3-yl)isoxazol-4-yl)methyl)pyridazin-3(2H)-one;

(S)-5-(7-(Difluoromethoxy)-5-oxa-2-azaspiro[3.4]octan-2-yl)-2-((5-methyl-3-(6-methylpyridin-3-yl)isoxazol-4-yl)methyl)pyridazin-3(2H)-one;

5-((2R,6S)-2,6-dimethylmorpholino)-2-((3-(5-fluoro-6-methylpyridin-3-yl)-5-methylisoxazol-4-yl)methyl)pyridazin-3(2H)-one;

5-(3-(2,2-difluoroethoxy)azetidin-1-yl)-2-((5-methyl-3-(6-methylpyridin-3-yl)isoxazol-4-yl)methyl)pyridazin-3(2H)-one;

2-((3-(5-fluoro-6-methylpyridin-3-yl)-5-methylisoxazol-4-yl)methyl)-5-(2-methoxypyridin-4-yl)pyridazin-3(2H)-one;

2-((3-(5-fluoro-6-methylpyridin-3-yl)-5-methylisoxazol-4-yl)methyl)-5-(5-oxa-2-azaspiro[3.4]octan-2-yl)pyridazin-3(2H)-one;

2-((3-(6-chloropyridin-3-yl)-5-methylisoxazol-4-yl)methyl)-5-(5-oxa-2-azaspiro[3.4]octan-2-yl)pyridazin-3(2H)-one;

2-((5-methyl-3-(6-methyl-3-pyridyl)isoxazol-4-yl)methyl)-5-(1-propylpyrazol-4-yl)pyridazin-3-one;

6-(1-((5-methyl-3-(6-methyl-3-pyridyl)isoxazol-4-yl)methyl)-6-oxo-pyridazin-4-yl)pyridine-2-carbonitrile;

2-((3-(6-chloropyridin-3-yl)-5-methylisoxazol-4-yl)methyl)-5-(3-methoxyazetidin-1-yl)pyridazin-3(2H)-one;

5-(3-ethoxyazetidin-1-yl)-2-((3-(5-fluoro-6-methylpyridin-3-yl)-5-methylisoxazol-4-yl)methyl)pyridazin-3(2H)-one;

2-((3-(6-chloropyridin-3-yl)-5-methylisoxazol-4-yl)methyl)-5-(2-methoxypyridin-4-yl)pyridazin-3(2H)-one;

2-((3-(6-chloropyridin-3-yl)-5-methylisoxazol-4-yl)methyl)-5-(1-methyl-1H-pyrazol-4-yl)pyridazin-3(2H)-one;

2-((5-methyl-3-(6-methylpyridin-3-yl)isoxazol-4-yl)methyl)-5-(5-oxa-2-azaspiro[3.5]nonan-2-yl)pyridazin-3(2H)-one;

2-((3-(6-chloropyridin-3-yl)-5-methylisoxazol-4-yl)methyl)-5-(7,7-difluoro-5-oxa-2-azaspiro[3.4]octan-2-yl)pyridazin-3(2H)-one;

2-((5-methyl-3-(6-methylpyridin-3-yl)isoxazol-4-yl)methyl)-5-(3-methylimidazo[1,2-a]pyridin-6-yl)pyridazin-3(2H)-one;

2-((3-(6-chloropyridin-3-yl)-5-methylisoxazol-4-yl)methyl)-5-((2RS,6SR)-2,6-dimethylmorpholino)pyridazin-3(2H)-one;

2-((3-(6-chloropyridin-3-yl)-5-methyl-1,2-oxazol-4-yl)methyl)-5-(3-ethoxyazetidin-1-yl)pyridazin-3-one;

2-((3-(6-chloropyridin-3-yl)-5-methylisoxazol-4-yl)methyl)-5-(1-ethyl-1H-pyrazol-4-yl)pyridazin-3(2H)-one;

2-((3-(6-chloropyridin-3-yl)-5-methylisoxazol-4-yl)methyl)-5-(1-cyclopropyl-1H-pyrazol-4-yl)pyridazin-3(2H)-one;

2-(1-((3-(6-chloropyridin-3-yl)-5-methylisoxazol-4-yl)methyl)-6-oxo-1,6-dihydropyridazin-4-yl)hexahydropyrrolo[1,2-a]pyrazin-6(2H)-one;

2-((3-(6-chloropyridin-3-yl)-5-methylisoxazol-4-yl)methyl)-5-(3-cyclopropoxyazetidin-1-yl)pyridazin-3(2H)-one;

(S)-7-(1-((3-(6-chloropyridin-3-yl)-5-methylisoxazol-4-yl)methyl)-6-oxo-1,6-dihydropyridazin-4-yl)hexahydroimidazo[1,5-a]pyrazin-3(2H)-one;

2-((5-methyl-3-(6-methylpyridin-3-yl)isoxazol-4-yl)methyl)-5-(3-oxa-9-azaspiro[5.5]undecan-9-yl)pyridazin-3(2H)-one;

(S)-2-((3-(6-chloropyridin-3-yl)-5-methylisoxazol-4-yl)methyl)-5-(2-methylmorpholino)pyridazin-3(2H)-one;

5-(2-methoxypyridin-4-yl)-2-((5-methyl-3-(5-(trifluoromethyl)pyrimidin-2-yl)isoxazol-4-yl)methyl)pyridazin-3(2H)-one;

5-(3-methoxyazetidin-1-yl)-2-((5-methyl-3-(5-(trifluoromethyl)pyrimidin-2-yl)isoxazol-4-yl)methyl)pyridazin-3(2H)-one;

(R)-2-((3-(6-chloropyridin-3-yl)-5-methylisoxazol-4-yl)methyl)-5-(7-fluoro-5-oxa-2-azaspiro[3.4]octan-2-yl)pyridazin-3(2H)-one;

(R)-7-(1-((3-(6-chloropyridin-3-yl)-5-methylisoxazol-4-yl)methyl)-6-oxo-1,6-dihydropyridazin-4-yl)hexahydroimidazo[1,5-a]pyrazin-3(2H)-one;

(S)-2-((3-(6-chloropyridin-3-yl)-5-methylisoxazol-4-yl)methyl)-5-(7-fluoro-5-oxa-2-azaspiro[3.4]octan-2-yl)pyridazin-3(2H)-one;

2-((3-(6-chloropyridin-3-yl)-5-methylisoxazol-4-yl)methyl)-5-(5-oxa-2-azaspiro[3.5]nonan-2-yl)pyridazin-3(2H)-one;

5-(3-(tert-butoxy)azetidin-1-yl)-2-((5-methyl-3-(6-methylpyridazin-3-yl)isoxazol-4-yl)methyl)pyridazin-3(2H)-one;

2-((5-methyl-3-(6-methylpyridazin-3-yl)isoxazol-4-yl)
  methyl)-5-(5-oxa-2-azaspiro[3.5]nonan-2-yl)pyridazin-3
  (2H)-one;
5-(3-((2-chloropyridin-4-yl)oxy)azetidin-1-yl)-2-((5-
  methyl-3-(6-methylpyridazin-3-yl)isoxazol-4-yl)methyl)
  pyridazin-3(2H)-one;
(R)-5-(7-methoxy-5-oxa-2-azaspiro[3.4]octan-2-yl)-2-((5-
  methyl-3-(6-(trifluoromethyl)pyridin-3-yl)isoxazol-4-yl)
  methyl)pyridazin-3(2H)-one;
5-(3-cyclobutoxyazetidin-1-yl)-2-((5-methyl-3-(6-meth-
  ylpyridazin-3-yl)isoxazol-4-yl)methyl)pyridazin-3(2H)-
  one;
5-(3-cyclopropoxyazetidin-1-yl)-2-((5-methyl-3-(6-meth-
  ylpyridazin-3-yl)isoxazol-4-yl)methyl)pyridazin-3(2H)-
  one;
(R)-2-((5-methyl-3-(6-methylpyridazin-3-yl)isoxazol-4-yl)
  methyl)-5-(7-methyl-5-oxa-2-azaspiro[3.4]octan-2-yl)
  pyridazin-3(2H)-one;
(S)-2-((5-methyl-3-(6-methylpyridazin-3-yl)isoxazol-4-yl)
  methyl)-5-(7-methyl-5-oxa-2-azaspiro[3.4]octan-2-yl)
  pyridazin-3(2H)-one;
(R)-5-(7-(difluoromethoxy)-5-oxa-2-azaspiro[3.4]octan-2-
  yl)-2-((5-methyl-3-(6-methylpyridazin-3-yl)isoxazol-4-
  yl)methyl)pyridazin-3(2H)-one;
5-((2S,6R)-2,6-dimethylmorpholin-4-yl)-2-((5-(fluorom-
  ethyl)-3-(6-methylpyridin-3-yl)-1,2-oxazol-4-yl)methyl)
  pyridazin-3-one;
5-(3-(2,2-difluoroethoxy)azetidin-1-yl)-2-((5-methyl-3-(6-
  (trifluoromethyl)pyridin-3-yl)isoxazol-4-yl)methyl)
  pyridazin-3(2H)-one;
2-((3-(6-chloropyridin-3-yl)-5-methylisoxazol-4-yl)
  methyl)-5-(3-(2,2-difluoroethoxy)azetidin-1-yl)
  pyridazin-3(2H)-one;
(S)-5-(7-(difluoromethoxy)-5-oxa-2-azaspiro[3.4]octan-2-
  yl)-2-((5-methyl-3-(6-methylpyridazin-3-yl)isoxazol-4-
  yl)methyl)pyridazin-3(2H)-one;
2-((5-methyl-3-(6-methylpyridazin-3-yl)isoxazol-4-yl)
  methyl)-5-(3-oxa-9-azaspiro[5.5]undecan-9-yl)
  pyridazin-3(2H)-one;
2-((3-(6-chloropyridin-3-yl)-5-methylisoxazol-4-yl)
  methyl)-5-(3-oxa-9-azaspiro[5.5]undecan-9-yl)
  pyridazin-3(2H)-one;
5-(3-cyclopropoxyazetidin-1-yl)-2-((5-methyl-3-(5-(trifluo-
  romethyl)pyrimidin-2-yl)isoxazol-4-yl)methyl)pyridazin-
  3(2H)-one;
5-(7,7-difluoro-5-oxa-2-azaspiro[3.4]octan-2-yl)-2-((5-
  methyl-3-(5-(trifluoromethyl)pyrimidin-2-yl)isoxazol-4-
  yl)methyl)pyridazin-3(2H)-one;
2-((3-(6-chloropyridin-3-yl)-5-methylisoxazol-4-yl)
  methyl)-5-(3-(trifluoromethoxy)azetidin-1-yl)pyridazin-3
  (2H)-one;
2-((3-(6-chloropyridazin-3-yl)-5-methylisoxazol-4-yl)
  methyl)-5-(3-methoxyazetidin-1-yl)pyridazin-3(2H)-one;
2-((3-(6-chloropyridazin-3-yl)-5-methylisoxazol-4-yl)
  methyl)-5-(3-cyclobutoxyazetidin-1-yl)pyridazin-3(2H)-
  one;
2-((3-(6-chloropyridin-3-yl)-5-methylisoxazol-4-yl)
  methyl)-5-(3-(2,2,2-trifluoroethoxy)azetidin-1-yl)
  pyridazin-3(2H)-one;
2-((3-(6-chloropyridin-3-yl)-5-methylisoxazol-4-yl)
  methyl)-5-(3-(difluoromethoxy)azetidin-1-yl)pyridazin-3
  (2H)-one;
2-((3-(6-chloropyridin-3-yl)-5-methylisoxazol-4-yl)
  methyl)-5-(1-oxa-8-azaspiro[4.5]decan-8-yl)pyridazin-3
  (2H)-one;
2-((3-(6-chloropyridin-3-yl)-5-methylisoxazol-4-yl)
  methyl)-5-(7-oxa-2-azaspiro[3.5]nonan-2-yl)pyridazin-3
  (2H)-one;
2-((3-(6-chloropyridin-3-yl)-5-methylisoxazol-4-yl)
  methyl)-5-(2-oxa-7-azaspiro[3.5]nonan-7-yl)pyridazin-3
  (2H)-one;
2-((5-cyclopropyl-3-(6-methylpyridazin-3-yl)isoxazol-4-yl)
  methyl)-5-(5-oxa-2-azaspiro[3.5]nonan-2-yl)pyridazin-3
  (2H)-one;
2-((3-(6-cyclopropylpyridin-3-yl)-5-methylisoxazol-4-yl)
  methyl)-5-(7,7-difluoro-5-oxa-2-azaspiro[3.4]octan-2-yl)
  pyridazin-3(2H)-one;
(R)-5-(3-(tert-butoxy)pyrrolidin-1-yl)-2-((5-methyl-3-(6-
  methylpyridazin-3-yl)isoxazol-4-yl)methyl)pyridazin-3
  (2H)-one;
2-((3-(6-chloropyridin-3-yl)-5-methylisoxazol-4-yl)
  methyl)-5-(4-methoxy-4-methylpiperidin-1-yl)pyridazin-
  3(2H)-one;
2-((3-(6-chloropyridin-3-yl)-5-methylisoxazol-4-yl)
  methyl)-5-(4-(pyridazin-4-yl)piperazin-1-yl)pyridazin-3
  (2H)-one;
2-((5-methyl-3-(6-methylpyridazin-3-yl)isoxazol-4-yl)
  methyl)-5-(3-((1,1,1-trifluoro-2-methylpropan-2-yl)oxy)
  azetidin-1-yl)pyridazin-3(2H)-one;
(S or R)-2-((3-(6-chloropyridin-3-yl)-5-methylisoxazol-4-
  yl)methyl)-5-(3-((1,1,1-trifluoropropan-2-yl)oxy)azeti-
  din-1-yl)pyridazin-3(2H)-one;
(R or S)-2-((3-(6-chloropyridin-3-yl)-5-methylisoxazol-4-
  yl)methyl)-5-(3-((1,1,1-trifluoropropan-2-yl)oxy)azeti-
  din-1-yl)pyridazin-3(2H)-one;
2-((3-(6-chloropyridin-3-yl)-5-methylisoxazol-4-yl)
  methyl)-5-((-6-methoxy-3-azabicyclo[3.1.0]hexan-3-yl)
  pyridazin-3(2H)-one;
4-chloro-5-(3-ethoxyazetidin-1-yl)-2-((5-methyl-3-(6-meth-
  ylpyridin-3-yl)isoxazol-4-yl)methyl)pyridazin-3(2H)-
  one;
2-((3-(6-chloropyridin-3-yl)-5-methylisoxazol-4-yl)
  methyl)-5-(7,7-difluoro-5-oxa-2-azaspiro[3.4]octan-2-yl)
  pyridazin-3(2H)-one;
2-((3-(6-chloropyridin-3-yl)-5-methylisoxazol-4-yl)
  methyl)-5-(1-oxa-7-azaspiro[3.5]nonan-7-yl)pyridazin-3
  (2H)-one;
5-(3-(tert-butoxy)azetidin-1-yl)-2-((3-(6-chloropyridazin-3-
  yl)-5-methylisoxazol-4-yl)methyl)pyridazin-3(2H)-one;
4-chloro-2-((3-(6-chloropyridin-3-yl)-5-methylisoxazol-4-
  yl)methyl)-5-(3-ethoxyazetidin-1-yl)pyridazin-3(2H)-
  one;
(S)-5-(8-fluoro-5-oxa-2-azaspiro[3.5]nonan-2-yl)-2-((5-
  methyl-3-(6-methylpyridin-3-yl)isoxazol-4-yl)methyl)
  pyridazin-3(2H)-one;
(R)-5-(8-fluoro-5-oxa-2-azaspiro[3.5]nonan-2-yl)-2-((5-
  methyl-3-(6-methylpyridin-3-yl)isoxazol-4-yl)methyl)
  pyridazin-3(2H)-one;
(R)-5-(7-fluoro-5-oxa-2-azaspiro[3.5]nonan-2-yl)-2-((5-
  methyl-3-(6-methylpyridin-3-yl)isoxazol-4-yl)methyl)
  pyridazin-3(2H)-one;
(S)-5-(7-fluoro-5-oxa-2-azaspiro[3.5]nonan-2-yl)-2-((5-
  methyl-3-(6-methylpyridin-3-yl)isoxazol-4-yl)methyl)
  pyridazin-3(2H)-one;
2-((3-(6-chloropyridin-3-yl)-5-methylisoxazol-4-yl)
  methyl)-5-(4-(pyrimidin-5-yl)piperazin-1-yl)pyridazin-3
  (2H)-one;
2-((3-(6-chloropyridin-3-yl)-5-methylisoxazol-4-yl)
  methyl)-5-(4-(pyridin-3-yl)piperazin-1-yl)pyridazin-3
  (2H)-one;

5-(3-ethoxyazetidin-1-yl)-2-((5-(fluoromethyl)-3-(6-methylpyridazin-3-yl)isoxazol-4-yl)methyl)pyridazin-3(2H)-one;

2-((3-(6-chloropyridin-3-yl)-5-methylisoxazol-4-yl)methyl)-5-(4-(4-methyl-1,2,5-oxadiazol-3-yl)piperazin-1-yl)pyridazin-3(2H)-one;

5-(3-methoxyazetidin-1-yl)-2-((5-methyl-3-(6-(trifluoromethyl)pyridazin-3-yl)isoxazol-4-yl)methyl)pyridazin-3(2H)-one;

5-(5-chloro-6-methoxypyridin-3-yl)-2-((3-(6-chloropyridazin-3-yl)-5-methylisoxazol-4-yl)methyl)pyridazin-3(2H)-one;

2-((3-(6-chloropyridin-3-yl)-5-methylisoxazol-4-yl)methyl)-5-(4-(4-methylpyrimidin-5-yl)piperazin-1-yl)pyridazin-3(2H)-one;

5-(4-(3-chloropyridazin-4-yl)piperazin-1-yl)-2-((3-(6-chloropyridin-3-yl)-5-methylisoxazol-4-yl)methyl)pyridazin-3(2H)-one;

2-((3-(6-chloropyridin-3-yl)-5-methylisoxazol-4-yl)methyl)-5-(4-(2-methylpyridin-3-yl)piperazin-1-yl)pyridazin-3(2H)-one;

2-((3-(6-chloropyridin-3-yl)-5-methylisoxazol-4-yl)methyl)-5-((2S,3S) or (2R,3R)-3-methoxy-2-methylazetidin-1-yl)pyridazin-3(2H)-one;

(S)-5-(8-fluoro-5-oxa-2-azaspiro[3.5]nonan-2-yl)-2-((5-methyl-3-(6-methylpyridazin-3-yl)isoxazol-4-yl)methyl)pyridazin-3(2H)-one;

(S)-5-(7-fluoro-5-oxa-2-azaspiro[3.5]nonan-2-yl)-2-((5-methyl-3-(6-methylpyridazin-3-yl)isoxazol-4-yl)methyl)pyridazin-3(2H)-one;

2-((3-(6-chloropyridin-3-yl)-5-methylisoxazol-4-yl)methyl)-5-((2R,3R) or (2S,3S)-3-hydroxy-2-methylazetidin-1-yl)pyridazin-3(2H)-one;

2-((3-(6-chloropyridin-3-yl)-5-methyl-1,2-oxazol-4-yl)methyl)-5-(4-(4-methoxypyrimidin-5-yl)piperazin-1-yl)pyridazin-3-one;

2-((3-(6-chloropyridin-3-yl)-5-methylisoxazol-4-yl)methyl)-5-((2S,3S) or (2R,3R)-3-ethoxy-2-methylazetidin-1-yl)pyridazin-3(2H)-one;

2-((3-(6-chloropyridin-3-yl)-5-methylisoxazol-4-yl)methyl)-5-(4-(4-cyclopropylpyrimidin-5-yl)piperazin-1-yl)pyridazin-3(2H)-one;

5-(4-(5-chloropyridazin-4-yl)piperazin-1-yl)-2-((3-(6-chloropyridin-3-yl)-5-methylisoxazol-4-yl)methyl)pyridazin-3(2H)-one;

2-((3-(6-chloropyridin-3-yl)-5-methylisoxazol-4-yl)methyl)-5-((2R,3R) or (2S,3S)-3-ethoxy-2-methylazetidin-1-yl)pyridazin-3(2H)-one;

2-((5-(fluoromethyl)-3-(6-methylpyridazin-3-yl)isoxazol-4-yl)methyl)-5-(5-oxa-2-azaspiro[3.4]octan-2-yl)pyridazin-3(2H)-one;

(R or S)-2-((3-(6-chloropyridin-3-yl)-5-methylisoxazol-4-yl)methyl)-5-(8-fluoro-5-oxa-2-azaspiro[3.5]nonan-2-yl)pyridazin-3(2H)-one;

(R or S)-2-((3-(6-chloropyridin-3-yl)-5-methylisoxazol-4-yl)methyl)-5-(7-fluoro-5-oxa-2-azaspiro[3.5]nonan-2-yl)pyridazin-3(2H)-one;

(S or R)-2-((3-(6-chloropyridin-3-yl)-5-methylisoxazol-4-yl)methyl)-5-(7-fluoro-5-oxa-2-azaspiro[3.5]nonan-2-yl)pyridazin-3(2H)-one;

2-((3-(6-chloropyridin-3-yl)-5-methylisoxazol-4-yl)methyl)-5-(4-(3-methylpyridazin-4-yl)piperazin-1-yl)pyridazin-3(2H)-one;

2-((3-(6-chloropyridin-3-yl)-5-methylisoxazol-4-yl)methyl)-5-(4-(4-chloropyrimidin-5-yl)piperazin-1-yl)pyridazin-3(2H)-one;

2-((3-(6-chloropyridin-3-yl)-5-methylisoxazol-4-yl)methyl)-5-(4-(5-methylpyridazin-4-yl)piperazin-1-yl)pyridazin-3(2H)-one;

2-((5-methyl-3-(6-methylpyridazin-3-yl)isoxazol-4-yl)methyl)-5-(1-oxa-9-azaspiro[5.5]undecan-9-yl)pyridazin-3(2H)-one;

2-((3-(6-chloropyridin-3-yl)-5-methylisoxazol-4-yl)methyl)-5-(6-methoxy-2-azaspiro[3.3]heptan-2-yl)pyridazin-3(2H)-one;

2-((3-(6-chloropyridin-3-yl)-5-methylisoxazol-4-yl)methyl)-5-(4-(3-methoxypyridin-4-yl)piperazin-1-yl)pyridazin-3(2H)-one;

2-((5-methyl-3-(6-methylpyridazin-3-yl)isoxazol-4-yl)methyl)-5-(3-(1-methylcyclopropoxy)azetidin-1-yl)pyridazin-3(2H)-one;

5-(3-(2,2-difluoroethoxy)azetidin-1-yl)-2-((5-methyl-3-(6-methylpyridazin-3-yl)isoxazol-4-yl)methyl)pyridazin-3(2H)-one;

(R)-2-((3-(6-chloropyridin-3-yl)-5-methylisoxazol-4-yl)methyl)-5-(7-methyl-5-oxa-2-azaspiro[3.5]nonan-2-yl)pyridazin-3(2H)-one;

(S)-2-((3-(6-chloropyridin-3-yl)-5-methylisoxazol-4-yl)methyl)-5-(7-methyl-5-oxa-2-azaspiro[3.5]nonan-2-yl)pyridazin-3(2H)-one;

(S)-5-(7-ethyl-5-oxa-2-azaspiro[3.4]octan-2-yl)-2-((5-methyl-3-(6-methylpyridazin-3-yl)isoxazol-4-yl)methyl)pyridazin-3(2H)-one;

5-(6,6-dimethyl-5-oxa-2-azaspiro[3.4]octan-2-yl)-2-((5-methyl-3-(6-methylpyridazin-3-yl)isoxazol-4-yl)methyl)pyridazin-3(2H)-one;

(S)-2-((5-methyl-3-(6-methylpyridazin-3-yl)isoxazol-4-yl)methyl)-5-(8-(trifluoromethyl)-5-oxa-2-azaspiro[3.5]nonan-2-yl)pyridazin-3(2H)-one;

(R)-2-((5-methyl-3-(6-methylpyridazin-3-yl)isoxazol-4-yl)methyl)-5-(8-(trifluoromethyl)-5-oxa-2-azaspiro[3.5]nonan-2-yl)pyridazin-3(2H)-one;

(R)-2-((5-methyl-3-(6-methylpyridazin-3-yl)isoxazol-4-yl)methyl)-5-(7-methyl-5-oxa-2-azaspiro[3.5]nonan-2-yl)pyridazin-3(2H)-one;

(S)-2-((5-methyl-3-(6-methylpyridazin-3-yl)isoxazol-4-yl)methyl)-5-(7-methyl-5-oxa-2-azaspiro[3.5]nonan-2-yl)pyridazin-3(2H)-one;

5-(6-(difluoromethoxy)-2-azaspiro[3.3]heptan-2-yl)-2-((5-methyl-3-(6-methylpyridazin-3-yl)isoxazol-4-yl)methyl)pyridazin-3(2H)-one;

2-((5-methyl-3-(6-methylpyridazin-3-yl)isoxazol-4-yl)methyl)-5-(5-oxa-2-azaspiro[3.6]decan-2-yl)pyridazin-3(2H)-one;

(S)-2-((5-methyl-3-(6-methylpyridazin-3-yl)isoxazol-4-yl)methyl)-5-(8-methyl-5-oxa-2-azaspiro[3.5]nonan-2-yl)pyridazin-3(2H)-one;

(R)-2-((5-methyl-3-(6-methylpyridazin-3-yl)isoxazol-4-yl)methyl)-5-(8-methyl-5-oxa-2-azaspiro[3.5]nonan-2-yl)pyridazin-3(2H)-one;

(R)-5-(7-fluoro-5-oxa-2-azaspiro[3.5]nonan-2-yl)-2-((5-methyl-3-(6-methylpyridazin-3-yl)isoxazol-4-yl)methyl)pyridazin-3(2H)-one;

(S)-2-((5-methyl-3-(6-methylpyridazin-3-yl)isoxazol-4-yl)methyl)-5-(7-(trifluoromethyl)-5-oxa-2-azaspiro[3.5]nonan-2-yl)pyridazin-3(2H)-one;

(R)-2-((5-methyl-3-(6-methylpyridazin-3-yl)isoxazol-4-yl)methyl)-5-(7-(trifluoromethyl)-5-oxa-2-azaspiro[3.5]nonan-2-yl)pyridazin-3(2H)-one;

(S)-2-((3-(6-chloropyridin-3-yl)-5-methylisoxazol-4-yl)methyl)-5-(8-methyl-5-oxa-2-azaspiro[3.5]nonan-2-yl)pyridazin-3(2H)-one;

(R)-2-((3-(6-chloropyridin-3-yl)-5-methylisoxazol-4-yl)methyl)-5-(7-(trifluoromethyl)-5-oxa-2-azaspiro[3.5]nonan-2-yl)pyridazin-3(2H)-one;
2-((5-ethyl-3-(6-methylpyridazin-3-yl)isoxazol-4-yl)methyl)-5-(5-oxa-2-azaspiro[3.5]nonan-2-yl)pyridazin-3(2H)-one;
(R)-2-((5-ethyl-3-(6-methylpyridazin-3-yl)isoxazol-4-yl)methyl)-5-(7-fluoro-5-oxa-2-azaspiro[3.5]nonan-2-yl)pyridazin-3(2H)-one;
5-((4S)-4-fluoro-1-oxa-9-azaspiro[5.5]undecan-9-yl)-2-((5-methyl-3-(6-methylpyridazin-3-yl)isoxazol-4-yl)methyl)pyridazin-3-one;
5-((4R)-4-fluoro-1-oxa-9-azaspiro[5.5]undecan-9-yl)-2-((5-methyl-3-(6-methylpyridazin-3-yl)isoxazol-4-yl)methyl)pyridazin-3-one;
2-((5-(fluoromethyl)-3-(6-methylpyridazin-3-yl)isoxazol-4-yl)methyl)-5-(5-oxa-2-azaspiro[3.5]nonan-2-yl)pyridazin-3(2H)-one;
(R)-5-(7-fluoro-5-oxa-2-azaspiro[3.5]nonan-2-yl)-2-((5-(fluoromethyl)-3-(6-methylpyridazin-3-yl)isoxazol-4-yl)methyl)pyridazin-3(2H)-one;
(R)-2-((3-(6-chloropyridin-3-yl)-5-methylisoxazol-4-yl)methyl)-5-(4-fluoro-1-oxa-9-azaspiro[5.5]undecan-9-yl)pyridazin-3(2H)-one;
(S)-2-((3-(6-chloropyridin-3-yl)-5-methylisoxazol-4-yl)methyl)-5-(4-fluoro-1-oxa-9-azaspiro[5.5]undecan-9-yl)pyridazin-3(2H)-one;
(R)-5-(7-fluoro-5-oxa-2-azaspiro[3.5]nonan-2-yl)-2-((5-methyl-3-(5-(trifluoromethyl)pyrimidin-2-yl)isoxazol-4-yl)methyl)pyridazin-3(2H)-one;
2-((3-(6-chloropyridin-3-yl)-5-methylisoxazol-4-yl)methyl)-5-(1-oxa-9-azaspiro[5.5]undecan-9-yl)pyridazin-3(2H)-one;
(R)-5-(7-fluoro-5-oxa-2-azaspiro[3.5]nonan-2-yl)-2-((5-methyl-3-(6-(trifluoromethyl)pyridazin-3-yl)isoxazol-4-yl)methyl)pyridazin-3(2H)-one;
2-((5-methyl-3-(6-(trifluoromethyl)pyridazin-3-yl)isoxazol-4-yl)methyl)-5-(5-oxa-2-azaspiro[3.5]nonan-2-yl)pyridazin-3(2H)-one;
or pharmaceutically acceptable salts thereof.

Further particular examples of a compound of formula (I) as described herein are selected from
5-((2S,6R)-2,6-dimethylmorpholin-4-yl)-2-((5-methyl-3-(6-methylpyridin-3-yl)-1,2-oxazol-4-yl)methyl)pyridazin-3-one;
5-(4-Cyclopropylpiperazin-1-yl)-2-((5-methyl-3-(6-methylpyridin-3-yl)isoxazol-4-yl)methyl)pyridazin-3(2H)-one;
(S)-2-((5-Methyl-3-(6-methylpyridin-3-yl)isoxazol-4-yl)methyl)-5-(2-methylmorpholino)pyridazin-3(2H)-one
2-((3-(6-chloropyridin-3-yl)-5-methylisoxazol-4-yl)methyl)-5-((2RS,6SR)-2,6-dimethylmorpholino)pyridazin-3(2H)-one;
2-((3-(6-chloropyridin-3-yl)-5-methylisoxazol-4-yl)methyl)-5-(3-cyclopropoxyazetidin-1-yl)pyridazin-3(2H)-one;
(S)-2-((3-(6-chloropyridin-3-yl)-5-methylisoxazol-4-yl)methyl)-5-(2-methylmorpholino)pyridazin-3(2H)-one;
(R)-5-(7-fluoro-5-oxa-2-azaspiro[3.5]nonan-2-yl)-2-((5-methyl-3-(6-methylpyridin-3-yl)isoxazol-4-yl)methyl)pyridazin-3(2H)-one;
(R or S)-2-((3-(6-chloropyridin-3-yl)-5-methylisoxazol-4-yl)methyl)-5-(7-fluoro-5-oxa-2-azaspiro[3.5]nonan-2-yl)pyridazin-3(2H)-one;
5-(3-(tert-butoxy)azetidin-1-yl)-2-((5-methyl-3-(6-methylpyridazin-3-yl)isoxazol-4-yl)methyl)pyridazin-3(2H)-one;
2-((5-methyl-3-(6-methylpyridazin-3-yl)isoxazol-4-yl)methyl)-5-(5-oxa-2-azaspiro[3.5]nonan-2-yl)pyridazin-3(2H)-one;
or pharmaceutically acceptable salts thereof.

Furthermore particular examples of a compound of formula (I) as described herein are selected from
(R or S)-2-((3-(6-chloropyridin-3-yl)-5-methylisoxazol-4-yl)methyl)-5-(7-fluoro-5-oxa-2-azaspiro[3.5]nonan-2-yl)pyridazin-3(2H)-one;
5-(3-(tert-butoxy)azetidin-1-yl)-2-((5-methyl-3-(6-methylpyridazin-3-yl)isoxazol-4-yl)methyl)pyridazin-3(2H)-one;
or pharmaceutically acceptable salts thereof.

Processes for the manufacture of a compound of formula (I) or (II) as described herein are also an object of the invention.

The preparation of compounds of formula (I) or (II) of the present invention may be carried out in sequential or convergent synthetic routes. Syntheses of the invention are shown in the following general schemes. The skills required for carrying out the reactions and purifications of the resulting products are known to those skilled in the art. The substituents and indices used in the following description of the processes have the significance given herein before unless indicated to the contrary.

In more detail, the compounds of formula (I) or (II) can be manufactured by the methods given below, by the methods given in the examples or by analogous methods. Appropriate reaction conditions for the individual reaction steps are known to a person skilled in the art. The reaction sequence is not limited to the one displayed in schemes 1-7, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The preparation of compounds of formula (I) and (II) of the present invention may be carried out in sequential or convergent synthetic routes. Syntheses of the compounds of the invention are shown in the following schemes 1-6 and in the description of 298 specific examples. The skills required for carrying out the reactions and purifications of the resulting products are known to those skilled in the art. The substituents and indices used in the following description of the processes have the significance given herein before unless indicated to the contrary.

In more detail, the compounds of formula (I) or (II) can be manufactured by the methods given below, by the methods given in the examples or by analogous methods. Appropriate reaction conditions for the individual reaction steps are known to a person skilled in the art. The reaction sequence is not limited to the one displayed in schemes 1-6, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula (I) or (II) and their pharmaceutically acceptable salts can be prepared by a process described below (Scheme 1)

35

Scheme 1: synthesis of pyridazinones; wherein all definitions are as described above and in the claims

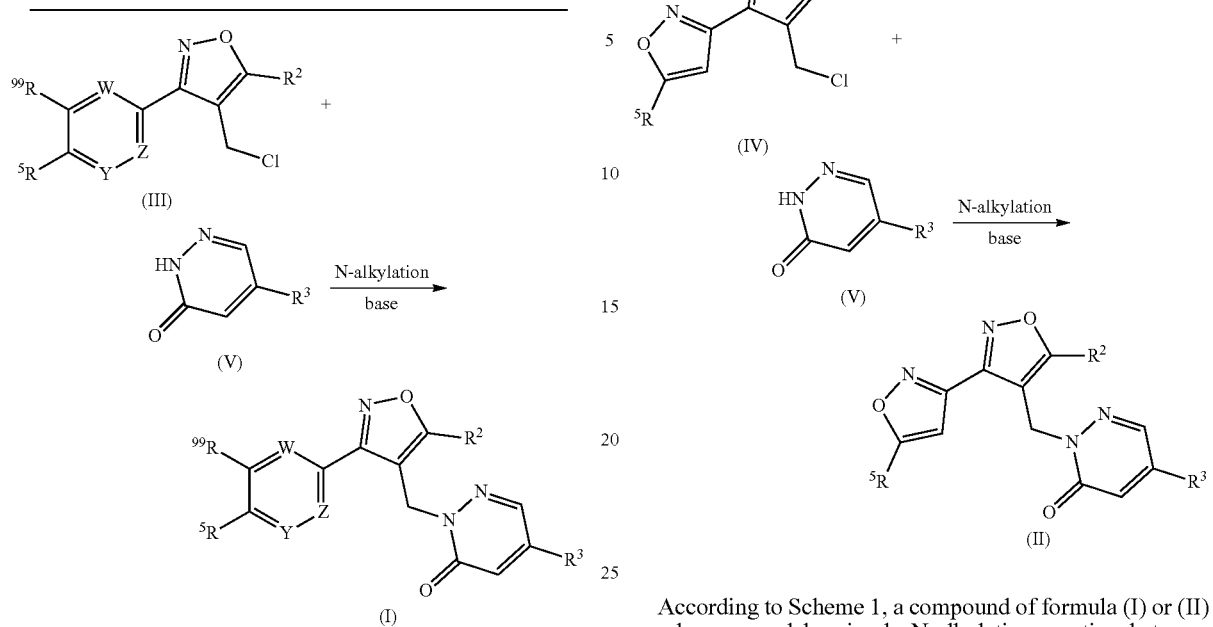

36

-continued

According to Scheme 1, a compound of formula (I) or (II) can be prepared by simple N-alkylation reaction between alkyl chlorides (III) or (IV) and a pyridazinone of formula (V) in presence of a base (e.g. $K_2C_3$).

Synthesis of alkyl chlorides (III) or (IV) is highlighted in Scheme 2.

Scheme 2: synthesis of alkyl chlorides (III) or (IV); wherein all definitions are as described above and in the claims

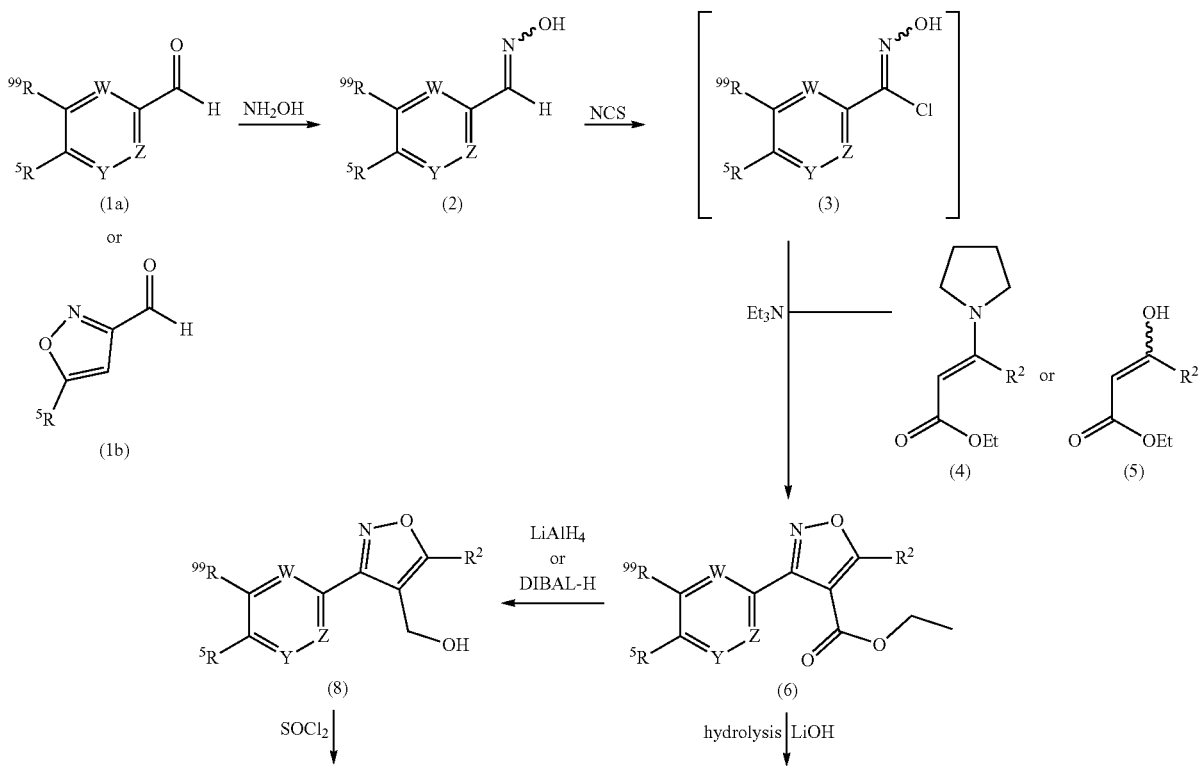

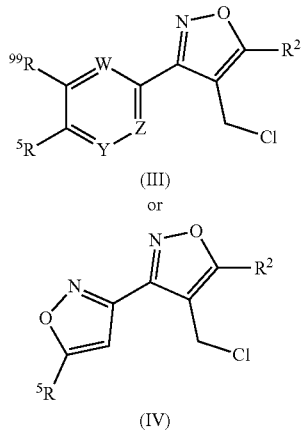

(III)

or

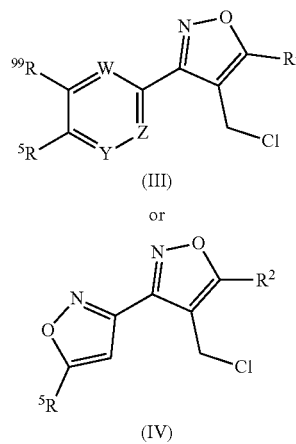

(IV)

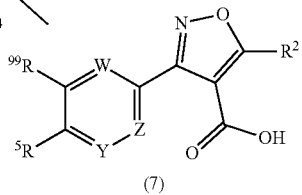

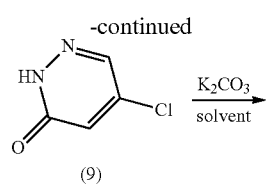

(7)

Commercially available aldehydes (1a) or (1b) are converted to corresponding oximes (2) by treatment with hydroxylamine hydrochloride in presence of a base (e.g. NaOH or Et$_3$N). Following electrophilic chlorination with N-chlorosuccinimide (NCS), the intermediate chloro-oximes (3), in presence of a base (Et$_3$N), undergo a 1,3-dipolar cycloaddition reaction with readily available enamines (4) or enols (5) to afford isoxazoles of formula (6). Their reduction to alcohols (8) can be accomplished directly with LiAH$_4$ or DIBAL-H at controlled temperature or in two-steps via hydrolysis to their corresponding carboxylic acids (7) followed by reduction (NaBH$_4$) by treatment with ethyl chloroformate in presence of a base (Et$_3$N). Final conversion to desired alkyl chlorides (III) or (IV) is accomplished by exposure to thionyl chloride.

Scheme 3: synthesis of building block (A-Z)

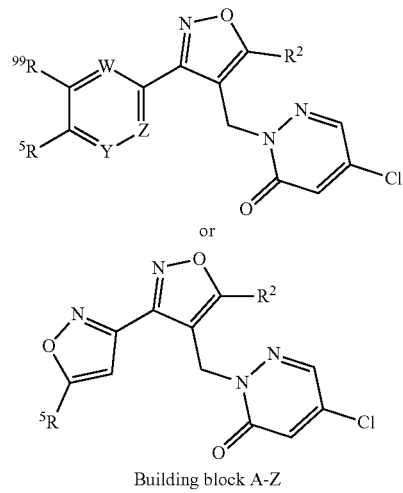

Building block A-Z

Conveniently, alkyl chlorides (III) or (IV) can be reacted in presence of a base (K$_2$CO$_3$) with commercially available 4-chloro-TH-pyridazin-6-one (9) to provide bench stable 5-chloro pyridazinones building block (A-Z) as shown in Scheme 3.

Scheme 4: synthesis of pyridazinones (I) or (II) from building block (A-Z); wherein R³ is amino substituted on the nitrogen atom by one or two substituents or substituted heterocycloalky; all other definitions are as described above and in the claims

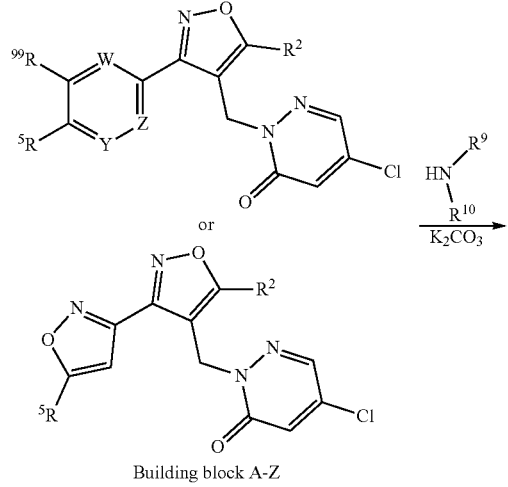

Scheme 5: synthesis of pyridazinones (I) or (II) from building block (A-Z); wherein R³ is aryl or heteroaryl; all other definitions are as described above and in the claims

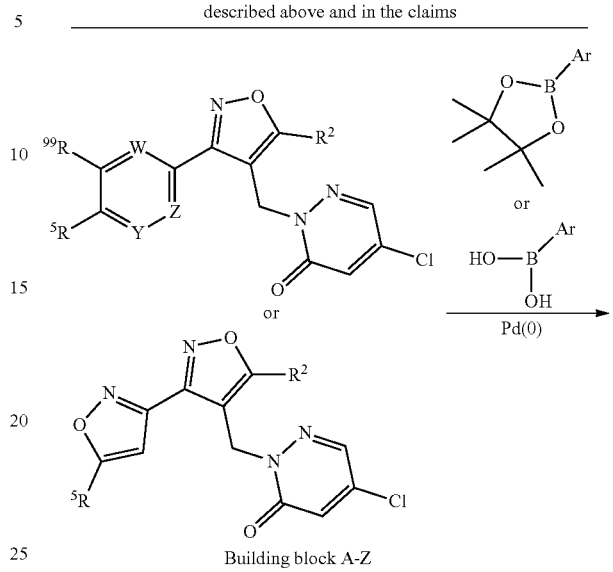

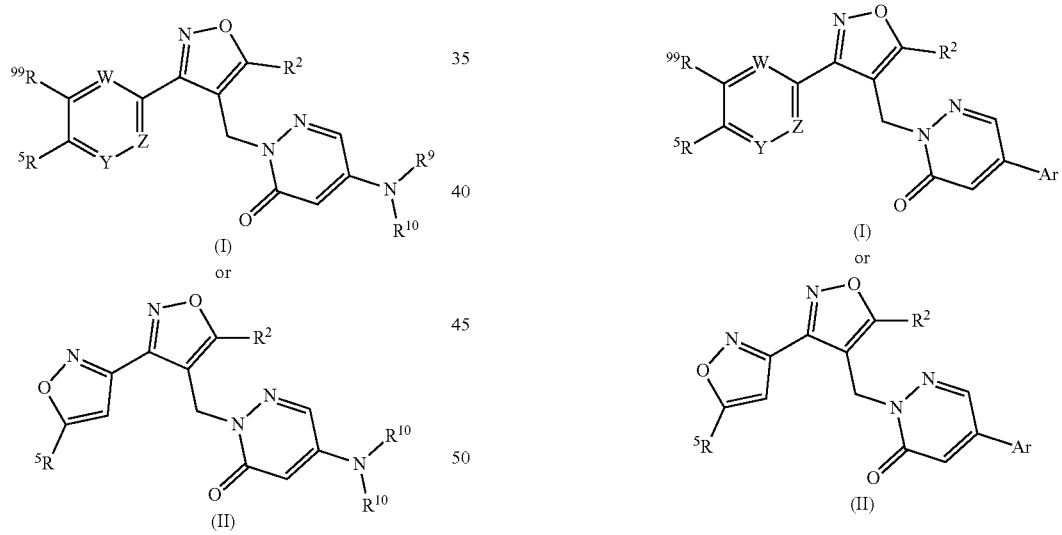

In certain embodiments of the invention where R³ is nitrogen, pyridazinones of formula (I) or (II) can be prepared by nucleophilic aromatic substitution reaction between building block (A-Z) and a primary (R⁹=H) or a secondary amine HNR⁹R¹⁰, including a large variety of heterocycloalkyl amines (Scheme 4).

In further embodiments of the invention, where R³ is heteroaryl or aryl, pyridazinones of formula (I) or (II) can be obtained by a palladium-mediated Suzuki coupling reaction between aryl-chloride building block (A-Z) and commercially available boronic acids or boranes (Scheme 5).

Scheme 6: alternative synthesis of pyridazinones (I); wherein $R^3$ is aryl or heteroaryl; all other definitions are as described above and in the claims

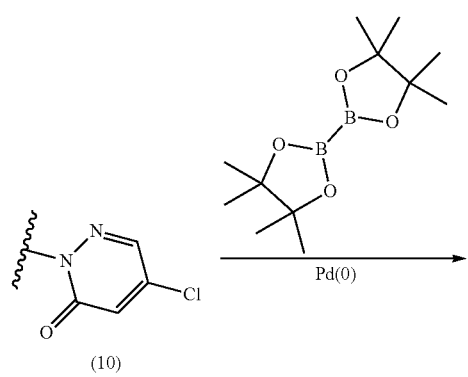

(10)

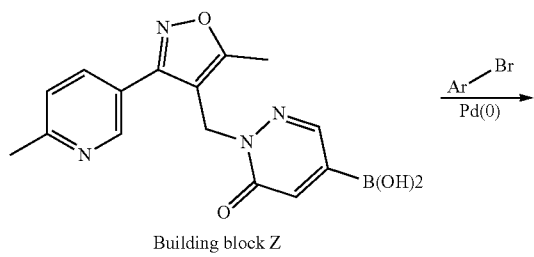

Building block Z

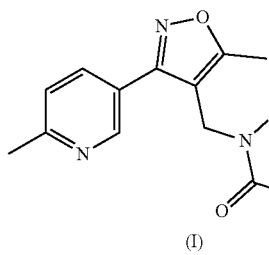

(I)

In alternative, as illustrated in Scheme 6, aryl-chlorides can be converted to corresponding boronic acids by a palladium-mediated process and used in the following Suzuki coupling with commercially available aryl bromides to access pyridazinones of formula (I).

Also an embodiment of the present invention is a process to prepare a compound of formula (I) or (II) as defined above comprising the reaction of a compound of formula (III) or (IV) with a compound of formula (V) in a presence of a base, particularly $K_2CO_3$.

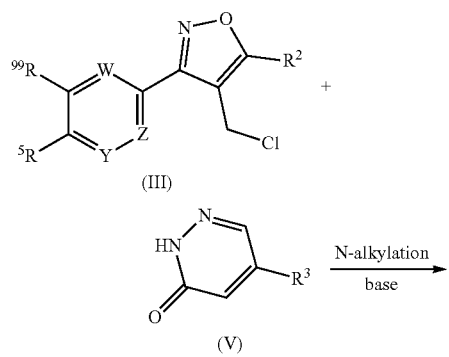

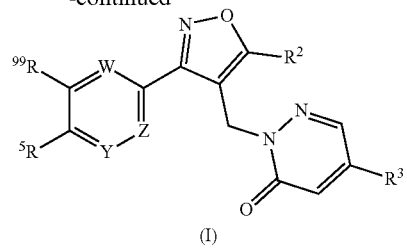

(I)

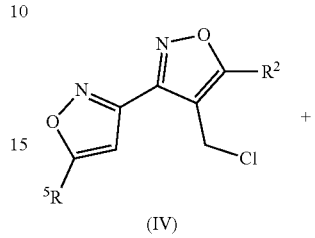

(IV)

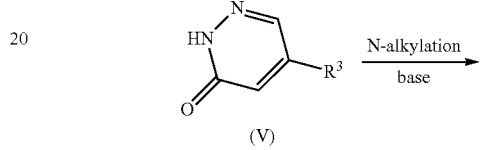

(V)

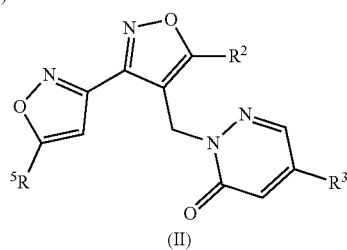

(II)

wherein $R^2$, $R^3$, $R^5$, $R^{99}$, W, Y and Z are as defined herein.

Also an object of the present invention is a compound according to formula (I) or (II), more particularly compounds of formula (I), as described herein for use as a therapeutically active substance.

Likewise an object of the present invention is a pharmaceutical composition comprising a compound according to formula (I) or (II), more particularly compounds of formula (I), as described herein and a therapeutically inert carrier.

A particular embodiment of the present invention is a compound according to formula (I) or (II), more particularly compounds of formula (I), as described herein for the treatment or prophylaxis, more particularly the treatment, of Alzheimer's disease, mild cognitive impairment (MCI), age-related cognitive decline, negative and/or cognitive symptoms associated with schizophrenia, bipolar disorders, autism spectrum disorder (ASD), Angelman syndrome, Rett syndrome, Prader-Willi syndrome, epilepsy, post-traumatic stress disorder (PTSD), amyotrophic lateral sclerosis (ALS), fragile-X disorder, more particularly autism spectrum disorder (ASD), Angelman syndrome, Alzheimer's disease, negative and/or cognitive symptoms associated with schizophrenia and post-traumatic stress disorder (PTSD).

The present invention also relates to the use of a compound according to formula (I) or (II), more particularly compounds of formula (I), as described herein for the preparation of a medicament for the treatment or prophylaxis, more particularly the treatment, of Alzheimer's disease, mild cognitive impairment (MCI), age-related cognitive decline, negative and/or cognitive symptoms associated with schizophrenia, bipolar disorders, autism spectrum disorder (ASD), Angelman syndrome, Rett syndrome, Prader- Willi syndrome, epilepsy, post-traumatic stress disorder (PTSD), amyotrophic lateral sclerosis (ALS), fragile-X disorder, more particularly autism spectrum disorder (ASD), Angelman syndrome, Alzheimer's disease, negative and/or cognitive symptoms associated with schizophrenia and post-traumatic stress disorder (PTSD).

Also an object of the invention is a method for the treatment or prophylaxis, more particularly the treatment, of Alzheimer's disease, mild cognitive impairment (MCI), age-related cognitive decline, negative and/or cognitive symptoms associated with schizophrenia, bipolar disorders, autism spectrum disorder (ASD), Angelman syndrome, Rett syndrome, Prader-Willi syndrome, epilepsy, post-traumatic stress disorder (PTSD), amyotrophic lateral sclerosis (ALS), fragile-X disorder, more particularly autism spectrum disorder (ASD), Angelman syndrome, Alzheimer's disease, negative and/or cognitive symptoms associated with schizophrenia and post-traumatic stress disorder (PTSD), which method comprises administering an effective amount of a compound according to formula (I) or (II), more particularly compounds of formula (I), as described herein.

Also an embodiment of the present invention are compounds of formula (I) or (II), more particularly compounds of formula (I), as described herein, when manufactured according to any one of the described processes.

Assay Procedures

Membrane Preparation and Binding Assay

The affinity of compounds at $GABA_A$ receptor subtypes was measured by competition for [3H]flumazenil (85 Ci/mmol; Roche) binding to HEK293 cells expressing rat (stably transfected) or human (transiently transfected) receptors of composition $\alpha1\beta3\gamma2$, $\alpha2\beta3\gamma2$, $\alpha3\beta3\gamma2$ and $\alpha5\beta3\gamma2$.

Cell pellets were suspended in Krebs-tris buffer (4.8 mM KCl, 1.2 mM CaCl2), 1.2 mM $MgCl_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 mL (96-well plates) which contained 100 mL of cell membranes, [3H]-Flumazenil at a concentration of 1 nM for $\alpha1$, $\alpha2$, $\alpha3$ subunits and 0.5 nM for $\alpha5$ subunits and the test compound in the range of $10\text{-}10^{-3} \times 10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. $K_i$ values were calculated using Excel-Fit (Microsoft) and are the means of two determinations.

The compounds of the accompanying examples were tested in the above described assay, and the preferred compounds were found to possess a $K_i$ value for displacement of [3H]-Flumazenil from $\alpha5$ subunits of the human $GABA_A$ receptor of 100 nM or less. Most preferred are compounds with a $K_i$ (nM)<35. In a preferred embodiment the compounds of the invention are binding selective for the $\alpha5$ subunit relative to the $\alpha1$, $\alpha2$ and $\alpha3$ subunit. Representative test results, obtained by the above described assay measuring binding affinity to HEK293 cells expressing human (h) receptors, are shown in the Table below.

Functional Expression of $GABA_A$ Receptors:

*Xenopus* Oocytes Preparation

*Xenopus laevis* oocytes at maturation stages V-VI were used for the expression of cloned mRNA encoding $GABA_A$ receptor subunits. Oocytes ready for RNA micro-injection were bought from Ecocyte, Castrop-Rauxel, Germany and stored in modified Barth's medium (composition in mM: NaCl 88, KCl 1, $NaHCO_3$ 2.4, HEPES 10, $MgSO_4$ 0.82, $CaNO_3$ 0.33, $CaCl_2$ 0.33, pH=7.5) at 20° C. until the experiment.

*Xenopus* Oocytes Microinjection

Oocytes were plated in 96-well plates to be used in an automated instrument (Robo-ocyte, MultiChannelSystems, Reutlingen, Germany) for microinjection and electrophysiological recordings. Approximately 50 nl of an aqueous solution containing the RNA transcripts for the subunits of the desired $GABA_A$ receptor was injected into each oocyte. RNA concentrations ranged between 0.3 and 16 ng/µl/subunit and were adjusted in pilot experiments to obtain GABA responses of a suitable size and a maximal effect of the reference modulator, Beta-CCM (β-CCM), a betacarboline negative allosteric modulator (NAM) at the $GABA_A$ receptor benzodiazepine (BZD) binding site or Midazolam, a benzodiazepine positive allosteric modulator (PAM) at the $GABA_A$ receptor benzodiazepine (BZD) binding site. The concentration of the γ2 subunit encoding RNA usually was 5- to 10-fold higher than the RNAs encoding the other subunits. Oocytes were kept in modified Barth's medium (composition in mM: NaCl 88, KCl 1, $NaHCO_3$ 4, HEPES 10, $MgSO_4$ 0.82, $CaNO_3$ 0.33, $CaCl_2$) 0.33, pH=7.5) at 20° C. until the experiment.

Electrophysiology

Electrophysiological experiments were performed on days 3 to 5 after the micro-injection of mRNA. During the experiment the oocytes were constantly superfused by a solution containing (in mM) NaCl 90, KCl 1, HEPES 5, $MgCl_2$ 1, $CaCl_2$) 1 (pH 7.4). Oocytes were impaled by two glass microelectrodes (resistance: 0.4 MΩ) which were filled with a solution containing KCl 1M+K-acetate 1.5 M and voltage-clamped to −80 mV. The recordings were performed at room temperature using the Roboocyte two-electrode voltage clamp system (Multichannelsystem). After an initial equilibration period of 1.5 min GABA was added for 1.5 min at a concentration evoking approximately 20% of a maximal current response ($EC_{20}$). After another rest interval of 2.5 min GABA was again added evoking a response of similar amplitude and shape. 0.5 min after the onset of this second GABA application the test compound, at a concentration corresponding to approximatively 30 fold its $K_i$, was added while GABA was still present. Current traces were recorded at a digitization rate of 10 Hz during and shortly before and after the GABA application.

Each compound and concentration was tested on at least 3 oocytes. Different oocytes were used for different compound concentrations. β-CCM, a negative allosteric modulator, or Midazolam, a positive allosteric modulators, were tested on a few (3-6) oocytes on each 96-well plate for a positive control at a maximally effective. β-CCM inhibited the GABA-evoked current by approximatively 50% (Fold increase ~0.5), while Midazolam potentiated the GABA-induced current by approximatively 150% (Fold increase ~2.5).

Data Analysis

For the analysis, the digitized current traces of the first and second GABA response were superimposed and, if necessary, rescaled to equal maximal amplitudes. The ratio between the two responses during the time interval of test compound application was calculated point by point. The extremum of the resulting "ratio trace" was taken as the efficacy ("Fold increase") of the compound expressed as "% modulation of GABA $EC_{20}$" (100*(Fold increase-1)). The results are shown in Table 1.

TABLE 1

| Example | Ki h-GABA-A α5β3γ2 (μM) | Fold increase h-GABA-A α5β3γ2 oocyte | Efficacy (GABA) % |
|---|---|---|---|
| 1 | 0.0102 | 1.63 | 63 |
| 2 | 0.0262 | 2.55 | 155 |
| 3 | 0.0106 | 2.1 | 110 |
| 4 | 0.0086 | 2.45 | 145 |
| 5 | 0.0016 | 2.55 | 155 |
| 6 | 0.0006 | 2.45 | 145 |
| 7 | 0.001 | 3.53 | 253 |
| 8 | 0.0264 | 2.68 | 168 |
| 9 | 0.0159 | 2.53 | 153 |
| 10 | 0.0219 | 3.22 | 222 |
| 11 | 0.0079 | 1.57 | 57 |
| 12 | 0.0038 | 2.14 | 114 |
| 13 | 0.0007 | 1.94 | 94 |
| 14 | 0.0015 | 2.66 | 166 |
| 15 | 0.0352 | 2.2 | 120 |
| 16 | 0.0026 | 2.39 | 139 |
| 22 | 0.0032 | 2.66 | 166 |
| 24 | 0.0146 | 3.03 | 203 |
| 25 | 0.0125 | 3.66 | 266 |
| 26 | 0.0284 | 3.47 | 247 |
| 27 | 0.0142 | 2 | 100 |
| 28 | 0.0006 | 2.36 | 136 |
| 29 | 0.0014 | 3.28 | 228 |
| 30 | 0.0005 | 3.16 | 216 |
| 31 | 0.0135 | 2.45 | 145 |
| 32 | 0.0127 | 3.88 | 288 |
| 33 | 0.0032 | 2.5 | 150 |
| 34 | 0.0043 | 3.22 | 222 |
| 35 | 0.0008 | 2.79 | 179 |
| 36 | 0.0138 | 2.45 | 145 |
| 38 | 0.0384 | 2.81 | 181 |
| 39 | 0.0032 | 2.98 | 198 |
| 40 | 0.0433 | 3.5 | 250 |
| 43 | 0.01 | 2.74 | 174 |
| 44 | 0.0095 | 2.81 | 181 |
| 45 | 0.0066 | 2.03 | 103 |
| 46 | 0.0152 | 2.07 | 107 |
| 49 | 0.013 | 2.67 | 167 |
| 50 | 0.0028 | 2.87 | 187 |
| 51 | 0.0033 | 2.82 | 182 |
| 52 | 0.0007 | 2.35 | 135 |
| 53 | 0.0098 | 2.52 | 152 |
| 54 | 0.0108 | 2.75 | 175 |
| 55 | 0.0434 | 1.85 | 85 |
| 56 | 0.0334 | 3.47 | 247 |
| 57 | 0.0562 | 2.98 | 198 |
| 58 | 0.0704 | 3.09 | 209 |
| 59 | 0.0154 | 2.57 | 157 |
| 60 | 0.0102 | 1.97 | 97 |
| 61 | 0.0154 | 1.76 | 76 |
| 62 | 0.0006 | 1.88 | 88 |
| 63 | 0.0059 | 1.41 | 41 |
| 64 | 0.0018 | 2.08 | 108 |
| 65 | 0.0047 | 2.42 | 142 |
| 66 | 0.0264 | 2.21 | 121 |
| 67 | 0.0105 | 2.07 | 107 |
| 68 | 0.0119 | 1.71 | 71 |
| 69 | 0.0389 | 2.55 | 155 |
| 70 | 0.0006 | 2.06 | 106 |
| 72 | 0.0402 | 2.67 | 167 |
| 74 | 0.0004 | 2.32 | 132 |
| 75 | 0.0036 | 2.04 | 104 |
| 76 | 0.0064 | 1.71 | 71 |
| 77 | 0.0304 | 2.49 | 149 |
| 78 | 0.0646 | 1.92 | 92 |

TABLE 1-continued

| Example | Ki h-GABA-A α5β3γ2 (μM) | Fold increase h-GABA-A α5β3γ2 oocyte | Efficacy (GABA) % |
|---|---|---|---|
| 79 | 0.0161 | 2.11 | 111 |
| 80 | 0.0086 | 2.33 | 133 |
| 81 | 0.0242 | 2.23 | 123 |
| 82 | 0.0328 | 3.45 | 245 |
| 83 | 0.0172 | 1.5 | 50 |
| 84 | 0.085 | 1.89 | 89 |
| 85 | 0.0181 | 2.34 | 134 |
| 86 | 0.0119 | 1.87 | 87 |
| 87 | 0.039 | 2.05 | 105 |
| 88 | 0.0334 | 2.03 | 103 |
| 89 | 0.0014 | 2.89 | 189 |
| 90 | 0.0248 | 2.09 | 109 |
| 91 | 0.0217 | 2.57 | 157 |
| 92 | 0.0256 | 2.67 | 167 |
| 93 | 0.0016 | 2.25 | 125 |
| 94 | 0.0078 | 2.36 | 136 |
| 95 | 0.0308 | 2.15 | 115 |
| 96 | 0.013 | 2.32 | 132 |
| 97 | 0.0086 | 2.06 | 106 |
| 98 | 0.0073 | 2.32 | 132 |
| 99 | 0.0144 | 2.34 | 134 |
| 100 | 0.0122 | 2.05 | 105 |
| 101 | 0.0032 | 2.46 | 146 |
| 102 | 0.0131 | 1.86 | 86 |
| 103 | 0.0297 | 2.41 | 141 |
| 104 | 0.0229 | 2.34 | 134 |
| 105 | 0.006 | 1.72 | 72 |
| 106 | 0.0062 | 2.36 | 136 |
| 107 | 0.0038 | 1.7 | 70 |
| 108 | 0.0114 | 2.04 | 104 |
| 109 | 0.0022 | 2.07 | 107 |
| 110 | 0.0012 | 2.42 | 142 |
| 111 | 0.0346 | 2.47 | 147 |
| 112 | 0.038 | 2.01 | 101 |
| 113 | 0.0078 | 1.91 | 91 |
| 114 | 0.024 | 1.81 | 81 |
| 115 | 0.0104 | 1.87 | 87 |
| 116 | 0.0308 | 1.84 | 84 |
| 117 | 0.0041 | 3.26 | 226 |
| 118 | 0.0092 | 3.1 | 210 |
| 119 | 0.0026 | 2.38 | 138 |
| 120 | 0.0073 | 2.72 | 172 |
| 123 | 0.0186 | 2.52 | 152 |
| 124 | 0.012 | 2.48 | 148 |
| 126 | 0.0094 | 2.34 | 134 |
| 127 | 0.0073 | 2.53 | 153 |
| 128 | 0.0111 | 2.2 | 120 |
| 129 | 0.0045 | 2.98 | 198 |
| 130 | 0.0251 | 2.87 | 187 |
| 131 | 0.017 | 2.05 | 105 |
| 132 | 0.0195 | 2.19 | 119 |
| 133 | 0.0812 | 2.72 | 172 |
| 134 | 0.0166 | 2.11 | 111 |
| 135 | 0.0281 | 2.19 | 119 |
| 136 | 0.0052 | 1.96 | 96 |
| 137 | 0.0229 | 2.1 | 110 |
| 138 | 0.0092 | 2.05 | 105 |
| 139 | 0.0193 | 2.32 | 132 |
| 140 | 0.0085 | 1.62 | 62 |
| 141 | 0.016 | 2.07 | 107 |
| 142 | 0.0154 | 1.48 | 48 |
| 143 | 0.0033 | 1.68 | 68 |
| 144 | 0.0032 | 1.2 | 20 |
| 145 | 0.0262 | 2.19 | 119 |
| 147 | 0.012 | 2.7 | 170 |
| 148 | 0.0084 | 3.48 | 248 |
| 149 | 0.0202 | 1.89 | 89 |
| 150 | 0.0304 | 1.85 | 85 |
| 151 | 0.0272 | 2.19 | 119 |
| 152 | 0.0287 | 2.16 | 116 |
| 153 | 0.0242 | 2.66 | 166 |
| 154 | 0.0237 | 3.44 | 244 |
| 155 | 0.0216 | 2.33 | 133 |
| 156 | 0.0026 | 1.66 | 66 |
| 157 | 0.0227 | 1.86 | 86 |

TABLE 1-continued

| Example | Ki h-GABA-A α5β3γ2 (μM) | Fold increase h-GABA-A α5β3γ2 oocyte | Efficacy (GABA) % |
|---|---|---|---|
| 158 | 0.0096 | 1.96 | 96 |
| 160 | 0.0074 | 1.43 | 43 |
| 161 | 0.0078 | 1.56 | 56 |
| 162 | 0.0188 | 1.4 | 40 |
| 163 | 0.0114 | 2.65 | 165 |
| 166 | 0.0017 | 2.49 | 149 |
| 167 | 0.0022 | 2.95 | 195 |
| 168 | 0.0094 | 2.4 | 140 |
| 169 | 0.0024 | 1.97 | 97 |
| 170 | 0.0022 | 2.11 | 111 |
| 171 | 0.0042 | 1.8 | 80 |
| 172 | 0.034 | 2.13 | 113 |
| 173 | 0.0297 | 1.8 | 80 |
| 174 | 0.0217 | 2.01 | 101 |
| 175 | 0.0066 | 1.86 | 86 |
| 176 | 0.0297 | 2.03 | 103 |
| 177 | 0.0184 | 2.21 | 121 |
| 178 | 0.0027 | 2.58 | 158 |
| 179 | 0.0297 | 2.33 | 133 |
| 180 | 0.039 | 2.96 | 196 |
| 181 | 0.0157 | 2.34 | 134 |
| 182 | 0.0189 | 3.09 | 209 |
| 183 | 0.0287 | 2.37 | 137 |
| 184 | 0.0288 | 2.25 | 125 |
| 185 | 0.0042 | 2.26 | 126 |
| 186 | 0.0374 | 2.6 | 160 |
| 188 | 0.0086 | 3.1 | 210 |
| 189 | 0.0282 | 2.8 | 180 |
| 190 | 0.0252 | 2.46 | 146 |
| 191 | 0.0059 | 2.26 | 126 |
| 192 | 0.0064 | 3.21 | 221 |
| 193 | 0.0072 | 1.95 | 95 |
| 194 | 0.0108 | 2.52 | 152 |
| 195 | 0.0172 | 2.18 | 118 |
| 196 | 0.0037 | 1.98 | 98 |
| 197 | 0.002 | 2.31 | 131 |
| 198 | 0.0018 | 2.31 | 131 |
| 199 | 0.0194 | 2.17 | 117 |
| 200 | 0.0186 | 1.86 | 86 |
| 201 | 0.0143 | 1.93 | 93 |
| 202 | 0.0042 | 1.96 | 96 |
| 203 | 0.0178 | 2.21 | 121 |
| 204 | 0.0151 | 2.6 | 160 |
| 205 | 0.002 | 3.53 | 253 |
| 206 | 0.0137 | 2.44 | 144 |
| 207 | 0.0148 | 1.75 | 75 |
| 208 | 0.0612 | 2.1 | 110 |
| 209 | 0.0527 | 1.94 | 94 |
| 210 | 0.026 | 2.43 | 143 |
| 211 | 0.0409 | 4.24 | 324 |
| 212 | 0.0416 | 2.18 | 118 |
| 213 | 0.0328 | 2.08 | 108 |
| 214 | 0.0083 | 1.74 | 74 |
| 215 | 0.05 | 2.19 | 119 |
| 216 | 0.0158 | 2.03 | 103 |
| 217 | 0.0123 | 1.85 | 85 |
| 218 | 0.0198 | 1.84 | 84 |
| 219 | 0.0026 | 3.47 | 247 |
| 220 | 0.0253 | 2.18 | 118 |
| 221 | 0.0312 | 1.99 | 99 |
| 222 | 0.0312 | 1.82 | 82 |
| 223 | 0.0276 | 3.15 | 215 |
| 224 | 0.0128 | 2.24 | 124 |
| 226 | 0.013 | 1.95 | 95 |
| 227 | 0.0044 | 2.49 | 149 |
| 228 | 0.0038 | 1.41 | 41 |
| 229 | 0.01 | 1.81 | 81 |
| 230 | 0.0451 | 2.27 | 127 |
| 232 | 0.037 | 2.04 | 104 |
| 233 | 0.0336 | 1.82 | 82 |
| 234 | 0.0044 | 1.93 | 93 |
| 235 | 0.0028 | 1.77 | 77 |
| 236 | 0.0029 | 2.36 | 136 |
| 237 | 0.0058 | 2.47 | 147 |
| 238 | 0.0068 | 2.28 | 128 |
| 239 | 0.001 | 1.67 | 67 |
| 240 | 0.0057 | 1.94 | 94 |
| 241 | 0.0054 | 1.8 | 80 |
| 242 | 0.003 | 1.8 | 80 |
| 243 | 0.0046 | 2.73 | 173 |
| 244 | 0.0388 | 2.4 | 140 |
| 245 | 0.0187 | 2.06 | 106 |
| 246 | 0.0034 | 2.3 | 130 |
| 247 | 0.0028 | 1.94 | 94 |
| 248 | 0.0246 | 2.07 | 107 |
| 249 | 0.0022 | 1.6 | 60 |
| 250 | 0.0033 | 1.46 | 46 |
| 251 | 0.0166 | 1.83 | 83 |
| 252 | 0.0042 | 1.86 | 86 |
| 253 | 0.031 | 2.56 | 156 |
| 254 | 0.0276 | 2.47 | 147 |
| 255 | 0.0146 | 1.99 | 99 |
| 256 | 0.0454 | 2.26 | 126 |
| 257 | 0.0366 | 2.08 | 108 |
| 258 | 0.0343 | 2.26 | 126 |
| 259 | 0.0362 | 2.93 | 193 |
| 260 | 0.0037 | 2.23 | 123 |
| 261 | 0.0036 | 1.77 | 77 |
| 262 | 0.0355 | 3.16 | 216 |
| 263 | 0.0042 | 3.05 | 205 |
| 264 | 0.003 | 1.93 | 93 |
| 265 | 0.0258 | 2.55 | 155 |
| 266 | 0.0358 | 2.36 | 136 |
| 268 | 0.0166 | 2.84 | 184 |
| 269 | 0.0014 | 1.7 | 70 |
| 270 | 0.0278 | 2.44 | 144 |
| 271 | 0.0073 | 1.9 | 90 |
| 272 | 0.0264 | 2.35 | 135 |
| 273 | 0.03 | 2.26 | 126 |
| 274 | 0.0158 | 2.1 | 110 |
| 275 | 0.0046 | 1.89 | 89 |
| 276 | 0.0362 | 2.02 | 102 |
| 277 | 0.0034 | 2.31 | 131 |
| 278 | 0.008 | 2.08 | 108 |
| 279 | 0.0086 | 1.87 | 87 |
| 280 | 0.0075 | 2.66 | 166 |
| 281 | 0.0094 | 2.05 | 105 |
| 282 | 0.0015 | 2.66 | 166 |
| 285 | 0.0026 | 1.84 | 84 |
| 286 | 0.0033 | 2.12 | 112 |
| 287 | 0.0038 | 1.77 | 77 |
| 288 | 0.0032 | 1.63 | 63 |
| 289 | 0.0022 | 1.68 | 68 |
| 291 | 0.0028 | 2.24 | 124 |
| 294 | 0.0418 | 2.17 | 117 |
| 295 | 0.016 | 1.74 | 74 |
| 296 | 0.0277 | 1.84 | 84 |
| 297 | 0.0107 | 2.3 | 130 |
| 298 | 0.0254 | 2.16 | 116 |
| 302 | 0.002 | 2.49 | 149 |
| 303 | 0.0237 | 2.38 | 138 |
| 305 | 0.0025 | 2 | 100 |
| 306 | 0.0012 | 2.01 | 101 |
| 310 | 0.0142 | 2.05 | 105 |
| 311 | 0.0024 | 1.88 | 88 |
| 312 | 0.0065 | 2.27 | 127 |
| 313 | 0.0079 | 2.03 | 103 |
| 315 | 0.004 | 2.4 | 140 |
| 316 | 0.0043 | 2 | 100 |
| 317 | 0.0049 | 1.68 | 68 |
| 318 | 0.0056 | 2.11 | 111 |
| 319 | 0.001 | 1.91 | 91 |
| 320 | 0.0248 | 3.26 | 226 |
| 321 | 0.0063 | 2.29 | 129 |
| 322 | 0.0711 | 1.73 | 73 |
| 323 | 0.0431 | 1.76 | 76 |
| 324 | 0.02 | 2.66 | 166 |
| 325 | 0.0032 | 2.78 | 178 |
| 326 | 0.0019 | 2.64 | 164 |
| 327 | 0.0036 | 2.22 | 122 |

TABLE 1-continued

| Example | Ki h-GABA-A α5β3γ2 (μM) | Fold increase h-GABA-A α5β3γ2 oocyte | Efficacy (GABA) % |
|---|---|---|---|
| 328 | 0.0126 | 1.7 | 70 |
| 329 | 0.0587 | 2.64 | 164 |
| 330 | 0.0488 | 2.59 | 159 |
| 331 | 0.0176 | 2.59 | 159 |
| 332 | 0.0026 | 1.65 | 65 |
| 333 | 0.0414 | 2.9 | 190 |
| 334 | 0.0059 | 2.05 | 105 |
| 335 | 0.0092 | 1.9 | 90 |

WO2009/071476 discloses reference compound RO-309 as example 309.

WO2009/071477 discloses reference compounds RO-035 as example 35, RO-036 as example 36, RO-039 as example 39 and RO-096 as example 96.

The reference compounds were also tested for their affinity towards the GABA$_A$ receptor α5β3γ2 subtypes as well as for their efficacy in GABA$_A$ α5β3γ2 overexpressing oocytes. The results are shown in Table 2.

TABLE 2

| Example | Ki h-GABA-A α5β3γ2 (μM) | Fold increase h-GABA-A α5β3γ2 oocyte | Efficacy (GABA) % |
|---|---|---|---|
| RO-035 | 0.0105 | 0.65 | −35 |
| RO-036 | 0.00945 | 0.72 | −28 |
| RO-039 | 0.00515 | 0.83 | −17 |
| RO-096 | 0.026 | 0.84 | −16 |
| RO-309 | 0.0006 | 0.83 | −17 |

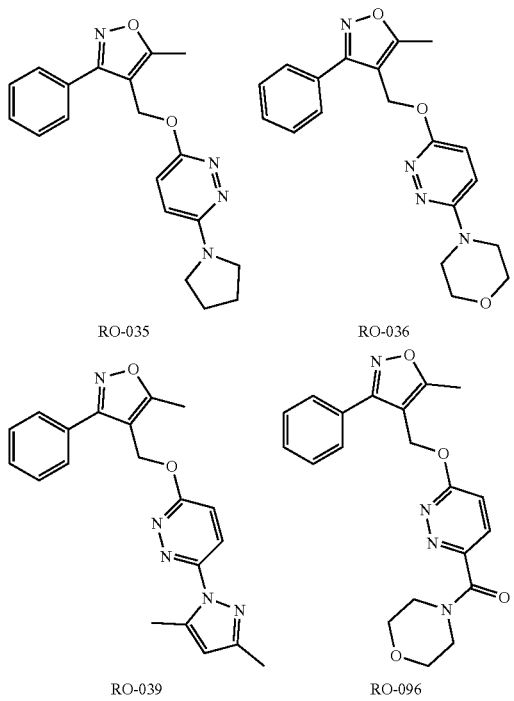

RO-035, RO-036, RO-039, RO-096, RO-309

The compounds of formula (I) or (II) and their pharmaceutically acceptable salts can be used as medicaments (e.g. in the form of pharmaceutical preparations). The pharmaceutical preparations can be administered internally, such as orally (e.g. in the form of tablets, coated tablets, dragees, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compounds of formula (I) or (II) and their pharmaceutically acceptable salts can be processed with pharmaceutically inert, inorganic or organic adjuvants for the production of tablets, coated tablets, dragees, hard gelatin capsules, injection solutions or topical formulations Lactose, corn starch or derivatives thereof, talc, stearic acid or its salts etc. can be used, for example, as such adjuvants for tablets, dragees and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg in can be administered either by single dose per day or per week, or by multiple doses (2 to 4) per day, or by multiple doses per week It will, however, be clear that the upper or lower limit given herein can be exceeded when this is shown to be indicated.

Preparation of Pharmaceutical Compositions Comprising Compounds of the Invention Tablets of the following composition are manufactured in the usual manner:

| Ingredient | mg/tablet | | | |
|---|---|---|---|---|
|  | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules of the following composition are manufactured:

| Ingredient | mg/capsule | | | |
|---|---|---|---|---|
|  | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

A compound of formula I lactose and corn starch are firstly mixed in a mixer and then in a comminuting machine. The mixture is returned to the mixer; the talc is added thereto and mixed thoapproximatively. The mixture is filled by machine into suitable capsules, e.g. hard gelatin capsules.

Injection solutions of the following composition are manufactured:

| Ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

Building Block A 5-chloro-2-[[5-methyl-3-(6-methyl-3-pyridyl)isoxazol-4-yl]methyl]pyridazin-3-one

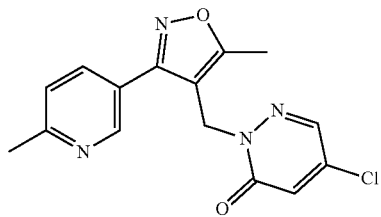 [SMILES: Cc1ccc(-c2noc(C)c2Cn2ncc(Cl)cc2=O)cn1]

a) (3E)-6-methylpyridine-3-carbaldehyde oxime

To a solution of 6-methylnicotinaldehyde (9.86 g, 77.3 mmol) in methanol (35 mL) was added under nitrogen hydroxylamine (50 wt. % in water, 5.93 mL, 101 mmol). The resulting suspension was stirred for 3 h at 40° C. and for 20 h at room temperature. Concentration by rotary evaporation under reduced pressure afforded the title compound (10.89 g, 98%) as an off-white solid. MS (ESI): 137.0 ([M+H]+).

b) ethyl 5-methyl-3-(6-methylpyridin-3-yl)isoxazole-4-carboxylate

To a solution of (E)-6-methylnicotinaldehyde oxime (10.89 g, 80.0 mmol) in DMF (95 mL) at 6° C. was added N-chlorosuccinimide (11.7 g, 88.0 mmol). Upon addition, the color of the reaction mixture changed from yellow to orange and the reaction was allowed to warm to room temperature. After 1 h, the mixture was heated to 50° C. for 2 h. The resulting brown suspension was cooled to 6° C. then (E)-ethyl 3-(pyrrolidin-1-yl)but-2-enoate (17.6 g, 96.0 mmol) was added and the reaction mixture was stirred at 50° C. overnight. After cooling to room temperature, water (95 mL) was added dropwise and the resulting brown suspension was filtered through a sintered funnel. The residue was washed with water then dried at high vacuum to afford the title compound (11.80 g, 60%) as a brown solid. MS (ESI): 247.1 ([M+H]+).

c) (5-methyl-3-(6-methylpyridin-3-yl)isoxazol-4-yl)methanol

To a solution of ethyl 5-methyl-3-(6-methylpyridin-3-yl)isoxazole-4-carboxylate (11.8 g, 47.9 mmol) in tetrahydrofurane (160 mL) at 2° C. was added under nitrogen over a period of 20 min lithium aluminium hydride (2.55 g, 67.1 mmol). After stirring at 4° C. for 1.5 h, water (2.61 mL) was carefully added and the mixture was stirred for further 50 min before being quenched by addition of aqueous NaOH (15 wt. %, 2.61 mL). The reaction mixture was stirred for 30 min at room temperature before addition of water (7.8 mL). After stirring for 1 h, the resulting suspension was filtered through a sintered funnel and the residue was washed with tetrahydrofurane (20 mL) to afford the title compound (9.08 g, 93%) as an orange solid. MS (ESI): 205.1 ([M+H]+).

d) 4-(chloromethyl)-5-methyl-3-(6-methyl-3-pyridyl)isoxazole

To a stirred suspension of (5-methyl-3-(6-methylpyridin-3-yl)isoxazol-4-yl)methanol (360 mg, 1.76 mmol) in dichloromethane (3.2 mL) was added under an atmosphere of nitrogen dropwise during 15 min at 0° C. thionyl chloride (257 µL, 3.53 mmol). Then the solution was stirred at 0° C. for 30 min. The reaction mixture was basified by the dropwise addition of a 1M solution of sodium hydrogen carbonate (20 mL). Then the organic layer was washed with water (30 mL) and the aqueous layers were extracted with dichloromethane (3×10 mL). The combined organic layers were dried over magnesium sulfate and concentrated in vacuo to afford the title compound (391 mg, 100%) as a white solid. MS (ESI): 223.1 ([M+H]+).

e) 5-chloro-2-[[5-methyl-3-(6-methyl-3-pyridyl)isoxazol-4-yl]methyl]pyridazin-3-one To a mixture of 4-(chloromethyl)-5-methyl-3-(6-methyl-3-pyridyl)isoxazole (870 mg, 3.91 mmol), 5-chloropyridazin-3(2H)-one (663 mg, 5.08 mmol) and potassium carbonate (1.35 g, 9.77 mmol) was added acetone (15 mL). The reaction mixture was stirred at room temperature for 17 h. Purification by flash chromatography (silica, gradient: 0% to 100% ethyl acetate in heptane) afforded the title compound (1.17 g, 94%) as an off-white solid. MS (ESI): 317.1 ([M+H]+).

Building Block B 5-chloro-2-[[5-(fluoromethyl)-3-(6-methyl-3-pyridyl)isoxazol-4-yl]methyl]pyridazin-3-one

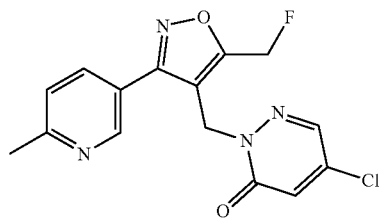 [SMILES: Cc1ccc(-c2noc(CF)c2Cn2ncc(Cl)cc2=O)cn1]

a) ethyl 4-fluoro-3-oxo-butanoate

To a stirred solution of ethyl acetate (9.59 g, 10.7 mL, 109 mmol) in anhydrous diethyl ether (100 mL) under argon at −78° C. (CO$_2$-acetone bath) was added over 30 min LDA (2.0 M solution in cyclohexane/ethylbenzene/THF, 59 mL, 118 mmol). The reaction mixture was stirred for 2 h at −78° C. then ethyl 2-fluoroacetate (10.5 g, 9.62 mL, 99 mmol) was added over 15 min. The CO2-Acetone bath was removed and the reaction was allowed to warm to room temperature and stirred overnight. The reaction was slowly poured into cold aqueous HCl (10 wt. %, 100 mL) and extracted with diethyl ether (3×50 mL). The combined organic extracts were washed with brine (30 mL), dried over sodium sulfate, filtered and evaporated at 35° C. under reduced pressure (650 mbar-200 mbar). The resulting colourless liquid was purified by distillation at reduced pressure using a 30 cm Vigreux column. Fractions collected at 13 mbar at 71° C. (vapor temperature) afforded the title compound (12.67 g, 86%) as a colourless liquid. MS (ESI): 149.1 ([M+H]+).

b) ethyl 5-(fluoromethyl)-3-(6-methylpyridin-3-yl)isoxazole-4-carboxylate

To a stirred solution of (E)-6-methylnicotinaldehyde oxime (1.00 g, 7.34 mmol) in anhydrous tetrahydrofurane (6.7 mL) at 6° C. was added N-chlorosuccinimide (1.10 g, 8.08 mmol). After 30 min, the mixture was heated to 50° C. for 1 h then all the solvent was removed under reduced pressure. The resulting residue (chloro-oxime) was dissolved in ethanol (6.7 mL) and stirred at room temperature for 30 min. In a separate flask, triethylamine (2.05 mL, 14.7 mmol) was added to a solution of ethyl 4-fluoro-3-oxobutanoate (1.65 g, 7.34 mmol) in tetrahydrofurane (6.6 mL) and the resulting suspension was stirred at room temperature. After 30 min, the suspension was cooled to 0° C. and the previously prepared suspension of chloro-oxime in ethanol was slowly added via cannula. The resulting yellow suspension was stirred for 3 h at room temperature. The reaction was diluted with ethyl acetate (100 mL) and the organic phase washed with water and brine, dried over sodium sulfate and concentrated in vacuo. Purification by flash chromatography (silica, 0% to 50% ethyl acetate in heptane) afforded the title compound (1.1 g, 57%) as a white solid. MS (ESI): 265.2 ([M+H]+).

c) (5-(fluoromethyl)-3-(6-methylpyridin-3-yl)isoxazol-4-yl)methanol

To a stirred suspension of ethyl 5-(fluoromethyl)-3-(6-methylpyridin-3-yl)isoxazole-4-carboxylate (404 mg, 1.53 mmol) in anhydrous toluene (4 mL) at −78° C. was added dropwise DIBAL-H (1.0 M in toluene, 1.84 mL, 1.84 mmol). The reaction was stirred at −78° C. for 30 min before being quenched by the addition of ethyl acetate (0.5 mL). After 15 min, the reaction was allowed to warm to 0° C. and saturated aqueous sodium bicarbonate (5 mL) was added. The mixture was stirred vigorously for 20 min then diluted with ethyl acetate (30 mL) and the organic phase washed with brine, dried over sodium sulfate and concentrated in vacuo. Purification by flash chromatography (silica, 0% to 100% ethyl acetate in heptane) afforded the title compound (193 mg, 57%) as a white solid. MS (ESI): 223.2 ([M+H]+).

d) 4-(chloromethyl)-5-(fluoromethyl)-3-(6-methyl-3-pyridyl)isoxazole

In analogy to experiment of building block A d, (5-(fluoromethyl)-3-(6-methylpyridin-3-yl)isoxazol-4-yl)methanol instead of (5-methyl-3-(6-methylpyridin-3-yl)

isoxazol-4-yl)methanol was converted into the title compound (0.207 g, 99%) which was obtained as a light yellow oil. MS (ESI): 241.0 ([M+H]⁺).

e) 5-chloro-2-[[5-(fluoromethyl)-3-(6-methyl-3-pyridyl)isoxazol-4-yl]methyl]pyridazin-3-one To a mixture of 4-(chloromethyl)-5-(fluoromethyl)-3-(6-methyl-3-pyridyl)isoxazole (218 mg, 0.906 mmol), 5-chloropyridazin-3(2H)-one (142 mg, 1.09 mmol) and potassium carbonate (0.376 g, 2.72 mmol) was added acetone (2.5 mL) and DMF (0.25 mL). The reaction mixture was heated to 50° C. for 1 h. The resulting suspension was filtered while still hot on a sintered funnel and rinsed with acetone (10 mL) then ethyl acetate (10 mL). The filtrate was concentrated in vacuo. Purification by flash chromatography (silica, 0% to 80% ethyl acetate in heptane) afforded the title compound (165 mg, 54%) as a yellow cristalline solid. MS (ESI): 335.1 ([M+H]+).

Building Block C 5-chloro-2-[[5-methyl-3-[6-(trifluoromethyl)-3-pyridyl]isoxazol-4-yl]methyl]pyridazin-3-one

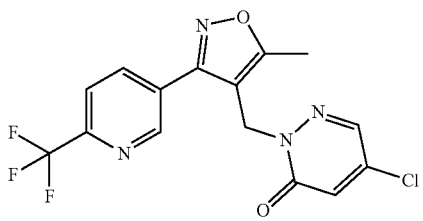 [SMILES: Cc1onc(-c2ccc(C(F)(F)F)nc2)c1Cn1ncc(Cl)cc1=O]

a) (3E)-6-(trifluoromethyl)pyridine-3-carbaldehyde oxime

In analogy to experiment of building block A a, 6-(trifluoromethyl)pyridine-3-carboxaldehyde instead of 6-methylnicotinaldehyde was converted into the title compound (10.94 g, 96%) which was obtained as a light yellow solid. MS (ESI): 191.1 ([M+H]⁺).

b) ethyl 5-methyl-3-(6-(trifluoromethyl)-3-pyridyl)isoxazole-4-carboxylate

In analogy to experiment of building block A b, (E)-ethyl 3-(pyrrolidin-1-yl)but-2-enoate, using (3E)-6-(trifluoromethyl)pyridine-3-carbaldehyde oxime instead of (E)-6-methylnicotinaldehyde oxime was converted into the title compound (7.95 g, 96%) which was obtained as a yellow solid. MS (ESI): 301.1 ([M+H]⁺).

c) 5-methyl-3-(6-(trifluoromethyl)-3-pyridyl)isoxazole-4-carboxylic acid

To a stirred solution of ethyl 5-methyl-3-(6-(trifluoromethyl)pyridin-3-yl)isoxazole-4-carboxylate (5.91 g, 19.7 mmol) in a mixture of tetrahydrofurane (21 mL), methanol (21 mL) and water (21 mL) at 0° C. was added lithium hydroxide monohydrate (2.03 g, 48.4 mmol). The ice bath was removed and the reaction mixture was stirred at room temperature for 2.5 h. The reaction mixture was re-cooled to 0° C. then acidified with aqueous citric acid (5 wt. %) to pH~5 (a precipitate was formed). The organic solvents were removed by rotary evaporation under reduced pressure. The resulting aqueous suspension was cooled to 0° C. then filtered on a sintered funnel. The collected solid was rinsed with ice cold water (50 mL) and dried under high vacuum to afford the title compound (4.88 g, 91% yield) as alight yellow solid. MS (ESI): 273.1 ([M+H]⁺).

d) (5-methyl-3-(6-(trifluoromethyl)-3-pyridyl)isoxazol-4-yl)methanol

In analogy to experiment of building block E c, 5-methyl-3-(6-(trifluoromethyl)-3-pyridyl)isoxazole-4-carboxylic acid instead of 3-(6-methyl-3-pyridyl)isoxazole-4-carboxylic acid was converted into the title compound (3.87 g, 84%) which was obtained as a light yellow solid. MS (ESI): 259.1 ([M+H]⁺).

e) 4-(chloromethyl)-5-methyl-3-[6-(trifluoromethyl)-3-pyridyl]isoxazole

In analogy to experiment of building block A d, (5-methyl-3-(6-(trifluoromethyl)-3-pyridyl)isoxazol-4-yl)methanol instead of (5-methyl-3-(6-methylpyridin-3-yl)isoxazol-4-yl)methanol was converted into the title compound (0.206 g, 96%) which was obtained as a brown solid. MS (ESI): 277.0 ([M+H]⁺).

f) 5-chloro-2-[[5-methyl-3-[6-(trifluoromethyl)-3-pyridyl]isoxazol-4-yl]methyl]pyridazin-3-one In analogy to experiment of building block B e, 4-(chloromethyl)-5-methyl-3-[6-(trifluoromethyl)-3-pyridyl]isoxazole instead of 4-(chloromethyl)-5-(fluoromethyl)-3-(6-methyl-3-pyridyl)isoxazole was converted into the title compound (0.142 g, 71%) which was obtained as an off-white solid. MS (ESI): 371.0 ([M+H]⁺).

Building Block D 5-chloro-2-[[3-(6-chloro-3-pyridyl)-5-methyl-isoxazol-4-yl]methyl]pyridazin-3-one

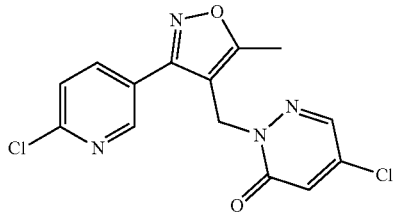 [SMILES: Cc1onc(-c2ccc(Cl)nc2)c1Cn1ncc(Cl)cc1=O]

a) (E)-6-chloronicotinaldehyde oxime

To a solution of 6-chloronicotinaldehyde (100 mg, 0.706 mmol) in acetonitrile (1 mL) were added hydroxylamine hydrochloride (73.6 mg, 1.06 mmol) and potassium phosphate tribasic (75 mg, 0.353 mmol). The mixture was stirred at room temperature for 30 min before addition of water (0.2 mL). After 1 h, the resulting suspension was diluted with water (5 mL) and the solid was collected through filtration on a sintered funnel then dried in vacuo to afford the title compound (57 mg, 51%) as a white solid. MS (ESI): 157.0 ([M+H]⁺).

b) ethyl 3-(6-chloropyridin-3-yl)-5-methylisoxazole-4-carboxylate

In analogy to experiment of building block A b, (E)-ethyl 3-(pyrrolidin-1-yl)but-2-enoate, using (E)-6-chloronicotinaldehyde oxime instead of (E)-6-methylnicotinaldehyde oxime, was converted into the title compound (92 mg, 78%) which was obtained as a white solid. MS (ESI): 267.1 ([M+H]$^+$).

c) (3-(6-chloropyridin-3-yl)-5-methylisoxazol-4-yl)methanol

To a stirred solution of ethyl 3-(6-chloropyridin-3-yl)-5-methylisoxazole-4-carboxylate (77 mg, 0.289 mmol) in anhydrous tetrahydrofurane (2 mL) at 0° C. was added dropwise DIBAL-H (1.0 M in hexane, 0.924 mL, 0.924 mmol). The resulting light yellow solution was allowed to warm to room temperature and stirred for 4.5 h before being re-cooled to 0° C. (ice bath) and quenched by addition of aqueous Na/K tartrate (10 wt. %, 7 mL). The mixture was vigorously stirred at room temperature (ice bath removed) for 30 min then diluted with ethyl acetate (10 mL). Upon addition of aqueous ammonium chloride (20 wt. %, 3 mL) and aqueous HCl (1.0 M, 1 mL) the aqueous layer was separated and extracted with ethyl acetate (2×15 mL). The combined organic extracts were dried over sodium sulfate, filtered and concentrated in vacuo. Purification by flash chromatography (silica, 0% to 100% ethyl acetate in heptane) afforded the title compound (48 mg, 74%) as a white solid. MS (ESI): 225.0 ([M+H]$^+$).

d) 4-(chloromethyl)-3-(6-chloro-3-pyridyl)-5-methyl-isoxazole

In analogy to experiment of building block A d, (3-(6-chloropyridin-3-yl)-5-methylisoxazol-4-yl)methanol instead of (5-methyl-3-(6-methylpyridin-3-yl)isoxazol-4-yl)methanol was converted into the title compound (44 mg, 88%) which was obtained as a white solid. MS (ESI): 243.0 ([M+H]$^+$.

e) 5-chloro-2-[[3-(6-chloro-3-pyridyl)-5-methyl-isoxazol-4-yl]methyl]pyridazin-3-one 4-(chloromethyl)-3-(6-chloropyridin-3-yl)-5-methyl-isoxazole (100 mg, 0.411 mmol), 5-chloropyridazin-3(2H)-one (78.5 mg, 0.601 mmol) and potassium carbonate (171 mg, 1.23 mmol) were suspended in N,N-dimethylacetamide (2 ml). The reaction mixture was stirred at 50° C. for 35 min, cooled to room temperature and diluted with water. The aqueous layer was extracted with ethyl acetate (3×). The combined organic layers were dried over sodium sulfate, filtered and concentrated in vacuo. Purification by flash chromatography (silica, 0% to 50% ethyl acetate in heptane) afforded the title compound (108 mg, 78%) as a white solid MS: 337.0; 339.1 [M+H]$^+$; 359.0 [M+Na]$^+$.

Building Block E

5-chloro-2-[[3-(6-methyl-3-pyridyl)isoxazol-4-yl]methyl]pyridazin-3-one

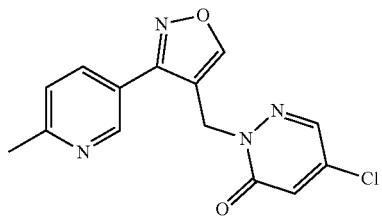 [SMILES: Cc1ccc(-c2nocc2Cn2ncc(Cl)cc2=O)cn1]

a) ethyl 3-(6-methyl-3-pyridyl)isoxazole-4-carboxylate

In analogy to experiment of building block A b, (E)-6-methylnicotinaldehyde oxime, using ethyl (E)-3-(dimethylamino)prop-2-enoate instead of (E)-ethyl 3-(pyrrolidin-1-yl)but-2-enoate, was converted into the title compound (2.45 g, 57%) which was obtained as a light brown oil. MS (ESI): 233.1 ([M+H]$^+$).

b) 3-(6-methyl-3-pyridyl)isoxazole-4-carboxylic acid

In analogy to experiment of building block C c, ethyl 3-(6-methyl-3-pyridyl)isoxazole-4-carboxylate instead of ethyl 5-methyl-3-(6-(trifluoromethyl)pyridin-3-yl)isoxazole-4-carboxylate was converted into the title compound (1.48 g, 70%) which was obtained as an off white solid. MS (ESI): 205.0 ([M+H]$^+$).

c) (3-(6-methyl-3-pyridyl)isoxazol-4-yl)methanol

To a stirred suspension of 3-(6-methyl-3-pyridyl)isoxazole-4-carboxylic acid (1.48 g, 7.25 mmol) in anhydrous tetrahydrofurane (24 mL) was added triethylamine (1.1 mL, 7.9 mmol). The resulting solution was cooled to −15° C. (NaCl/ice bath) before a solution of ethyl chloroformate (0.73 mL, 7.6 mmol) in tetrahydrofurane (4 mL) was added dropwise. After 2 h, the resulting white precipitate was filtered through a sintered funnel and the collected solid rinsed with a minimal amount of tetrahydrofurane. The filtrate was re-cooled to −15° C. (NaCl/ice bath) and a solution of sodium borohydride (686 mg, 18.1 mmol) in water (16 mL) was added dropwise. Upon addition, the reaction mixture was allowed to warm to room temperature and stirred for 3 h. A further amount of sodium borohydride (137 mg, 3.62 mmol) was added and the mixture was stirred at room temperature for 1 h. The reaction was quenched by the addition of aqueous NaOH (2.0 M, 30 mL) then extracted with ethyl acetate (2×160 mL). The combined organic extracts were dried over sodium sulfate and concentrated in vacuo. Purification by flash chromatography (silica, 0% to 100% ethyl acetate in heptane) afforded the title compound (606 mg, 44%) as an off-white solid. MS (ESI): 191.1 ([M+H]$^+$).

d) 4-(chloromethyl)-3-(6-methyl-3-pyridyl)isoxazole

In analogy to experiment of building block A d, (3-(6-methyl-3-pyridyl)isoxazol-4-yl)methanol instead of (5-methyl-3-(6-methylpyridin-3-yl)isoxazol-4-yl)methanol was converted into the title compound (329 mg, 95%) which was obtained as a brown oil. MS (ESI): 209.1 ([M+H]⁺.

e) 5-chloro-2-[[3-(6-methyl-3-pyridyl)isoxazol-4-yl]methyl]pyridazin-3-one

In analogy to experiment of building block B e, 4-(chloromethyl)-3-(6-methyl-3-pyridyl)isoxazole instead of 4-(chloromethyl)-5-(fluoromethyl)-3-(6-methyl-3-pyridyl) isoxazole was converted into the title compound (0.320 g, 66%) which was obtained as a yellow oil. MS (ESI): 303.1 ([M+H]⁺).

Building Block F 5-chloro-2-[[5-methyl-3-(6-methylpyridazin-3-yl)isoxazol-4-yl]methyl]pyridazin-3-one

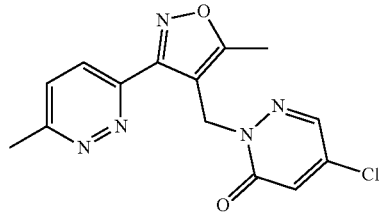 [SMILES: Cc1ccc(-c2noc(C)c2Cn2ncc(Cl)cc2=O)nn1]

a) (E)-6-methylpyridazine-3-carbaldehyde oxime

To a stirred solution of 6-methylpyridazine-3-carbaldehyde (880 mg, 7.21 mmol) in ethanol (1.25 mL) were added hydroxylamine hydrochloride (551 mg, 7.93 mmol) followed by aqueous NaOH (2.0 M, 9.2 mL, 18.4 mmol). The reaction mixture was stirred at room temperature for 3 h then treated with acetic acid to pH~5. The resulting precipitate was collected by filtration and dried at high vacuum to afford the title compound (943 mg, 95%) as an off-white solid. MS (ESI): 138.1 ([M+H]⁺).

b) ethyl 5-methyl-3-(6-methylpyridazin-3-yl)isoxazole-4-carboxylate

In analogy to experiment of building block A b, (E)-6-methylpyridazine-3-carbaldehyde oxime instead of (E)-6-methylnicotinaldehyde oxime was converted into the title compound (1.15 g, 67%) which was obtained as a brown oil. MS (ESI): 248.1 ([M+H]⁺).

c) (5-methyl-3-(6-methylpyridazin-3-yl)isoxazol-4-yl)methanol

To a stirred suspension of calcium chloride (1.8 g, 16.2 mmol) in a mixture of anhydrous tetrahydrofurane (50 mL) and ethanol (33 mL) at 0° C. were added ethyl 5-methyl-3-(6-methylpyridazin-3-yl)isoxazole-4-carboxylate (1.0 g, 4.04 mmol) followed by sodium borohydride (1.22 g, 32.4 mmol, portion-wise addition). The mixture was stirred at 0° C. for 30 min then allowed to warm to room temperature and stirred for further 1 h. The reaction mixture was re-cooled to 0° C. and quenched by addition of saturated aqueous ammonium chloride. The organic solvents were removed by rotary evaporation under reduced pressure and the resulting aqueous layer was extracted with dichloromethane (2×50 mL). The combined organic extracts were washed with brine, dried over magnesium sulfate and concentrated in vacuo. Purification by flash chromatography (silica, 20% to 100% ethyl acetate in heptane) afforded the title compound (407 mg, 49%) as a yellow solid. MS (ESI): 206.1 ([M+H]⁺).

d) 4-(chloromethyl)-5-methyl-3-(6-methylpyridazin-3-yl)isoxazole

In analogy to experiment of building block A d, (5-methyl-3-(6-methylpyridazin-3-yl)isoxazol-4-yl)methanol instead of (5-methyl-3-(6-methylpyridin-3-yl)isoxazol-4-yl)methanol was converted into the title compound (320 mg, 98%) which was obtained as a light brown solid. MS (ESI): 224.1 ([M+H]⁺.

e) 5-chloro-2-[[5-methyl-3-(6-methylpyridazin-3-yl)isoxazol-4-yl]methyl]pyridazin-3-one In analogy to experiment of building block D e, 4-(chloromethyl)-5-methyl-3-(6-methylpyridazin-3-yl)isoxazole instead of 4-(chloromethyl)-3-(6-chloropyridin-3-yl)-5-methylisoxazole was converted into the title compound (0.455 g, 67%) which was obtained as a light brown solid. MS (ESI): 318.2 ([M+H]⁺).

Building Block G 5-chloro-2-[[5-(difluoromethyl)-3-(6-methyl-3-pyridyl)isoxazol-4-yl]methyl]pyridazin-3-one

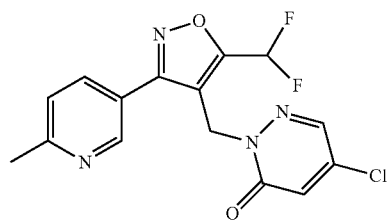 [SMILES: Cc1ccc(-c2noc(C(F)F)c2Cn2ncc(Cl)cc2=O)cn1]

a) (Z)-4,4-difluoro-3-pyrrolidin-1-yl-but-2-enoate

To a stirred solution of ethyl 4,4-difluoro-3-oxobutanoate (1.6 mL, 15.5 mmol) in cyclohexane (11 mL) was added pyrrolidine (1.4 mL, 16.9 mmol). The reaction was heated to 110° C. overnight using a Dean-Stark trap before being cooled to room temperature. The reaction mixture was filtered directly through a pad of sodium sulfate and the filtrate concentrated in vacuo to afford the title compound (2.49 g, 62%) as a brown oil. MS (ESI): 220.2 ([M+H]⁺).

b) ethyl 5-(difluoromethyl)-3-(6-methyl-3-pyridyl)isoxazole-4-carboxylate

In analogy to experiment of building block A b, (3E)-6-methylpyridine-3-carbaldehyde oxime, using ethyl (Z)-4,4-difluoro-3-pyrrolidin-1-yl-but-2-enoate instead of (E)-ethyl 3-(pyrrolidin-1-yl)but-2-enoate was converted into the title compound (362 mg, 58%) which was obtained as an orange oil. MS (ESI): 283.2 ([M+H]⁺).

c) (5-(difluoromethyl)-3-(6-methyl-3-pyridyl)isoxazol-4-yl)methanol

To a stirred solution of ethyl 5-(difluoromethyl)-3-(6-methylpyridin-3-yl)isoxazole-4-carboxylate (0.490 g, 1.56 mmol) in anhydrous toluene (16 mL) at −78° C. was added dropwise DIBAL-H (1.0 M in toluene, 3.2 mL, 3.2 mmol). The reaction was stirred at −78° C. for 3.5 h before the addition of a further amount of DIBAL-H (1.0 M in toluene, 0.78 mL, 0.78 mmol). After 1.5 h, the reaction mixture was carefully quenched by the addition of aqueous Na/K tartrate (10 wt. %, 10 mL). The biphasic mixture was allowed to warm to room temperature and stirred vigorously for 1 h before being extracted with ethyl acetate (2×40 mL). The combined organic extracts were washed with water (5 mL) and brine (5 mL), dried over sodium sulfate and concentrated in vacuo. Purification by flash chromatography (silica, 0% to 70% ethyl acetate in heptane) afforded the title compound (165 mg, 44%) as a light yellow solid. MS (ESI): 241.1 ([M+H]$^+$).

d) 4-(chloromethyl)-5-(difluoromethyl)-3-(6-methyl-3-pyridyl)isoxazole

In analogy to experiment of building block A d, (5-(difluoromethyl)-3-(6-methyl-3-pyridyl)isoxazol-4-yl)methanol instead of (5-methyl-3-(6-methylpyridin-3-yl)isoxazol-4-yl)methanol was converted into the title compound (300 mg, 97%) which was obtained as a light grey oil. MS (ESI): 224.1 ([M+H]$^+$).

e) 5-chloro-2-[[5-(difluoromethyl)-3-(6-methyl-3-pyridyl)isoxazol-4-yl]methyl]pyridazin-3-one In analogy to experiment of building block B e, 4-(chloromethyl)-5-(difluoromethyl)-3-(6-methyl-3-pyridyl)isoxazole instead of 4-(chloromethyl)-5-(fluoromethyl)-3-(6-methyl-3-pyridyl)isoxazole was converted into the title compound (0.237 g, 58%) which was obtained as a yellow oil. MS (ESI): 353.1 ([M+H]$^+$).

Building Block H 5-chloro-2-[[3-(6-cyclopropyl-3-pyridyl)-5-methyl-isoxazol-4-yl]methyl]pyridazin-3-one

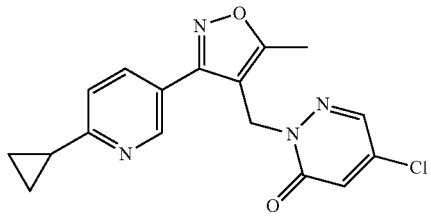 [SMILES: Cc1onc(-c2ccc(C3CC3)nc2)c1Cn1ncc(Cl)cc1=O]

a) (Z)—N-((6-bromopyridin-3-yl)methylidene)hydroxylamine

To a stirred solution of hydroxylamine hydrochloride (11.0 g, 161 mmol) in ethanol (300 mL) was added triethylamine (33.0 mL, 242 mmol) and the reaction was stirred at room temperature for 30 min before addition of 6-bromopyridine-3-carbaldehyde (15.0 g, 80.6 mmol). The reaction mixture was heated at reflux for 1 h then all the volatiles were removed by rotary evaporation under reduced pressure. The resulting residue was diluted with water and extracted with ethyl acetate (2×200 mL). The combined organic extracts were washed with brine, dried over sodium sulfate and concentrated in vacuo. Purification by flash chromatography (silica, 10% ethyl acetate in hexane) afforded the title compound (12.5 g, 77%) as a white solid. MS (ESI): 201.3 ([M+H]$^+$).

b) ethyl 3-(6-bromo-3-pyridyl)-5-methyl-isoxazole-4-carboxylate

In analogy to experiment of building block A b, (Z)—N-((6-bromopyridin-3-yl)methylidene)hydroxylamine instead of (E)-6-methylnicotinaldehyde oxime was converted into the title compound (16 g, 86%) which was obtained as a brown oil. MS (ESI): 311.0 ([M+H]$^+$).

c) ethyl 3-(6-cyclopropyl-3-pyridyl)-5-methyl-isoxazole-4-carboxylate

A round-bottomed flask was charged with ethyl 3-(6-bromo-3-pyridyl)-5-methyl-isoxazole-4-carboxylate (8.00 g, 25.7 mmol), cyclopropyl boronic acid (8.80 g, 102 mmol), $K_3PO_4$ (19.0 g, 90 mmol), tricyclohexylphosphine (2.89 g, 10.2 mmol) and Pd(OAc)$_2$ (1.16 g, 5.14 mmol). The flask was degassed by alternative evacuation and back filling with argon. A previously degassed 10:1 solution of toluene/water (264 mL) was added and the resulting mixture was flushed with argon for 15 min. The reaction mixture was stirred at 100° C. for 3 h before being cooled to room temperature and filtered directly through a plug of celite. The filter cake was rinsed with ethyl acetate and the filtrate concentrated in vacuo. Purification by flash chromatography (silica, 10% ethyl acetate in hexanes) afforded the title compound (5.5 g, 78%) as a yellow solid. MS (ESI): 272.7 ([M+H]$^+$).

d) (3-(6-cyclopropyl-3-pyridyl)-5-methyl-isoxazol-4-yl)methanol

To a stirred solution of ethyl 3-(6-cyclopropyl-3-pyridyl)-5-methyl-isoxazole-4-carboxylate (2.7 g, 11.4 mmol) in anhydrous tetrahydrofurane (20 mL) at −10° C. was added dropwise lithium alumimium hydride (1.0 M in tetrahydrofurane, 13.7 mL, 13.7 mmol). After 30 min, the reaction mixture was allowed to warm to 0° C. before being quenched by the addition of sodium sulfate decahydrate. The reaction was filtered directly through a plug of celite. The filter cake was rinsed with ethyl acetate and the filtrate concentrated in vacuo to afford the title compound (1.8 g, 81%) as an off white solid. MS (ESI): 236.1 ([M+H]$^+$).

e) 4-(chloromethyl)-3-(6-cyclopropyl-3-pyridyl)-5-methyl-isoxazole

In analogy to experiment of building block A d, (5-(difluoromethyl)-3-(6-methyl-3-pyridyl)isoxazol-4-yl)methanol instead of (5-methyl-3-(6-methylpyridin-3-yl)isoxazol-4-yl)methanol was converted into the title compound (157 mg, 93%) which was obtained as a white solid. MS (ESI): 249.1 ([M+H]$^+$.

f) 5-chloro-2-[[3-(6-cyclopropyl-3-pyridyl)-5-methyl-isoxazol-4-yl]methyl]pyridazin-3-one In analogy to experiment of building block B e, 4-(chloromethyl)-3-(6-cyclopropyl-3-pyridyl)-5-methyl-isoxazole instead of 4-(chloromethyl)-5-(fluoromethyl)-3-(6-methyl-3-pyridyl)isoxazole was converted into the title compound (0.110 g, 69%) which was obtained as an off-white solid. MS (ESI): 343.0 ([M+H]$^+$).

Building Block I 5-chloro-2-[[5-cyclopropyl-3-(6-methylpyridazin-3-yl)isoxazol-4-yl]methyl]pyridazin-3-one

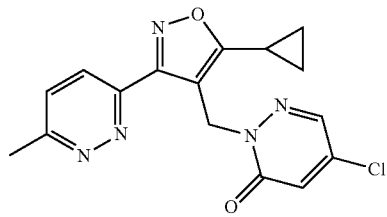 [SMILES: Cc1ccc(-c2noc(C3CC3)c2Cn2ncc(Cl)cc2=O)nn1]

a) ethyl 5-cyclopropyl-3-(6-methylpyridazin-3-yl)isoxazole-4-carboxylate

In analogy to experiment of building block A b, 6-methylpyridazine-3-carbaldehyde oxime, using ethyl 3-cyclopropyl-3-(pyrrolidin-1-yl)acrylate instead of (E)-ethyl 3-(pyrrolidin-1-yl)but-2-enoate was converted into the title compound (352 mg, 42%) which was obtained as an orange oil. MS (ESI): 274.1 ([M+H]$^+$).

b) 5-cyclopropyl-3-(6-methylpyridazin-3-yl)isoxazole-4-carboxylic acid

In analogy to experiment of building block C c, ethyl 5-cyclopropyl-3-(6-methylpyridazin-3-yl)isoxazole-4-carboxylate instead of ethyl 5-methyl-3-(6-(trifluoromethyl)pyridin-3-yl)isoxazole-4-carboxylate was converted into the title compound (260 mg, 95%) which was obtained as an orange solid. MS (ESI): 246.1 ([M+H]$^+$).

c) (5-cyclopropyl-3-(6-methylpyridazin-3-yl)isoxazol-4-yl)methanol

In analogy to experiment of building block E c, 5-cyclopropyl-3-(6-methylpyridazin-3-yl)isoxazole-4-carboxylic acid instead of 3-(6-methyl-3-pyridyl)isoxazole-4-carboxylic acid was converted into the title compound (85 mg, 47%) which was obtained as an orange solid. MS (ESI): 232.1 ([M+H]$^+$).

d) 4-(chloromethyl)-5-cyclopropyl-3-(6-methylpyridazin-3-yl)isoxazole

In analogy to experiment of building block A d, (5-cyclopropyl-3-(6-methylpyridazin-3-yl)isoxazol-4-yl)methanol instead of (5-methyl-3-(6-methylpyridin-3-yl)isoxazol-4-yl)methanol was converted into the title compound (38 mg, 99%) which was obtained as a white solid. MS (ESI): 250.1 ([M+H]$^+$.

e) 5-chloro-2-[[5-cyclopropyl-3-(6-methylpyridazin-3-yl)isoxazol-4-yl]methyl]pyridazin-3-one In analogy to experiment of building block B e, 4-(chloromethyl)-5-cyclopropyl-3-(6-methylpyridazin-3-yl)isoxazole instead of 4-(chloromethyl)-5-(fluoromethyl)-3-(6-methyl-3-pyridyl)isoxazole was converted into the title compound (30 mg, 88%) which was obtained as an off-white solid. MS (ESI): 344.3 ([M+H]$^+$).

Building Block J 5-chloro-2-[[3-(5-fluoro-6-methyl-3-pyridyl)-5-methyl-isoxazol-4-yl]methyl]pyridazin-3-one

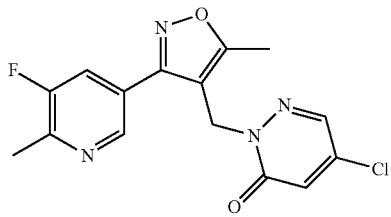 [SMILES: Cc1ncc(-c2noc(C)c2Cn2ncc(Cl)cc2=O)cc1F]

a) (3E)-5-fluoro-6-methyl-pyridine-3-carbaldehyde oxime

To a stirred suspension of 5-fluoro-6-methyl-pyridine-3-carbaldehyde (450 mg, 3.23 mmol) in ethanol (0.7 mL) was added under argon ice-cold water (4.3 mL) and hydroxylamine hydrochloride (247 mg, 3.56 mmol). After 10 min, aqueous NaOH (2.0 M, 4.12 mL, 8.25 mmol) was added dropwise and the reaction mixture was stirred at room temperature for 3 h. The resulting colourless solution was treated with acetic acid to pH~5 (a white precipitate was formed). After stirring for 15 min, the precipitate was collected by filtration on a sintered funnel, washed with water and dried at high vacuum to afford the title compound (383 mg, 77%) as a white solid. MS (ESI): 155.1 ([M+H]$^+$).

b) ethyl 3-(5-fluoro-6-methyl-3-pyridyl)-5-methyl-isoxazole-4-carboxylate

To a stirred solution of (3E)-5-fluoro-6-methyl-pyridine-3-carbaldehyde oxime (380 mg, 2.47 mmol) in DMF (5 mL) at room temperature was added N-chlorosuccinimide (329 mg, 2.47 mmol). The reaction was stirred at room temperature for 3.5 h before addition of (E)-ethyl 3-(pyrrolidin-1-yl)but-2-enoate (452 mg, 2.47 mmol). The mixture was heated to 50° C. overnight to obtain a clear brown solution. After cooling to room temperature, the reaction was diluted with ethyl acetate (50 mL) and washed with water (50 mL) and brine (50 mL), dried over magnesium sulfate and concentrated in vacuo. Purification by flash chromatography (silica, 0% to 30% ethyl acetate in heptane) afforded the title compound (475 mg, 73%) as a light brown solid. MS (ESI): 265.2 ([M+H]$^+$).

c) (3-(5-fluoro-6-methylpyridin-3-yl)-5-methyl-1,2-oxazol-4-yl)methanol

To a stirred solution of ethyl 3-(5-fluoro-6-methyl-3-pyridyl)-5-methyl-isoxazole-4-carboxylate (470 mg, 1.78 mmol) in anhydrous tetrahydrofurane (10 mL) at 0° C. was carefully added under argon lithium alumimium hydride (94.5 mg, 2.49 mmol). The reaction mixture was allowed to warm to room temperature for 2 h before being re-cooled to 0° C. and carefully quenched by addition of water (0.1 mL). After gas evolution had ceased, aqueous NaOH (4.0 M, 0.1 mL) was added followed by water (0.35 mL) and the mixture was stirred at 0° C. for 30 min. The resulting light yellow suspension was filtered off and the cake was rinsed with tetrahydrofurane. The filtrate was concentrated in vacuo and purified by flash chromatography (silica, 0% to 5% MeOH in dichloromethane) to afford the title compound (221 mg, 56%) as a yellow solid. MS (ESI): 223.2 ([M+H]+).

d) 4-(chloromethyl)-3-(5-fluoro-6-methyl-3-pyridyl)-5-methyl-isoxazole

In analogy to experiment of building block A d, (3-(5-fluoro-6-methylpyridin-3-yl)-5-methyl-1,2-oxazol-4-yl)methanol instead of (5-methyl-3-(6-methylpyridin-3-yl)isoxazol-4-yl)methanol was converted into the title compound (193 mg, 81%) which was obtained as a white solid. MS (ESI): 241.1 ([M+H]+.

e) 5-chloro-2-[[3-(5-fluoro-6-methyl-3-pyridyl)-5-methyl-isoxazol-4-yl]methyl]pyridazin-3-one In analogy to experiment of building block B e, 4-(chloromethyl)-3-(5-fluoro-6-methyl-3-pyridyl)-5-methyl-isoxazole instead of 4-(chloromethyl)-5-(fluoromethyl)-3-(6-methyl-3-pyridyl)isoxazole was converted into the title compound (279 mg, 82%) which was obtained as an off-white solid. MS (ESI): 335.1 ([M+H]+).

Building Block K

5-chloro-2-[[5-(fluoromethyl)-3-(6-methylpyridazin-3-yl)isoxazol-4-yl]methyl]pyridazin-3-one

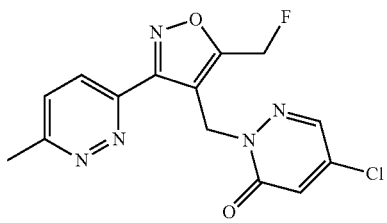 [SMILES: Cc1ccc(-c2noc(CF)c2Cn2ncc(Cl)cc2=O)nn1]

a) ethyl (E)-4-fluoro-3-pyrrolidin-1-yl-but-2-enoate

To a stirred solution of ethyl 4-fluoro-3-oxo-butanoate (1.0 g, 6.75 mmol) in cyclohexane (10 mL) was added dropwise (caution exothermic) pyrrolidine (0.60 mL, 7.22 mmol) followed by a catalytic amount of p-toluenesulfonic acid monohydrate (64.2 mg, 0.338 mmol). The mixture was stirred at room temperature for 30 min then the bottom flask was equipped with a Dean-Stark trap and heated at reflux overnight. The reaction mixture was cooled to room temperature then all the volatiles were removed by rotary evaporation under reduced pressure. The resulting crude residue (orange oil) was used directly in the following step without further purification.

b) ethyl 5-(fluoromethyl)-3-(6-methylpyridazin-3-yl)isoxazole-4-carboxylate

To a stirred suspension of (E)-6-methylpyridazine-3-carbaldehyde oxime (350 mg, 2.55 mmol) in DMF (5 mL) at 6° C. was added N-chlorosuccinimide (375 mg, 2.81 mmol). Upon addition, the color of the reaction mixture changed from yellow to orange and the reaction was allowed to warm to room temperature. After 1 h, the mixture was heated to 50° C. for 2 h. The resulting brown suspension was re-cooled to 6° C. then a solution of ethyl (E)-4-fluoro-3-pyrrolidin-1-yl-but-2-enoate (685 mg, 3.06 mmol, purity 90%) in DMF (1.0 mL) was added dropwise and the reaction mixture was stirred at 50° C. overnight. After cooling to room temperature, the reaction was diluted with water (20 mL) and extracted with ethyl acetate (3×40 mL). The combined organic extracts were washed with brine, dried over sodium sulfate and concentrated in vacuo. Purification by flash chromatography (silica, 0% to 50% ethyl acetate in heptane) afforded the title compound (498 mg, 74%) as an orange oil. MS (ESI): 266.1 ([M+H]+).

c) (5-(fluoromethyl)-3-(6-methylpyridazin-3-yl)isoxazol-4-yl)methanol

To a stirred suspension of ethyl 5-(fluoromethyl)-3-(6-methylpyridazin-3-yl)isoxazole-4-carboxylate (498 mg, 1.88 mmol) in anhydrous toluene (16 mL) at −78° C. was added dropwise DIBAL-H (1.0 M in toluene, 5.63 mL, 5.63 mmol). The reaction was stirred at −78° C. for 1 h then allowed to warm to room temperature and stirred overnight. The reaction mixture was cooled to 0° C. then quenched by addition of aqueous NaOH (1.0 M, 15 mL) followed by ethyl acetate (20 mL). The mixture was diluted with water (20 mL) and extracted with ethyl acetate (3×40 mL). The combined organic extracts were washed with brine, dried over sodium sulfate and concentrated in vacuo. Purification by flash chromatography (silica, 0% to 100% ethyl acetate in heptane) afforded the title compound (105 mg, 25%) as a light yellow powder. MS (ESI): 224.2 ([M+H]+).

d) 4-(chloromethyl)-5-(fluoromethyl)-3-(6-methylpyridazin-3-Yl)isoxazole

In analogy to experiment of building block A d, (5-(fluoromethyl)-3-(6-methylpyridazin-3-yl)isoxazol-4-yl)methanol instead of (5-methyl-3-(6-methylpyridin-3-yl)isoxazol-4-yl)methanol was converted into the title compound (267 mg, 97%) which was obtained as a brown oil. MS (ESI): 242.1 ([M+H]+.

e) 5-chloro-2-[[5-(fluoromethyl)-3-(6-methylpyridazin-3-yl)isoxazol-4-yl]methyl]pyridazin-3-one In analogy to experiment of building block B e, 4-(chloromethyl)-5-(fluoromethyl)-3-(6-methylpyridazin-3-yl)isoxazole instead of 4-(chloromethyl)-5-(fluoromethyl)-3-(6-methyl-3-pyridyl)isoxazole was converted into the title compound (75 mg, 20%) which was obtained as a yellow oil. MS (ESI): 336.1 ([M+H]+).

Building Block L

5-chloro-2-[[3-(4-fluorophenyl)-5-methyl-isoxazol-4-yl]methyl]pyridazin-3-one

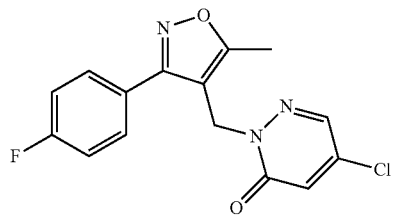 [SMILES: Cc1onc(-c2ccc(F)cc2)c1Cn1ncc(Cl)cc1=O]

Preparation of [3-(4-fluorophenyl)-5-methyl-isoxazol-4-yl]methanol described in the following patents: US 20090143371, US 20090143385, WO 2010127975, WO 2013057123, WO 2013057124 a) 4-(chloromethyl)-3-(4-fluorophenyl)-5-methyl-isoxazole

In analogy to experiment of building block A d, [3-(4-fluorophenyl)-5-methyl-isoxazol-4-yl]methanol instead of (5-methyl-3-(6-methylpyridin-3-yl)isoxazol-4-yl)methanol was converted into the title compound (1.09 g, 95%) which was obtained as an off-white solid. MS (ESI): 226.1 ([M+H]$^+$.

b) 5-chloro-2-[[3-(4-fluorophenyl)-5-methyl-isoxazol-4-yl]methyl]pyridazin-3-one In analogy to experiment of building block B e, 4-(chloromethyl)-3-(4-fluorophenyl)-5-methyl-isoxazole instead of 4-(chloromethyl)-5-(fluoromethyl)-3-(6-methyl-3-pyridyl) isoxazole was converted into the title compound (0.822 g, 76%) which was obtained as an off-white solid. MS (ESI): 320.1 ([M+H]$^+$).

Building Block M 5-chloro-2-[[3-(5-chloro-2-pyridyl)-5-methyl-isoxazol-4-yl]methyl]pyridazin-3-one

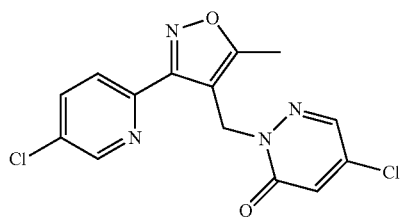 [SMILES: Cc1onc(-c2ccc(Cl)cn2)c1Cn1ncc(Cl)cc1=O]

Preparation of [3-(5-chloro-2-pyridyl)-5-methyl-isoxazol-4-yl]methanol described in the following patents: US 20090143371, US 20090143385 a) 4-(chloromethyl)-3-(5-chloro-2-pyridyl)-5-methyl-isoxazole

In analogy to experiment of building block A d, [3-(5-chloro-2-pyridyl)-5-methyl-isoxazol-4-yl]methanol instead of (5-methyl-3-(6-methylpyridin-3-yl)isoxazol-4-yl)methanol was converted into the title compound (0.566 g, 95%) which was obtained as an off-white solid. MS (ESI): 243.1 ([M+H]$^+$.

b) 5-chloro-2-[[3-(5-chloro-2-pyridyl)-5-methyl-isoxazol-4-yl]methyl]pyridazin-3-one In analogy to experiment of building block B e, 4-(chloromethyl)-3-(5-chloro-2-pyridyl)-5-methyl-isoxazole instead of 4-(chloromethyl)-5-(fluoromethyl)-3-(6-methyl-3-pyridyl)isoxazole was converted into the title compound (0.374 g, 76%) which was obtained as an off-white solid. MS (ESI): 337.0 ([M+H]$^+$).

Building Block N 5-chloro-2-[[3-(5-chloro-2-pyridyl)-5-cyclopropyl-isoxazol-4-yl]methyl]pyridazin-3-one

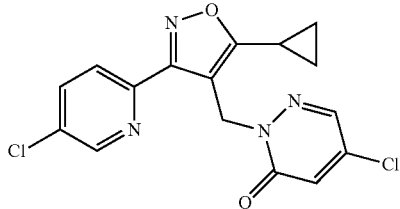 [SMILES: O=c1cc(Cl)cnn1Cc1c(-c2ccc(Cl)cn2)noc1C1CC1]

a) (2E)-5-chloropyridine-2-carbaldehyde oxime

In analogy to experiment of building block J a, 5-chloro-2-formylpyridine instead of 5-fluoro-6-methyl-pyridine-3-carbaldehyde was converted into the title compound (4.23 g, 96%) which was obtained as a white solid. MS (ESI): 157.0 ([M+H]$^+$).

b) ethyl 3-(5-chloro-2-pyridyl)-5-methyl-isoxazole-4-carboxylate

To a stirred solution of (2E)-5-chloropyridine-2-carbaldehyde oxime (1.8 g, 11.5 mmol) in DMF (24 mL) at room temperature was added N-chlorosuccinimide (1.71 g, 12.8 mmol) in three portions. The reaction was stirred at room temperature for 3 h before addition of (E)-ethyl 3-(pyrrolidin-1-yl)but-2-enoate (2.63 g, 14.4 mmol). The mixture was heated to 50° C. overnight to obtain a clear brown solution. After cooling to room temperature, the reaction was diluted with TBME (100 mL) and washed with water (30 mL) and brine (30 mL), dried over magnesium sulfate and concentrated in vacuo. Purification by flash chromatography (silica, 0% to 15% ethyl acetate in heptane) afforded the title compound (2.60 g, 85%) as a light yellow oil. MS (ESI): 267.1 ([M+H]$^+$).

c) [3-(5-chloro-2-pyridyl)-5-methyl-isoxazol-4-yl]methanol

To a stirred solution of ethyl 3-(5-chloro-2-pyridyl)-5-methyl-isoxazole-4-carboxylate (800 mg, 3 mmol) in anhydrous tetrahydrofurane (16 mL) at 0° C. was carefully added under argon a 1.0 M solution of lithium alumimium hydride in tetrahydrofurane (1.5 mL, 1.5 mmol). The reaction mixture was stirred at 0° C. for 1 h before being re-cooled to −15° C. and carefully quenched by addition of water (0.06 mL). After gas evolution had ceased, aqueous NaOH (4.0 M, 0.06 mL) was added followed by water (0.17 mL) and the mixture was stirred at room temperature for 1.25 h. After the addition of sodium sulfate the resulting suspension was filtered off and the cake was rinsed with tetrahydrofurane. The filtrate was concentrated in vacuo and purified by flash chromatography (silica, 0% to 30% ethyl acetate in heptane) to afford the title compound (545 mg, 81%) as a light yellow solid. MS (ESI): 225.1 ([M+H]$^+$).

d) 4-(chloromethyl)-3-(5-chloro-2-pyridyl)-5-cyclopropyl-isoxazole

In analogy to experiment of building block A d, [3-(5-chloro-2-pyridyl)-5-methyl-isoxazol-4-yl]methanol instead of (5-methyl-3-(6-methylpyridin-3-yl)isoxazol-4-yl)methanol was converted into the title compound (0.554 g, 96%) which was obtained as light yellow solid. MS (ESI): 269.1 ([M+H]+).

e) 5-chloro-2-[[3-(5-chloro-2-pyridyl)-5-cyclopropyl-isoxazol-4-yl]methyl]pyridazin-3-one In analogy to experiment of building block B e, 4-(chloromethyl)-3-(5-chloro-2-pyridyl)-5-cyclopropyl-isoxazole instead of 4-(chloromethyl)-5-(fluoromethyl)-3-(6-methyl-3-pyridyl)isoxazole was converted into the title compound (0.418 g, 79%) which was obtained as an off-white solid. MS (ESI): 363.1 ([M+H]+).

Building Block O 5-chloro-2-[[5-methyl-3-(5-methylisoxazol-3-yl)isoxazol-4-yl]methyl]pyridazin-3-one

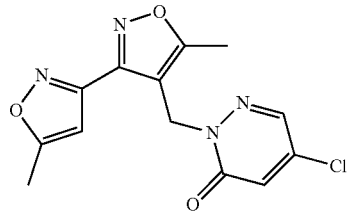 [SMILES: Cc1cc(-c2noc(C)c2Cn2ncc(Cl)cc2=O)no1]

a) (5-methylisoxazol-3-yl)methanol

To a stirred solution of 5-methyl-isoxazole-3-carboxylic acid methyl ester (5 g, 35.4 mmol) in methanol (50 mL) was added at 0° C. sodium borohydride (2.94 g, 77.9 mmol). Then the reaction mixture was allowed to stir at 25° C. for 2 h. After the addition of water the reaction mixture was extracted with ethyl acetate (2×100 mL). The organic layer were washed with brine, dried over sodium sulfate and concentrated. Purification by flash chromatography (silica, 0% to 30% ethyl acetate in heptane) afforded the title compound (3.8 g, 76%) as an off-colourless oil. MS (ESI): 114.0 ([M+H]+).

b) 5-methylisoxazole-3-carbaldehyde

To a solution of (5-methylisoxazol-3-yl)methanol (2 g, 17.6 mmol) in dry dichloromethane (20 mL) was added MnO$_2$ (15.3 g, 176 mmol) at 0° C. and the reaction mixture was stirred at 25° C. for 7 h. The black solid was filtered through celite and the filtrate was concentrated to afford the title compound (1.5 g, 76%) as brown oil. MS (ESI): 209.1 ([M+H]+).

c) (3E)-5-methylisoxazole-3-carbaldehyde oxime

To a stirred solution of 5-methylisoxazole-3-carbaldehyde (250 mg, 2.25 mmol) in methanol (3 mL) was added hydroxylamine (50% in water; 2.25 mL, 27.0 mmol) at 0° C. and the reaction mixture was stirred at 25° C. for 2 h. Then the reaction mixture was extracted with ethyl acetate and the organic layer was washed with brine, dried over sodium sulfate then concentrated to afford the title compound (200 mg, 70%) as white solid. MS (ESI): 183.9 ([M+H]+).

d) ethyl 5-methyl-3-(5-methylisoxazol-3-yl)isoxazole-4-carboxylate

To a solution of (3E)-5-methylisoxazole-3-carbaldehyde oxime (1.1 g, 8.73 mmol) in DMF (15 mL) was added N-chlorosuccinimide (1.75 g, 13.1 mmol) under inert atmosphere at 0° C. in portion wise and the reaction mixture was stirred at 25° C. for 2 h. To this solution was added ethyl (2E)-3-(pyrrolidin-1-yl)but-2-enoate (4 g, 21.8 mmol) in DMF (5 mL) at 25° C. and the reaction mixture was stirred at 25° C. for 16 h. Then the reaction mixture was concentrated in the dark and the resulting residue was diluted with ethyl acetate (50 mL) and was washed with Na2CO3 (1M in H2O), water (100 mL) and brine. The combined organic layers were dried over sodium sulfate and concentrated in vacuo. Purification by flash chromatography (silica, 0% to 20% ethyl acetate in heptane) afforded the title compound (1.5 g, 73%) as white solid. MS (ESI): 237 ([M+H]+).

e) [5-methyl-3-(5-methyl-1,2-oxazol-3-yl)-1,2-oxazol-4-yl]methanol

To a solution of ethyl 5-methyl-3-(5-methylisoxazol-3-yl)isoxazole-4-carboxylate (2.7 g, 11.4 mmol) in tetrahydrofurane (20 mL) was added dropwise a 1 M solution of lithium aluminium hydride in tetrahydrofurane (13.7 mL, 13.7 mmol) at −10° C. and the reaction mixture was stirred at same temperature for 30 min. The reaction mixture was quenched with sodium sulfate decahydrate at 0° C. and reaction mass was filtered through celite pad. Filtrate was evaporated to afford the title compound (1.8 g, 81%) as an off white solid. MS (ESI): 195.1 ([M+H]+).

f) 4-(chloromethyl)-5-methyl-3-(5-methylisoxazol-3-yl)isoxazole

In analogy to experiment of building block A d, [5-methyl-3-(5-methyl-1,2-oxazol-3-yl)-1,2-oxazol-4-yl]methanol instead of (5-methyl-3-(6-methylpyridin-3-yl)isoxazol-4-yl)methanol was converted into the title compound (0.422 g, 92%) which was obtained as a light brown solid. MS (ESI): 213.1 ([M+H]+).

g) 5-chloro-2-[[5-methyl-3-(5-methylisoxazol-3-yl)isoxazol-4-yl]methyl]pyridazin-3-one In analogy to experiment of building block B e, 4-(chloromethyl)-5-methyl-3-(5-methylisoxazol-3-yl)isoxazole instead of 4-(chloromethyl)-5-(fluoromethyl)-3-(6-methyl-3-pyridyl)isoxazole was converted into the title compound (0.495 g, 87%) which was obtained as an off-white solid (ESI): 307.1 ([M+H]+).

Building Block P 5-chloro-2-[[3-[6-(trifluoromethyl)-3-pyridyl]isoxazol-4-yl]methyl]pyridazin-3-one

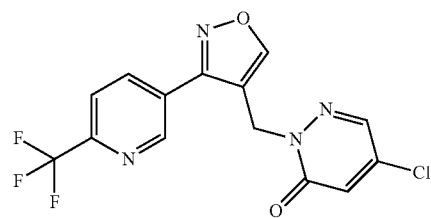 [SMILES: O=c1cc(Cl)cnn1Cc1conc1-c1ccc(C(F)(F)F)nc1]

a) (3E)-6-(trifluoromethyl)pyridine-3-carbaldehyde oxime

In analogy to experiment of building block A a, 6-(trifluoromethyl)pyridine-3-carbaldehyde instead of 6-methylnicotinaldehyde was converted into the title compound (5.28 g, 100%) which was obtained as a white solid. MS (ESI): 191.1 ([M+H]$^+$).

b) ethyl 3-[6-(trifluoromethyl)-3-pyridyl]isoxazole-4-carboxylate

In analogy to experiment of building block A b, (3E)-6-(trifluoromethyl)pyridine-3-carbaldehyde oxime instead of (E)-6-methylnicotinaldehyde oxime and using ethyl 3-(dimethylamino)acrylate instead of (E)-ethyl 3-(pyrrolidin-1-yl)but-2-enoate was converted into the title compound (1.70 g, 75%) which was obtained as a light yellow oil. MS (ESI): 287.2 ([M+H]$^+$).

c) 3-[6-(trifluoromethyl)-3-pyridyl]isoxazole-4-carboxylic acid

To a stirred solution of ethyl 3-[6-(trifluoromethyl)-3-pyridyl]isoxazole-4-carboxylate (1.43 g, 5.70 mmol) in tetrahydrofurane (6 mL) and methanol (6 mL) was added at 0° C. lithium hydroxide monohydrate (586 mg, 13.9 mmol) followed by the addition of water (6 mL). Then the ice bath was removed and the reaction mixture was stirred at room temperature for 1.5 h. After cooling to 0° C. the reaction mixture was acidified with 5% citric acid-solution to pH 5. The suspension was filtered and rinsed with water. The organic solvents of the filtrate were evaporated and the aqueous residue was extracted with ethyl acetate (3×100 mL). The organic layers were combined, dried over sodium sulfate and was combined with the off-white solid above and concentrated to afford the title compound (1.00 g, 66%) as a light yellow solid. MS (ESI): 259.1 ([M+H]$^+$).

d) [3-[6-(trifluoromethyl)-3-pyridyl]isoxazol-4-yl]methanol

To a stirred solution of 3-[6-(trifluoromethyl)-3-pyridyl]isoxazole-4-carboxylic acid (0.97 g, 3.76 mmol) in tetrahydrofurane (12 mL) and triethylamine (0.56 mL, 4.02 mmol) was added dropwise at −15° C. a solution of ethyl chloroformate (0.38 mL, 3.96 mmol) in tetrahydrofurane (3 mL). After stirring at −15° C. for 2 h the suspension was filtered off and was washed with a minimal amount of tetrahydrofurane. Then the filtrate was cooled to −15° C. and a solution of sodium borohydride (355 mg, 9.39 mmol) in water (10 mL) was added dropwise at −15° C. After the addition was complete, the ice bath was removed and the reaction mixture was stirred at room temperature for 2.5 h. The reaction mixture was extracted with ethyl acetate (80 mL) and a 2 M solution of NaOH (15 mL). The aqueous layer was back-extracted with ethyl acetate (80 mL). The organic layers were combined, dried over sodium sulfate, filtered and concentrated to afford the title compound (885 mg, 87%) as a yellow solid. MS (ESI): 245.1 ([M+H]$^+$).

e) 4-(chloromethyl)-3-[6-(trifluoromethyl)-3-pyridyl]isoxazole

In analogy to experiment of building block A d, [3-[6-(trifluoromethyl)-3-pyridyl]isoxazol-4-yl]methanol instead of (5-methyl-3-(6-methylpyridin-3-yl)isoxazol-4-yl)methanol was converted into the title compound (0.403 g, 94%) which was obtained as a yellow oil. MS (ESI): 263.0 ([M+H]$^+$).

f) 5-chloro-2-[[3-[6-(trifluoromethyl)-3-pyridyl]isoxazol-4-yl]methyl]pyridazin-3-one In analogy to experiment of building block B e, 4-(chloromethyl)-3-[6-(trifluoromethyl)-3-pyridyl]isoxazole instead of 4-(chloromethyl)-5-(fluoromethyl)-3-(6-methyl-3-pyridyl)isoxazole was converted into the title compound (0.281 g, 58%) which was obtained as an off-white solid. MS (ESI): 357.0 ([M+H]$^+$).

Building Block Q 5-chloro-2-[[3-(4-chlorophenyl)-5-methyl-isoxazol-4-yl]methyl]pyridazin-3-one

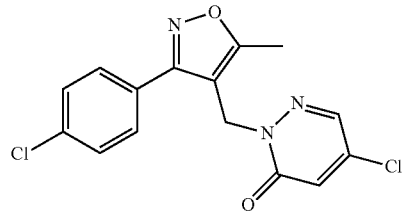 [SMILES: Cc1onc(-c2ccc(Cl)cc2)c1Cn1ncc(Cl)cc1=O]

Preparation of [3-(4-chlorophenyl)-5-methyl-isoxazol-4-yl]methanol described in the following patents: US 20090143371, WO 2013057123.

a) 4-(chloromethyl)-3-(4-chlorophenyl)-5-methyl-isoxazole

In analogy to experiment of building block A d, [3-(4-chlorophenyl)-5-methyl-isoxazol-4-yl]methanol instead of (5-methyl-3-(6-methylpyridin-3-yl)isoxazol-4-yl)methanol was converted into the title compound (2.20 g, 91%) which was obtained as an off-white solid. MS (ESI): 242.0 ([M+H]$^+$).

b) 5-chloro-2-[[3-(4-chlorophenyl)-5-methyl-isoxazol-4-yl]methyl]pyridazin-3-one In analogy to experiment of building block A e, 4-(chloromethyl)-3-(4-chlorophenyl)-5-methyl-isoxazole instead of 4-(chloromethyl)-5-methyl-3-(6-methyl-3-pyridyl)isoxazole was converted into the title compound (1.62 g, 57%) which was obtained as an off-white solid. MS (ESI): 336.1 ([M+H]$^+$).

Building Block R 5-chloro-2-[[5-methyl-3-[5-(trifluoromethyl)pyrimidin-2-yl]isoxazol-4-yl]methyl]pyridazin-3-one

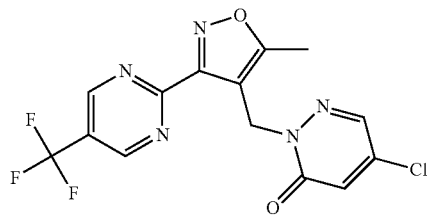 [SMILES: Cc1onc(-c2ncc(C(F)(F)F)cn2)c1Cn1ncc(Cl)cc1=O]

a) (2E)-5-(trifluoromethyl)pyrimidine-2-carbaldehyde oxime

In analogy to experiment of building block J a, 5-(trifluoromethyl)pyrimidine-2-carbaldehyde instead of 5-fluoro-6-methyl-pyridine-3-carbaldehyde was converted into the title compound (0.769 g, 79%) which was obtained as a brown solid. MS (ESI): 192.1 ([M+H]$^+$).

b) ethyl 5-methyl-3-[5-(trifluoromethyl)pyrimidin-2-yl]isoxazole-4-carboxylate In analogy to experiment of building block J b, (2E)-5-(trifluoromethyl)pyrimidine-2-carbaldehyde oxime instead of (3E)-5-fluoro-6-methyl-pyridine-3-carbaldehyde oxime was converted into the title compound (0.735 g, 61%) which was obtained as a yellow solid. MS (ESI): 302.1 ([M+H]$^+$).

c) 5-methyl-3-[5-(trifluoromethyl)pyrimidin-2-yl]isoxazole-4-carboxylic acid In analogy to experiment of building block P c, ethyl 5-methyl-3-[5-(trifluoromethyl)pyrimidin-2-yl]isoxazole-4-carboxylate instead of ethyl 3-[6-(trifluoromethyl)-3-pyridyl]isoxazole-4-carboxylate was converted into the title compound (0.720 g, 86%) which was obtained as a light yellow solid. MS (ESI): 274.1 ([M+H]$^+$).

d) [5-methyl-3-[5-(trifluoromethyl)pyrimidin-2-yl]isoxazol-4-yl]methanol

In analogy to experiment of building block P d, 5-methyl-3-[5-(trifluoromethyl)pyrimidin-2-yl]isoxazole-4-carboxylic acid instead of 3-[6-(trifluoromethyl)-3-pyridyl]isoxazole-4-carboxylic acid was converted into the title compound (107 mg, 28%) which was obtained as a light yellow solid. MS (ESI): 260.0 ([M+H]$^+$).

e) 4-(chloromethyl)-5-methyl-3-[5-(trifluoromethyl)pyrimidin-2-yl]isoxazole

In analogy to experiment of building block A d, [5-methyl-3-[5-(trifluoromethyl)pyrimidin-2-yl]isoxazol-4-yl]methanol instead of (5-methyl-3-(6-methylpyridin-3-yl)isoxazol-4-yl)methanol was converted into the title compound (303 mg, 100%) which was obtained as a light brown solid. MS (ESI): 277.9 ([M+H]$^+$).

f) 5-chloro-2-[[5-methyl-3-[5-(trifluoromethyl)pyrimidin-2-yl]isoxazol-4-yl]methyl]pyridazin-3-one In analogy to experiment of building block B e, 4-(chloromethyl)-5-methyl-3-[5-(trifluoromethyl)pyrimidin-2-yl]isoxazole instead of 4-(chloromethyl)-5-(fluoromethyl)-3-(6-methyl-3-pyridyl)isoxazole was converted into the title compound (235 mg, 73%) which was obtained as an off-white solid. MS (ESI): 372.4 ([M+H]$^+$).

Building Block S 5-chloro-2-[[3-(6-chloropyridazin-3-yl)-5-methyl-isoxazol-4-yl]methyl]pyridazin-3-one

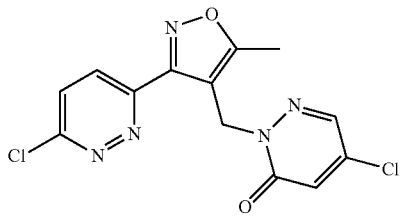 [SMILES: Cc1onc(-c2ccc(Cl)nn2)c1Cn1ncc(Cl)cc1=O]

a) (3E)-6-chloropyridazine-3-carbaldehyde oxime

In analogy to experiment of building block D a, 6-chloropyridazine-3-carbaldehyde instead of 6-chloronicotinaldehyde was converted into the title compound (1.028 g, 98%) which was obtained as a brown solid. MS (ESI): 158.0 ([M+H]$^+$).

b) ethyl 3-(6-chloropyridazin-3-yl)-5-methyl-isoxazole-4-carboxylate

In analogy to experiment of building block J b, (3E)-6-chloropyridazine-3-carbaldehyde oxime instead of (3E)-5-fluoro-6-methyl-pyridine-3-carbaldehyde oxime was converted into the title compound (0.224 g, 66%) which was obtained as a yellow solid. MS (ESI): 306.1 ([M+H]$^+$).

c) [3-(6-chloropyridazin-3-yl)-5-methyl-isoxazol-4-yl]methanol

In analogy to experiment of building block D c, ethyl 3-(6-chloropyridazin-3-yl)-5-methyl-isoxazole-4-carboxylate instead of ethyl 3-(6-chloropyridin-3-yl)-5-methyl-isoxazole-4-carboxylate was converted into the title compound (81 mg, 32%) which was obtained as a light yellow solid. MS (ESI): 226.1 ([M+H]$^+$).

d) 4-(chloromethyl)-3-(6-chloropyridazin-3-yl)-5-methyl-isoxazole

In analogy to experiment of building block A d, [3-(6-chloropyridazin-3-yl)-5-methyl-isoxazol-4-yl]methanol instead of (5-methyl-3-(6-methylpyridin-3-yl)isoxazol-4-yl)methanol was converted into the title compound (83 mg, 96%) which was obtained as a light yellow solid. MS (ESI): 244.1; 246.0 ([M+H]$^+$).

e) 5-chloro-2-[[3-(6-chloropyridazin-3-yl)-5-methyl-isoxazol-4-yl]methyl]pyridazin-3-one A mixture of 4-(chloromethyl)-3-(6-chloropyridazin-3-yl)-5-methyl-isoxazole (66 mg, 0.270 mmol), 5-chloropyridazin-3(2H)-one (38.8 mg, 0.297 mmol) and potassium carbonate (74.7 mg, 0.541 mmol) in N,N-dimethylacetamide (1.3 mL) was stirred at room temperature for 5 h. The mixture was diluted with water and extracted with ethyl acetate (3×). The combined extracts were dried over sodium sulfate, filtered and concentrated in vacuo. The crude residue was purified by flash chromatography (silica, 0% to 100% ethyl acetate in heptane) to afford the title compound (72 mg, 79%) as a white solid. MS (ESI): 338.0; 340.0 ([M+H]+).

Building Block T 5-chloro-2-[[5-methyl-3-[6-(trifluoromethyl)pyridazin-3-yl]isoxazol-4-yl]methyl]pyridazin-3-one

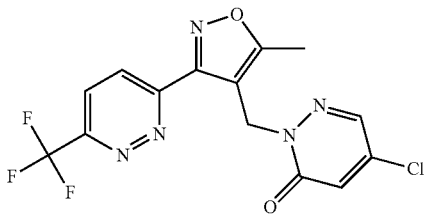 [SMILES: Cc1onc(-c2ccc(C(F)(F)F)nn2)c1Cn1ncc(Cl)cc1=O]

a) (3E)-6-chloropyridazine-3-carbaldehyde oxime

To a solution of 6-(trifluoromethyl)pyridazine-3-carbaldehyde (900 mg, 5.11 mmol) in a mixture of acetonitrile (8.1 ml) and water (0.900 mL) were added hydroxylamine hydrochloride (533 mg, 7.67 mmol) and potassium phosphate tribasic (542 mg, 2.56 mmol). The mixture was stirred at room temperature for 30 min. The resulting orange mixture was poured into an ice bath and diluted with water. The aqueous layer was extracted three times with ethyl acetate. The combined organic layers were dried over sodium sulfate, filtered and concetrated in vacuo to provide the title compound (550 mg, 56%) as an orange solid. MS(ESI): 190.2 ([M+H]+).

b) ethyl 5-methyl-3-[6-(trifluoromethyl)pyridazin-3-yl]isoxazole-4-carboxylate

In analogy to experiment of building block J b, (3E)-6-chloropyridazine-3-carbaldehyde oxime instead of (3E)-5-fluoro-6-methyl-pyridine-3-carbaldehyde oxime was converted into the title compound (0.744 g, 86%) which was obtained as a yellow solid. MS (ESI): 302.4 ([M+H]+).

c) [5-methyl-3-[6-(trifluoromethyl)pyridazin-3-yl]isoxazol-4-yl]methanol

A solution of ethyl 5-methyl-3-(6-(trifluoromethyl)pyridazin-3-yl)isoxazole-4-carboxylate (100 mg, 0.332 mmol) in toluene (2.21 mL) was cooled to −68° C. After 10 min, a solution of DIBAL-H (1.0 M in toluene, 0.670 mL, 0.667 mmol) was added dropwise at −68° C. within 3 min. After complete addition, the solution was stirred at −68° C. for 30 min. The reaction was quenched at −68° C. by a dropwise addition of aqueous NaOH (1.0 M, 2.5 mL). The mixture was allowed to warm to room temperature before being partitioned between water (35 mL) and ethyl acetate (50 mL). The phases were separated. The aqueous layer was extracted with ethyl acetate (3×30 mL). The combined organic layers were washed with brine (1×50 mL), dried over sodium sulfate, filtered and concentrated in vacuo to provide the title compound (78 mg, 91%) as a white solid. The compound was used without further purification. MS (ESI) m/z: 260.1 ([M+H]+).

d) 4-(chloromethyl)-5-methyl-3-[6-(trifluoromethyl)pyridazin-3-yl]isoxazole

In analogy to experiment of building block A d, [5-methyl-3-[6-(trifluoromethyl)pyridazin-3-yl]isoxazol-4-yl]methanol instead of (5-methyl-3-(6-methylpyridin-3-yl)isoxazol-4-yl)methanol was converted into the title compound (80 mg, 95%) which was obtained as a brown solid. MS (ESI): 244.1; 277.8 ([M+H]+).

e) 5-chloro-2-[[5-methyl-3-[6-(trifluoromethyl)pyridazin-3-yl]isoxazol-4-yl]methyl]pyridazin-3-one In analogy to experiment of building block B e, 4-(chloromethyl)-5-methyl-3-[6-(trifluoromethyl)pyridazin-3-yl]isoxazole instead of 4-(chloromethyl)-5-(fluoromethyl)-3-(6-methyl-3-pyridyl)isoxazole was converted into the title compound (60.2 mg, 59%) which was obtained as an off-white solid. MS (ESI): 371.9 ([M+H]+).

Building Block U 5-chloro-2-[[5-ethyl-3-(6-methylpyridazin-3-yl)isoxazol-4-yl]methyl]pyridazin-3-one

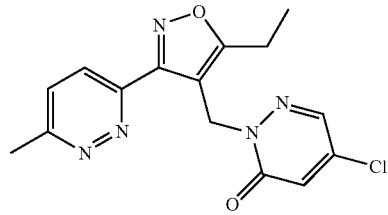 [SMILES: CCc1onc(-c2ccc(C)nn2)c1Cn1ncc(Cl)cc1=O]

a) ethyl 5-ethyl-3-(6-methylpyridazin-3-yl)isoxazole-4-carboxylate

In analogy to experiment of building block A b, (E)-6-methylpyridazine-3-carbaldehyde oxime instead of (3E)-5-fluoro-6-methyl-pyridine-3-carbaldehyde oxime, using (Z)-ethyl 3-(pyrrolidin-1-yl)pent-2-enoate instead of (E)-ethyl 3-(pyrrolidin-1-yl)but-2-enoate, was converted into the title compound (179 mg, 63%) which was obtained as a yellow oil. MS (ESI): 262.2 ([M+H]+).

b) [5-ethyl-3-(6-methylpyridazin-3-yl)isoxazol-4-Yl]methanol

In analogy to experiment of building block K c, ethyl 5-ethyl-3-(6-methylpyridazin-3-yl)isoxazole-4-carboxylate instead of ethyl 5-(fluoromethyl)-3-(6-methylpyridazin-3-yl)isoxazole-4-carboxylate was converted into the title compound (80 mg, 41%) which was obtained as a white powder. MS (ESI): 220.1 ([M+H]+).

c) 4-(chloromethyl)-5-ethyl-3-(6-methylpyridazin-3-yl)isoxazole

In analogy to experiment of building block A d, [5-ethyl-3-(6-methylpyridazin-3-yl)isoxazol-4-yl]methanol instead of (5-methyl-3-(6-methylpyridin-3-yl)isoxazol-4-yl)methanol was converted into the title compound (85 mg, 98%) which was obtained as a light brown solid. MS (ESI): 238.1; 240.0 ([M+H]+).

e) 5-chloro-2-[[5-ethyl-3-(6-methylpyridazin-3-yl)isoxazol-4-yl]methyl]pyridazin-3-one In analogy to experiment of building block B e, 4-(chloromethyl)-5-ethyl-3-(6-methylpyridazin-3-yl)isoxazole instead of 4-(chloromethyl)-5-(fluoromethyl)-3-(6-methyl-3-pyridyl)isoxazole was converted into the title compound (84 mg, 71%) which was obtained as a light yellow oil. MS (ESI): 332.0 ([M+H]$^+$).

Building Block V 5-chloro-2-[[3-(5-chloro-3-fluoro-2-pyridyl)-5-methyl-isoxazol-4-yl]methyl]pyridazin-3-one

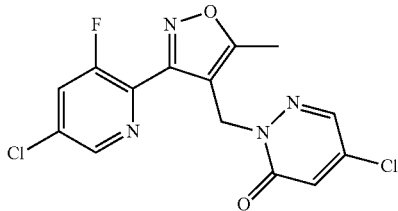 [SMILES: Cc1onc(-c2ncc(Cl)cc2F)c1Cn1ncc(Cl)cc1=O]

a) (2E)-5-chloro-3-fluoro-pyridine-2-carbaldehyde oxime

In analogy to experiment of building block J a, 5-chloro-3-fluoro-pyridine-2-carbaldehyde instead of 5-fluoro-6-methyl-pyridine-3-carbaldehyde was converted into the title compound (791 mg, 98%) which was obtained as a light yellow solid. MS (ESI): 185.0 ([M+H]$^+$).

b) ethyl 3-(5-chloro-3-fluoro-2-pyridyl)-5-methyl-isoxazole-4-carboxylate

To a stirred solution of (2E)-5-chloro-3-fluoro-pyridine-2-carbaldehyde oxime (0.785 g, 4.5 mmol) in DMF (16 mL) at room temperature was added N-chlorosuccinimide (0.661 g, 4.95 mmol) in four portions. The reaction was stirred at room temperature for 2.5 h and at 50° C. for 1 h before addition of (E)-ethyl 3-(pyrrolidin-1-yl)but-2-enoate (0.989 g, 5.4 mmol) at room temperature. The mixture was heated to 50° C. overnight to obtain a clear brown solution. After cooling to room temperature, the reaction was diluted with TBME (100 mL) and washed with water (30 mL) and brine (30 mL), dried over magnesium sulfate and concentrated in vacuo. Purification by flash chromatography (silica, 0% to 15% ethyl acetate in heptane) afforded the title compound (1.19 g, 89%) which was obtained as a light yellow solid. MS (ESI): 285.1 ([M+H]$^+$).

c) 3-(5-chloro-3-fluoro-2-pyridyl)-5-methyl-isoxazole-4-carboxylic acid

To a stirred solution of ethyl 3-(5-chloro-3-fluoro-2-pyridyl)-5-methyl-isoxazole-4-carboxylate (1.19 g, 8.91 mmol) in tetrahydrofurane (4.4 mL) and methanol (4.4 mL) was added at 0° C. lithium hydroxide monohydrate (408 mg, 9.73 mmol) followed by the addition of water (4.4 mL). Then the ice bath was removed and the reaction mixture was stirred at room temperature for 1.5 h. After cooling to 0° C. the reaction mixture was acidified with 5% citric acid-solution to pH 5. The suspension was filtered and rinsed with water. The organic solvents of the filtrate were evaporated and the aqueous residue was extracted with ethyl acetate (3×100 mL). The organic layers were combined, dried over sodium sulfate and was combined with the off-white solid above and concentrated to afford the title compound (769 mg, 76%) which was obtained as an off-white solid. MS (ESI): 257.0 ([M+H]$^+$).

d) [3-(5-chloro-3-fluoro-2-pyridyl)-5-methyl-isoxazol-4-yl]methanol

To a stirred solution of 3-(5-chloro-3-fluoro-2-pyridyl)-5-methyl-isoxazole-4-carboxylic acid (0.760 g, 2.96 mmol) in anhydrous tetrahydrofurane (9.0 mL) and triethylamine (0.44 mL, 3.16 mmol) was added at −15° C. under argon a solution of ethyl chloroformate (0.30 mL, 3.12 mmol) in tetrahydrofurane (3 mL). The reaction mixture was stirred at −15° C. for 3 h. Then the reaction mixture was filtered off and was washed with tetrahydrofurane. The filtrate was cooled to −15° C. and a solution of sodium borohydride (280 mg, 7.4 mmol) in water (8 mL) was added dropwise at −15° C. After the addition was complete, the ice bath was removed and the reaction mixture was stirred at room temperature for 2.5 h. The reaction mixture was extracted with ethyl acetate (80 mL) and 2 M solution of NaOH (10 mL). The aqueous layer was back-extracted with ethyl acetate (80 mL). Then the organic layers were combined, dried over sodium sulfate and purified by flash chromatography (silica, 0% to 100% ethyl acetate in heptane) to afford the title compound (513 mg, 71%) which was obtained as an off-white solid. MS (ESI): 243.1 ([M+H]$^+$).

e) 3-(5-chloro-3-fluoro-2-pyridyl)-4-(chloromethyl)-5-methyl-isoxazole

In analogy to experiment of building block A d, [3-(5-chloro-3-fluoro-2-pyridyl)-5-methyl-isoxazol-4-yl]methanol instead of (5-methyl-3-(6-methylpyridin-3-yl)isoxazol-4-yl)methanol was converted into the title compound (430 mg, 97%) which was obtained as a light brown solid. MS (ESI): 244.1; 261.0 ([M+H]$^+$).

f) 5-chloro-2-[[5-methyl-3-[6-(trifluoromethyl)pyridazin-3-yl]isoxazol-4-yl]methyl]pyridazin-3-one In analogy to experiment of building block B e, 3-(5-chloro-3-fluoro-2-pyridyl)-4-(chloromethyl)-5-methyl-isoxazole instead of 4-(chloromethyl)-5-(fluoromethyl)-3-(6-methyl-3-pyridyl)isoxazole was converted into the title compound (420 mg, 86%) which was obtained as an off-white solid. MS (ESI): 355.0 ([M+H]$^+$).

Building Block Z

[1-[[5-methyl-3-(6-methyl-3-pyridyl)isoxazol-4-yl]methyl]-6-oxo-pyridazin-4-yl]boronic acid

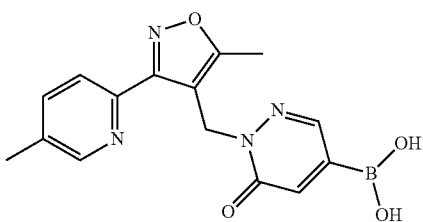 [SMILES: Cc1ccc(-c2noc(C)c2Cn2ncc(B(O)O)cc2=O)nc1]

A round-bottomed flask was charged with 5-chloro-2-[[5-methyl-3-(6-methyl-3-pyridyl)isoxazol-4-yl]methyl]pyridazin-3-one (building block A, 1.00 g, 3.16 mmol), 4,4,5,5-tetramethyl-2-(4,4,5,5-tetramethyl-1,3,2-dioxaborolan-2-yl)-1,3,2-dioxaborolane (1.20 g, 4.74 mmol), potassium acetate dry (775 mg, 7.89 mmol), (19.0 g, 90 mmol), 9,9-dimethyl-4,5-bis(diphenylphosphino)xanthene (183 mg, 0.316 mmol) and tris(dibenzylideneacetone)dipalladium (0) (145 mg, 0.158 mmol). The flask was degassed by alternative evacuation and back filling with argon. Previously degassed 1,4-dioxane (20 mL) was added and the resulting mixture was flushed with argon for 15 min. The reaction mixture was stirred at 100° C. for 16 h before being cooled to room temperature and filtered directly through a plug of celite. The filter cake was rinsed with ethyl acetate and the filtrate concentrated in vacuo. Purification by preparative HPLC (column: C-18, eluent: $H_2O$ and $CH_3CN$ with 0.05% $HCO_2H$) afforded the title compound (506 mg, 46%) as a white powder. MS (ESI): 327.2 ([M+H]$^+$).

Preparation of Amines and Heterocyclic Compounds (2R,3R)-2-methylazetidin-3-ol hydrochloride

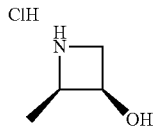

a) (2R,3R)-1-benzhydryl-2-methylazetidin-3-ol

To a solution of 2-(bromomethyl)-3-methyloxirane (7.2 g, 40.5 mmol) in methanol (24 mL) was added diphenylmethanamine (8.21 mL, 47.5 mmol). After stirring at room temperature for 2 days the reaction mixture was stirred at 70° C. for 4 days. Then the mixture was concentrated in vacuo, diluted with ethyl acetate (50 mL) and was washed twice with a 1M solution of $K_2CO_3$, water (50 mL) and brine (50 mL). The aqueous layers were backextracted with ethyl acetate (50 mL). The combined organic extracts were washed with brine, dried over magnesium sulfate and concentrated in vacuo. Purification by flash chromatography (silica, 20% to 100% ethyl acetate in heptane) and HPLC afforded the title compound (1.19 g, 12%) as a white solid. MS (ESI): 254.2 ([M+H]$^+$). Purification by Chiral HPLC afforded the title compound (430 mg) as a white solid. MS (ESI): 254.2 ([M+H]$^+$).

b) (2R,3R)-2-methylazetidin-3-ol hydrochloride

To a solution of (2R,3R)-1-benzhydryl-2-methylazetidin-3-ol (443 mg, 1.75 mmol) in methanol (10 mL) was added under an atmosphere of argon palladium on carbon 10% (184 mg, 0.173 mmol). The flask was carefully evacuated and backfilled with hydrogen for five times and was vigorously stirred at room temperature under an atmosphere of hydrogen for 48 h. The reaction mixture was filtered over Hyflo and was washed well with methanol. The filtrate was concentrated in vacuo. After the addition of acetonitrile (30 mL) the mixture was concentrated and dried under high vacuum to afford the title crude compound (480 mg, purity <450, 100%) as an off-white solid. MS (ESI): 88.1 ([M+H]$^+$).

(2S,3S)-2-methylazetidin-3-ol hydrochloride

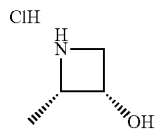

a) (2S,3S)-1-benzhydryl-2-methylazetidin-3-ol

In analogy to experiment of (2R,3R)-1-benzhydryl-2-methylazetidin-3-ol, 2-(bromomethyl)-3-methyloxirane was converted into the title compound (478 mg) which was obtained as a white solid. MS (ESI): 254.2 ([M+H]$^+$).

b) (2S,3S)-2-methylazetidin-3-ol hydrochloride

In analogy to experiment of (2R,3R)-2-methylazetidin-3-ol hydrochloride, (2S,3S)-1-benzhydryl-2-methylazetidin-3-ol instead of (2R,3R)-1-benzhydryl-2-methylazetidin-3-ol was converted into the title compound (260 mg, purity <88%, 100%) which was obtained as a white solid. MS (ESI): 88.1 ([M+H]$^+$).

6,6-dimethyl-5-oxa-2-azaspiro[3.4]octane hydrochloride

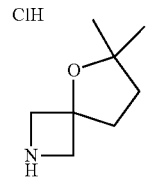

a) 1-benzhydryl-3-(3-hydroxy-3-methyl-butyl)azetidin-3-ol

A solution of 4-chloro-2-methylbutan-2-ol (775 mg, 6.32 mmol) in tetrahydrofurane (3 mL) was cooled under an atmosphere of nitrogen to −30° C. Then methylmagnesium chloride 3 M in tetrahydrofurane (2.11 mL, 6.32 mmol) was added dropwise below −20° C. Then the reaction mixture was allowed to warm to room temperature and magnesium powder (230 mg, 9.48 mmol) was added. Then 1,2-dibromoethane (5.5 µl, 0.063 mmol) was added and the reaction mixture was stirred at reflux for 3 h. After one and two h 1,2-dibromoethane (5. µL, 0.063 mmol) was added. After cooling to room temperature a solution of 1-benzhydrylazetidin-3-one (500 mg, 2.11 mmol) in tetrahydrofurane (3 mL) was added dropwise. Then the reaction mixture was stirred at room temperature for 18 h. After cooling to 0° C. a saturated aqueous ammonium chloride (20 mL) was added carefully. The reaction mixture was filtered off and was washed well with ethyl acetate (20 mL). The aqueous layer was extracted tree times with ethyl acetate (10 mL). Then the combined organic extract was dried over magnesium sulfate and concentrated. Purification by flash chromatography (silica, 30% to 70% ethyl acetate in heptane) afforded the title compound (250 mg, 37%) as a light yellow oil. MS (ESI): 326.3 ([M+H]⁺).

b) 2-benzhydryl-6,6-dimethyl-5-oxa-2-azaspiro[3.4]octane

To a solution of 1-benzhydryl-3-(3-hydroxy-3-methyl-butyl)azetidin-3-ol (240 mg, 0.737 mmol) in tetrahydrofurane (2.4 mL) was added at room temperature N,N-diisopropylethylamine (322 µL, 1.84 mmol), DMAP (9.01 mg, 0.074 mmol) and methanesulfonyl chloride (63.2 µL, 0.811 mmol). After stirring at room temperature for 15 minutes the solution was stirred at 70° C. for 18 h. After cooling to room temperature N,N-diisopropylethylamine (322 µL, 1.84 mmol), DMAP (9.01 mg, 0.074 mmol) and methanesulfonyl chloride (63.2 µL, 0.811 mmol) was added and the reaction mixture was stirred at room temperature for 24 h. Then the reaction mixture was diluted with ethyl acetate (15 mL) and was washed with sodium carbonate 1 M (15 mL). The aqueous layer was extracted with ethyl acetate (15 mL). The combined organic layers were dried over magnesium sulfate, filtered and concentrated in vacuo. Purification by flash chromatography (silica, 0% to 50% ethyl acetate in heptane) afforded the title compound (60 mg, 27%) as a light yellow oil. MS (ESI): 308.3 ([M+H]⁺).

c) 6,6-dimethyl-5-oxa-2-azaspiro[3.4]octane hydrochloride

Under an atmosphere of nitrogen 2-benzhydryl-6,6-dimethyl-5-oxa-2-azaspiro[3.4]octane (58 mg, 0.189 mmol) was dissolved in methanol (3 mL). Then palladium on carbon 10% (7 mg, 0.007 mmol) and a 1 M aqueous solution of hydrochloric acid (226 µL, 0.226 mmol) was added. The reaction mixture was stirred under an atmosphere of hydrogen for 18 h. Then the reaction mixture was filtered over Hyflo and was washed well with methanol. The filtrate was concentrated and was dried on high vacuum to afford the title crude compound (55 mg, purity <61% 100% yield) as an off-white solid. MS (ESI): 142.1 ([M+H]⁺).

(1-methylcyclopropyl)-piperazin-1-yl-methanone hydrochloride

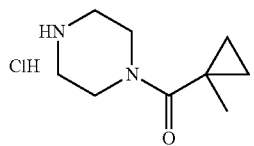

a) tert-butyl 4-(1-methylcyclopropanecarbonyl)piperazine-1-carboxylate

To a solution of tert-butyl piperazine-1-carboxylate (1.56 g, 8.4 mmol) in DMF (12 mL) at 0° C. was added under nitrogen N,N-diisopropylethylamine (5.43 g, 7.34 mL, 42 mmol) and 1-methylcyclopropanecarboxylic acid (1.01 g, 10.1 mmol). Then TBTU (3.24 g, 10.1 mmol) was added and the mixture was stirred at room temperature overnight. The mixture was concentrated in vacuo. Then the residue was diluted with ethyl acetate (50 mL) and the organic phase washed with a 1 M solution of sodium carbonate (50 ml), water (50 mL) and brine (50 mL), dried over magnesium sulfate and concentrated in vacuo. The residue was precipitated by addition of cold heptane (30 mL) and then filtered off. The collected product was washed with further heptane then dried under high vacuum to afford the title compound (1.92 g, 85%) as a white solid. MS (ESI): 269.2 ([M+H]⁺).

b) (1-methylcyclopropyl)-piperazin-1-yl-methanone hydrochloride

To a stirred suspension of tert-butyl 4-(1-methylcyclopropanecarbonyl)piperazine-1-carboxylate (1.92 g, 7.15 mmol) in 1,4-dioxane (15 mL) at 0° C. was added a 4.0 M solution of HCl in dioxane (8.94 mL, 35.8 mmol). Then the ice bath was removed and the suspension was stirred at room temperature for 2 h and finally at 60° C. for 4 h before being cooled to room temperature. The resulting suspension was filtered through a sintered funnel. The collected hydrochloride salt was washed with further 1,4-dioxane then dried under high vaccum to afford the title compound (1.63 g, 99%) as a white solid. MS (ESI): 169.1 ([M+H]⁺).

2-cyclopropyl-2,6-diazaspiro[3.3]heptane 2,2,2-trifluoroacetic acid

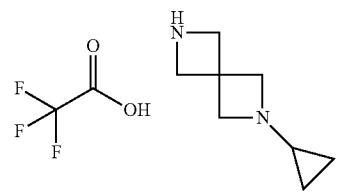

a) tert-butyl 6-cyclopropyl-2,6-diazaspiro[3.3]heptane-2-carboxylate

To a stirred solution of tert-Butyl 2,6-diazaspiro[3.3]heptane-2-carboxylate hemioxalate (2.01 g, 4.13 mmol) in anhydrous in tetrahydrofurane (5.2 mL) and methanol (5.2 mL) under argon at room temperature was added (1-Ethoxy-cyclopropoxy)trimethylsilane (3.4 mL, 16.9 mmol) followed by Sodium Cyanoborohydride (779 mg, 12.4 mmol) and Acetic acid (0.76 mL, 13.3 mmol). The reaction mixture was stirred at 50° C. overnight. After cooling to room temperature, water (4 mL) and 2M NaOH (16 mL) were added and the mixture was stirred at room temperature. After 10 min, the reaction was diluted with dichloromethane (50 mL) and the organic phase washed with brine, dried over sodium sulfate and concentrated in vacuo. Purification by flash chromatography (silica, 0% to 5% methanol in dichloromethane) afforded the title compound (1.434 g, 73%) as a colourless oil. MS (ESI): 239.1 ([M+H]⁺).

b) 2-Cyclopropyl-2,6-diazaspiro[3.3]heptane bis(2,2,2-trifluoroacetate)

To a stirred solution of tert-Butyl 6-cyclopropyl-2,6-diazaspiro[3.3]heptane-2-carboxylate (0.480 g, 2.01 mmol) in dichloromethane (5.2 mL) at 0° C. was added Trifluoroacetic acid (1.63 g, 1.1 ml). The reaction mixture was stirred at 0° C. for 1 h before allowed to warm up at room temperature for 1 h. The reaction mixture was concentrated to afford the title compound (1.350 g, 50% pure, 92% yield) as a colourless oil. MS (ESI): 139.1 ([M+H]$^+$).

(S)-5-Oxa-2-azaspiro[3.4]octan-7-ol 2,2,2-trifluoroacetic acid

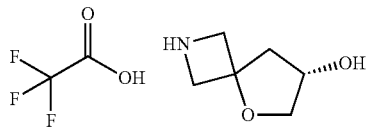 [SMILES: O=C(O)C(F)(F)F ; O[C@@H]1COC2(CNC2)C1]

a) (7S)-5-oxa-2-azaspiro[3.4]octan-7-ol;2,2,2-trifluoroacetic acid (S)-tert-Butyl 7-hydroxy-5-oxa-2-azaspiro[3.4]octane-2-carboxylate (0.210 g, 916 µmol) was dissolved in dichloromethane (2.4 mL) and the colourless solution was cooled to 0° C. Trifluoroacetic acid (0.38 mL, 4.93 mmol) was added dropwise at 0° C. After the addition was complete, the ice bath was removed and the reaction mixture was stirred at room temperature for 2 h. The reaction mixture was concentrated to afford the title compound (342 mg, 92%) as a colourless oil. MS (ESI): 130.1 ([M+H]$^+$).

(7R)-5-oxa-2-azaspiro[3.4]octan-7-ol 2,2,2-trifluoroacetic acid

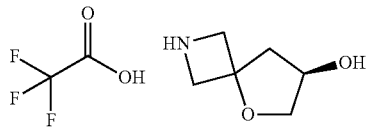 [SMILES: O=C(O)C(F)(F)F ; O[C@H]1COC2(CNC2)C1]

a) (7R)-5-oxa-2-azaspiro[3.4]octan-7-ol;2,2,2-trifluoroacetic acid (R)-tert-Butyl 7-hydroxy-5-oxa-2-azaspiro[3.4]octane-2-carboxylate (0.220 g, 960 µmol) was dissolved in dichloromethane (2.4 mL) and the colourless solution was cooled to 0° C. Trifluoroacetic acid (0.38 mL, 4.93 mmol) was added dropwise at 0° C. After the addition was complete, the ice bath was removed and the reaction mixture was stirred at room temperature for 2 h. The reaction mixture was concentrated to afford the title compound (367 mg, 94%) as a colourless oil. MS (ESI): 130.1 ([M+H]$^+$).

3-(cyclopropoxy)azetidine 2,2,2-trifluoroacetic acid

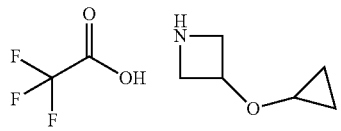

To a stirred solution of tert-Butyl 3-cyclopropoxyazetidine-1-carboxylate (43 mg, 202 µmol) in dichloromethane (0.6 mL) at 0° C. was added Trifluoroacetic acid (0.09 mL, 1.17 mmol). The reaction mixture was stirred at 0° C. for 1 h before allowed to warm up at room temperature for 2 h. The reaction mixture was concentrated to afford the title compound as a colourless oil which was used in the next step without further purification. MS (ESI): 113.2 ([M+H]$^+$).

3-(2,2,2-trifluoroethoxy)azetidine 2,2,2-trifluoroacetic acid

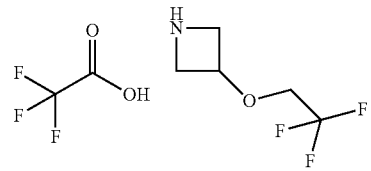

To a stirred solution of tert-Butyl 3-(2,2,2-trifluoroethoxy)azetidine-1-carboxylate (80 mg, 313 µmol) in dichloromethane (0.6 mL) at 0° C. was added Trifluoroacetic acid (0.13 mL, 1.69 mmol). The reaction mixture was stirred at 0° C. for 1 h before allowed to warm up at room temperature for 2.5 h. The reaction mixture was concentrated to afford the title compound as a colourless oil which was used in the next step without further purification.

MS (ESI): 155.1 ([M+H]$^+$).

(7R)-7-fluoro-5-oxa-2-azoniaspiro[3.4]octane 2,2,2-trifluoroacetic acid

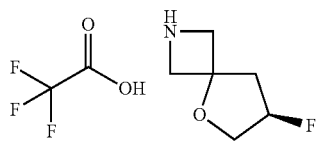

To a stirred solution of (R)-tert-Butyl 7-fluoro-5-oxa-2-azaspiro[3.4]octane-2-carboxylate (70 mg, 303 µmol) in dichloromethane (0.6 mL) at 0° C. was added Trifluoroacetic acid (130 µl, 1.69 mmol). The reaction mixture was stirred at room temperature for 2.5 h. The reaction mixture was concentrated to afford the title compound as a colourless oil which was used in the next step without further purification. MS (ESI): 131.1 ([M+H]$^+$).

(7S)-7-fluoro-5-oxa-2-azoniaspiro[3.4]octane 2,2,2-trifluoroacetic acid

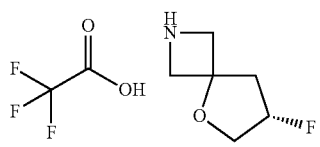

To a stirred solution of (S)-tert-Butyl 7-fluoro-5-oxa-2-azaspiro[3.4]octane-2-carboxylate (70 mg, 303 µmol) in dichloromethane (0.9 mL) at 0° C. was added Trifluoroacetic acid (0.13 mL, 1.69 mmol). The reaction mixture was stirred at room temperature for 2.5 h. The reaction mixture was concentrated to afford the title compound as a colourless oil which was used in the next step without further purification. MS (ESI): 131.1 ([M+H]⁺).

(7R)-7-(difluoromethoxy)-5-oxa-2-azoniaspiro[3.4] octane 2,2,2-trifluoroacetic acid

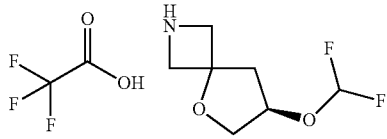

To a stirred solution of (R)-tert-Butyl 7-(difluoromethoxy)-5-oxa-2-azaspiro[3.4]octane-2-carboxylate (109 mg, 390 µmol) in dichloromethane (0.9 mL) at 0° C. was added Trifluoroacetic acid (0.17 ml, 2.21 mmol). The reaction mixture was stirred at room temperature for 2 h. The reaction mixture was concentrated to afford the title compound as a colourless oil which was used in the next step without further purification. MS (ESI): 179.3 ([M+H]⁺).

(7S)-7-(difluoromethoxy)-5-oxa-2-azaspiro[3.4]octane 2,2,2-trifluoroacetic acid

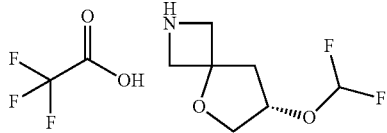

To a stirred solution of (S)-tert-Butyl 7-(difluoromethoxy)-5-oxa-2-azaspiro[3.4]octane-2-carboxylate (95 mg, 340 µmol) in dichloromethane (0.6 mL) at 0° C. was added Trifluoroacetic acid (0.16 ml, 2.08 mmol). The reaction mixture was stirred at room temperature for 2 h. The reaction mixture was concentrated to afford the title compound as a colourless oil which was used in the next step without further purification. MS (ESI): 179.3 ([M+H]⁺).

3-(cyclopropoxy)azetidine

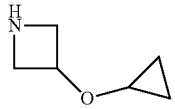

a) tert-butyl 3-vinyloxvazetidine-1-carboxylate

In a 100 ml round-bottomed flask, tert-Butyl 3-hydroxyazetidine-1-carboxylate (1.50 g, 8.66 mmol), Palladium (II) acetate (20 mg, 89.1 µmol) and 4,7-Diphenyl-1,10-phenanthroline (29 mg, 87.2 µmol) were dissolved in Butyl vinyl ether (22 mL, 171 mmol) and Triethylamine (1.0 mL, 7.17 mmol). The reaction mixture was stirred at 75° C. over the weekend. The reaction mixture was cooled to room temperature, adsorbed on Isolute HM-N and purified by flash chromatography (silica, 0% to 10% ethyl acetate in heptane) to afford the title compound (1.139 g, 66%) as a yellow oil. MS (ESI): inconclusive; mass not found.

¹H NMR (CHLOROFORM-d, 300 MHz): δ (ppm) 6.37 (dd, J=14.4, 7.0 Hz, 1H), 4.53-4.64 (m, 1H), 4.17 (dd, J=9.7, 6.5 Hz, 2H), 4.08 (dd, J=6.9, 2.4 Hz, 1H), 3.97 (dd, J=14.5, 2.4 Hz, 1H), 3.90 (dd, J=9.9, 4.2 Hz, 2H), 1.44 (s, 9H).

b) 3-(cyclopropoxy)azetidine

In a 50 ml 3-neck round-bottomed flask, Diethylzinc (1.0 M solution in Hexanes, 4.0 mL, 4 mmol) was added to 4.0 mL dichloromethane and cooled to 0° C. A solution of Trifluoroacetic acid (0.30 mL, 3.89 mmol) in dichloromethane (2.0 mL) was added very slowly via syringe. Upon stirring for 20 min, a solution of diiodomethane (0.32 mL, 3.97 mmol) in dichloromethane (2.0 mL) was added at 0° C. After an additional 20 min of stirring, a solution of tert-Butyl 3-(vinyloxy)azetidine-1-carboxylate (0.395 g, 1.98 mmol) in dichloromethane (3 mL) was added at 0° C. After the addition was complete, the ice bath was removed and the reaction mixture was stirred at room temperature overnight. The reaction mixture was quenched with saturated aqueous ammonium chloride (10 mL) and extracted with dichloromethane (40 mL). The aqueous layer was back-extracted twice with dichloromethane (40 mL). The organic layers were combined, dried over sodium sulfate, filtered and concentrated to afford an orange oil, which is not product. The aqueous layer was basified with 5M NaOH to pH 10. Then, the aqueous layer was extracted four times with dichloromethane. The organic layers were combined, dried over sodium sulfate, filtered and concentrated to afford the title compound (270 mg, 48%) as a yellow oil. MS (ESI): 114.1 ([M+H]⁺).

(7R)-7-methoxy-5-oxa-2-azaspiro[3.4]octane hydrochloride

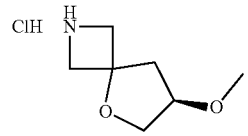

a) tert-butyl (7R)-7-methoxy-5-oxa-2-azaspiro[3.4] octane-2-carboxylate (R)-tert-butyl 7-hydroxy-5-oxa-2-azaspiro[3.4]octane-2-carboxylate (200 mg, 741 µmol) was dissolved in DMF (2 mL) and tetrahydrofurane (2 mL). Sodium hydride (60%, 47.4 mg, 1.19 mmol) was added and the reaction mixture stirred at room temperature for 30 min. Iodomethane (92.7 µl, 1.48 mmol) was then added, and the reaction mixture stirred at room temperature overnight. The reaction mixture was quenched with water, then extracted with ethyl acetate (2×100 mL). The combined organic layers were washed with water (3×10 mL) and brine (10 mL), dried over sodium sulfate, filtered and concentrated. The crude material was purified by ISCO combiflash chromatography (silica, 0% to 5% methanol in dichloromethane to afford the title compound as a colourless oil (124 mg, 65%). MS: 188.1 ([M−C₄H₈+H]⁺).

b) (R)-7-methoxy-5-oxa-2-azaspiro[3.4]octane hydrochloride

To a stirred solution of (R)-tert-butyl 7-methoxy-5-oxa-2-azaspiro[3.4]octane-2-carboxylate (124 mg, 484 µmol) in 1,4-Dioxane (2 mL) was added a 4.0 M solution of HCl in dioxane (1.82 mL, 7.26 mmol). The reaction was stirred at room temperature overnight. The resulting precipitate was filtered through a sintered funnel, washed with further 1,4-dioxane then dried under high vaccum to afford the title compound (95.8 mg, 99%) as a white solid. MS (ESI): 144.0 ([M+H]$^+$).

7-methyl-5-oxa-2-azaspiro[3.4]octane 2,2,2-trifluoroacetic acid

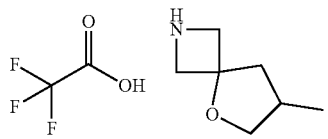

Tert-butyl 7-methyl-5-oxa-2-azaspiro[3.4]octane-2-carboxylate (70 mg, 308 μmol) was dissolved in dichloromethane (0.7 mL) and the colourless solution was cooled to 0° C. Trifluoroacetic acid (0.14 ml, 1.82 mmol) was added dropwise at 0° C. After the addition was complete, the ice bath was removed and the reaction mixture was stirred at room temperature for 2 h. The reaction mixture was concentrated to afford the title compound (39.2 mg, 99%) as a colourless oil. MS (ESI): 127.1 ([M+H]$^+$).

(7R)-7-(difluoromethoxy)-5-oxa-2-azaspiro[3.4] octane hydrochloride

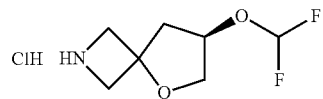 [SMILES: Cl ; FC(F)O[C@H]1COC2(CNC2)C1]

To a stirred solution of (R)-tert-butyl 7-(difluoromethoxy)-5-oxa-2-azaspiro[3.4]octane-2-carboxylate (70 mg, 251 μmol) in Dioxane (1 mL) was added a 4.0 M solution of HCl in dioxane (940 μl, 3.76 mmol). The reaction was stirred at room temperature overnight. The resulting suspension was filtered through a sintered funnel and dried under high vacuum to yield the title compound (51.3 mg, 95%) as as a white solid. MS (ESI): 180.1 ([M+H]$^+$).

(7S)-7-(difluoromethoxy)-5-oxa-2-azaspiro[3.4]octane 2,2,2-trifluoroacetic acid

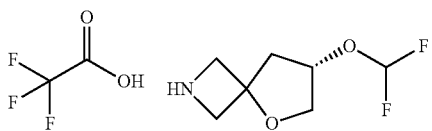 [SMILES: O=C(O)C(F)(F)F ; FC(F)O[C@@H]1COC2(CNC2)C1]

a) tert-butyl 7-benzoyloxy-5-oxa-2-azaspiro[3.4] octane-2-carboxylate

In a 10 mL 2-neck round-bottomed flask, tert-Butyl 7-hydroxy-5-oxa-2-azaspiro[3.4]octane-2-carboxylate (0.200 g, 872 μmol) was dissolved in dichloromethane (3.4 mL) and the colourless solution was cooled to 0° C. Pyridine (0.22 mL, 2.72 mmol) was added followed by dropwise addition of benzoyl chloride (0.20 mL, 1.72 mmol). After the addition was complete, the ice bath was removed and the reaction mixture was stirred at room temperature for 2 h. The reaction mixture was extracted with dichloromethane (20 mL) and 1M HCl (5 mL). The aqueous layer was back-extracted with dichloromethane (20 mL). The organic layers were combined, dried over sodium sulfate, filtered and concentrated. Purification by flash chromatography (silica, 0% to 30% ethyl acetate in heptane) afforded the title compound (257 mg, 89%) as a white solid. MS (ESI): 278.2 ([M–C$_4$H$_8$+H]$^+$).

b) tert-butyl (7S)-7-benzoyloxy-5-oxa-2-azaspiro [3.4]octane-2-carboxylate and tert-butyl (7R)-7-benzoyloxy-5-oxa-2-azaspiro[3.4]octane-2-carboxylate tert-Butyl 7-(benzoyloxy)-5-oxa-2-azaspiro[3.4]octane-2-carboxylate (1.160 g, 3.48 mmol) was separated by chiral preparative HPLC, affording
(−) enantiopure (S)-title compound (470 mg, 41%) as a colourless oil. MS (ESI): inconclusive; mass not found.
(+) enantiopure (R)-title compound (549 mg, 47%) as a colourless oil. MS (ESI): inconclusive; mass not found.

c) (S)-tert-butyl 7-hydroxy-5-oxa-2-azaspiro[3.4] octane-2-carboxylate

In a sealed flask, (S)-tert-butyl 7-(benzoyloxy)-5-oxa-2-azaspiro[3.4]octane-2-carboxylate (100 mg, 300 μmol) was dissolved in ammonia, 7N in methanol (1.71 mL, 12 mmol) and stirred at room temperature overnight. The reaction mixture was concentrated in vacuo.

Purification by flash chromatography (silica, 0% to 70% ethyl acetate in heptane) afforded the title compound (68.4 mg, 85%). as a colourless oil. MS (ESI): inconclusive; mass not found.

d) (S)-tert-butyl 7-(difluoromethoxy)-5-oxa-2-azaspiro[3.4]octane-2-carboxylate (S)-tert-butyl 7-hydroxy-5-oxa-2-azaspiro[3.4]octane-2-carboxylate (300 mg, 1.31 mmol) was dissolved in acetonitrile (8.0 mL) and copper (I) iodide (49.8 mg, 262 μmol) was added. The reaction mixture was heated to 45° C. Then, a solution of 2,2-difluoro-2-(fluorosulfonyl)acetic acid (270 μl, 2.62 mmol) in acetonitrile (84.0 mL) was added dropwise over a period of 40 min at 45° C. The reaction mixture was stirred at 45° C. for 3 h. The reaction mixture was cooled to room temperature and saturated aqueous sodium bicarbonate (30 mL) was added. The product was extracted with ethyl acetate (2×30 mL). The combined organic phases were washed with water (3×20 mL), and brine (30 mL) then dried over sodium sulfate, filtered and concentrated in vacuo. Purification by flash chromatography (silica, 0% to 30% ethyl acetate in heptane) afforded the title compound (193 mg, 57%) as a colourless oil. MS (ESI): inconclusive; mass not found.

e) (7S)-7-(difluoromethoxy)-5-oxa-2-azaspiro[3.4] octane;2,2,2-trifluoroacetic acid To a stirred solution of (S)-tert-butyl 7-(difluoromethoxy)-5-oxa-2-azaspiro[3.4]octane-2-carboxylate (170 mg, 609 μmol) in dichloromethane (3.04 mL) was added TFA (469 µl, 6.09 mmol). The reaction was stirred at room temperature overnight. The resultant precipitate was dried under high vacuum to yield the title compound (206.6 mg, 116%) as a light yellow oil. MS (ESI): 180.1 ([M+H-114]$^+$).

3-(2,2,2-trifluoroethoxy)azetidine bis-2,2,2-trifluoroacetic acid

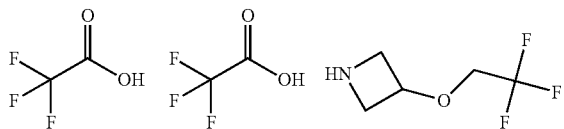

a) tert-butyl 3-(2,2,2-trifluoroethoxy)azetidine-1-carboxylate

To a solution of tert-Butyl-3-hydroxyazetidine-1-carboxylate (500 mg, 2.89 mmol) dissolved in DMF (8.0 mL) was added Sodium hydride, 60% dispersion in mineral oil (173 mg, 4.33 mmol). The reaction mixture was stirred at room temperature for 30 min. The reaction mixture was cooled to 0° C. 2,2,2-Trifluoroethyl trifluoromethanesulfonate (0.67 ml, 4.65 mmol) was added dropwise at 0° C. After the addition was complete, the ice bath was removed and the reaction mixture was stirred at room temperature overnight. The reaction mixture was quenched with water and then extracted with TBME (90 mL) and water (15 mL). The aqueous layer was back-extracted with TBME (90 mL). The combined organic layers were washed with water (3×15 mL) and brine (15 mL), dried over sodium sulfate, filtered and evaporated under reduced pressure. Purification by flash chromatography (silica, 0% to 30% ethyl acetate in heptane) afforded the title compound (428 mg, 58%) as a light yellow oil. MS (ESI): 256.3 ([M+H]$^+$).

b) 3-(2,2,2-trifluoroethoxy)azetidine-Bis 2,2,2-trifluoroacetic acid

To a solution of tert-butyl 3-(2,2,2-trifluoroethoxy)azetidine-1-carboxylate (340 mg, 1.33 mmol) in dichloromethane (3.5 mL) under nitrogen at 0° C., was added trifluoroacetic acid (616 µl, 7.99 mmol). The reaction mixture was stirred at room temperature for 3 h. The reaction mixture was concentrated to afford the title compound (463 mg, 91%) as a colourless oil. MS (ESI): 156.1 ([M+H]$^+$).

3-(2,2,2-trifluoro-1,1-dimethyl-ethoxy)azetidine hydrochloride

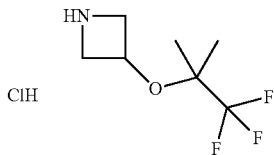

a) (1-Benzhydrylazetidin-3-yl)methanesulfonate

To a solution of 1-(Diphenylmethyl)-3-hydroxyazetidine (1.087 g, 4.54 mmol) in dichloromethane (6.0 mL) was added Triethylamine (1.27 mL, 9.08 mmol) and the reaction mixture was cooled to 0° C. At that temperature, Methanesulfonyl chloride (425 µL, 5.45 mmol) was added dropwise. The reaction mixture was stirred at 0° C. for 30 min and at room temperature for 1 h. The reaction mixture was poured into Water (5 mL) and extracted with dichloromethane (20 mL). The combined organic layers were dried over sodium sulfate, filtered and concentrated to afford the title compound (1.563 g, 100%) as a yellow oil, which was used without further purification. MS (ESI): 318.2 ([M+H]$^+$).

b) 1-benzhydryl-3-(2,2,2-trifluoro-1,1-dimethyl-ethoxy)azetidine

To a solution of 1,1,1-trifluoro-2-methylpropan-2-ol (144 mg, 123 µL, 1.12 mmol) in DMF (1 mL) was added sodium hydride 60% (44.9 mg, 1.12 mmol). After stirring at room temperature for 30 min, 1-benzhydrylazetidin-3-yl methanesulfonate (178 mg, 561 µmol) was added. The suspension was stirred at 7 0° C. for 18 h, at 110° C. for 2 h and finally at 130° C. for 4 h. After cooling to room temperature, the reaction mixture was diluted with ethyl acetate (20 mL) and water (10 mL). The aqueous layer was back-extracted with ethyl acetate (20 mL). The organic layers were washed with brine (20 mL). The organic layers were combined, dried over sodium sulfate, filtered and concentrated in vacuo. Purification by flash chromatography (silica, 0% to 40% ethyl acetate in heptane) afforded the title compound (71 mg, 36%) as a brown oil. MS (ESI): 350.2 ([M+H]$^+$).

c) 3-(2,2,2-trifluoro-1,1-dimethyl-ethoxy)azetidine hydrochloride

To a solution of 1-benzhydryl-3-((1,1,1-trifluoro-2-methylpropan-2-yl)oxy)azetidine (71 mg, 203 µmol) in methanol (4 mL) was added hydrochloric acid 4 M in dioxane (152 µL, 610 µmol). Under an atmosphere of argon palladium on charcoal (10%, 35 mg, 32.9 µmol) was added. The vial was then degassed by alternative evacuation and back filling with hydrogen. The reaction mixture was heated at 50° C. for 8 h. The reaction mixture was filtered over Hyflo and washed with methanol. The filtrate was concentrated in vacuo to afford the title compound (77.3 mg, 100%) as a off-white solid. MS (ESI): 184.1 ([M+H]$^+$).

3-(2,2,2-trifluoro-1-methyl-ethoxy)azetidine-2,2,2-trifluoroacetic acid

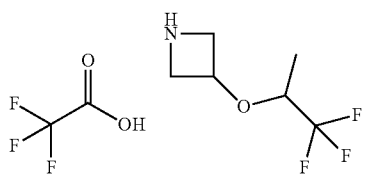

a) tert-butyl 3-(2,2,2-trifluoro-1-methyl-ethoxy)azetidine-1-carboxylate

To a suspension of sodium hydride (60%, 166 mg, 4.16 mmol) in N,N-Dimethylformamide (3 mL) was added dropwise a solution of tert-butyl 3-hydroxyazetidine-1-carboxylate (600 mg, 3.46 mmol) in N,N-Dimethylformamide (3 mL) under ice bath cooling. After the addition was complete, the mixture was stirred at room temperature for 30 min. A solution of 1,1,1-trifluoropropan-2-yl trifluoromethanesulfonate (1.02 g, 4.16 mmol) in N,N-Dimethylformamide (3 mL) was added dropwise at 0° C. The mixture was stirred at room temperature for 3 h, cooled in an ice bath and quenched with a saturated aqueous sodium bicarbonate solution. The mixture was diluted with water and extracted ethyl acetate (3×). The combined extracts were dried over sodium sulfate, filtered and concentrated in vacuo. Purification by flash chromatography (silica, 0% to 50% EtOAc in heptane) afforded the title compound (215 mg, 23%) as a colourless oil. MS (ESI): 214.1 ([M+H-56]$^+$).

b) 2,2,2-trifluoroacetic acid;3-(2,2,2-trifluoro-1-methyl-ethoxy)azetidine

A solution of tert-butyl 3-((1,1,1-trifluoropropan-2-yl)oxy)azetidine-1-carboxylate (215 mg, 798 μmol) in dichloromethane (3.3 mL) was cooled in an ice bath. Trifluoroacetic acid (306 μL, 3.99 mmol) was added. The mixture was stirred at room temperature for 3 h. Trifluoroacetic acid (306 μL, 3.99 mmol) was added and the mixture was stirred at room temperature for 1 h. The solvent was removed in vacuo to afford the title compound (254 mg, 100%) as alight yellow oil. MS (ESI): 170.0 ([M+H]$^+$).

(R)-7-fluoro-5-oxa-2-azaspiro[3.5]nonane hydrochloride or enantiomer F

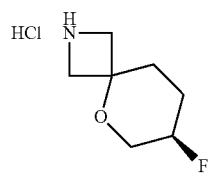

a) 2-fluoroprop-2-en-1-ol

To a mixture of lithium aluminium hydride (131.2 g, 3.46 mol) in diethyl ether (3 L) was carefully added AlCl3 (63.0 mL, 1.15 mol) at −5° C. The mixture was stirred at −5° C. for 30 min, then methyl 2-fluoroprop-2-enoate (240 g, 2.31 mol) was added dropwise at −5° C. The mixture was stirred at −5° C. for other 3.5 h. Wet sodium sulfate was added at 0° C. and the mixture was filtered. The filtrate was isolated by atmospheric distillation at 50° C. affording the title compound (163.0 g, 46%) as colourless liquid in ether. 1H NMR (400 MHz, CDCl3): 4.63 (dd, J1=2.8 Hz, J2=17.2 Hz, 1H), 4.53 (dd, J1=2.8 Hz, J2=51.6 Hz, 1H), 4.08 (dd, J1=3.2 Hz, J2=10.8 Hz, 1H), 3.30 (m, 1H).

b) 2-fluoroprop-2-enyl methanesulfonate

To a mixture of 2-fluoroprop-2-en-1-ol (160.0 g, 1.05 mol) and triethylamine (219 mL, 1.58 mol) in dichloromethane (400 mL) was added MsCl (97.6 mL, 1.26 mol) at −30° C. The mixture was stirred at −30° C. for 1 h. The mixture was diluted with dichloromethane (500 mL) and washed with water (3×700 mL). The organic phase was dried with sodium sulfate, filtered and concentrated in vacuo to afford the title compound (119.3 g, crude) as a yellow oil. 1H NMR (400 MHz, CDCl3): 4.95 (dd, J1=3.6 Hz, J2=15.2 Hz, 1H), 4.86-4.70 (m, 3H), 3.08 (s, 3H).

c) tert-butyl 3-allyl-3-hydroxyazetidine-1-carboxylate

To a mixture of tert-butyl 3-oxoazetidine-1-carboxylate (150.0 g, 876 mmol) in tetrahydrofurane (1 L) was added allylmagnesium bromide (1 M, 876 mL) at −78° C. The mixture was stirred at −78° C. for 1.5 h, then quenched with saturated aqueous ammonium chloride (10 L) and extracted with ethyl acetate (3×2 L). The combined organic phase was dried with sodium sulfate, filtered and concentrated in vacuo to afford the title compound (192.5 g, crude) as an orange oil. MS (ESI): 158.1 ([M−C4H8+H]$^+$).

d) tert-butyl 3-allyl-3-((2-fluoroallyl)oxy)azetidine-1-carboxylate

To a mixture of tert-butyl 3-allyl-3-hydroxyazetidine-1-carboxylate (150.0 g, 703 mmol) in DMF (750 mL) was added sodium hydride (60%, 42.2 g, 1.05 mol) at 0° C. and stirred for 1 h. 2-Fluoroprop-2-enyl methanesulfonate (119.2 g, 773 mmol) was added to the mixture at 0° C. and stirred for 1 h. The mixture was quenched with saturated aqueous ammonium chloride (1.5 L) and extracted with MTBE (3×800 mL). The combined organic phase was washed with water (3×500 mL), dried with sodium sulfate, filtered and concentrated in vacuo. Purification by chromatography (silica, petroleum ether/ethyl acetate) afforded the title compound (80.0 g, crude) as an orange oil. The product was used for next step directly. 1H NMR (400 MHz, CDCl3): 5.86-5.76 (m, 1H), 5.25-5.20 (m, 2H), 4.77 (d, J1=16.4 Hz, 1H), 4.62 (d, J1=48.4 Hz, 1H), 3.99-3.92 (m, 4H), 3.80-3.73 (m, 2H), 2.58-2.54 (m, 2H), 1.47 (s, 9H).

e) tert-butyl 7-fluoro-5-oxa-2-azaspiro[3.5]non-7-ene-2-carboxylate

To a solution of tert-butyl 3-allyl-3-((2-fluoroallyl)oxy)azetidine-1-carboxylate (1.51 g, 5.57 mmol) in dry degassed toluene (928 mL) under argon at room temperature, was added (1,3-dimesitylimidazolidin-2-ylidene)(2-isopropoxybenzylidene)ruthenium(VI)chloride (349 mg, 557 μmol). The mixture was stirred at 100° C. for 1.5 hr, then filtered over dicalite. The filtrate was concentrated in vacuo. Purification by flash chromatography (silica, ethyl acetate/heptane) afforded the title compound (1.28 g, 95%) as a green oil. MS (ESI): 188.1 ([M−C4H8+H]$^+$).

f) tert-butyl 7-fluoro-5-oxa-2-azaspiro[3.5]nonane-2-carboxylate

To a solution of tert-butyl 7-fluoro-5-oxa-2-azaspiro[3.5]non-7-ene-2-carboxylate (1.26 g, 5.18 mmol) in methanol (51.8 mL) at room temperature was added Pd—C (10%, 276 mg, 259 μmol). The mixture was stirred under hydrogen atmosphere at room temperature for 18 h. The reaction mixture was filtered through a pad of dicalite and washed with methanol. The filtrate was concentrated in vacuo affording the title compound (1.18 g, 93%) as a green solid. MS (ESI): 190.1 ([M−C4H8+H]$^+$).

g) 7-fluoro-5-oxa-2-azaspiro[3.5]nonane hydrochloride

To a solution of tert-butyl 7-fluoro-5-oxa-2-azaspiro[3.5]nonane-2-carboxylate (1.18 g, 4.81 mmol) in dichloromethane (14.5 mL) at room temperature, was added HCl in dioxan (4M, 6.01 ml, 24.1 mmol). The mixture was stirred h) (S)-benzyl 7-fluoro-5-oxa-2-azaspiro[3.5]nonane-2-carboxylate and (R)-benzyl 7-fluoro-5-oxa-2-azaspiro[3.5]nonane-2-carboxylate To a suspension of 7-fluoro-5-oxa-2-azaspiro[3.5]nonane hydrochloride (4.43 g, 23.9 mmol) in dichloromethane (44.4 mL) at 0-5° C., was added triethylamine (10.4 ml, 74.6 mmol) and benzyl chloroformate (7.13 ml, 49.9 mmol). The mixture was stirred at room temperature. After 2 h, triethylamine (2.5 ml, 17.9 mmol) and benzyl chloroformate (1.71 ml, 12.0 mmol) were added. After 3 h stirring at room temperature, the reaction mixture was diluted with 1 M HCl. The aqueous layer was extracted with dichloromethane. The combined organic layers were dried over sodium sulfate, filtered and concentrated in vacuo. The mixture was separated by chiral preparative HPLC (Chiralpak AD, 60:40 heptane/ethanol, 203 nm), affording
(+) enantiopure (S)-title compound or enantiomer (2.06 g, 31%) as an orange oil, MS (ESI): 280.2 ([M+H]$^+$).
(−) enantiopure (R)-title compound or enantiomer (2.07 g, 31%) as an orange oil, MS (ESI): 280.2 ([M+H]$^+$).

i) (R)-7-fluoro-5-oxa-2-azaspiro[3.5]nonane hydrochloride or enantiomer

To a solution of (R)-benzyl 7-fluoro-5-oxa-2-azaspiro[3.5]nonane-2-carboxylate or enantiomer (2 g, 7.16 mmol) in methanol (71.6 mL) at room temperature was added Pd—C (10%, 762 mg, 716 μmol) and aqueous HCl (4N, 2.15 ml, 8.59 mmol). The mixture was stirred under hydrogen atmosphere at room temperature for 18 h. The reaction mixture was filtered through a pad of dicalite and washed with methanol. The filtrate was concentrated in vacuo affording the title compound (1.27 g, 97%) as an off-white solid. MS (ESI): 146.2 ([M+H]$^+$), specific optical rotation: −41.488° (methanol, 0.667 g/100 mL).

(S)-7-fluoro-5-oxa-2-azaspiro[3.5]nonane hydrochloride or enantiomer

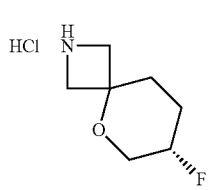

To a solution of (S)-benzyl 7-fluoro-5-oxa-2-azaspiro[3.5]nonane-2-carboxylate or enantiomer (2 g, 7.16 mmol) in methanol (71.6 mL) at room temperature was added Pd—C (10%, 762 mg, 716 μmol) and HCl (aq.) (4N, 2.15 ml, 8.59 mmol). The mixture was stirred under hydrogen atmosphere at room temperature for 19 h. The reaction mixture was filtered through a pad of dicalite and washed with methanol. The filtrate was concentrated in vacuo affording the title compound (1.10 g, 85%) as an off-white solid. MS (ESI): 146.2 ([M+H]$^+$), specific optical rotation: +38.593° (methanol, 0.667 g/100 mL).

(R)-7-methyl-5-oxa-2-azaspiro[3.5]nonane hydrochloride or enantiomer

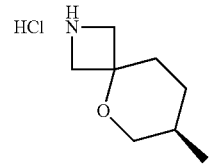

a) tert-butyl 3-allyl-3-((2-methylallyl)oxy)azetidine-1-carboxylate

In analogy to the experimental procedure of tert-butyl 3-allyl-3-((2-fluoroallyl)oxy)azetidine-1-carboxylate, 3-bromo-2-methylprop-1-ene was converted into the title compound (1.05 g, 84%) which was obtained as a light yellow liquid. MS (ESI): 265.5 ([M+H]$^+$).

b) tert-butyl 7-methyl-5-oxa-2-azaspiro[3.5]non-7-ene-2-carboxylate

To a solution of tert-butyl 3-allyl-3-((2-methylallyl)oxy)azetidine-1-carboxylate (1.02 g, 3.82 mmol) in dry degassed dichloromethane (636 mL) under Argon at room temperature, was added Grubbs 11 (324 mg, 382 μmol). The mixture was stirred at 40° C. for 19 hr. The reaction mixture was concentrated in vacuo. Purification by flash chromatography (silica, ethyl acetate/heptane) afforded thre title compound (859 mg, 94%) as a brown oil.
MS (ESI): 184.4 ([M−C$_4$H$_8$+H]$^+$).

c) tert-butyl 7-methyl-5-oxa-2-azaspiro[3.5]nonane-2-carboxylate

In analogy to the experimental procedure of tert-butyl 7-fluoro-5-oxa-2-azaspiro[3.5]nonane-2-carboxylate, tert-butyl 7-methyl-5-oxa-2-azaspiro[3.5]non-7-ene-2-carboxylate was converted into the title compound (807 mg, 100%) which was obtained as a colourless oil. MS (ESI): 186.5 ([M−C$_4$H$_8$+H]$^+$).

d) 7-methyl-5-oxa-2-azaspiro[3.5]nonane hydrochloride

In analogy to the experimental procedure of 7-fluoro-5-oxa-2-azaspiro[3.5]nonane hydrochloride, tert-butyl 7-methyl-5-oxa-2-azaspiro[3.5]nonane-2-carboxylate was converted into the title compound (592 mg, 100%) which was obtained as a light grey solid. MS (ESI): 142.3 ([M+H]$^+$).

e) (S)-benzyl 7-methyl-5-oxa-2-azaspiro[3.5]nonane-2-carboxylate and (R)-benzyl 7-methyl-5-oxa-2-azaspiro[3.5]nonane-2-carboxylate In analogy to the experimental procedure of (S)-benzyl 7-fluoro-5-oxa-2-azaspiro[3.5]nonane-2-carboxylate and (R)-benzyl 7-fluoro-5-oxa-2-azaspiro[3.5]nonane-2-carboxylate, 7-methyl-5-oxa-2-azaspiro[3.5]nonane hydrochloride was converted into benzyl 7-methyl-5-oxa-2-azaspiro[3.5]nonane-2-carboxylate. The mixture was separated by chiral SFC (AD-H, 10% Ethanol) affording (+) enantiopure (S)-title compound or enantiomer (8.60 g, 42%) as a yellow oil, MS (ESI): 276.0 ([M+H]⁺), specific optical rotation: +31.6090 (methanol, 0.1 g/l)
(−) enantiopure (R)-title compound or enantiomer (9.01 g, 44%) as a yellow oil, MS (ESI): 276.1 ([M+H]⁺), specific optical rotation: −35.979° (methanol, 0.1 g/l).

f) (R)-7-methyl-5-oxa-2-azaspiro[3.5]nonane hydrochloride or enantiomer

In analogy to the experimental procedure of (R)-7-fluoro-5-oxa-2-azaspiro[3.5]nonane hydrochloride or enantiomer, (R)-benzyl 7-methyl-5-oxa-2-azaspiro[3.5]nonane-2-carboxylate or enantiomer was converted into the title compound (5.82 g, 100%) which was obtained as a white solid. MS (ESI): 142.3 ([M+H]⁺).

7-(trifluoromethyl)-5-oxa-2-azaspiro[3.5]nonane hydrochloride

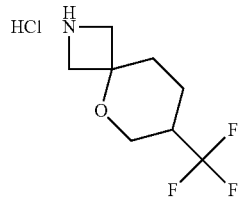 [SMILES: Cl ; FC(F)(F)C1CCC2(CNC2)OC1]

a) tert-butyl 3-allyl-3-((2-(trifluoromethyl)allyl)oxy)azetidine-1-carboxylate

In analogy to the experimental procedure of tert-butyl 3-allyl-3-((2-fluoroallyl)oxy)azetidine-1-carboxylate, 2-(trifluoromethyl)prop-2-enyl 4-methylbenzenesulfonate (*J. Org. Chem.*, 2006, 71, 7527-7532) was converted into the title compound (3.2 g, 54%) which was obtained as a light brown liquid. MS (ESI): 266.2 ([M−C₄H₈+H]⁺).

b) tert-butyl 7-(trifluoromethyl)-5-oxa-2-azaspiro[3.5]non-7-ene-2-carboxylate

In analogy to the experimental procedure of tert-butyl 7-fluoro-5-oxa-2-azaspiro[3.5]non-7-ene-2-carboxylate, tert-butyl 3-allyl-3-((2-(trifluoromethyl)allyl)oxy)azetidine-1-carboxylate was converted into the title compound (146 mg, 70%) which was obtained as a yellow solid. MS (ESI): 238.1 ([M−C₄H₈+H]⁺).

c) tert-butyl 7-(trifluoromethyl)-5-oxa-2-azaspiro[3.5]nonane-2-carboxylate

In analogy to the experimental procedure of tert-butyl 7-fluoro-5-oxa-2-azaspiro[3.5]nonane-2-carboxylate, tert-butyl 7-(trifluoromethyl)-5-oxa-2-azaspiro[3.5]non-7-ene-2-carboxylate was converted into the title compound (147 mg, 91%) which was obtained as a light grey solid. MS (ESI): 240.2 ([M−C₄H₈+H]⁺).

d) 7-(trifluoromethyl)-5-oxa-2-azaspiro[3.5]nonane hydrochloride

In analogy to the experimental procedure of 7-fluoro-5-oxa-2-azaspiro[3.5]nonane hydrochloride, tert-butyl 7-(trifluoromethyl)-5-oxa-2-azaspiro[3.5]nonane-2-carboxylate was converted into the title compound (111 mg, 97%) which was obtained as a grey solid. MS (ESI): 196.1 ([M+H]⁺).

8-fluoro-5-oxa-2-azaspiro[3.5]nonane hydrochloride

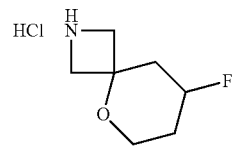

a) tert-butyl 3-(2-fluoroallyl)-3-hydroxyazetidine-1-carboxylate

To a previously degassed solution of tetrahydrofuran (2.5 mL) and Water (2.5 mL) at room temperature, was added tert-butyl 3-oxoazetidine-1-carboxylate (250 mg, 1.46 mmol), indium (50.3 mg, 438 µmol) and 3-bromo-2-fluoroprop-1-ene (223 mg, 1.61 mmol). The mixture was stirred at 30° C. for 3.5 hr, then diluted with ethyl acetate. The aqueous layer was extracted with ethyl acetate (2×). The combined organic layers were dried over sodium sulfate, filtered and concentrated in vacuo. Purification by flash chromatography esilica, ethyl acetate/heptane) afforded the title compound (130 mg, 39%) as a colourless oil. MS (ESI): 230.1 ([M+H]⁺).

b) tert-butyl 3-(allyloxy)-3-(2-fluoroallyl)azetidine-1-carboxylate

In analogy to the experimental procedure of tert-butyl 3-allyl-3-((2-fluoroallyl)oxy)azetidine-1-carboxylate, tert-butyl 3-(2-fluoroallyl)-3-hydroxyazetidine-1-carboxylate and 3-bromoprop-1-ene were converted into the title compound (130 mg, 85%) which was obtained as a colourless oil. MS (ESI): 216.2 ([M−C₄H₈+H]⁺).

c) tert-butyl 8-fluoro-5-oxa-2-azaspiro[3.5]non-7-ene-2-carboxylate

In analogy to the experimental procedure of tert-butyl 7-methyl-5-oxa-2-azaspiro[3.5]non-7-ene-2-carboxylate, tert-butyl 3-(allyloxy)-3-(2-fluoroallyl)azetidine-1-carboxylate was converted into the title compound (40 mg, 37%) which was obtained as a brown oil. MS (ESI): 188.1 ([M−C₄H₈+H]⁺).

d) tert-butyl 8-fluoro-5-oxa-2-azaspiro[3.5]nonane-2-carboxylate

In analogy to the experimental procedure of tert-butyl 7-fluoro-5-oxa-2-azaspiro[3.5]nonane-2-carboxylate, tert-butyl 8-fluoro-5-oxa-2-azaspiro[3.5]non-7-ene-2-carboxylate was converted into the title compound.

e) 8-fluoro-5-oxa-2-azaspiro[3.5]nonane hydrochloride

In analogy to the experimental procedure of 7-fluoro-5-oxa-2-azaspiro[3.5]nonane hydrochloride, tert-butyl 8-fluoro-5-oxa-2-azaspiro[3.5]nonane-2-carboxylate was converted into the title compound.

97

8-(trifluoromethyl)-5-oxa-2-azaspiro[3.5]nonane hydrochloride

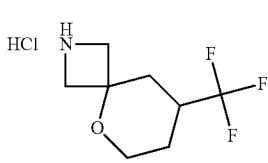 [SMILES: Cl ; FC(F)(F)C1CCOC2(CNC2)C1]

a) tert-butyl 3-hydroxy-3-(2-(trifluoromethyl)allyl) azetidine-1-carboxylate In analogy to the experimental procedure of tert-butyl 3-(allyloxy)-3-(2-fluoroallyl)azetidine-1-carboxylate, tert-butyl 3-oxoazetidine-1-carboxylate and 2-(bromomethyl)-3,3,3-trifluoroprop-1-ene were converted into the title compound (1.17 g, 36%) which was obtained as a white solid. MS (ESI): 182.2 ($[M-C_4H_8+H]^+$).

b) tert-butyl 3-(allyloxy)-3-(2-(trifluoromethyl)allyl) azetidine-1-carboxylate In analogy to the experimental procedure of tert-butyl 3-allyl-3-((2-fluoroallyl)oxy)azetidine-1-carboxylate, tert-butyl 3-hydroxy-3-(2-(trifluoromethyl)allyl)azetidine-1-carboxylate and 3-bromoprop-1-ene were converted into the title compound (194 mg, 68%) which was obtained as a colourless oil. MS (ESI): 266.2 ($[M-C_4H_8+H]^+$).

c) tert-butyl 8-(trifluoromethyl)-5-oxa-2-azaspiro[3.5]non-7-ene-2-carboxylate In analogy to the experimental procedure of tert-butyl 7-fluoro-5-oxa-2-azaspiro[3.5]non-7-ene-2-carboxylate, tert-butyl 3-(allyloxy)-3-(2-(trifluoromethyl)allyl)azetidine-1-carboxylate was converted into the title compound (900 mg, 79%) which was obtained as a brown solid. MS (ESI): 294.2 ($[M+H]^+$).

d) tert-butyl 8-(trifluoromethyl)-5-oxa-2-azaspiro[3.5]nonane-2-carboxylate In analogy to the experimental procedure of tert-butyl 7-fluoro-5-oxa-2-azaspiro[3.5]nonane-2-carboxylate, tert-butyl 8-(trifluoromethyl)-5-oxa-2-azaspiro[3.5]non-7-ene-2-carboxylate was converted into the title compound (628 mg, 99%) which was obtained as a light grey solid. MS (ESI): 240.5 ($[M-C_4H_8+H]^+$).

d) 8-(trifluoromethyl)-5-oxa-2-azaspiro[3.5]nonane hydrochloride

In analogy to the experimental procedure of 7-fluoro-5-oxa-2-azaspiro[3.5]nonane hydrochloride, tert-butyl 8-(trifluoromethyl)-5-oxa-2-azaspiro[3.5]nonane-2-carboxylate was converted into the title compound (537 mg, 100%) which was obtained as a grey solid. MS (ESI): 196.4 ($[M+H]^+$).

98

8-methyl-5-oxa-2-azaspiro[3.5]nonane hydrochloride

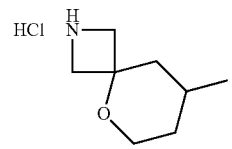

a) tert-butyl 3-hydroxy-3-(2-(trifluoromethyl)allyl) azetidine-1-carboxylate In analogy to the experimental procedure of tert-butyl 3-(allyloxy)-3-(2-fluoroallyl)azetidine-1-carboxylate, tert-butyl 3-oxoazetidine-1-carboxylate and 3-bromo-2-methyl-prop-1-ene were converted into the title compound (789 mg, 30%) which was obtained as a colourless oil. MS (ESI): 172.4 ($[M-C_4H_8+H]^+$).

b) tert-butyl 3-(allyloxy)-3-(2-(trifluoromethyl)allyl) azetidine-1-carboxylate In analogy to the experimental procedure of tert-butyl 3-allyl-3-((2-fluoroallyl)oxy)azetidine-1-carboxylate, tert-butyl 3-hydroxy-3-(2-methylallyl)azetidine-1-carboxylate and 3-bromoprop-1-ene were converted into the title compound (670 mg, 72%) which was obtained as a yellow oil. MS (ESI): 212.5 ($[M-C_4H_8+H]^+$).

c) tert-butyl 8-methyl-5-oxa-2-azaspiro[3.5]non-7-ene-2-carboxylate

In analogy to the experimental procedure of tert-butyl 7-fluoro-5-oxa-2-azaspiro[3.5]non-7-ene-2-carboxylate, tert-butyl 3-(allyloxy)-3-(2-methylallyl)azetidine-1-carboxylate was converted into the title compound (560 mg, 93%) which was obtained as a green oil. MS (ESI): 183.9 ($[M+H]^+$).

d) tert-butyl 8-methyl-5-oxa-2-azaspiro[3.5]nonane-2-carboxylate

In analogy to the experimental procedure of tert-butyl 7-fluoro-5-oxa-2-azaspiro[3.5]nonane-2-carboxylate, tert-butyl 8-methyl-5-oxa-2-azaspiro[3.5]non-7-ene-2-carboxylate was converted into the title compound (423 mg, 75%) which was obtained as a light brown solid. MS(ESI): 186.1 ($[M-C_4H_8+H]^+$).

e) 8-methyl-5-oxa-2-azaspiro[3.5]nonane hydrochloride

In analogy to the experimental procedure of 7-fluoro-5-oxa-2-azaspiro[3.5]nonane hydrochloride, tert-butyl 8-methyl-5-oxa-2-azaspiro[3.5]nonane-2-carboxylate was converted into the title compound (312 mg, 100%) which was obtained as an orange solid. MS (ESI): 142.3 ($[M+H]^+$).

4-fluoro-1-oxa-9-azaspiro[5.5]undecane

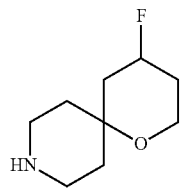

a) 9-benzyl-1-oxa-9-azaspiro[5.5]undecan-4-ol

To a mixture of 1-benzyl-4-piperidone (4.9 mL, 26.42 mmol) and 3-buten-1-ol (1.91 g, 26.42 mmol) was slowly added sulfuric acid (70%, 10.0 mL, 26.42 mmol) at 0° C. The reaction mixture was vigorously stirred overnight, than diluted with water (100 mL) and the pH was adjusted to 7-8 with sodium bicarbonate. The organic layer was extracted with ethyl acetate (2×200 mL). The combined organic phases were washed with brine, dried over sodium sulfate and concentrated in vacuo. Purification by chromatography (NH-functionalised silica, ethyl acetate/hexane) afforded the title compound (5 g, 65% yield)) as a colourless liquid. MS (ESI): 262.5 ([M+H]$^+$).

b) 9-benzyl-4-fluoro-1-oxa-9-azaspiro[5.5]undecane

To a stirred solution of triethylamine trihydrofluoride (1.87 mL, 11.48 mmol) in dichloromethane (50 mL) at room temperature were successively added Xtalfluor-e (1.97 g, 8.61 mmol) and 9-benzyl-1-oxa-9-azaspiro[5.5]undecan-4-ol (1.5 g, 5.74 mmol) After 24 h, the reaction mixture was cooled down to 0-5° C., quenched with 5% aq sodium bicarbonate solution and the resulting mixture was extracted with dichloromethane. The combined organic phase was washed with brine, dried over sodium sulfate and concentrated in vacuo. Purification by HPLC afforded the title compound (505 mg, 33%) as a colourless oil. MS (ESI): 263.9 ([M+H]$^+$).

c) 4-fluoro-1-oxa-9-azaspiro[5.5]undecane

In analogy to the experimental procedure of tert-butyl 7-fluoro-5-oxa-2-azaspiro[3.5]nonane-2-carboxylate, 9-benzyl-4-fluoro-1-oxa-9-azaspiro[5.5]undecane was converted into the title compound (329 mg, 73%) which was obtained as an off-white solid. MS (ESI): 172.3 ([M+H]$^+$).

Example 1

N-methyl-N-[(3S)-1-[1-[[5-methyl-3-(6-methyl-3-pyridyl)isoxazol-4-yl]methyl]-6-oxo-pyridazin-4-yl]pyrrolidin-3-yl]acetamide

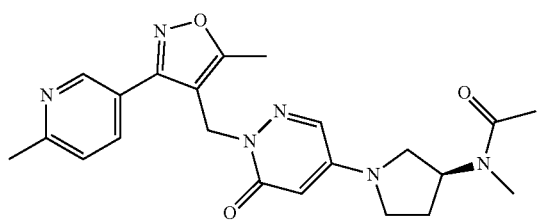 [SMILES: CC(=O)N(C)[C@H]1CCN(c2cnn(Cc3c(-c4ccc(C)nc4)noc3C)c(=O)c2)C1]

To a solution of 5-chloro-2-[[5-methyl-3-(6-methyl-3-pyridyl)isoxazol-4-yl]methyl]pyridazin-3-one (building block A, 88.5 mg, 0.279 mmol) in DMSO (1 mL) was added under an atmosphere of argon N-methyl-N-(pyrrolidin-3-yl)acetamide (55.7 µL, 0.419 mmol) and potassium carbonate (116 mg, 0.838 mmol). The vial was capped and heated to 80° C. for 18 h. The reaction mixture was diluted with EtOAc (20 mL) and was washed with water (15 mL) and brine (15 mL). The aqueous layers were extracted twice with EtOAc (20 mL). The combined organic extracts were dried (MgSO$_4$), filtered and concentrated in vacuo. Purification by flash chromatography (silica, gradient: 0% to 10% MeOH in CH$_2$Cl$_2$) afforded the racemic title compound (107 mg, 90%) as an off-white foam. MS (ESI): 423.3 ([M+H]$^+$).

Separation of the enantiomers by chiral HPLC (column: Chiralpak AD) afforded the (+)-title compound which was obtained as an off-white foam.

Example 2

N-methyl-N-[(3R)-1-[1-[[5-methyl-3-(6-methyl-3-pyridyl)isoxazol-4-yl]methyl]-6-oxo-pyridazin-4-yl]pyrrolidin-3-yl]acetamide

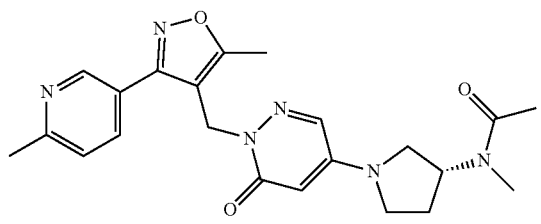 [SMILES: CC(=O)N(C)[C@@H]1CCN(c2cnn(Cc3c(-c4ccc(C)nc4)noc3C)c(=O)c2)C1]

In analogy to experiment of example 1, separation of the enantiomers by chiral HPLC (column: Chiralcel OD) afforded the (−)-title compound (39 mg) which was obtained as an off-white foam. MS (ESI): 423.2 ([M+H]$^+$).

Example 3

5-[(3R)-3-hydroxypyrrolidin-1-yl]-2-[[5-methyl-3-(6-methyl-3-pyridyl)isoxazol-4-yl]methyl]pyridazin-3-one

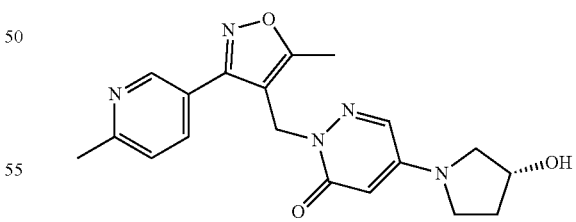

To a stirred suspension of 5-chloro-2-[[5-methyl-3-(6-methyl-3-pyridyl)isoxazol-4-yl]methyl]pyridazin-3-one (building block A, 300 mg, 0.947 mmol) and (R)-3-hydroxypyrrolidine (0.14 mL, 1.73 mmol) in DMSO (0.5 mL) and acetonitrile (3 mL) was added potassium carbonate (393 mg, 2.84 mmol) Then the reaction mixture was stirred at 70° C. for 18 h. After cooling to room temperature the reaction mixture was diluted with EtOAc (80 mL) was washed three times with water (10 mL) and brine (10 mL). The aqueous layers were back extracted twice with EtOAc (80 mL). The combined organic extracts were dried (Na$_2$SO$_4$), filtered and concentrated in vacuo. Purification by flash chromatography (silica, gradient: 0% to 10% MeOH in CH$_2$Cl$_2$) afforded the title compound (341 mg, 93%) as an off-white foam. MS (ESI): 368.2 ([M+H]$^+$).

Example 4

5-[(3S)-3-hydroxypyrrolidin-1-yl]-2-[[5-methyl-3-(6-methyl-3-pyridyl)isoxazol-4-yl]methyl]pyridazin-3-one

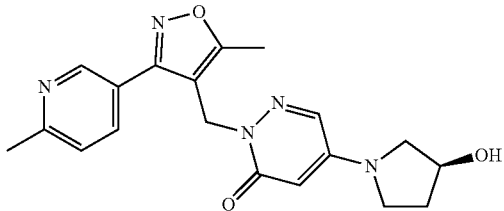 [SMILES: Cc1ccc(-c2noc(C)c2Cn2ncc(N3CC[C@H](O)C3)cc2=O)cn1]

In analogy to experiment of example 3, 5-chloro-2-[[5-methyl-3-(6-methyl-3-pyridyl)isoxazol-4-yl]methyl]pyridazin-3-one, using (S)-3-hydroxypyrrolidine instead of (R)-3-hydroxypyrrolidine, was converted into the title compound (378 mg, 82%) which was obtained as a white solid. MS (ESI): 368.2 ([M+H]$^+$).

Example 5

5-(4-hydroxy-1-piperidyl)-2-[[5-methyl-3-(6-methyl-3-pyridyl)isoxazol-4-yl]methyl]pyridazin-3-one

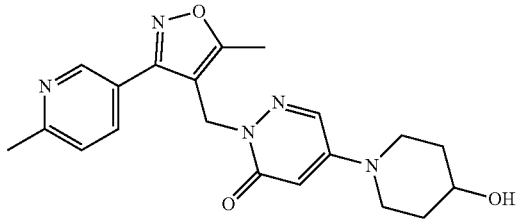 [SMILES: Cc1ccc(-c2noc(C)c2Cn2ncc(N3CCC(O)CC3)cc2=O)cn1]

To a stirred solution of 5-chloro-2-[[5-methyl-3-(6-methyl-3-pyridyl)isoxazol-4-yl]methyl]pyridazin-3-one (building block A, 51.2 mg, 0.162 mmol) in acetonitrile (1 mL) under an atmosphere of argon was added potassium carbonate (67 mg, 0.49 mmol) and piperidin-4-ol (24.5 mg, 0.242 mmol). The vial was capped and heated to 80° C. for 18 h. After cooling to room temperature the reaction mixture was diluted with EtOAc (20 mL) and was washed with water (15 mL) and brine (15 mL). The aqueous layers were extracted twice with EtOAc (20 mL). The combined organic extracts were dried (MgSO$_4$), filtered and concentrated in vacuo. Purification by flash chromatography (silica, gradient: 0% to 10% MeOH in CH$_2$Cl$_2$) afforded the title compound (341 mg, 93%) as an off-white foam. MS (ESI): 382.3 ([M+H]$^+$).

Example 6

5-(2,2-dimethylmorpholin-4-yl)-2-((5-methyl-3-(6-methylpyridin-3-yl)-1,2-oxazol-4-yl)methyl)pyridazin-3-one

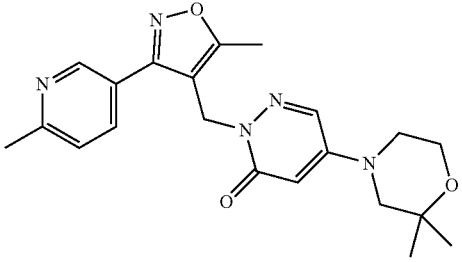

In analogy to experiment of example 5, 5-chloro-2-[[5-methyl-3-(6-methyl-3-pyridyl)isoxazol-4-yl]methyl]pyridazin-3-one, using 2,2-dimethylmorpholine instead of piperidin-4-ol, was converted into the title compound (40.6 mg, 64%) which was obtained as an off-white foam. MS (ESI): 396.3 ([M+H]$^+$).

Example 7

5-(cis-2,6-dimethylmorpholin-4-yl)-2-((5-methyl-3-(6-methylpyridin-3-yl)-1,2-oxazol-4-yl)methyl)pyridazin-3-one

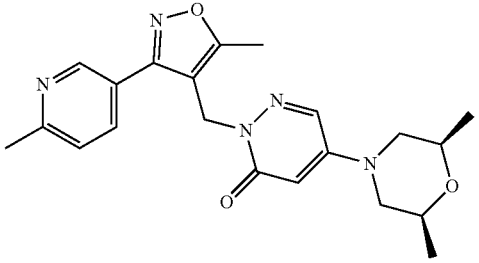

In analogy to experiment of example 3, 5-chloro-2-[[5-methyl-3-(6-methyl-3-pyridyl)isoxazol-4-yl]methyl]pyridazin-3-one, using cis-2,6-dimethylmorpholine instead of (R)-3-hydroxypyrrolidine, was converted into the title compound (205 mg, 71%) which was obtained as a white solid. MS (ESI): 396.2 ([M+H]$^+$).

Example 8 ethyl 1-(1-((5-methyl-3-(6-methylpyridin-3-yl)-1,2-oxazol-4-yl)methyl)-6-oxopyridazin-4-yl)piperidine-4-carboxylate

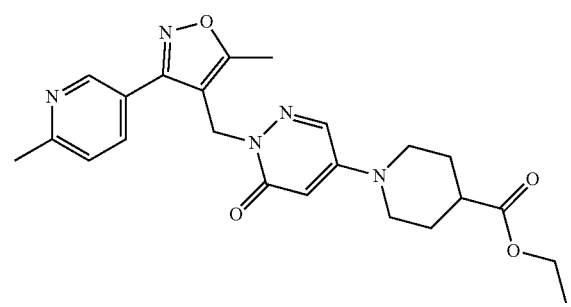 [SMILES: CCOC(=O)C1CCN(c2cnn(Cc3c(-c4ccc(C)nc4)noc3C)c(=O)c2)CC1]

In analogy to experiment of example 5, 5-chloro-2-[[5-methyl-3-(6-methyl-3-pyridyl)isoxazol-4-yl]methyl]pyridazin-3-one, using ethyl piperidine-4-carboxylate instead of piperidin-4-ol, was converted into the title compound (181 mg, 71%) which was obtained as an off-white solid. MS (ESI): 438.3 ([M+H]+).

Example 9

5-(4-(cyclopropanecarbonyl)piperazin-1-yl)-2-((5-methyl-3-(6-methylpyridin-3-yl)isoxazol-4-yl)methyl)pyridazin-3(2H)-one

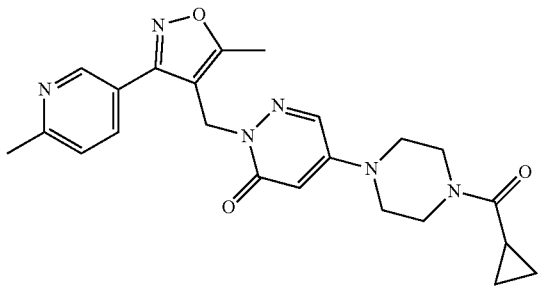 [SMILES: Cc1ccc(-c2noc(C)c2Cn2ncc(N3CCN(C(=O)C4CC4)CC3)cc2=O)cn1]

In analogy to experiment of example 5, 5-chloro-2-[[5-methyl-3-(6-methyl-3-pyridyl)isoxazol-4-yl]methyl]pyridazin-3-one, using cyclopropyl(piperazin-1-yl)methanone instead of piperidin-4-ol, was converted into the title compound (142 mg, 64%) which was obtained as a white solid. MS (ESI): 435.4 ([M+H]+).

Example 10

2-((5-methyl-3-(6-methylpyridin-3-yl)isoxazol-4-yl)methyl)-5-(4-(1-methylcyclopropanecarbonyl)piperazin-1-yl)pyridazin-3(2H)-one

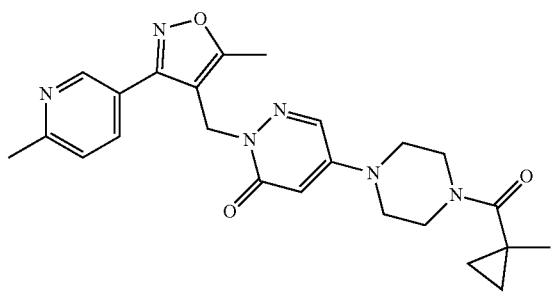

In analogy to experiment of example 5, 5-chloro-2-[[5-methyl-3-(6-methyl-3-pyridyl)isoxazol-4-yl]methyl]pyridazin-3-one, using (1-methylcyclopropyl)(piperazin-1-yl)methanone hydrochloride instead of piperidin-4-ol, was converted into the title compound (36.7 mg, 59%) which was obtained as a white solid. MS (ESI): 449.3 ([M+H]+).

Example 11

2-((3-(4-Fluorophenyl)-5-methylisoxazol-4-yl)methyl)-5-morpholinopyridazin-3(2H)-one

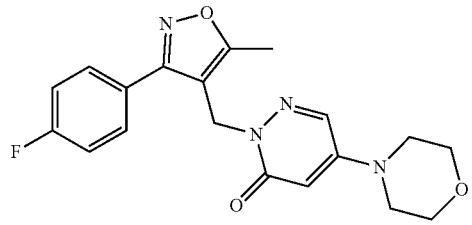 [SMILES: Cc1onc(-c2ccc(F)cc2)c1Cn1ncc(N2CCOCC2)cc1=O]

In analogy to experiment of example 3, 5-chloro-2-[[3-(4-fluorophenyl)-5-methyl-isoxazol-4-yl]methyl]pyridazin-3-one (building block L), using morpholine instead of (R)-3-hydroxypyrrolidine, was converted into the title compound (36 mg, 41%) which was obtained as a light yellow solid. MS (ESI): 371.2 ([M+H]+).

Example 12

5-(cis-2,6-Dimethylmorpholino)-2-((3-(4-fluorophenyl)-5-methylisoxazol-4-yl)methyl)pyridazin-3(2H)-one

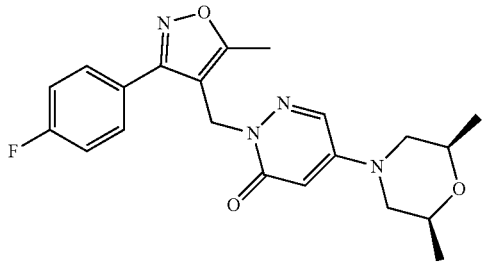 [SMILES: Cc1onc(-c2ccc(F)cc2)c1Cn1ncc(N2C[C@@H](C)O[C@@H](C)C2)cc1=O]

In analogy to experiment of example 3, 5-chloro-2-[[3-(4-fluorophenyl)-5-methyl-isoxazol-4-yl]methyl]pyridazin-3-one (building block L), using cis-2,6-dimethylmorpholine instead of (R)-3-hydroxypyrrolidine, was converted into the title compound (64 mg, 52%) which was obtained as a light yellow solid. MS (ESI): 399.3 ([M+H]+).

Example 13

2-((3-(5-Chloropyridin-2-yl)-5-methylisoxazol-4-yl)methyl)-5-(cis-2,6-dimethylmorpholino)pyridazin-3(2H)-one

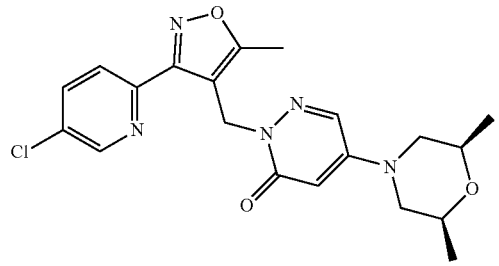 [SMILES: Cc1onc(-c2ccc(Cl)cn2)c1Cn1ncc(N2C[C@@H](C)O[C@@H](C)C2)cc1=O]

In analogy to experiment of example 3, 5-chloro-2-[[3-(5-chloro-2-pyridyl)-5-methyl-isoxazol-4-yl]methyl]pyridazin-3-one (building block M), using cis-2,6-dimethylmorpholine instead of (R)-3-hydroxypyrrolidine, was converted into the title compound (66 mg, 68%) which was obtained as a light yellow solid. MS (ESI): 416.2 ([M+H]⁺).

Example 14

2-((3-(5-Chloropyridin-2-yl)-5-cyclopropylisoxazol-4-yl)methyl)-5-(cis-2,6-dimethylmorpholino)pyridazin-3(2H)-one

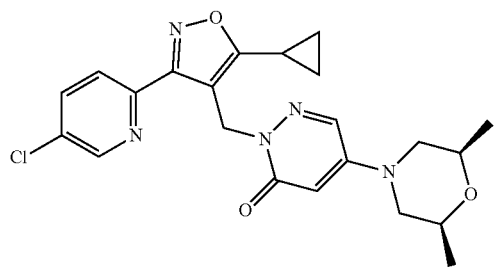 [SMILES: C[C@@H]1CN(c2cnn(Cc3c(-c4ccc(Cl)cn4)noc3C3CC3)c(=O)c2)C[C@H](C)O1]

In analogy to experiment of example 3, 5-chloro-2-[[3-(5-chloro-2-pyridyl)-5-cyclopropyl-isoxazol-4-yl]methyl]pyridazin-3-one (building block N), using cis-2,6-dimethyl-morpholine instead of (R)-3-hydroxypyrrolidine, was converted into the title compound (19 mg, 19%) which was obtained as a light yellow foam. MS (ESI): 442.3 ([M+H]⁺).

Example 15

2-((3-(4-Fluorophenyl)-5-methylisoxazol-4-yl)methyl)-5-(4-(1-methylcyclopropanecarbonyl)piperazin-1-yl)pyridazin-3(2H)-one

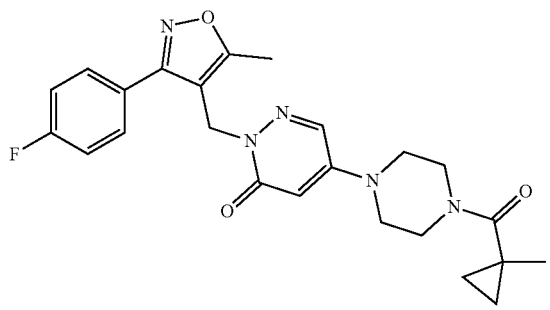 [SMILES: Cc1onc(-c2ccc(F)cc2)c1Cn1ncc(N2CCN(C(=O)C3(C)CC3)CC2)cc1=O]

In analogy to experiment of example 3, 5-chloro-2-[[3-(4-fluorophenyl)-5-methyl-isoxazol-4-yl]methyl]pyridazin-3-one (building block L), using (1-methylcyclopropyl)-piperazin-1-yl-methanone hydrochloride instead of (R)-3-hydroxypyrrolidine, was converted into the title compound (210 mg, 52%) which was obtained as a light yellow solid. MS (ESI): 452.3 ([M+H]⁺).

Example 16

2-((3-(5-Chloropyridin-2-yl)-5-methylisoxazol-4-yl)methyl)-5-(4-(1-methylcyclopropanecarbonyl)piperazin-1-yl)pyridazin-3(2H)-one

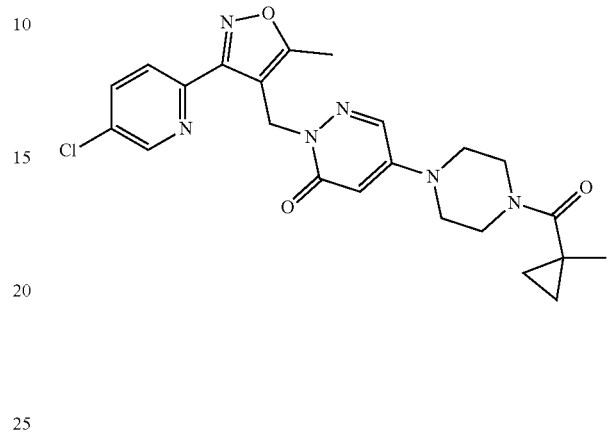

In analogy to experiment of example 3, 5-chloro-2-[[3-(5-chloro-2-pyridyl)-5-methyl-isoxazol-4-yl]methyl]pyridazin-3-one (building block M), using (1-methylcyclopropyl)-piperazin-1-yl-methanone hydrochloride instead of (R)-3-hydroxypyrrolidine, was converted into the title compound (33 mg, 33%) which was obtained as an off-white solid. MS (ESI): 469.3 ([M+H]⁺).

Example 22

2-[[5-methyl-3-(6-methyl-3-pyridyl)isoxazol-4-yl]methyl]-5-morpholino-pyridazin-3-one

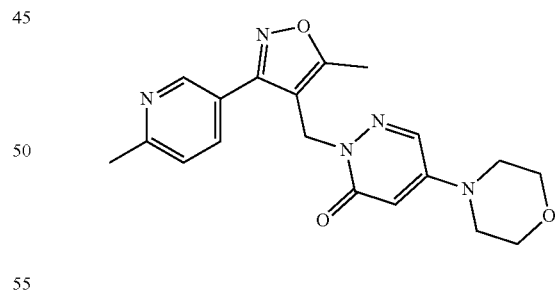

In analogy to experiment of example 5, 5-chloro-2-[[5-methyl-3-(6-methyl-3-pyridyl)isoxazol-4-yl]methyl]pyridazin-3-one, using morpholine instead of piperidin-4-ol, was converted into the title compound (61 mg, 88%) which was obtained as a light yellow solid. MS (ESI): 368.2 ([M+H]⁺).

Example 24

2-[[5-methyl-3-(6-methyl-3-pyridyl)isoxazol-4-yl]methyl]-5-[4-(trifluoromethyl)-1-piperidyl]pyridazin-3-one

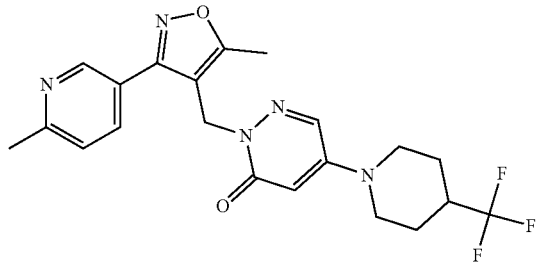 [SMILES: Cc1ccc(-c2noc(C)c2Cn2ncc(N3CCC(C(F)(F)F)CC3)cc2=O)cn1]

In analogy to experiment of example 5, 5-chloro-2-[[5-methyl-3-(6-methyl-3-pyridyl)isoxazol-4-yl]methyl]pyridazin-3-one, using 4-(trifluoromethyl)piperidine instead of (R)-3-hydroxypyrrolidine, was converted into the title compound (70 mg, 85%) which was obtained as an off white solid. MS (ESI): 434.2 ([M+H]$^+$).

Example 25

2-((3-(5-Chloropyridin-2-yl)-5-cyclopropylisoxazol-4-yl)methyl)-5-(4-(cyclopropanecarbonyl)piperazin-1-yl)pyridazin-3(2H)-one

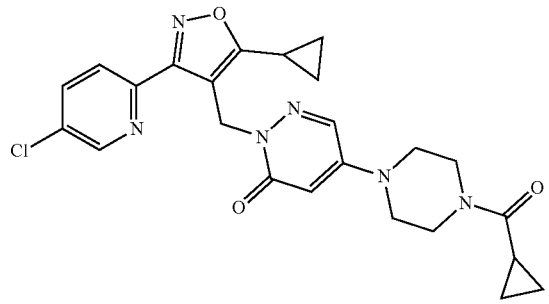 [SMILES: O=C(C1CC1)N1CCN(c2cnn(Cc3c(-c4ccc(Cl)cn4)noc3C3CC3)c(=O)c2)CC1]

In analogy to experiment of example 3, 5-chloro-2-[[3-(5-chloro-2-pyridyl)-5-cyclopropyl-isoxazol-4-yl]methyl]pyridazin-3-one (building block N), using cyclopropyl(piperazin-1-yl)methanone instead of (R)-3-hydroxypyrrolidine, was converted into the title compound (49 mg, 62%) which was obtained as an off-white solid. MS (ESI): 481.3 ([M+H]$^+$).

Example 26

2-((3-(5-Chloropyridin-2-yl)-5-cyclopropylisoxazol-4-yl)methyl)-5-(4-(1-methylcyclopropanecarbonyl)piperazin-1-yl)pyridazin-3(2H)-one

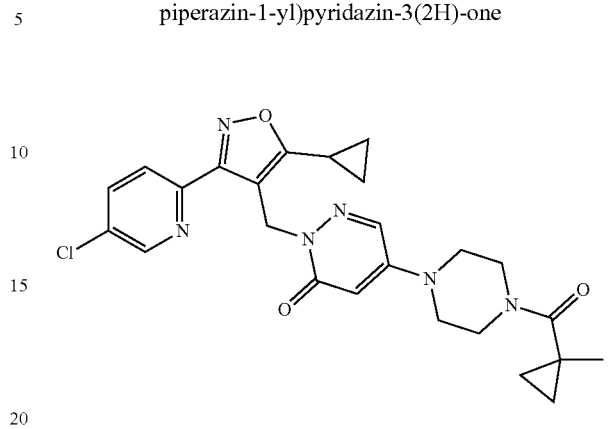

In analogy to experiment of example 3, 5-chloro-2-[[3-(5-chloro-2-pyridyl)-5-cyclopropyl-isoxazol-4-yl]methyl]pyridazin-3-one (building block N), using (1-methylcyclopropyl)(piperazin-1-yl)methanone hydrochloride instead of (R)-3-hydroxypyrrolidine, was converted into the title compound (48 mg, 58%) which was obtained as an off-white foam. MS (ESI): 495.2 ([M+H]$^+$).

Example 27

N-cyclopropyl-1-[1-[[5-methyl-3-(6-methyl-3-pyridyl)isoxazol-4-yl]methyl]-6-oxo-pyridazin-4-yl]piperidine-4-carboxamide

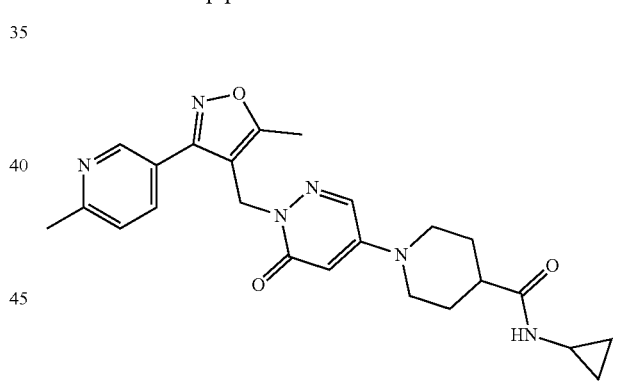

a) ethyl 1-[1-[[5-methyl-3-(6-methyl-3-pyridyl)isoxazol-4-yl]methyl]-6-oxo-pyridazin-4-yl]piperidine-4-carboxylate In analogy to experiment of example 5, 5-chloro-2-[[5-methyl-3-(6-methyl-3-pyridyl)isoxazol-4-yl]methyl]pyridazin-3-one, using ethyl piperidine-4-carboxylate instead of piperidin-4-ol, was converted into the title compound (40.6 mg, 64%) which was obtained as an off-white solid. MS (ESI): 438.3 ([M+H]$^+$).

b) 1-[1-[[5-methyl-3-(6-methyl-3-pyridyl)isoxazol-4-yl]methyl]-6-oxo-pyridazin-4-yl]piperidine-4-carboxylic acid To a solution of ethyl 1-[1-[[5-methyl-3-(6-methyl-3-pyridyl)isoxazol-4-yl]methyl]-6-oxo-pyridazin-4-yl]piperidine-4-carboxylate (170 mg, 0.389 mmol) in THF (0.9 mL) and methanol (0.9 mL) was added lithium hydroxide monohydrate (50 mg, 1.19 mmol) followed by water (0.9 mL). The reaction mixture was stirred at room temperature for 2.5 h. Then the reaction mixture was acidified with 5% citric acid-solution and then extracted with EtOAc. The aqueous layer was back extracted with EtOAc. The organic layers were washed with water and brine. The organic layers were combined, dried over sodium sulfate, filtered and concentrated to afford the title compound (145 mg, 91%) as a light yellow foam. MS (ESI): 410.2 ([M+H]$^+$).

c) N-cyclopropyl-1-[1-[[5-methyl-3-(6-methyl-3-pyridyl)isoxazol-4-yl]methyl]-6-oxo-pyridazin-4-yl]piperidine-4-carboxamide To a solution of 1-[1-[[5-methyl-3-(6-methyl-3-pyridyl)isoxazol-4-yl]methyl]-6-oxo-pyridazin-4-yl]piperidine-4-carboxylic acid (50 mg, 0.11 mmol) in EtOAc (2 mL) was added cyclopropylamine (16 µL, 0.23 mmol), triethylamine (100 µL, 0.72 mmol) and propylphosphonic anhydride solution >50 wt. % in EtOAc (0.14 mL, 0.24 mmol) and the reaction mixture was stirred at room temperature overnight. After the addition of cyclopropylamine (16 µL, 0.23 mmol) and propylphosphonic anhydride solution >50 wt. % in EtOAc (70 µL, 0.12 mmol) the reaction mixture was stirred at 50° C. for 4 h. After cooling to room temperature the reaction mixture was extracted with EtOAc (30 mL) and saturated solution of NaHCO$_3$(5 mL). The aqueous layer was back extracted with EtOAc (30 mL). The organic layers were washed with water (5 mL) and brine (5 mL). The organic layers were combined, dried over sodium sulfate, filtered and concentrated. Purification by flash chromatography (silica, gradient: 0% to 10% MeOH in CH$_2$Cl$_2$) afforded the title compound (43 mg, 87%) as an off-white solid. MS (ESI): 449.3 ([M+H]$^+$).

Example 28

2-[[5-methyl-3-(6-methyl-3-pyridyl)isoxazol-4-yl]methyl]-5-[(1R,5S)-8-oxa-3-azabicyclo[3.2.1]octan-3-yl]pyridazin-3-one

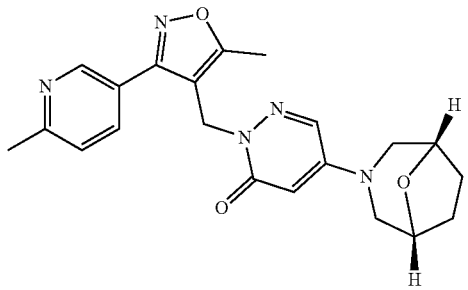 [SMILES: Cc1ccc(-c2noc(C)c2Cn2ncc(N3C[C@H]4CC[C@@H](C3)O4)cc2=O)cn1]

In analogy to experiment of example 3, 5-chloro-2-[[5-methyl-3-(6-methyl-3-pyridyl)isoxazol-4-yl]methyl]pyridazin-3-one, using (1R,5S)-8-oxa-3-azabicyclo[3.2.1]octane hydrochloride instead of (R)-3-hydroxypyrrolidine, was converted into the title compound (76 mg, 87%) which was obtained as an off-white solid. MS (ESI): 394.2 ([M+H]$^+$).

Example 29

5-[(2S,6S)-2,6-dimethylmorpholin-4-yl]-2-[[5-methyl-3-(6-methyl-3-pyridyl)isoxazol-4-yl]methyl]pyridazin-3-one or enantiomer

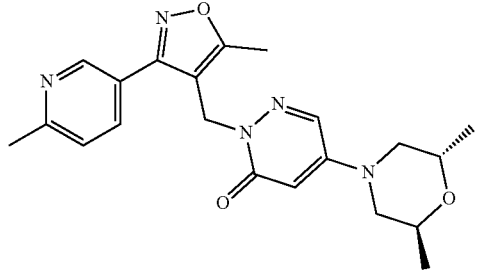

In analogy to experiment of example 5, 5-chloro-2-[[5-methyl-3-(6-methyl-3-pyridyl)isoxazol-4-yl]methyl]pyridazin-3-one, using trans-2,6-dimethylmorpholine instead of piperidin-4-ol, was converted into the racemic title compound (109 mg, 87%) which was obtained as a yellow foam. MS (ESI): 396.3 ([M+H]$^+$). Separation of the enantiomers by chiral HPLC (column: Reprosil Chiral-NR) afforded the (+)-title compound (33 mg) which was obtained as a light yellow foam. MS (ESI): 396.2 ([M+H]$^+$).

Example 30

5-[(2R,6R)-2,6-dimethylmorpholin-4-yl]-2-[[5-methyl-3-(6-methyl-3-pyridyl)isoxazol-4-yl]methyl]pyridazin-3-one or enantiomer

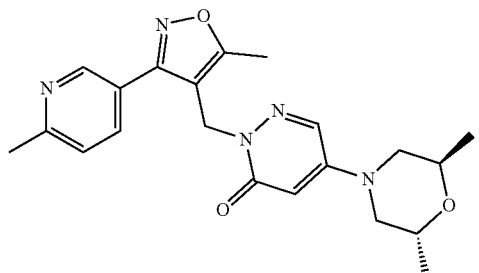

In analogy to experiment of example 29, separation of the enantiomers by chiral HPLC (column: Reprosil Chiral-NR) afforded the (−)-title compound (37 mg) which was obtained as a light yellow foam. MS (ESI): 396.2 ([M+H]$^+$).

Example 31

2-[[5-methyl-3-(6-methyl-3-pyridyl)isoxazol-4-yl]methyl]-5-[4-(2,2,2-trifluoroethyl)piperazin-1-yl]pyridazin-3-one

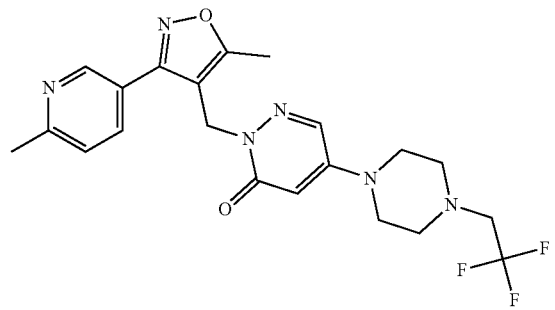 [SMILES: Cc1ccc(-c2noc(C)c2Cn2ncc(N3CCN(CC(F)(F)F)CC3)cc2=O)cn1]

In analogy to experiment of example 3, 5-chloro-2-[[5-methyl-3-(6-methyl-3-pyridyl)isoxazol-4-yl]methyl]pyridazin-3-one, using 1-(2,2,2-trifluoroethyl)piperazine hydrochloride instead of (R)-3-hydroxypyrrolidine, was converted into the title compound (81 mg, 82%) which was obtained as an off-white solid. MS (ESI): 449.2 ([M+H]$^+$).

Example 32

5-(cis-2,6-dimethylmorpholin-4-yl)-2-[[3-(6-methyl-3-pyridyl)isoxazol-4-yl]methyl]pyridazin-3-one

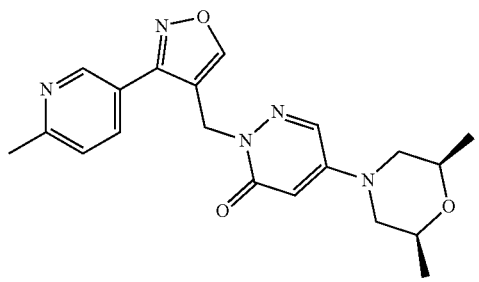

In analogy to experiment of example 3, 5-chloro-2-[[3-(6-methyl-3-pyridyl)isoxazol-4-yl]methyl]pyridazin-3-one (building block E), using cis-2,6-dimethylmorpholine instead of (R)-3-hydroxypyrrolidine, was converted into the title compound (436 mg, 77%) which was obtained as an off-white foam. MS (ESI): 382.2 ([M+H]$^+$).

Example 33

2-[[5-methyl-3-(6-methyl-3-pyridyl)isoxazol-4-yl]methyl]-5-(3-oxa-6-azabicyclo[3.1.1]heptan-6-yl)pyridazin-3-one

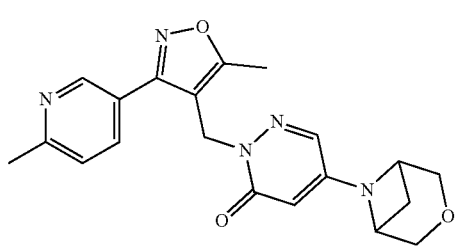 [SMILES: Cc1ccc(-c2noc(C)c2Cn2ncc(N3C4COCC3C4)cc2=O)cn1]

In analogy to experiment of example 3, 5-chloro-2-[[5-methyl-3-(6-methyl-3-pyridyl)isoxazol-4-yl]methyl]pyridazin-3-one, using 3-oxa-6-azabicyclo[3.1.1]heptane 2,2,2-trifluoroacetate instead of (R)-3-hydroxypyrrolidine, was converted into the title compound (51 mg, 77%) which was obtained as a light yellow foam. MS (ESI): 380.2 ([M+H]$^+$).

Example 34

1-[1-[[5-methyl-3-(6-methyl-3-pyridyl)isoxazol-4-yl]methyl]-6-oxo-pyridazin-4-yl]piperidine-4-carbonitrile

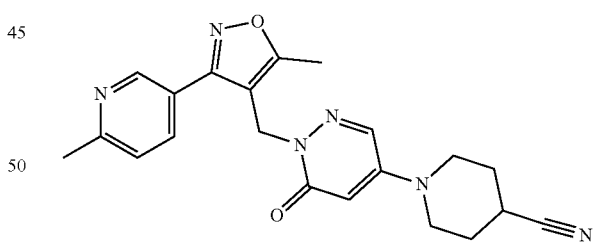

In analogy to experiment of example 3, 5-chloro-2-[[5-methyl-3-(6-methyl-3-pyridyl)isoxazol-4-yl]methyl]pyridazin-3-one, using piperidine-4-carbonitrile instead of (R)-3-hydroxypyrrolidine, was converted into the title compound (38 mg, 69%) which was obtained as a light yellow foam. MS (ESI): 391.2 ([M+H]$^+$).

Example 35

2-[[5-methyl-3-(6-methyl-3-pyridyl)isoxazol-4-yl]methyl]-5-(3-oxa-8-azabicyclo[3.2.1]octan-8-yl)pyridazin-3-one

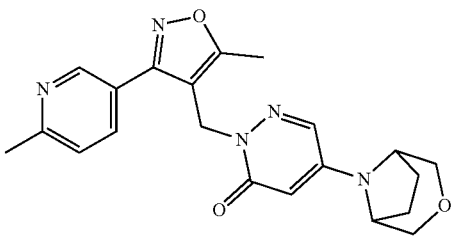 [SMILES: Cc1ccc(-c2noc(C)c2Cn2ncc(N3C4CCC3COC4)cc2=O)cn1]

In analogy to experiment of example 3, 5-chloro-2-[[5-methyl-3-(6-methyl-3-pyridyl)isoxazol-4-yl]methyl]pyridazin-3-one, using 3-oxa-8-azabicyclo[3.2.1]octane hydrochloride instead of (R)-3-hydroxypyrrolidine, was converted into the title compound (29 mg, 52%) which was obtained as a light yellow foam. MS (ESI): 394.2 ([M+H]$^+$).

Example 36

5-(4-cyclopropylpiperazin-1-yl)-2-[[5-methyl-3-(6-methyl-3-pyridyl)isoxazol-4-yl]methyl]pyridazin-3-one

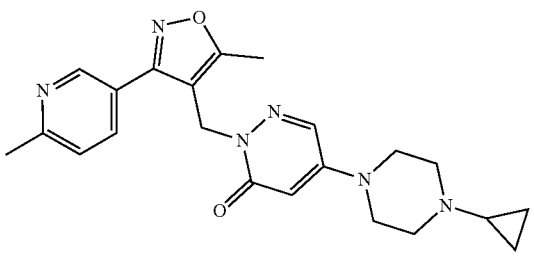 [SMILES: Cc1ccc(-c2noc(C)c2Cn2ncc(N3CCN(C4CC4)CC3)cc2=O)cn1]

In analogy to experiment of example 3, 5-chloro-2-[[5-methyl-3-(6-methyl-3-pyridyl)isoxazol-4-yl]methyl]pyridazin-3-one, using 1-cyclopropylpiperazine hydrochloride instead of (R)-3-hydroxypyrrolidine, was converted into the title compound (65 mg, 84%) which was obtained as an off-white solid. MS (ESI): 407.2 ([M+H]$^+$).

Example 38

2-[[5-methyl-3-(6-methyl-3-pyridyl)isoxazol-4-yl]methyl]-5-(2-oxa-6-azaspiro[3.3]heptan-6-yl)pyridazin-3-one

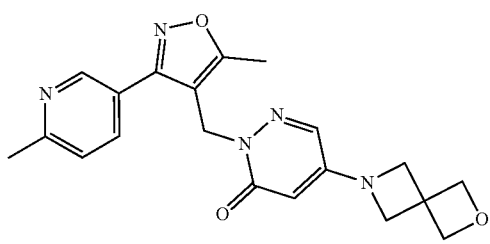 [SMILES: Cc1ccc(-c2noc(C)c2Cn2ncc(N3CC4(COC4)C3)cc2=O)cn1]

In analogy to experiment of example 3, 5-chloro-2-[[5-methyl-3-(6-methyl-3-pyridyl)isoxazol-4-yl]methyl]pyridazin-3-one, using 2-oxa-6-azaspiro[3.3]heptane oxalate instead of (R)-3-hydroxypyrrolidine, was converted into the title compound (55 mg, 66%) which was obtained as an off-white solid. MS (ESI): 380.1 ([M+H]$^+$).

Example 39

5-(cis-2,6-dimethylmorpholin-4-yl)-2-[[5-methyl-3-[6-(trifluoromethyl)-3-pyridyl]isoxazol-4-yl]methyl]pyridazin-3-one

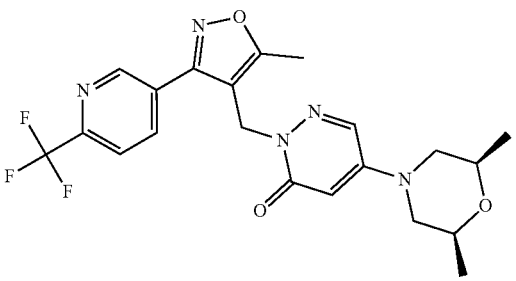 [SMILES: Cc1onc(-c2ccc(C(F)(F)F)nc2)c1Cn1ncc(N2C[C@@H](C)O[C@@H](C)C2)cc1=O]

In analogy to experiment of example 3, 5-chloro-2-[[5-methyl-3-[6-(trifluoromethyl)-3-pyridyl]isoxazol-4-yl]methyl]pyridazin-3-one (building block C), using cis-2,6-dimethylmorpholine instead of (R)-3-hydroxypyrrolidine, was converted into the title compound (72 mg, 91%) which was obtained as an off-white foam. MS (ESI): 450.2 ([M+H]$^+$).

Example 40

5-[4-(1-methylcyclopropanecarbonyl)piperazin-1-yl]-2-[[5-methyl-3-[6-(trifluoromethyl)-3-pyridyl]isoxazol-4-yl]methyl]pyridazin-3-one

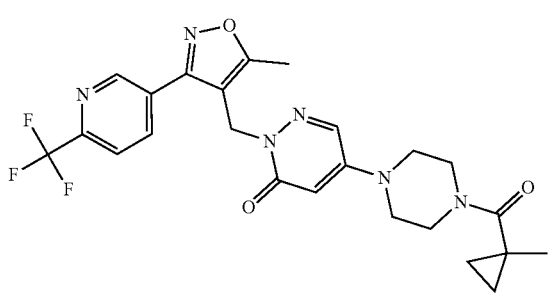 [SMILES: Cc1onc(-c2ccc(C(F)(F)F)nc2)c1Cn1ncc(N2CCN(C(=O)C3(C)CC3)CC2)cc1=O]

In analogy to experiment of example 3, 5-chloro-2-[[5-methyl-3-[6-(trifluoromethyl)-3-pyridyl]isoxazol-4-yl]methyl]pyridazin-3-one (building block C), using (1-Methylcyclopropyl)(piperazin-1-yl)methanone hydrochloride instead of (R)-3-hydroxypyrrolidine, was converted into the title compound (49 mg, 56%) which was obtained as an off-white foam. MS (ESI): 503.2 ([M+H]$^+$).

Example 43

2-(1-((5-methyl-3-(6-methylpyridin-3-yl)isoxazol-4-yl)methyl)-6-oxo-1,6-dihydropyridazin-4-yl)hexahydropyrrolo[1,2-a]pyrazin-6(2H)-one

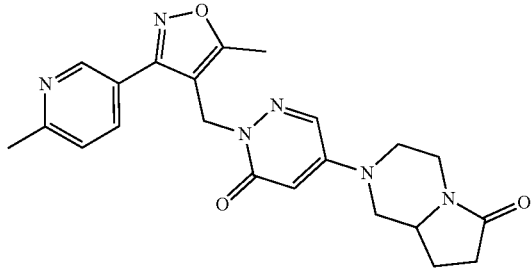

In analogy to experiment of example 3, 5-chloro-2-[[5-methyl-3-(6-methyl-3-pyridyl)isoxazol-4-yl]methyl]pyridazin-3-one, using hexahydropyrrolo[1,2-a]pyrazin-6(2H)-one instead of (R)-3-hydroxypyrrolidine, was converted into the title compound (20 mg, 15%) which was obtained as a yellow solid. MS (ESI): 421.2.1 ([M+H]$^+$).

Example 44

7-(1-((5-methyl-3-(6-methylpyridin-3-yl)isoxazol-4-yl)methyl)-6-oxo-1,6-dihydropyridazin-4-yl)tetrahydro-1H-oxazolo[3,4-a]pyrazin-3(5H)-one

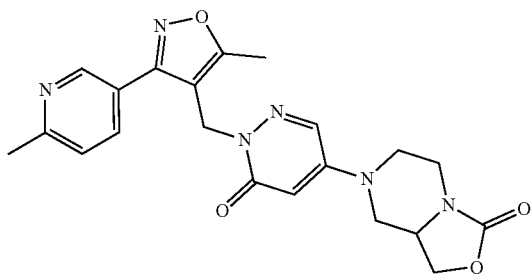 [SMILES: Cc1ccc(-c2noc(C)c2Cn2ncc(N3CCN4C(=O)OCC4C3)cc2=O)cn1]

In analogy to experiment of example 3, 5-chloro-2-[[5-methyl-3-(6-methyl-3-pyridyl)isoxazol-4-yl]methyl]pyridazin-3-one, using tetrahydro-1H-oxazolo[3,4-a]pyrazin-3(5H)-one hydrochloride instead of (R)-3-hydroxypyrrolidine, was converted into the title compound (46 mg, 37%) which was obtained as a yellow solid. MS (ESI): 423.2 ([M+H]$^+$).

Example 45

5-(dimethylamino)-2-((5-methyl-3-(6-methylpyridin-3-yl)isoxazol-4-yl)methyl)pyridazin-3(2H)-one

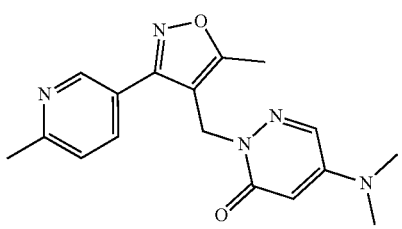

In analogy to experiment of example 64, 5-chloro-2-[[5-methyl-3-(6-methyl-3-pyridyl)isoxazol-4-yl]methyl]pyridazin-3-one, using dimethylamine instead of N-methylcyclopropanamine oxalate, was converted into the title compound (19 mg, 19%) which was obtained as a light yellow solid. MS (ESI): 326.1 ([M+H]$^+$).

Example 46

2-[[5-methyl-3-(6-methyl-3-pyridyl)isoxazol-4-yl]methyl]-5-(2-oxa-7-azaspiro[3.5]nonan-7-yl)pyridazin-3-one

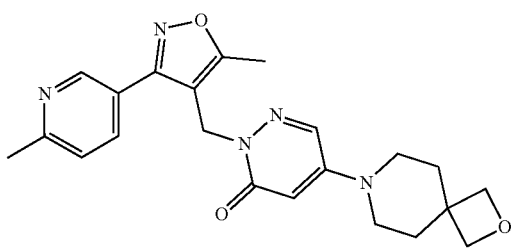 [SMILES: Cc1ccc(-c2noc(C)c2Cn2ncc(N3CCC4(CC3)COC4)cc2=O)cn1]

In analogy to experiment of example 3, 5-chloro-2-[[5-methyl-3-(6-methyl-3-pyridyl)isoxazol-4-yl]methyl]pyridazin-3-one, using 2-oxa-7-azaspiro[3.5]nonane 2,2,2-trifluoroacetate instead of (R)-3-hydroxypyrrolidine, was converted into the title compound (60 mg, 78%) which was obtained as an off-white foam. MS (ESI): 408.2 ([M+H]$^+$).

Example 49

5-[(3aR,6aS)-1,3,3a,4,6,6a-hexahydrofuro[3,4-c]pyrrol-5-yl]-2-[[5-methyl-3-(6-methyl-3-pyridyl)isoxazol-4-yl]methyl]pyridazin-3-one

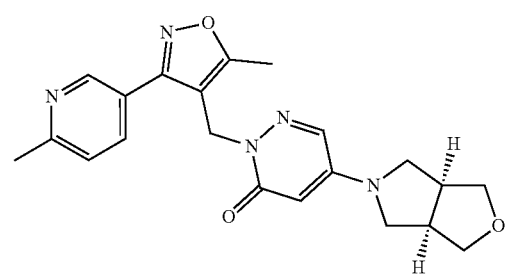 [SMILES: Cc1ccc(-c2noc(C)c2Cn2ncc(N3C[C@H]4COC[C@H]4C3)cc2=O)cn1]

In analogy to experiment of example 3, 5-chloro-2-[[5-methyl-3-(6-methyl-3-pyridyl)isoxazol-4-yl]methyl]pyridazin-3-one, using (3aR,6aS)-3,3a,4,5,6,6a-hexahydro-1H-furo[3,4-c]pyrrole hydrochloride instead of (R)-3-hydroxypyrrolidine, was converted into the title compound (59 mg, 68%) which was obtained as an off-white foam. MS (ESI): 394.2 ([M+H]$^+$).

Example 50

2-[[5-methyl-3-(6-methyl-3-pyridyl)isoxazol-4-yl]methyl]-5-[(3R)-3-methylpiperazin-1-yl]pyridazin-3-one

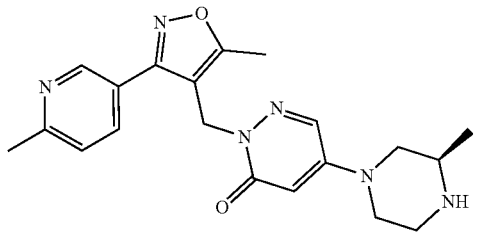

a) tert-butyl (2R)-2-methyl-4-[1-[[5-methyl-3-(6-methyl-3-pyridyl)isoxazol-4-yl]methyl]-6-oxo-pyridazin-4-yl]piperazine-1-carboxylate In analogy to experiment of example 3, 5-chloro-2-[[5-methyl-3-(6-methyl-3-pyridyl)isoxazol-4-yl]methyl]pyridazin-3-one, using tert-butyl (2R)-2-methylpiperazine-1-carboxylate instead of (R)-3-hydroxypyrrolidine, was converted into the title compound (123 mg, 74%) which was obtained as an off-white foam. MS (ESI): 481.3 ([M+H]$^+$).

b) 2-[[5-methyl-3-(6-methyl-3-pyridyl)isoxazol-4-yl]methyl]-5-[(3R)-3-methylpiperazin-1-yl]pyridazin-3-one To a solution of tert-butyl (2R)-2-methyl-4-[1-[[5-methyl-3-(6-methyl-3-pyridyl)isoxazol-4-yl]methyl]-6-oxo-pyridazin-4-yl]piperazine-1-carboxylate (120 mg, 0.250 mmol) in dioxane (1.2 mL) was added a 4 M solution of hydrochloric acid in dioxane (0.35 mL, 1.4 mmol) at room temperature. The reaction mixture was stirred at 60° C. for 1 h. Then the reaction mixture was concentrated and the residue was extracted with dichloromethane (30 mL) and a saturated solution of NaHCO$_3$ (5 mL). The aqueous layer was back extracted twice with dichloromethane (30 mL). The organic layers were combined, dried over sodium sulfate, filtered and concentrated to afford the title compound (85 mg, 90%) as a light brown oil. MS (ESI): 381.2 ([M+H]$^+$).

Example 51

2-[[5-methyl-3-(6-methyl-3-pyridyl)isoxazol-4-yl]methyl]-5-[(3S)-3-methylpiperazin-1-yl]pyridazin-3-one

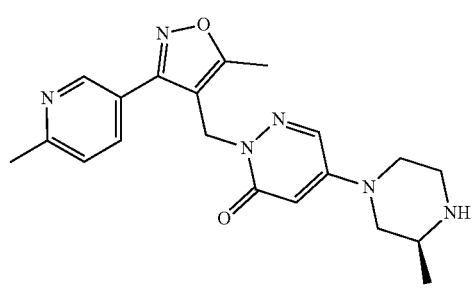 [SMILES: Cc1ccc(-c2noc(C)c2Cn2ncc(N3CCN[C@@H](C)C3)cc2=O)cn1]

a) tert-butyl (2S)-2-methyl-4-[1-[[5-methyl-3-(6-methyl-3-pyridyl)isoxazol-4-yl]methyl]-6-oxo-pyridazin-4-yl]piperazine-1-carboxylate In analogy to experiment of example 3, 5-chloro-2-[[5-methyl-3-(6-methyl-3-pyridyl)isoxazol-4-yl]methyl]pyridazin-3-one, using tert-butyl (2S)-2-methylpiperazine-1-carboxylate instead of (R)-3-hydroxypyrrolidine, was converted into the title compound (123 mg, 74%) which was obtained as an off-white foam. MS (ESI): 481.3 ([M+H]$^+$).

b) 2-[[5-methyl-3-(6-methyl-3-pyridyl)isoxazol-4-yl]methyl]-5-[(3S)-3-methylpiperazin-1-yl]pyridazin-3-one In analogy to experiment of example 50 b, tert-butyl (2S)-2-methyl-4-[1-[[5-methyl-3-(6-methyl-3-pyridyl)isoxazol-4-yl]methyl]-6-oxo-pyridazin-4-yl]piperazine-1-carboxylate instead of tert-butyl (2R)-2-methyl-4-[1-[[5-methyl-3-(6-methyl-3-pyridyl)isoxazol-4-yl]methyl]-6-oxo-pyridazin-4-yl]piperazine-1-carboxylate was converted into the title compound (84 mg, 88%) which was obtained as alight yellow oil. MS (ESI): 381.3 ([M+H]$^+$).

Example 52

2-[[3-(5-chloro-3-fluoro-2-pyridyl)-5-methyl-isoxazol-4-yl]methyl]-5-(cis-2,6-dimethylmorpholin-4-yl)pyridazin-3-one

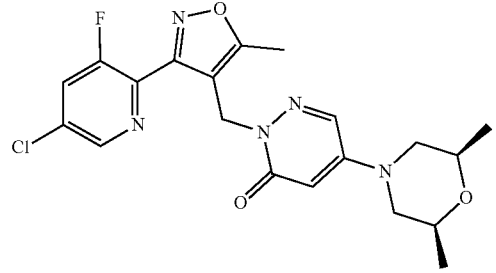 [SMILES: Cc1onc(-c2ncc(Cl)cc2F)c1Cn1ncc(N2C[C@@H](C)O[C@@H](C)C2)cc1=O]

In analogy to experiment of example 3, 5-chloro-2-[[3-(5-chloro-3-fluoro-2-pyridyl)-5-methyl-isoxazol-4-yl]methyl]pyridazin-3-one (building block V), using cis-2,6-dimethylmorpholine instead of (R)-3-hydroxypyrrolidine, was converted into the title compound (57 mg, 78%) which was obtained as an off-white solid. MS (ESI): 434.2 ([M+H]$^+$).

Example 53

2-[[3-(5-chloro-3-fluoro-2-pyridyl)-5-methyl-isoxazol-4-yl]methyl]-5-[4-(1-methylcyclopropanecarbonyl)piperazin-1-yl]pyridazin-3-one

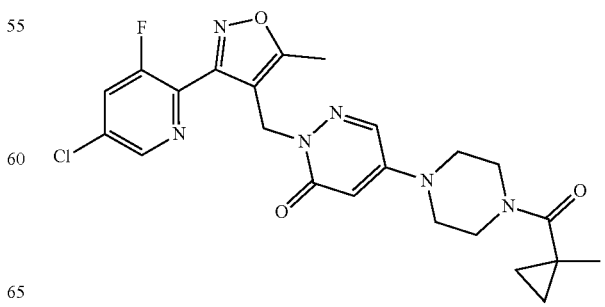

In analogy to experiment of example 3, 5-chloro-2-[[3-(5-chloro-3-fluoro-2-pyridyl)-5-methyl-isoxazol-4-yl]methyl]pyridazin-3-one (building block V), using (1-methylcyclopropyl)(piperazin-1-yl)methanone hydrochloride instead of (R)-3-hydroxypyrrolidine, was converted into the title compound (53 mg, 60%) which was obtained as an off-white solid. MS (ESI): 487.2 ([M+H]$^+$).

Example 54

5-[4-(3,5-dimethyl-1,2,4-triazol-4-yl)-1-piperidyl]-2-[[5-methyl-3-(6-methyl-3-pyridyl)isoxazol-4-yl]methyl]pyridazin-3-one

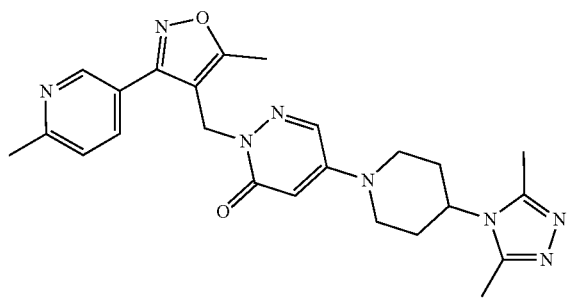 [SMILES: Cc1ccc(-c2noc(C)c2Cn2ncc(N3CCC(n4c(C)nnc4C)CC3)cc2=O)cn1]

In analogy to experiment of example 3, 5-chloro-2-[[5-methyl-3-(6-methyl-3-pyridyl)isoxazol-4-yl]methyl]pyridazin-3-one, using 4-(3,5-dimethyl-1,2,4-triazol-4-yl)piperidine instead of (R)-3-hydroxypyrrolidine, was converted into the title compound (56 mg, 62%) which was obtained as an off-white foam. MS (ESI): 461.3 ([M+H]$^+$).

Example 55

5-(4-(3,5-Dimethyl-4H-1,2,4-triazol-4-yl)piperidin-1-yl)-2-((3-(4-fluorophenyl)-5-methylisoxazol-4-yl)methyl)pyridazin-3(2H)-one

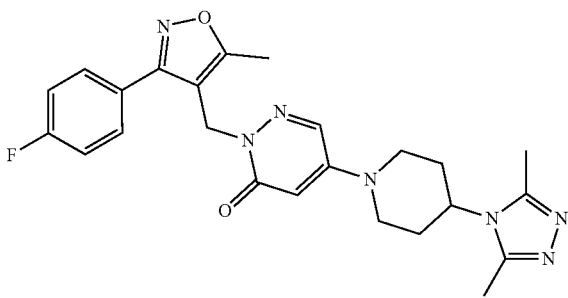 [SMILES: Cc1onc(-c2ccc(F)cc2)c1Cn1ncc(N2CCC(n3c(C)nnc3C)CC2)cc1=O]

In analogy to experiment of example 3, 5-chloro-2-[[3-(4-fluorophenyl)-5-methyl-isoxazol-4-yl]methyl]pyridazin-3-one (building block L), using 4-(3,5-dimethyl-1,2,4-triazol-4-yl)piperidine instead of (R)-3-hydroxypyrrolidine, was converted into the title compound (68 mg, 78%) which was obtained as an off-white solid. MS (ESI): 464.3 ([M+H]$^+$).

Example 56

(3R)—N-cyclopropyl-1-[1-[[5-methyl-3-(6-methyl-3-pyridyl)isoxazol-4-yl]methyl]-6-oxo-pyridazin-4-yl]pyrrolidine-3-carboxamide

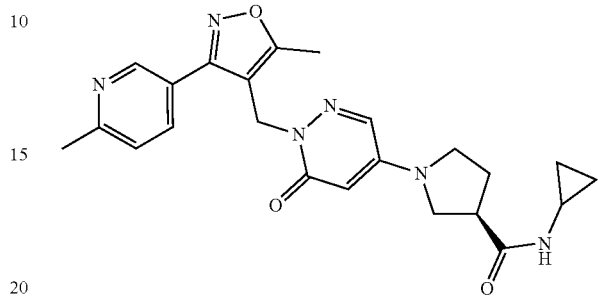

a) ethyl (3R)-1-[1-[[5-methyl-3-(6-methyl-3-pyridyl)isoxazol-4-yl]methyl]-6-oxo-pyridazin-4-yl]pyrrolidine-3-carboxylate In analogy to experiment of example 3, 5-chloro-2-[[5-methyl-3-(6-methyl-3-pyridyl)isoxazol-4-yl]methyl]pyridazin-3-one, using ethyl (3R)-pyrrolidine-3-carboxylate hydrochloride instead of (R)-3-hydroxypyrrolidine, was converted into the title compound (147 mg, 88%) which was obtained as a colorless oil. MS (ESI): 424.2 ([M+H]$^+$).

b) (3R)-1-[1-[[5-methyl-3-(6-methyl-3-pyridyl)isoxazol-4-yl]methyl]-6-oxo-pyridazin-4-yl]pyrrolidine-3-carboxylic acid In analogy to experiment of example 27b, using ethyl (3R)-1-[1-[[5-methyl-3-(6-methyl-3-pyridyl)isoxazol-4-yl]methyl]-6-oxo-pyridazin-4-yl]pyrrolidine-3-carboxylate instead of ethyl 1-[1-[[5-methyl-3-(6-methyl-3-pyridyl)isoxazol-4-yl]methyl]-6-oxo-pyridazin-4-yl]piperidine-4-carboxylate was converted into the title compound (82 mg, 74%) which was obtained as an off-white foam. MS (ESI): 396.2 ([M+H]$^+$).

c) (3R)—N-cyclopropyl-1-[1-[[5-methyl-3-(6-methyl-3-pyridyl)isoxazol-4-yl]methyl]-6-oxo-pyridazin-4-yl]pyrrolidine-3-carboxamide To a solution of (3R)-1-[1-[[5-methyl-3-(6-methyl-3-pyridyl)isoxazol-4-yl]methyl]-6-oxo-pyridazin-4-yl]pyrrolidine-3-carboxylic acid (11.4 mg, 0.200 mmol) in DMF (0.6 mL) was added N,N-diisopropylethylamine (70 µL, 0.401 mmol) followed by TBTU (34 mg, 0.11 mmol). The reaction mixture was stirred at room temperature overnight. The reaction mixture was extracted with EtOAc (30 mL) and water (3 mL). The aqueous layer was back extracted with EtOAc (30 mL). The organic layers were washed with water (3 mL) and brine (3 mL). The organic layers were combined, dried over sodium sulfate, filtered and concentrated. Purification by flash chromatography (silica, gradient: 0% to 10% MeOH in CH$_2$Cl$_2$) afforded the title compound (23 mg, 55%) as an off-white solid. MS (ESI): 435.2 ([M+H]$^+$).

Example 57

(3S)—N-cyclopropyl-1-[1-[[5-methyl-3-(6-methyl-3-pyridyl)isoxazol-4-yl]methyl]-6-oxo-pyridazin-4-yl]pyrrolidine-3-carboxamide

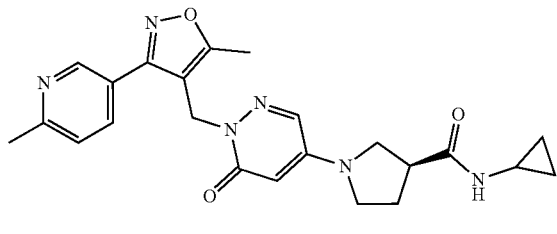 [SMILES: Cc1ccc(-c2noc(C)c2Cn2ncc(N3CC[C@H](C(=O)NC4CC4)C3)cc2=O)cn1]

a) ethyl (3S)-1-[1-[[5-methyl-3-(6-methyl-3-pyridyl)isoxazol-4-yl]methyl]-6-oxo-pyridazin-4-yl]pyrrolidine-3-carboxylate In analogy to experiment of example 3, 5-chloro-2-[[5-methyl-3-(6-methyl-3-pyridyl)isoxazol-4-yl]methyl]pyridazin-3-one, using ethyl (3S)-pyrrolidine-3-carboxylate hydrochloride instead of (R)-3-hydroxypyrrolidine, was converted into the title compound (146 mg, 88%) which was obtained as a colorless oil. MS (ESI): 424.2 ([M+H]$^+$).

b) (3S)-1-[1-[[5-methyl-3-(6-methyl-3-pyridyl)isoxazol-4-yl]methyl]-6-oxo-pyridazin-4-yl]pyrrolidine-3-carboxylic acid In analogy to experiment of example 27b, using ethyl (3S)-1-[1-[[5-methyl-3-(6-methyl-3-pyridyl)isoxazol-4-yl]methyl]-6-oxo-pyridazin-4-yl]pyrrolidine-3-carboxylate instead of ethyl 1-[1-[[5-methyl-3-(6-methyl-3-pyridyl)isoxazol-4-yl]methyl]-6-oxo-pyridazin-4-yl]piperidine-4-carboxylate was converted into the title compound (75 mg, 68%) which was obtained as an off-white solid. MS (ESI): 396.2 ([M+H]$^+$).

c) (3S)—N-cyclopropyl-1-[1-[[5-methyl-3-(6-methyl-3-pyridyl)isoxazol-4-yl]methyl]-6-oxo-pyridazin-4-yl]pyrrolidine-3-carboxamide In analogy to experiment of example 56c, using (3S)-1-[1-[[5-methyl-3-(6-methyl-3-pyridyl)isoxazol-4-yl]methyl]-6-oxo-pyridazin-4-yl]pyrrolidine-3-carboxylic acid instead of (3R)-1-[1-[[5-methyl-3-(6-methyl-3-pyridyl)isoxazol-4-yl]methyl]-6-oxo-pyridazin-4-yl]pyrrolidine-3-carboxylic acid was converted into the title compound (30 mg, 59%) which was obtained as an off-white solid. MS (ESI): 435.3 ([M+H]$^+$).

Example 58

5-(2-cyclopropyl-2,6-diazaspiro[3.3]heptan-6-yl)-2-[[5-methyl-3-(6-methyl-3-pyridyl)isoxazol-4-yl]methyl]pyridazin-3-one

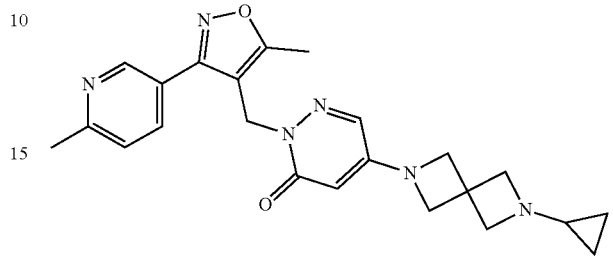

In analogy to experiment of example 3, 5-chloro-2-[[5-methyl-3-(6-methyl-3-pyridyl)isoxazol-4-yl]methyl]pyridazin-3-one, using 2-cyclopropyl-2,6-diazaspiro[3.3]heptane 2,2,2-trifluoroacetate instead of (R)-3-hydroxypyrrolidine, was converted into the title compound (393 mg, 83%) which was obtained as an off-white foam. MS (ESI): 419.2 ([M+H]$^+$).

Example 59

5-[(3R)-4-cyclopropyl-3-methyl-piperazin-1-yl]-2-[[5-methyl-3-(6-methyl-3-pyridyl)isoxazol-4-yl]methyl]pyridazin-3-one

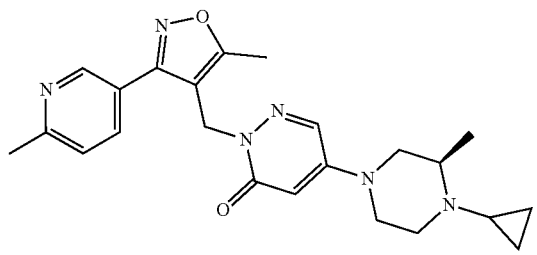 [SMILES: Cc1ccc(-c2noc(C)c2Cn2ncc(N3CCN(C4CC4)[C@H](C)C3)cc2=O)cn1]

To a solution of 2-[[5-methyl-3-(6-methyl-3-pyridyl)isoxazol-4-yl]methyl]-5-[(3R)-3-methylpiperazin-1-yl]pyridazin-3-one (85 mg, 0.201 mmol) in THF (0.4 mL) and methanol (0.4 mL) was added (1-ethoxycyclopropoxy)-trimethyl-silane (85 μL, 0.42 mmol), sodium cyanoborohydride (20 mg, 0.32 mmol) and acetic acid (20 μL, 0.35 mmol). The reaction mixture was stirred at 50° C. overnight. Then the reaction mixture was cooled to room temperature, quenched with a 2M solution of NaOH (3 mL) and then extracted with dichloromethane (30 mL). The aqueous layers were back extracted with dichloromethane (30 mL). The organic layers were combined, dried over sodium sulfate, filtered and concentrated. Purification by flash chromatography (silica, gradient: 0% to 5% MeOH in CH$_2$Cl$_2$) afforded the title compound (61 mg, 72%) as an off-white foam. MS (ESI): 421.3 ([M+H]$^+$).

Example 60

5-[(3S)-4-cyclopropyl-3-methyl-piperazin-1-yl]-2-[[5-methyl-3-(6-methyl-3-pyridyl)isoxazol-4-yl]methyl]pyridazin-3-one

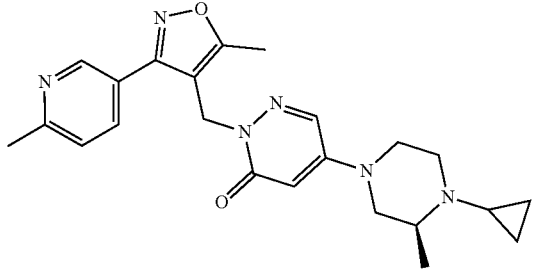 [SMILES: Cc1ccc(-c2noc(C)c2Cn2ncc(N3CCN(C4CC4)[C@@H](C)C3)cc2=O)cn1]

In analogy to experiment of example 59, using 2-[[5-methyl-3-(6-methyl-3-pyridyl)isoxazol-4-yl]methyl]-5-[(3S)-3-methylpiperazin-1-yl]pyridazin-3-one instead of 2-[[5-methyl-3-(6-methyl-3-pyridyl)isoxazol-4-yl]methyl]-5-[(3R)-3-methylpiperazin-1-yl]pyridazin-3-one was converted into the title compound (266 mg, 68%) which was obtained as a light yellow foam. MS (ESI): 421.2 ([M+H]$^+$).

Example 61

5-[4-(2-methoxyphenyl)-1-piperidyl]-2-[[5-methyl-3-(6-methyl-3-pyridyl)isoxazol-4-yl]methyl]pyridazin-3-one

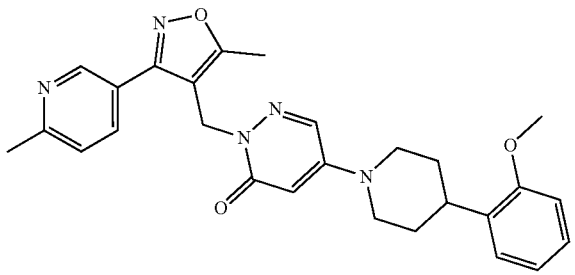 [SMILES: COc1ccccc1C1CCN(c2cnn(Cc3c(-c4ccc(C)nc4)noc3C)c(=O)c2)CC1]

In analogy to experiment of example 3, 5-chloro-2-[[5-methyl-3-(6-methyl-3-pyridyl)isoxazol-4-yl]methyl]pyridazin-3-one, using 4-(2-methoxyphenyl)piperidine instead of (R)-3-hydroxypyrrolidine, was converted into the title compound (34 mg, 23%) which was obtained as an off-white solid. MS (ESI): 472.3 ([M+H]$^+$)

5-(cis-2,6-dimethylmorpholin-4-yl)-2-[[5-methyl-3-(5-methylisoxazol-3-yl)isoxazol-4-yl]methyl]pyridazin-3-one

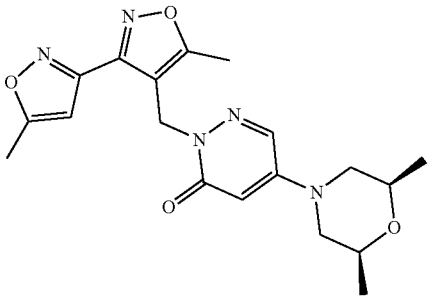

In analogy to experiment of example 3, 5-chloro-2-[[5-methyl-3-(5-methylisoxazol-3-yl)isoxazol-4-yl]methyl]pyridazin-3-one (building block O), using cis-2,6-dimethylmorpholine instead of (R)-3-hydroxypyrrolidine, was converted into the title compound (67 mg, 88%) which was obtained as an off-white solid. MS (ESI): 386.2 ([M+H]$^+$).

Example 63

5-(4-cyclopropylpiperazin-1-yl)-2-[[5-methyl-3-(5-methylisoxazol-3-yl)isoxazol-4-yl]methyl]pyridazin-3-one

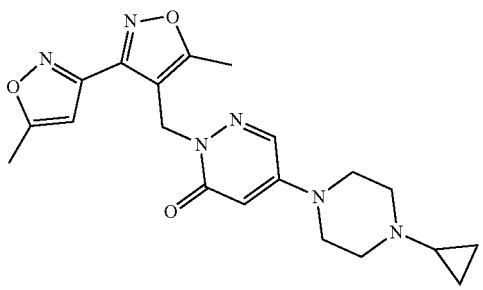 [SMILES: Cc1cc(-c2noc(C)c2Cn2ncc(N3CCN(C4CC4)CC3)cc2=O)no1]

In analogy to experiment of example 3, 5-chloro-2-[[5-methyl-3-(5-methylisoxazol-3-yl)isoxazol-4-yl]methyl]pyridazin-3-one (building block O), using 1-cyclopropylpiperazine hydrochloride instead of (R)-3-hydroxypyrrolidine, was converted into the title compound (70 mg, 91%) which was obtained as an off-white solid. MS (ESI): 397.2 ([M+H]$^+$).

Example 64

5-(cyclopropyl(methyl)amino)-2-((5-methyl-3-(6-methylpyridin-3-yl)isoxazol-4-yl)methyl)pyridazin-3(2H)-one

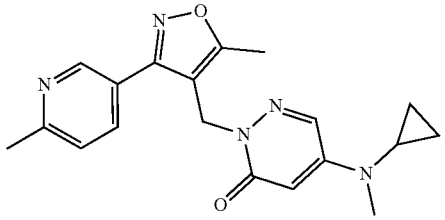 [SMILES: Cc1ccc(-c2noc(C)c2Cn2ncc(N(C)C3CC3)cc2=O)cn1]

To a solution of 5-chloro-2-[[5-methyl-3-(6-methyl-3-pyridyl)isoxazol-4-yl]methyl]pyridazin-3-one (building block A, 50 mg, 0.158 mmol) in EtOH (5 mL) was added under an atmosphere of argon triethylamine (0.219 mL, 1.58 mmol) and N-methylcyclopropanamine oxalate (254 mg, 1.58 mmol). The vial was capped and heated to 110° C. for 17 h. The reaction mixture was diluted with EtOAc (20 mL) and was washed with water (15 mL) and brine (15 mL). The aqueous layers were extracted twice with EtOAc (20 mL). The combined organic extracts were dried (MgSO$_4$), filtered and concentrated in vacuo. Purification by flash chromatography (silica, gradient: 0% to 10% MeOH in CH$_2$Cl$_2$) afforded the title compound (40 mg, 68%) as a light brown gum. MS (ESI): 352.2 ([M+H]$^+$).

Example 65

5-(methyl(oxetan-3-yl)amino)-2-((5-methyl-3-(6-methylpyridin-3-yl)isoxazol-4-yl)methyl)pyridazin-3(2H)-one

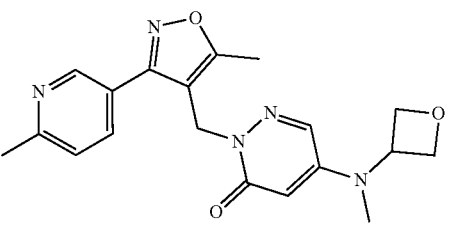 [SMILES: Cc1ccc(-c2noc(C)c2Cn2ncc(N(C)C3COC3)cc2=O)cn1]

In analogy to experiment of example 64, 5-chloro-2-[[5-methyl-3-(6-methyl-3-pyridyl)isoxazol-4-yl]methyl]pyridazin-3-one, using N-methyloxetan-3-amine instead of N-methylcyclopropanamine oxalate, was converted into the title compound (12 mg, 20%) which was obtained as a light brown waxy solid. MS (ESI): 368.2 ([M+H]$^+$).

Example 66

5-(4-cyclopropylpiperazin-1-yl)-2-[[5-methyl-3-[6-(trifluoromethyl)-3-pyridyl]isoxazol-4-yl]methyl]pyridazin-3-one

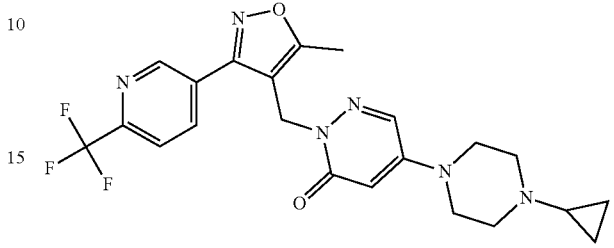

In analogy to experiment of example 3, 5-chloro-2-[[5-methyl-3-[6-(trifluoromethyl)-3-pyridyl]isoxazol-4-yl]methyl]pyridazin-3-one (building block C), using 1-cyclopropylpiperazine hydrochloride instead of (R)-3-hydroxypyrrolidine, was converted into the title compound (70 mg, 87%) which was obtained as an off-white solid. MS (ESI): 461.2 ([M+H]$^+$).

Example 67

2-((5-methyl-3-(6-methylpyridin-3-yl)isoxazol-4-yl)methyl)-5-phenylpyridazin-3(2H)-one

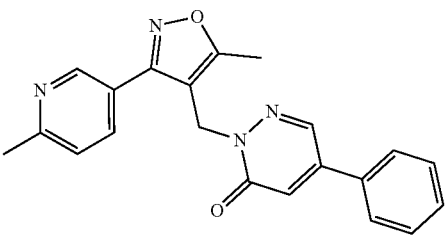 [SMILES: Cc1ccc(-c2noc(C)c2Cn2ncc(-c3ccccc3)cc2=O)cn1]

A round-bottomed flask was charged with 5-chloro-2-[[5-methyl-3-(6-methyl-3-pyridyl)isoxazol-4-yl]methyl]pyridazin-3-one (building block A, 60 mg, 0.189 mmol), phenylboronic acid (46.2 mg, 0.379 mmol), aqueous sodium carbonate (2.0 M, 0.21 mL, 0.420 mmol) and 1,1-bis(diphenylphosphino)ferrocenedichloropalladium(II) (4.25 mg, 0.0581 mmol). The flask was degassed by alternative evacuation and back filling with argon. A previously degassed 1,4-dioxane (3.0 mL) was added and the resulting mixture was flushed with argon for 10 min. The reaction mixture was stirred at 100° C. for 16 h before being cooled to room temperature and filtered directly through a plug of celite. The filter cake was rinsed with EtOAc and the filtrate concentrated in vacuo. Purification by flash chromatography (silica, 5% MeOH in CH$_2$Cl$_2$) afforded the title compound (64 g, 94%) as a white solid. MS (ESI): 359.1 ([M+H]$^+$).

Example 68

5-(4-fluorophenyl)-2-[[5-methyl-3-(6-methylpyridin-3-yl)-1,2-oxazol-4-yl]methyl]pyridazin-3-one

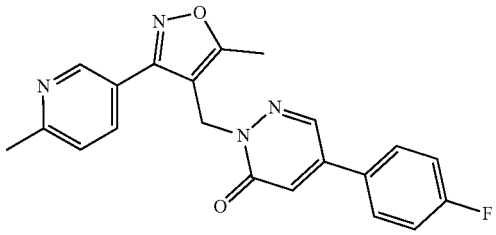 [SMILES: Cc1ccc(-c2noc(C)c2Cn2ncc(-c3ccc(F)cc3)cc2=O)cn1]

In analogy to experiment of example 67, 5-chloro-2-[[5-methyl-3-(6-methyl-3-pyridyl)isoxazol-4-yl]methyl]pyridazin-3-one, using (4-fluorophenyl)boronic acid instead of phenylboronic acid, was converted into the title compound (51 mg, 86%) which was obtained as an off-white solid. MS (ESI): 377.1 ([M+H]$^+$).

Example 69

5-(2-azaspiro[3.3]heptan-2-yl)-2-[[5-methyl-3-(6-methyl-3-pyridyl)isoxazol-4-yl]methyl]pyridazin-3-one

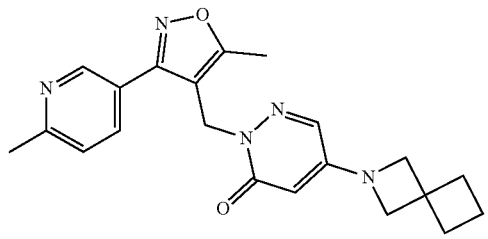 [SMILES: Cc1ccc(-c2noc(C)c2Cn2ncc(N3CC4(CCC4)C3)cc2=O)cn1]

In analogy to experiment of example 3, 5-chloro-2-[[5-methyl-3-(6-methyl-3-pyridyl)isoxazol-4-yl]methyl]pyridazin-3-one, using 2-azaspiro[3.3]heptane hydrochloride instead of (R)-3-hydroxypyrrolidine, was converted into the title compound (67 mg, 94%) which was obtained as an off-white solid. MS (ESI): 378.1 ([M+H]$^+$).

Example 70

5-((2-hydroxy-2-methylpropyl)(methyl)amino)-2-((5-methyl-3-(6-methylpyridin-3-yl)isoxazol-4-yl)methyl)pyridazin-3(2H)-one

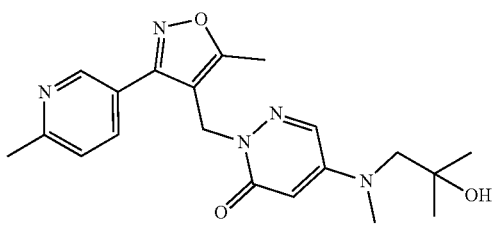 [SMILES: Cc1ccc(-c2noc(C)c2Cn2ncc(N(C)CC(C)(C)O)cc2=O)cn1]

In analogy to experiment of example 64, 5-chloro-2-[[5-methyl-3-(6-methyl-3-pyridyl)isoxazol-4-yl]methyl]pyridazin-3-one, using 2-methyl-1-(methylamino)propan-2-ol instead of N-methylcyclopropanamine oxalate, was converted into the title compound (21 mg, 33%) which was obtained as an off-white gum. MS (ESI): 384.2 ([M+H]$^+$).

Example 72

5-(cis-2,6-dimethylmorpholin-4-yl)-2-[[3-[6-(trifluoromethyl)-3-pyridyl]isoxazol-4-yl]methyl]pyridazin-3-one

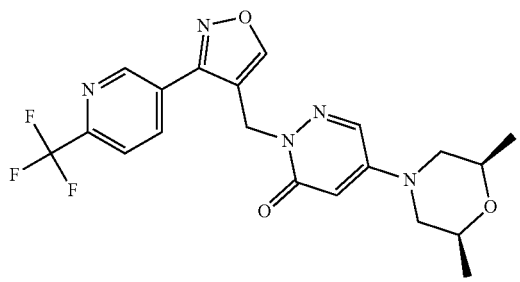 [SMILES: C[C@@H]1CN(c2cnn(Cc3conc3-c3ccc(C(F)(F)F)nc3)c(=O)c2)C[C@H](C)O1]

In analogy to experiment of example 3, 5-chloro-2-[[3-[6-(trifluoromethyl)-3-pyridyl]isoxazol-4-yl]methyl]pyridazin-3-one (building block P), using cis-2,6-dimethylmorpholine instead of (R)-3-hydroxypyrrolidine, was converted into the title compound (60 mg, 82%) which was obtained as an off-white solid. MS (ESI): 436.1 ([M+H]$^+$).

Example 74

5-(4,7-diazaspiro[2.5]octan-7-yl)-2-[[5-methyl-3-(6-methyl-3-pyridyl)isoxazol-4-yl]methyl]pyridazin-3-one

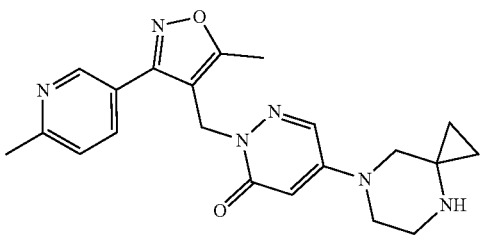 [SMILES: Cc1ccc(-c2noc(C)c2Cn2ncc(N3CCNC4(CC4)C3)cc2=O)cn1]

a) tert-butyl 7-[1-[[5-methyl-3-(6-methyl-3-pyridyl)isoxazol-4-yl]methyl]-6-oxo-pyridazin-4-yl]-4,7-diazaspiro[2.5]octane-4-carboxylate In analogy to experiment of example 3, 5-chloro-2-[[5-methyl-3-(6-methyl-3-pyridyl)isoxazol-4-yl]methyl]pyridazin-3-one, using tert-butyl 4,7-diazaspiro[2.5]octane-4-carboxylate hydrochloride instead of (R)-3-hydroxypyrrolidine, was converted into the title compound (146 mg, 85%) which was obtained as an off-white solid. MS (ESI): 493.3 ([M+H]$^+$).

b) 5-(4,7-diazaspiro[2.5]octan-7-yl)-2-[[5-methyl-3-(6-methyl-3-pyridyl)isoxazol-4-yl]methyl]pyridazin-3-one To a solution of tert-butyl 7-[1-[[5-methyl-3-(6-methyl-3-pyridyl)isoxazol-4-yl]methyl]-6-oxo-pyridazin-4-yl]-4,7-diazaspiro[2.5]octane-4-carboxylate (105 mg, 0.213 mmol) in dichloromethane (0-7 mL) was added at 0° C. trifluoroacetic acid (0.14 mL, 1.8 mmol). After stirring for 2.5 h at room temperature the reaction mixture was concentrated. Then the residue was extracted with dichloromethane (30 mL) and saturated NaHCO$_3$-solution (5 mL). The aqueous layer was back extracted with dichloromethane (30 mL). The organic layers were combined, dried over sodium sulfate, filtered and concentrated to afford the tile compound (63 mg, 75%) as an off-white solid. MS (ESI): 393.1 ([M+H]$^+$).

Example 75

2-[[5-methyl-3-(6-methyl-3-pyridyl)isoxazol-4-yl]methyl]-5-piperazin-1-yl-pyridazin-3-one

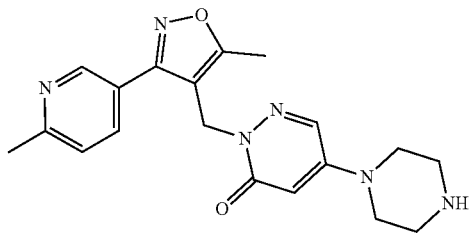 [SMILES: Cc1ccc(-c2noc(C)c2Cn2ncc(N3CCNCC3)cc2=O)cn1]

a) tert-butyl 4-[1-[[5-methyl-3-(6-methyl-3-pyridyl)isoxazol-4-yl]methyl]-6-oxo-pyridazin-4-yl]piperazine-1-carboxylate In analogy to experiment of example 3, 5-chloro-2-[[5-methyl-3-(6-methyl-3-pyridyl)isoxazol-4-yl]methyl]pyridazin-3-one, using tert-butyl piperazine-1-carboxylate instead of (R)-3-hydroxypyrrolidine, was converted into the title compound (337 mg, 76%) which was obtained as a light yellow solid. MS (ESI): 467.3 ([M+H]$^+$).

b) 2-[[5-methyl-3-(6-methyl-3-pyridyl)isoxazol-4-yl]methyl]-5-piperazin-1-yl-pyridazin-3-one In analogy to experiment of example 74b, using tert-butyl 4-[1-[[5-methyl-3-(6-methyl-3-pyridyl)isoxazol-4-yl]methyl]-6-oxo-pyridazin-4-yl]piperazine-1-carboxylate instead of tert-butyl 7-[1-[[5-methyl-3-(6-methyl-3-pyridyl)isoxazol-4-yl]methyl]-6-oxo-pyridazin-4-yl]-4,7-diazaspiro[2.5]octane-4-carboxylate was converted into the title compound (247 mg, 94%) which was obtained as a light yellow foam. MS (ESI): 367.2 ([M+H]$^+$).

Example 76

5-(4-methoxyphenyl)-2-[[5-methyl-3-(6-methylpyridin-3-yl)-1,2-oxazol-4-yl]methyl]pyridazin-3-one

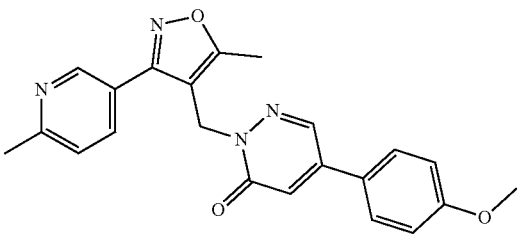

In analogy to experiment of example 67, 5-chloro-2-[[5-methyl-3-(6-methyl-3-pyridyl)isoxazol-4-yl]methyl]pyridazin-3-one, using (4-methoxyphenyl)boronic acid instead of phenylboronic acid, was converted into the title compound (17 mg, 28%) which was obtained as a light brown solid. MS (ESI): 389.1 ([M+H]$^+$).

Example 77

5-(2,6-diazaspiro[3.3]heptan-2-yl)-2-[[5-methyl-3-(6-methyl-3-pyridyl)isoxazol-4-yl]methyl]pyridazin-3-one

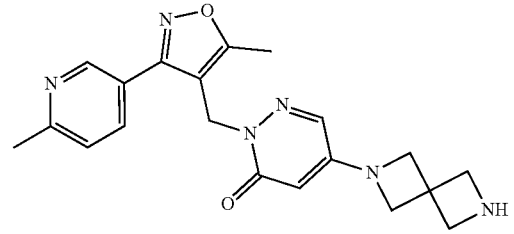 [SMILES: Cc1ccc(-c2noc(C)c2Cn2ncc(N3CC4(CNC4)C3)cc2=O)cn1]

a) tert-butyl 6-[1-[[5-methyl-3-(6-methyl-3-pyridyl)isoxazol-4-yl]methyl]-6-oxo-pyridazin-4-yl]-2,6-diazaspiro[3.3]heptane-2-carboxylate In analogy to experiment of example 3, 5-chloro-2-[[5-methyl-3-(6-methyl-3-pyridyl)isoxazol-4-yl]methyl]pyridazin-3-one, using tert-butyl 2,6-diazaspiro[3.3]heptane-2-carboxylate instead of (R)-3-hydroxypyrrolidine, was converted into the title compound (131 mg, 91%) which was obtained as an off-white foam. MS (ESI): 479.3 ([M+H]$^+$).

b) 5-(2,6-diazaspiro[3.3]heptan-2-yl)-2-[[5-methyl-3-(6-methyl-3-pyridyl)isoxazol-4-yl]methyl]pyridazin-3-one In analogy to experiment of example 74b, using tert-butyl 6-[1-[[5-methyl-3-(6-methyl-3-pyridyl)isoxazol-4-yl]methyl]-6-oxo-pyridazin-4-yl]-2,6-diazaspiro[3.3]heptane-2-carboxylate instead of tert-butyl 7-[1-[[5-methyl-3-(6-methyl-3-pyridyl)isoxazol-4-yl]methyl]-6-oxo-pyridazin-4-yl]-4,7-diazaspiro[2.5]octane-4-carboxylate was converted into the title compound (34 mg, 43%) which was obtained as an off-white foam. MS (ESI): 379.2 ([M+H]$^+$).

Example 78

2-((5-methyl-3-(6-methylpyridin-3-yl)isoxazol-4-yl)methyl)-5-(methylamino)pyridazin-3(2H)-one

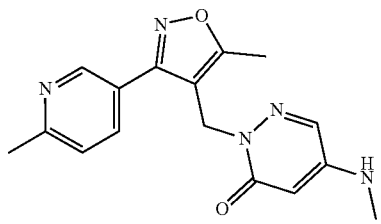

In analogy to experiment of example 64, 5-chloro-2-[[5-methyl-3-(6-methyl-3-pyridyl)isoxazol-4-yl]methyl]pyridazin-3-one, using methylamine (33% solution in ethanol) instead of N-methylcyclopropanamine oxalate, was converted into the title compound (95 mg, 88%) which was obtained as a light brown solid. MS (ESI): 312.2 ([M+H]+).

Example 79

5-(4-ethoxyphenyl)-2-((5-methyl-3-(6-methylpyridin-3-yl)isoxazol-4-yl)methyl)pyridazin-3(2H)-one

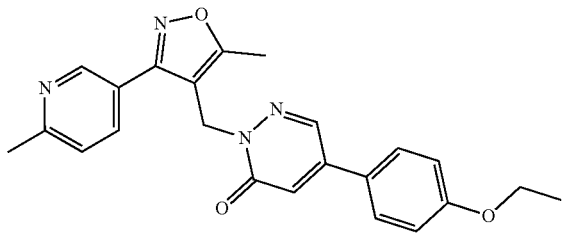 [SMILES: CCOc1ccc(-c2cnn(Cc3c(-c4ccc(C)nc4)noc3C)c(=O)c2)cc1]

In analogy to experiment of example 67, 5-chloro-2-[[5-methyl-3-(6-methyl-3-pyridyl)isoxazol-4-yl]methyl]pyridazin-3-one, using (4-ethoxyphenyl)boronic acid instead of phenylboronic acid, was converted into the title compound (59 mg, 93%) which was obtained as a light brown solid. MS (ESI): 403.2 ([M+H]+).

Example 80

5-(3-fluoro-4-methoxyphenyl)-2-((5-methyl-3-(6-methylpyridin-3-yl)isoxazol-4-yl)methyl)pyridazin-3(2H)-one

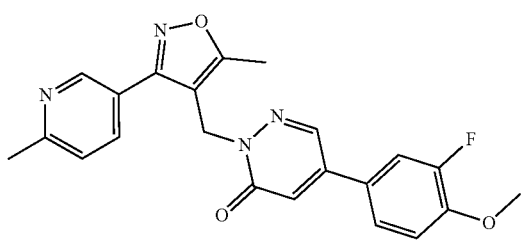

In analogy to experiment of example 67, 5-chloro-2-[[5-methyl-3-(6-methyl-3-pyridyl)isoxazol-4-yl]methyl]pyridazin-3-one, using (3-fluoro-4-methoxyphenyl)boronic acid instead of phenylboronic acid, was converted into the title compound (60 mg, 94%) which was obtained as an off-white solid. MS (ESI): 407.1 ([M+H]+).

Example 81

5-(6-methoxypyridin-3-yl)-2-((5-methyl-3-(6-methylpyridin-3-yl)isoxazol-4-yl)methyl)pyridazin-3(2H)-one

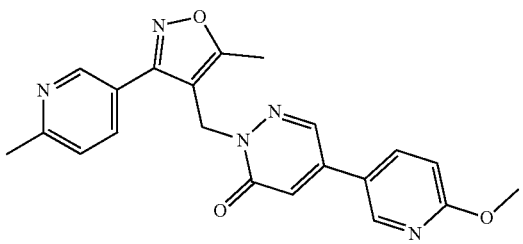

In analogy to experiment of example 67, 5-chloro-2-[[5-methyl-3-(6-methyl-3-pyridyl)isoxazol-4-yl]methyl]pyridazin-3-one, using 2-methoxy-5-(4,4,5,5-tetramethyl-1,3,2-dioxaborolan-2-yl)pyridine instead of phenylboronic acid, was converted into the title compound (26 mg, 42%) which was obtained as a light yellow solid. MS (ESI): 390.1 ([M+H]+).

Example 82

5-(6-methyl-2,6-diazaspiro[3.3]heptan-2-yl)-2-[[5-methyl-3-(6-methyl-3-pyridyl)isoxazol-4-yl]methyl]pyridazin-3-one

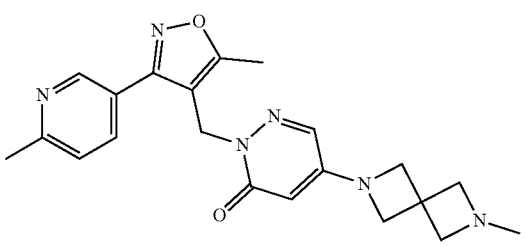

In analogy to experiment of example 3, 5-chloro-2-[[5-methyl-3-(6-methyl-3-pyridyl)isoxazol-4-yl]methyl]pyridazin-3-one, using 2-methyl-2,6-diazaspiro[3.3]heptane instead of (R)-3-hydroxypyrrolidine, was converted into the title compound (29 mg, 38%) which was obtained as an off-white solid. MS (ESI): 393.2 ([M+H]+).

Example 83

2-((5-methyl-3-(6-methylpyridin-3-yl)isoxazol-4-yl)methyl)-5-(trifluoromethyl)phenyl)pyridazin-3(2H)-one

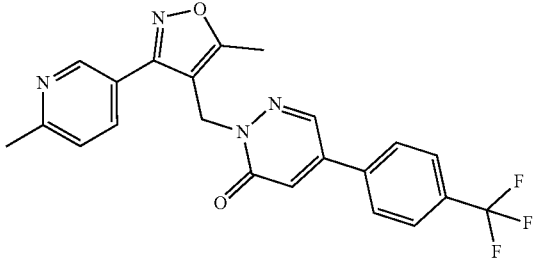 [SMILES: Cc1ccc(-c2noc(C)c2Cn2ncc(-c3ccc(C(F)(F)F)cc3)cc2=O)cn1]

In analogy to experiment of example 67, 5-chloro-2-[[5-methyl-3-(6-methyl-3-pyridyl)isoxazol-4-yl]methyl]pyridazin-3-one, using (4-(trifluoromethyl)phenyl)boronic acid instead of phenylboronic acid, was converted into the title compound (38 mg, 57%) which was obtained as a light brown solid. MS (ESI): 427.2 ([M+H]+).

Example 84

5-(5-methoxypyridin-2-yl)-2-((5-methyl-3-(6-methylpyridin-3-yl)isoxazol-4-yl)methyl)pyridazin-3(2H)-one

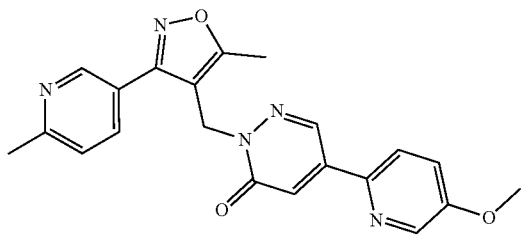

In analogy to experiment of example 67, 5-chloro-2-[[5-methyl-3-(6-methyl-3-pyridyl)isoxazol-4-yl]methyl]pyridazin-3-one, using 5-methoxy-2-(4,4,5,5-tetramethyl-1,3,2-dioxaborolan-2-yl)pyridine instead of phenylboronic acid, was converted into the title compound (8.2 mg, 11%) which was obtained as a brown solid. MS (ESI): 390.1 ([M+H]+).

Example 85

1-[1-[[5-methyl-3-(6-methyl-3-pyridyl)isoxazol-4-yl]methyl]-6-oxo-pyridazin-4-yl]azetidine-3-carbonitrile

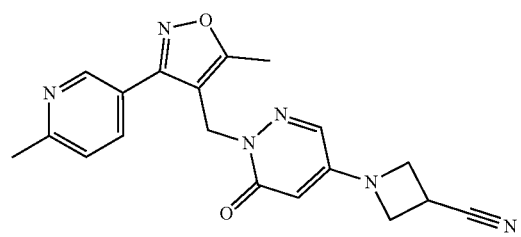 [SMILES: Cc1ccc(-c2noc(C)c2Cn2ncc(N3CC(C#N)C3)cc2=O)cn1]

In analogy to experiment of example 3, 5-chloro-2-[[5-methyl-3-(6-methyl-3-pyridyl)isoxazol-4-yl]methyl]pyridazin-3-one, using azetidine-3-carbonitrile hydrochloride instead of (R)-3-hydroxypyrrolidine, was converted into the title compound (45 mg, 56%) which was obtained as an off-white foam. MS (ESI): 363.2 ([M+H]+).

Example 86

2-[[3-(5-chloro-2-pyridyl)-5-methyl-isoxazol-4-yl]methyl]-5-(2-cyclopropyl-2,6-diazaspiro[3.3]heptan-6-yl)pyridazin-3-one

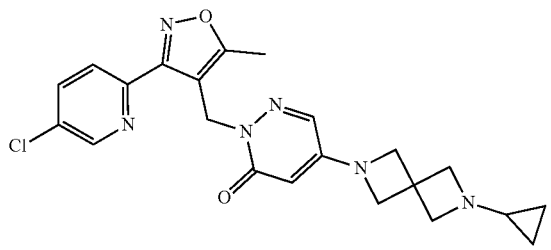 [SMILES: Cc1onc(-c2ccc(Cl)cn2)c1Cn1ncc(N2CC3(C2)CN(C2CC2)C3)cc1=O]

In analogy to experiment of example 3, 5-chloro-2-[[3-(5-chloro-2-pyridyl)-5-methyl-isoxazol-4-yl]methyl]pyridazin-3-one (building block M), using 2-cyclopropyl-2,6-diazaspiro[3.3]heptane bis(2,2,2-trifluoroacetate) instead of (R)-3-hydroxypyrrolidine, was converted into the title compound (74 mg, 81%) which was obtained as a white solid. MS (ESI): 439.2 ([M+H]+).

Example 87

5-(2-cyclopropyl-2,6-diazaspiro[3.3]heptan-6-yl)-2-[[5-methyl-3-(5-methylisoxazol-3-yl)isoxazol-4-yl]methyl]pyridazin-3-one

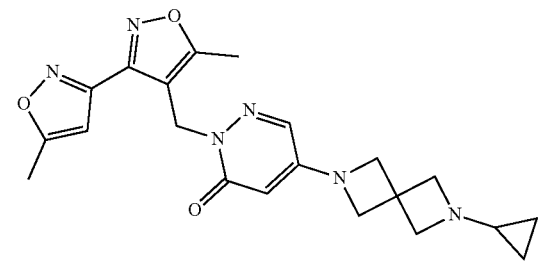 [SMILES: Cc1cc(-c2noc(C)c2Cn2ncc(N3CC4(C3)CN(C3CC3)C4)cc2=O)no1]

In analogy to experiment of example 3, 5-chloro-2-[[5-methyl-3-(5-methylisoxazol-3-yl)isoxazol-4-yl]methyl]pyridazin-3-one (building block O), using 2-cyclopropyl-2,6-diazaspiro[3.3]heptane 2,2,2-trifluoroacetic acid instead of (R)-3-hydroxypyrrolidine, was converted into the title compound (63 mg, 79%) which was obtained as an off-white solid. MS (ESI): 409.2 ([M+H]+).

Example 88

2-((5-methyl-3-(6-methylpyridin-3-yl)isoxazol-4-yl)methyl)-5-(((tetrahydro-2H-pyran-4-yl)methyl)amino)pyridazin-3(2H)-one

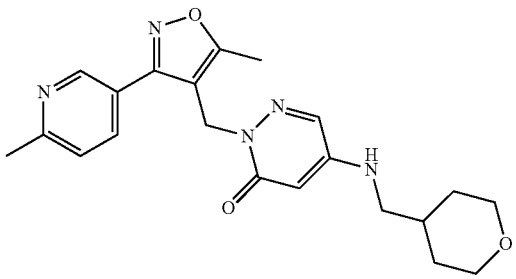 [SMILES: Cc1ccc(-c2noc(C)c2Cn2ncc(NCC3CCOCC3)cc2=O)cn1]

In analogy to experiment of example 64, 5-chloro-2-[[5-methyl-3-(6-methyl-3-pyridyl)isoxazol-4-yl]methyl]pyridazin-3-one, using (tetrahydro-2H-pyran-4-yl)methanamine instead of N-methylcyclopropanamine oxalate, was converted into the title compound (80 mg, 85%) which was obtained as an off-white solid. MS (ESI): 396.2 ([M+H]$^+$).

Example 89

2-[[5-methyl-3-(6-methyl-3-pyridyl)isoxazol-4-yl]methyl]-5-[(2S)-2-methylmorpholin-4-yl]pyridazin-3-one

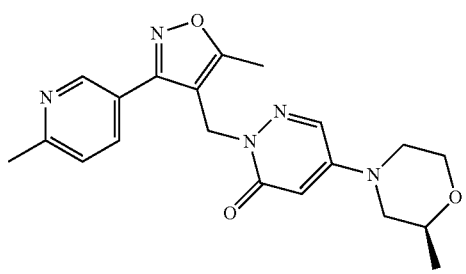 [SMILES: Cc1ccc(-c2noc(C)c2Cn2ncc(N3CCO[C@@H](C)C3)cc2=O)cn1]

In analogy to experiment of example 3, 5-chloro-2-[[5-methyl-3-(6-methyl-3-pyridyl)isoxazol-4-yl]methyl]pyridazin-3-one, using (2S)-2-methylmorpholine hydrochloride instead of (R)-3-hydroxypyrrolidine, was converted into the title compound (65 mg, 89%) which was obtained as an off-white foam. MS (ESI): 382.2 ([M+H]$^+$).

Example 90

5-[(3R)-3-tert-butoxypyrrolidin-1-yl]-2-[[5-methyl-3-(6-methyl-3-pyridyl)isoxazol-4-yl]methyl]pyridazin-3-one

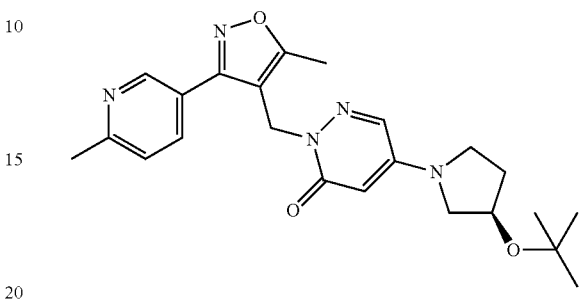

In analogy to experiment of example 3, 5-chloro-2-[[5-methyl-3-(6-methyl-3-pyridyl)isoxazol-4-yl]methyl]pyridazin-3-one, using (3R)-3-tert-butoxypyrrolidine oxalate instead of (R)-3-hydroxypyrrolidine, was converted into the title compound (74 mg, 92%) which was obtained as an off-white foam. MS (ESI): 424.3 ([M+H]$^+$).

Example 91

5-[(2S)-2-methylmorpholin-4-yl]-2-[[3-(6-methyl-3-pyridyl)isoxazol-4-yl]methyl]pyridazin-3-one

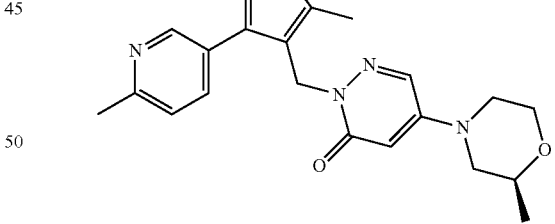

In analogy to experiment of example 3, 5-chloro-2-[[3-(6-methyl-3-pyridyl)isoxazol-4-yl]methyl]pyridazin-3-one (building block E), using (S)-2-methylmorpholine hydrochloride instead of (R)-3-hydroxypyrrolidine, was converted into the title compound (54 mg, 74%) which was obtained as an off-white foam. MS (ESI): 368.2 ([M+H]$^+$).

Example 92

5-[(2R)-2-methylmorpholin-4-yl]-2-[[3-(6-methyl-3-pyridyl)isoxazol-4-yl]methyl]pyridazin-3-one

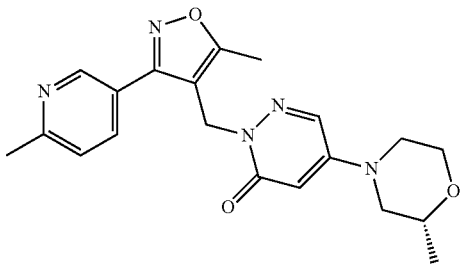 [SMILES: Cc1ccc(-c2noc(C)c2Cn2ncc(N3CCO[C@H](C)C3)cc2=O)cn1]

In analogy to experiment of example 3, 5-chloro-2-[[3-(6-methyl-3-pyridyl)isoxazol-4-yl]methyl]pyridazin-3-one (building block E), using (R)-2-methylmorpholine hydrochloride instead of (R)-3-hydroxypyrrolidine, was converted into the title compound (54 mg, 74%) which was obtained as an off-white foam. MS (ESI): 368.2 ([M+H]+).

Example 93

5-[(3R,5S)-3,5-dimethylpiperazin-1-yl]-2-[[5-methyl-3-(6-methyl-3-pyridyl)isoxazol-4-yl]methyl]pyridazin-3-one

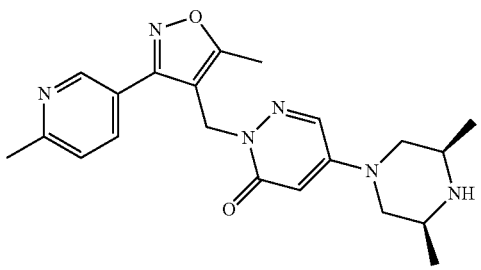

a) tert-butyl cis-2,6-dimethyl-4-[1-[[5-methyl-3-(6-methyl-3-pyridyl)isoxazol-4-yl]methyl]-6-oxo-pyridazin-4-yl]piperazine-1-carboxylate In analogy to experiment of example 3, 5-chloro-2-[[5-methyl-3-(6-methyl-3-pyridyl)isoxazol-4-yl]methyl]pyridazin-3-one, using tert-butyl cis-2,6-dimethylpiperazine-1-carboxylate instead of (R)-3-hydroxypyrrolidine, was converted into the title compound (546 mg, 71%) which was obtained as an orange solid. MS (ESI): 495.5 ([M+H]+).

b) 5-[(3R,5S)-3,5-dimethylpiperazin-1-yl]-2-[[5-methyl-3-(6-methyl-3-pyridyl)isoxazol-4-yl]methyl]pyridazin-3-one In analogy to experiment of example 74 b, using tert-butyl cis-2,6-dimethyl-4-[1-[[5-methyl-3-(6-methyl-3-pyridyl)isoxazol-4-yl]methyl]-6-oxo-pyridazin-4-yl]piperazine-1-carboxylate instead of tert-butyl 7-[1-[[5-methyl-3-(6-methyl-3-pyridyl)isoxazol-4-yl]methyl]-6-oxo-pyridazin-4-yl]-4,7-diazaspiro[2.5]octane-4-carboxylate was converted into the title compound (234 mg, 87%) which was obtained as an orange oil. MS (ESI): 395.3 ([M+H]+).

Example 94

2-[[5-methyl-3-(6-methyl-3-pyridyl)isoxazol-4-yl]methyl]-5-(3-phenoxyazetidin-1-yl)pyridazin-3-one

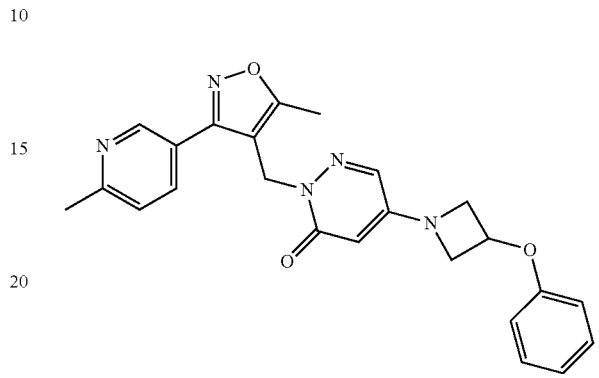

In analogy to experiment of example 3, 5-chloro-2-[[5-methyl-3-(6-methyl-3-pyridyl)isoxazol-4-yl]methyl]pyridazin-3-one, using 3-phenoxyazetidine hydrochloride instead of (R)-3-hydroxypyrrolidine, was converted into the title compound (73 mg, 90%) which was obtained as an off-white foam. MS (ESI): 430.3 ([M+H]+).

Example 95

2-[[5-methyl-3-(6-methyl-3-pyridyl)isoxazol-4-yl]methyl]-5-(5-oxa-2-azaspiro[3.4]octane-2-yl)pyridazin-3-one

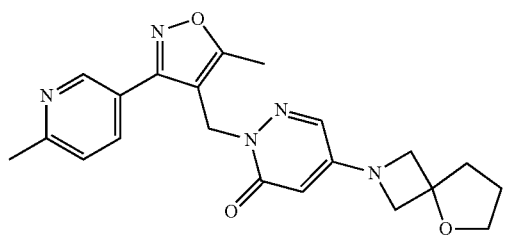 [SMILES: Cc1ccc(-c2noc(C)c2Cn2ncc(N3CC4(CCCO4)C3)cc2=O)cn1]

In analogy to experiment of example 3, 5-chloro-2-[[5-methyl-3-(6-methyl-3-pyridyl)isoxazol-4-yl]methyl]pyridazin-3-one, using 5-oxa-2-azaspiro[3.4]octane hydrochloride instead of (R)-3-hydroxypyrrolidine, was converted into the title compound (68 mg, 91%) which was obtained as an off-white foam. MS (ESI): 394.2 ([M+H]+).

Example 96

5-((1-cyclopropylazetidin-3-yl)amino)-2-((5-methyl-3-(6-methylpyridin-3-yl)isoxazol-4-yl)methyl)pyridazin-3(2H)-one

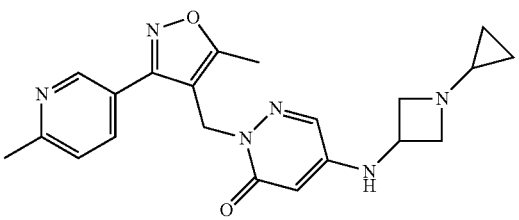 [SMILES: Cc1ccc(-c2noc(C)c2Cn2ncc(NC3CN(C4CC4)C3)cc2=O)cn1]

a) tert-butyl 3-[[1-[[5-methyl-3-(6-methyl-3-pyridyl)isoxazol-4-yl]methyl]-6-oxo-pyridazin-4-yl]amino]azetidine-1-carboxylate In analogy to experiment of example 64, 5-chloro-2-[[5-methyl-3-(6-methyl-3-pyridyl)isoxazol-4-yl]methyl]pyridazin-3-one, using tert-butyl 3-aminoazetidine-1-carboxylate instead of N-methylcyclopropanamine oxalate, was converted into the title compound (292 mg, 87%) which was obtained as a light yellow viscous oil. MS (ESI): 453.2 ([M+H]$^+$).

b) 5-(azetidin-3-ylamino)-2-[[5-methyl-3-(6-methyl-3-pyridyl)isoxazol-4-yl]methyl]pyridazin-3-one In analogy to experiment of example 50 b, tert-butyl 3-[[1-[[5-methyl-3-(6-methyl-3-pyridyl)isoxazol-4-yl]methyl]-6-oxo-pyridazin-4-yl]amino]azetidine-1-carboxylate instead of tert-butyl (2R)-2-methyl-4-[1-[[5-methyl-3-(6-methyl-3-pyridyl)isoxazol-4-yl]methyl]-6-oxo-pyridazin-4-yl]piperazine-1-carboxylate was converted into the title compound (55 mg, 38%) which was obtained as a white foam. MS (ESI): 353.1 ([M+H]$^+$).

c) 5-((1-cyclopropylazetidin-3-yl)amino)-2-((5-methyl-3-(6-methylpyridin-3-yl)isoxazol-4-yl)methyl)pyridazin-3(2H)-one In analogy to experiment of example 59, 5-(azetidin-3-ylamino)-2-[[5-methyl-3-(6-methyl-3-pyridyl)isoxazol-4-yl]methyl]pyridazin-3-one instead of 2-[[5-methyl-3-(6-methyl-3-pyridyl)isoxazol-4-yl]methyl]-5-[(3R)-3-methylpiperazin-1-yl]pyridazin-3-one was converted into the title compound (24 mg, 46%) which was obtained as a white foam. MS (ESI): 393.3 ([M+H]$^+$).

Example 97

5-(azetidin-1-yl)-2-[[5-methyl-3-(6-methyl-3-pyridyl)isoxazol-4-yl]methyl]pyridazin-3-one

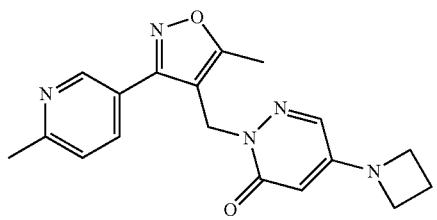 [SMILES: Cc1ccc(-c2noc(C)c2Cn2ncc(N3CCC3)cc2=O)cn1]

In analogy to experiment of example 5, 5-chloro-2-[[5-methyl-3-(6-methyl-3-pyridyl)isoxazol-4-yl]methyl]pyridazin-3-one, using azetidine instead of piperidin-4-ol, was converted into the title compound (331 mg, 91%) which was obtained as a white solid. MS (ESI): 338.2 ([M+H]$^+$).

Example 98

5-(3-hydroxy-3-methyl-azetidin-1-yl)-2-[[5-methyl-3-(6-methyl-3-pyridyl)isoxazol-4-yl]methyl]pyridazin-3-one

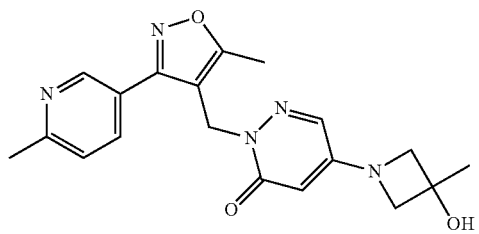

In analogy to experiment of example 3, 5-chloro-2-[[5-methyl-3-(6-methyl-3-pyridyl)isoxazol-4-yl]methyl]pyridazin-3-one, using 3-methylazetidin-3-ol hydrochloride instead of (R)-3-hydroxypyrrolidine, was converted into the title compound (260 mg, 93%) which was obtained as a white foam. MS (ESI): 368.3 ([M+H]$^+$).

Example 99

5-(3-ethoxyazetidin-1-yl)-2-[[5-methyl-3-(6-methyl-3-pyridyl)isoxazol-4-yl]methyl]pyridazin-3-one

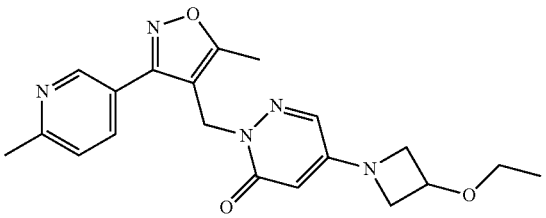 [SMILES: CCOC1CN(c2cnn(Cc3c(-c4ccc(C)nc4)noc3C)c(=O)c2)C1]

In analogy to experiment of example 3, 5-chloro-2-[[5-methyl-3-(6-methyl-3-pyridyl)isoxazol-4-yl]methyl]pyridazin-3-one, using 3-ethoxyazetidine hydrochloride instead of (R)-3-hydroxypyrrolidine, was converted into the title compound (449 mg, 83%) which was obtained as an off-white powder. MS (ESI): 382.2 ([M+H]$^+$).

Example 100

2-[[5-methyl-3-(6-methyl-3-pyridyl)isoxazol-4-yl]methyl]-5-(6-oxa-3-azabicyclo[3.1.1]heptan-3-yl)pyridazin-3-one

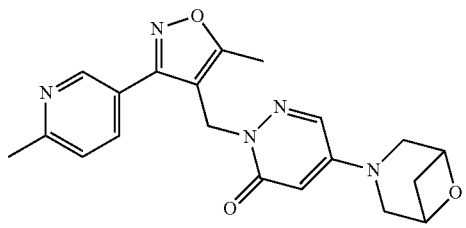 [SMILES: Cc1ccc(-c2noc(C)c2Cn2ncc(N3CC4CC(C3)O4)cc2=O)cn1]

In analogy to experiment of example 3, 5-chloro-2-[[5-methyl-3-(6-methyl-3-pyridyl)isoxazol-4-yl]methyl]pyridazin-3-one, using 6-oxa-3-azabicyclo[3.1.1]heptane oxalate instead of (R)-3-hydroxypyrrolidine, was converted into the title compound (43 mg, 72%) which was obtained as an off-white solid. MS (ESI): 380.3 ([M+H]$^+$).

Example 101

5-[4-(2-methoxy-3-pyridyl)piperazin-1-yl]-2-[[5-methyl-3-(6-methyl-3-pyridyl)isoxazol-4-yl]methyl]pyridazin-3-one

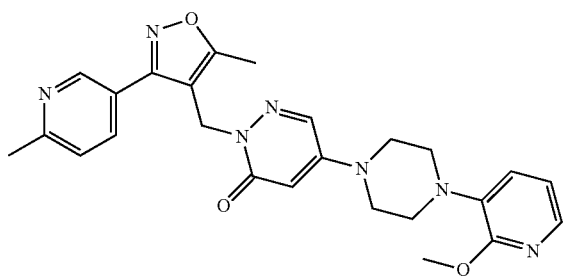 [SMILES: COc1ncccc1N1CCN(c2cnn(Cc3c(-c4ccc(C)nc4)noc3C)c(=O)c2)CC1]

To a solution of 2-[[5-methyl-3-(6-methyl-3-pyridyl)isoxazol-4-yl]methyl]-5-piperazin-1-yl-pyridazin-3-one (70 mg, 0.19 mmol) in toluene (1 mL) was added 3-bromo-2-methoxypyridine (35 µl, 0.23 mmol) and sodium tert-butoxide (46 mg, 0.48 mmol). The flask was evacuated and backfilled with argon. After the addition of tris(dibenzylideneacetone)dipalladium (0) chloroform adduct (18 mg, 0.017 mmol) and rac-BINAP (24 mg, 0.039 mmol) the reaction mixture was heated to 100° C. for 18 h. After cooling to room temperature the reaction mixture was then extracted with EtOAc (30 mL) and water (3 mL). The aqueous layer was back extracted twice with EtOAc (30 mL). The organic layers were washed twice with water (3 mL) and with brine (3 mL). The organic layers were combined, dried over sodium sulfate, filtered and concentrated. Purification by flash chromatography (silica, gradient: 0% to 10% MeOH in CH$_2$C$_2$) afforded the title compound (35 mg, 39%) as a light yellow foam. MS (ESI): 474.3 ([M+H]$^+$).

Example 102

5-(dimethylamino)-2-[[3-(5-fluoro-6-methyl-3-pyridyl)-5-methyl-isoxazol-4-yl]methyl]pyridazin-3-one

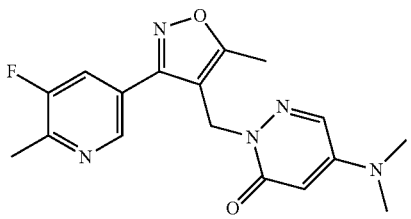

To a stirred solution of 4-(dimethylamino)-1H-pyridazin-6-one (80 mg, 0.57 mmol) in dimethylformamide (2.5 mL) under nitrogen at room temperature were added Cs$_2$CO$_3$ (654 mg, 2.01 mmol) and 4-(chloromethyl)-3-(5-fluoro-6-methyl-3-pyridyl)-5-methyl-isoxazole (207 mg, 0.86 mmol). The sealed tube was capped and heated to 60° C. for 4 h. After cooling to room temperature the reaction mixture was filtered off through a sintered funnel and rinsed with the minimal amount of dimethylformamide (~1.0 mL). The filtrate was purified directly by preparative HPLC (column: YMC Triart C-18, eluent: CH$_3$CN and 10 mm NH$_4$OAc in water) to provide the title compound (74 mg, 37%) as an off-white solid. MS (ESI): 344.0 ([M+H]$^+$).

Example 103

2-((5-methyl-3-(6-methyl-3-pyridyl)isoxazol-4-yl)methyl)-5-(1-methylpyrazol-4-yl)pyridazin-3-one

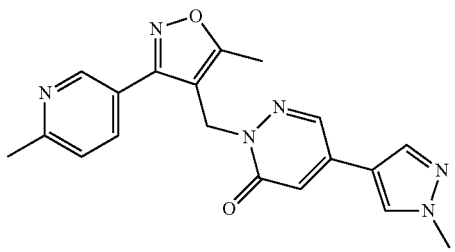

In analogy to experiment of example 67, 5-chloro-2-[[5-methyl-3-(6-methyl-3-pyridyl)isoxazol-4-yl]methyl]pyridazin-3-one, using (1-methyl-1H-pyrazol-4-yl)boronic acid instead of phenylboronic acid, was converted into the title compound (299 mg, 52%) which was obtained as an off-white solid. MS (ESI): 363.2 ([M+H]$^+$).

Example 104

5-(3-methoxyazetidin-1-yl)-2-[[5-methyl-3-(6-methyl-3-pyridyl)isoxazol-4-yl]methyl]pyridazin-3-one

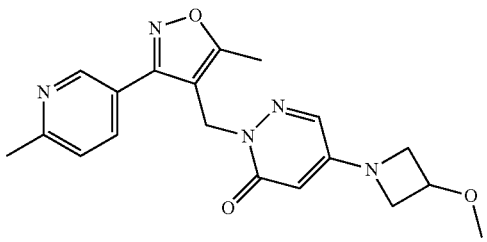

In analogy to experiment of example 3, 5-chloro-2-[[5-methyl-3-(6-methyl-3-pyridyl)isoxazol-4-yl]methyl]pyridazin-3-one, using 3-methoxyazetidine hydrochloride instead of (R)-3-hydroxypyrrolidine, was converted into the title compound (31 mg, 53%) which was obtained as an off-white solid. MS (ESI): 368.3 ([M+H]$^+$).

Example 105

5-(3-hydroxyazetidin-1-yl)-2-[[5-methyl-3-(6-methyl-3-pyridyl)isoxazol-4-yl]methyl]pyridazin-3-one

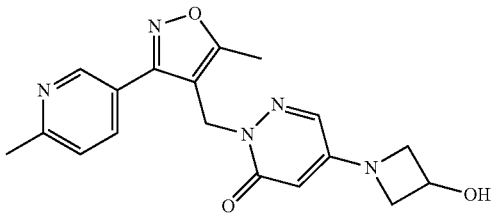 [SMILES: Cc1ccc(-c2noc(C)c2Cn2ncc(N3CC(O)C3)cc2=O)cn1]

In analogy to experiment of example 3, 5-chloro-2-[[5-methyl-3-(6-methyl-3-pyridyl)isoxazol-4-yl]methyl]pyridazin-3-one, using 3-hydroxyazetidine hydrochloride instead of (R)-3-hydroxypyrrolidine, was converted into the title compound (108 mg, 97%) which was obtained as an off-white solid. MS (ESI): 354.2 ([M+H]$^+$).

Example 106

2-((5-methyl-3-(6-methylpyridin-3-yl)isoxazol-4-yl)methyl)-5-(2-methylpyridin-4-yl)pyridazin-3(2H)-one

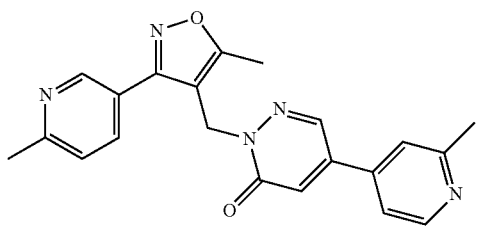

In analogy to experiment of example 67, 5-chloro-2-[[5-methyl-3-(6-methyl-3-pyridyl)isoxazol-4-yl]methyl]pyridazin-3-one, using (2-methylpyridin-4-yl)boronic acid instead of phenylboronic acid, was converted into the title compound (58 mg, 98%) which was obtained as a light brown solid. MS (ESI): 374.1 ([M+H]$^+$).

Example 107

5-(2-methoxypyridin-4-yl)-2-((5-methyl-3-(6-methylpyridin-3-yl)isoxazol-4-yl)methyl)pyridazin-3(2H)-one

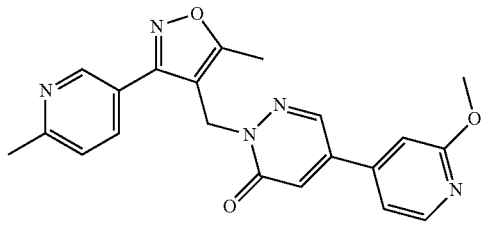 [SMILES: COc1cc(-c2cnn(Cc3c(-c4ccc(C)nc4)noc3C)c(=O)c2)ccn1]

In analogy to experiment of example 67, 5-chloro-2-[[5-methyl-3-(6-methyl-3-pyridyl)isoxazol-4-yl]methyl]pyridazin-3-one, using (2-methoxypyridin-4-yl)boronic acid instead of phenylboronic acid, was converted into the title compound (289 mg, 78%) which was obtained as a white solid. MS (ESI): 390.2 ([M+H]$^+$).

Example 108

2-((5-methyl-3-(6-methylpyridin-3-yl)isoxazol-4-yl)methyl)-5-(2-(trifluoromethyl)pyridin-4-yl)pyridazin-3(2H)-one

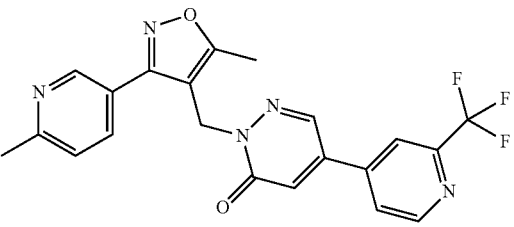 [SMILES: Cc1ccc(-c2noc(C)c2Cn2ncc(-c3ccnc(C(F)(F)F)c3)cc2=O)cn1]

In analogy to experiment of example 67, 5-chloro-2-[[5-methyl-3-(6-methyl-3-pyridyl)isoxazol-4-yl]methyl]pyridazin-3-one, using (2-(trifluoromethyl)pyridin-4-yl)boronic acid instead of phenylboronic acid, was converted into the title compound (32 mg, 48%) which was obtained as a light grey solid. MS (ESI): 428.2 ([M+H]$^+$)

Example 109

5-[4-(2-ethylimidazol-1-yl)-1-piperidyl]-2-[[5-methyl-3-(6-methyl-3-pyridyl)isoxazol-4-yl]methyl]pyridazin-3-one

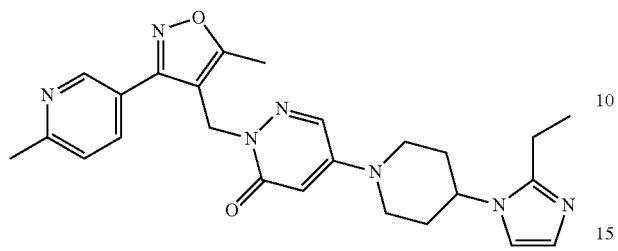

In analogy to experiment of example 3, 5-chloro-2-[[5-methyl-3-(6-methyl-3-pyridyl)isoxazol-4-yl]methyl]pyridazin-3-one, using 4-(2-ethylimidazol-1-yl)piperidine 2,2,2-trifluoroacetate instead of (R)-3-hydroxypyrrolidine, was converted into the title compound (72 mg, 76%) which was obtained as an off-white foam. MS (ESI): 460.3 ([M+H]$^+$).

Example 110

5-[4-(2-methylimidazol-1-yl)-1-piperidyl]-2-[[5-methyl-3-(6-methyl-3-pyridyl)isoxazol-4-yl]methyl]pyridazin-3-one

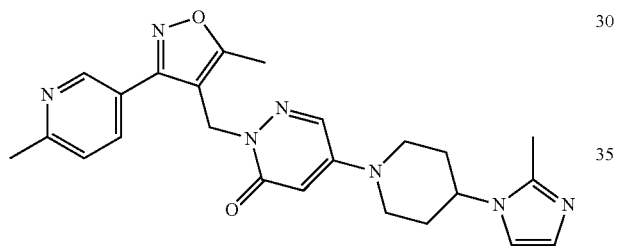

In analogy to experiment of example 3, 5-chloro-2-[[5-methyl-3-(6-methyl-3-pyridyl)isoxazol-4-yl]methyl]pyridazin-3-one, using 4-(2-methylimidazol-1-yl)piperidine 2,2,2-trifluoroacetate instead of (R)-3-hydroxypyrrolidine, was converted into the title compound (66 mg, 78%) which was obtained as an off-white solid. MS (ESI): 446.3 ([M+H]$^+$).

Example 111

5-[3-(cyclopropylmethoxy)azetidin-1-yl]-2-[[5-methyl-3-(6-methyl-3-pyridyl)isoxazol-4-yl]methyl]pyridazin-3-one

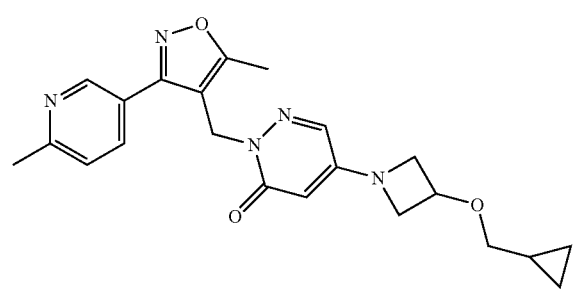 [SMILES: Cc1ccc(-c2noc(C)c2Cn2ncc(N3CC(OCC4CC4)C3)cc2=O)cn1]

In analogy to experiment of example 3, 5-chloro-2-[[5-methyl-3-(6-methyl-3-pyridyl)isoxazol-4-yl]methyl]pyridazin-3-one, using 3-(cyclopropylmethoxy)azetidine 2,2,2-trifluoroacetate instead of (R)-3-hydroxypyrrolidine, was converted into the title compound (67 mg, 87%) which was obtained as a colorless oil. MS (ESI): 408.3 ([M+H]$^+$).

Example 112

5-(3-isopropoxyazetidin-1-yl)-2-[[5-methyl-3-(6-methyl-3-pyridyl)isoxazol-4-yl]methyl]pyridazin-3-one

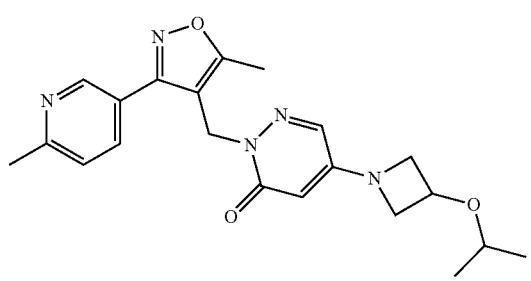 [SMILES: Cc1ccc(-c2noc(C)c2Cn2ncc(N3CC(OC(C)C)C3)cc2=O)cn1]

In analogy to experiment of example 3, 5-chloro-2-[[5-methyl-3-(6-methyl-3-pyridyl)isoxazol-4-yl]methyl]pyridazin-3-one, using 3-Isopropoxyazetidine 2,2,2-trifluoroacetate instead of (R)-3-hydroxypyrrolidine, was converted into the title compound (52 mg, 93%) which was obtained as a colorless oil. MS (ESI): 396.3 ([M+H]$^+$).

Example 113

5-(3,4-dimethoxyphenyl)-2-((5-methyl-3-(6-methyl-3-pyridyl)isoxazol-4-yl)methyl)pyridazin-3-one

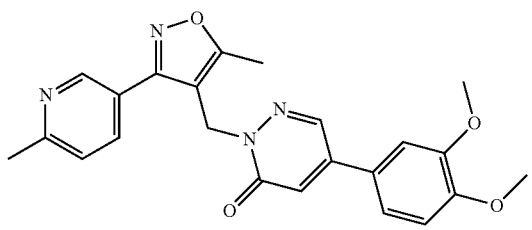

In analogy to experiment of example 145, 5-chloro-2-[[5-methyl-3-(6-methyl-3-pyridyl)isoxazol-4-yl]methyl]pyridazin-3-one, using (3,4-dimethoxyphenyl)boronic acid instead of (6-methoxypyridin-2-yl)boronic acid, was converted into the title compound (52 mg, 39%) which was obtained as an off-white solid. MS (ESI): 419.0 ([M+H]$^+$).

Example 114

2-((5-methyl-3-(6-methyl-3-pyridyl)isoxazol-4-yl)methyl)-5-(4-(trifluoromethoxy)phenyl)pyridazin-3-one

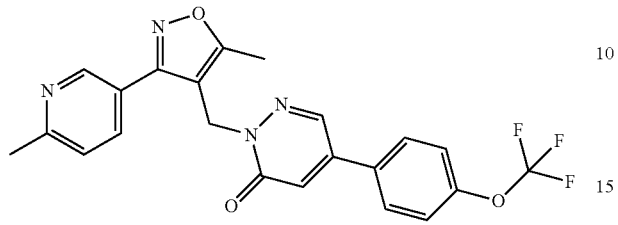

In analogy to experiment of example 145, 5-chloro-2-[[5-methyl-3-(6-methyl-3-pyridyl)isoxazol-4-yl]methyl]pyridazin-3-one, using [4-(trifluoromethoxy)phenyl]boronic acid instead of (6-methoxypyridin-2-yl)boronic acid, was converted into the title compound (54 mg, 38%) which was obtained as an off-white solid. MS (ESI): 442.9 ([M+H]$^+$).

Example 115

5-(4-isopropoxyphenyl)-2-((5-methyl-3-(6-methyl-3-pyridyl)isoxazol-4-yl)methyl)pyridazin-3-one

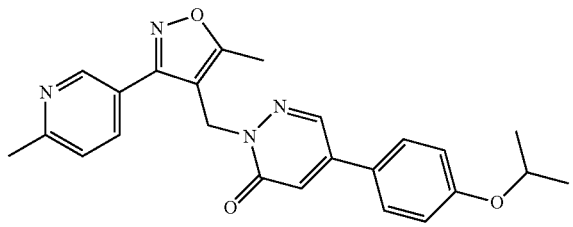 [SMILES: Cc1ccc(-c2noc(C)c2Cn2ncc(-c3ccc(OC(C)C)cc3)cc2=O)cn1]

In analogy to experiment of example 145, 5-chloro-2-[[5-methyl-3-(6-methyl-3-pyridyl)isoxazol-4-yl]methyl]pyridazin-3-one, using (4-isopropoxyphenyl)boronic acid instead of (6-methoxypyridin-2-yl)boronic acid, was converted into the title compound (54 mg, 41%) which was obtained as an off-white solid. MS (ESI): 417.0 ([M+H]$^+$).

Example 116

5-[6-(dimethylamino)-3-pyridyl]-2-((5-methyl-3-(6-methyl-3-pyridyl)isoxazol-4-yl)methyl)pyridazin-3-one

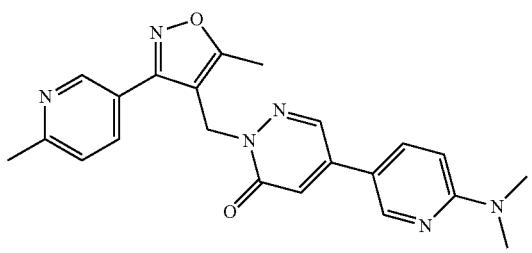

In analogy to experiment of example 145, 5-chloro-2-[[5-methyl-3-(6-methyl-3-pyridyl)isoxazol-4-yl]methyl]pyridazin-3-one, using [6-(dimethylamino)-3-pyridyl]boronic acid instead of (6-methoxypyridin-2-yl)boronic acid, was converted into the title compound (29 mg, 23%) which was obtained as a yellow solid. MS (ESI): 403.1 ([M+H]$^+$).

Example 117

5-(3-hydroxy-3-(trifluoromethyl)azetidin-1-yl)-2-((5-methyl-3-(6-methylpyridin-3-yl)isoxazol-4-yl)methyl)pyridazin-3(2H)-one

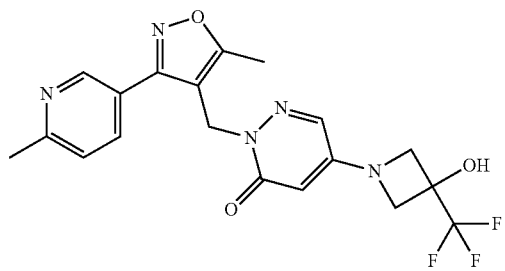 [SMILES: Cc1ccc(-c2noc(C)c2Cn2ncc(N3CC(O)(C(F)(F)F)C3)cc2=O)cn1]

In analogy to experiment of example 64, 5-chloro-2-[[5-methyl-3-(6-methyl-3-pyridyl)isoxazol-4-yl]methyl]pyridazin-3-one, using 3-(trifluoromethyl)azetidin-3-ol hydrochloride instead of N-methylcyclopropanamine oxalate, was converted into the title compound (45 mg, 68%) which was obtained as a light brown solid. MS (ESI): 422.1 ([M+H]$^+$).

Example 118

5-(3-hydroxy-3-methylpyrrolidin-1-yl)-2-((5-methyl-3-(6-methylpyridin-3-yl)isoxazol-4-yl)methyl)pyridazin-3(2H)-one

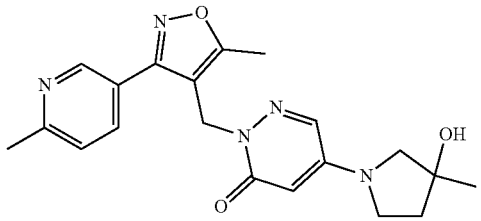

In analogy to experiment of example 64, 5-chloro-2-[[5-methyl-3-(6-methyl-3-pyridyl)isoxazol-4-yl]methyl]pyridazin-3-one, using 3-methylpyrrolidin-3-ol instead of N-methylcyclopropanamine oxalate, was converted into the title compound (34 mg, 57%) which was obtained as a colorless viscous oil. MS (ESI): 382.2 ([M+H]$^+$).

Example 119

5-(4-hydroxy-4-methylpiperidin-1-yl)-2-((5-methyl-3-(6-methylpyridin-3-yl)isoxazol-4-yl)methyl)pyridazin-3(2H)-one

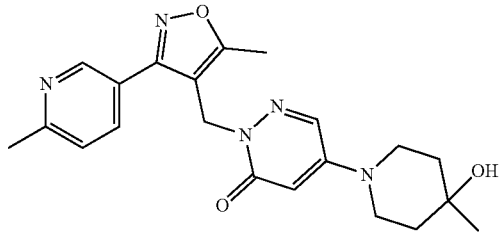 [SMILES: Cc1ccc(-c2noc(C)c2Cn2ncc(N3CCC(C)(O)CC3)cc2=O)cn1]

In analogy to experiment of example 64, 5-chloro-2-[[5-methyl-3-(6-methyl-3-pyridyl)isoxazol-4-yl]methyl]pyridazin-3-one, using 4-methylpiperidin-4-ol instead of N-methylcyclopropanamine oxalate, was converted into the title compound (60 mg, 96%) which was obtained as a colorless viscous oil. MS (ESI): 396.2 ([M+H]$^+$).

Example 120

5-((3S)-3-(2-hydroxypropan-2-yl)pyrrolidin-1-yl)-2-((5-methyl-3-(6-methylpyridin-3-yl)-1,2-oxazol-4-yl)methyl)pyridazin-3-one

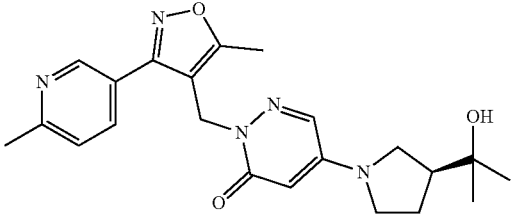 [SMILES: Cc1ccc(-c2noc(C)c2Cn2ncc(N3CC[C@H](C(C)(C)O)C3)cc2=O)cn1]

In analogy to experiment of example 64, 5-chloro-2-[[5-methyl-3-(6-methyl-3-pyridyl)isoxazol-4-yl]methyl]pyridazin-3-one, using (S)-2-(pyrrolidin-3-yl)propan-2-ol instead of N-methylcyclopropanamine oxalate, was converted into the title compound (60 mg, 93%) which was obtained as a white solid. MS (ESI): 410.4 ([M+H]$^+$).

Example 123

5-[3-(4-fluorophenoxy)azetidin-1-yl]-2-[[5-methyl-3-(6-methyl-3-pyridyl)isoxazol-4-yl]methyl]pyridazin-3-one

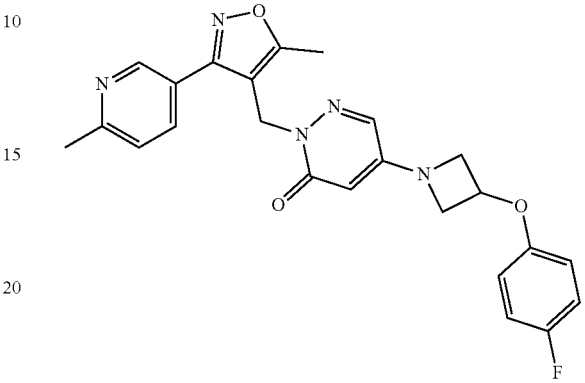

In analogy to experiment of example 3, 5-chloro-2-[[5-methyl-3-(6-methyl-3-pyridyl)isoxazol-4-yl]methyl]pyridazin-3-one, using 3-(4-fluorophenoxy)azetidine instead of (R)-3-hydroxypyrrolidine, was converted into the title compound (49 mg, 58%) which was obtained as an off-white foam. MS (ESI): 448.3 ([M+H]$^+$).

Example 124

2-[[5-methyl-3-(6-methyl-3-pyridyl)isoxazol-4-yl]methyl]-5-[3-(2-pyridyloxy)azetidin-1-yl]pyridazin-3-one

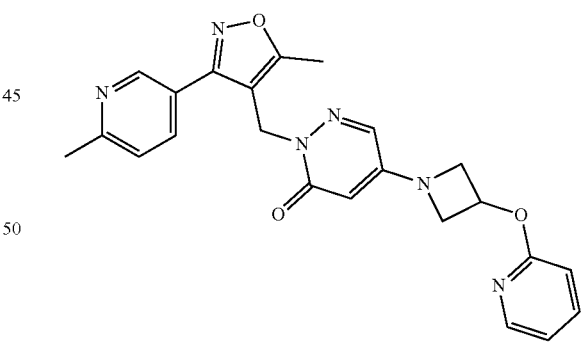

In analogy to experiment of example 3, 5-chloro-2-[[5-methyl-3-(6-methyl-3-pyridyl)isoxazol-4-yl]methyl]pyridazin-3-one, using 2-(azetidin-3-yloxy)pyridine bis(2,2,2-trifluoroacetate) instead of (R)-3-hydroxypyrrolidine, was converted into the title compound (93 mg, 98%) which was obtained as an off-white foam. MS (ESI): 431.3 ([M+H]$^+$).

Example 126

2-[[5-methyl-3-(6-methyl-3-pyridyl)isoxazol-4-yl]methyl]-5-[3-(3-pyridyloxy)azetidin-1-yl]pyridazin-3-one

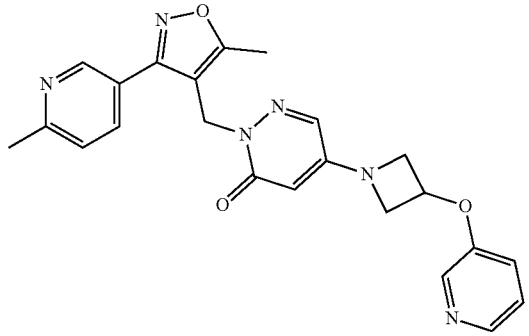 [SMILES: Cc1ccc(-c2noc(C)c2Cn2ncc(N3CC(Oc4cccnc4)C3)cc2=O)cn1]

In analogy to experiment of example 3, 5-chloro-2-[[5-methyl-3-(6-methyl-3-pyridyl)isoxazol-4-yl]methyl]pyridazin-3-one, using 3-(azetidin-3-yloxy)pyridine 2,2,2-trifluoroacetate instead of (R)-3-hydroxypyrrolidine, was converted into the title compound (46 mg, 48%) which was obtained as an off-white solid. MS (ESI): 431.4 ([M+H]+).

Example 127

5-[3-(3-fluorophenoxy)azetidin-1-yl]-2-[[5-methyl-3-(6-methyl-3-pyridyl)isoxazol-4-yl]methyl]pyridazin-3-one

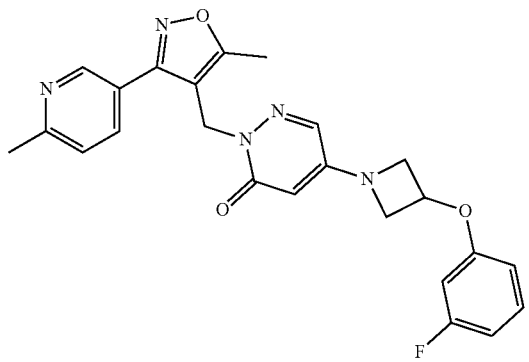 [SMILES: Cc1ccc(-c2noc(C)c2Cn2ncc(N3CC(Oc4cccc(F)c4)C3)cc2=O)cn1]

In analogy to experiment of example 3, 5-chloro-2-[[5-methyl-3-(6-methyl-3-pyridyl)isoxazol-4-yl]methyl]pyridazin-3-one, using 3-(3-fluorophenoxy)azetidine 2,2,2-trifluoroacetate instead of (R)-3-hydroxypyrrolidine, was converted into the title compound (67 mg, 79%) which was obtained as a white foam. MS (ESI): 448.4 ([M+H]+).

Example 128

5-[3-(2-fluorophenoxy)azetidin-1-yl]-2-[[5-methyl-3-(6-methyl-3-pyridyl)isoxazol-4-yl]methyl]pyridazin-3-one

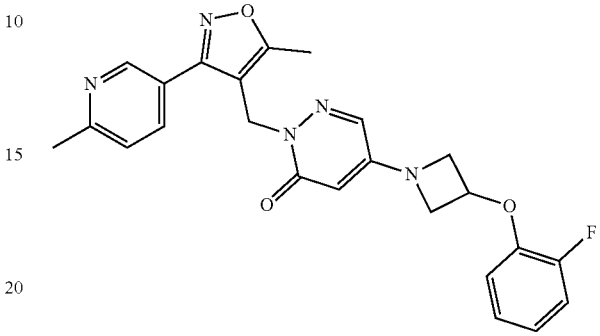

In analogy to experiment of example 3, 5-chloro-2-[[5-methyl-3-(6-methyl-3-pyridyl)isoxazol-4-yl]methyl]pyridazin-3-one, using 3-(2-fluorophenoxy)azetidine 2,2,2-trifluoroacetate instead of (R)-3-hydroxypyrrolidine, was converted into the title compound (65 mg, 77%) which was obtained as a white foam. MS (ESI): 448.4 ([M+H]+).

Example 129

2-[[5-methyl-3-(6-methyl-3-pyridyl)isoxazol-4-yl]methyl]-5-[3-(4-pyridyloxy)azetidin-1-yl]pyridazin-3-one

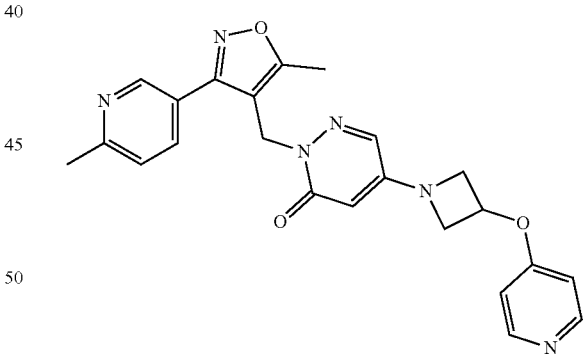

In analogy to experiment of example 3, 5-chloro-2-[[5-methyl-3-(6-methyl-3-pyridyl)isoxazol-4-yl]methyl]pyridazin-3-one, using 4-(azetidin-3-yloxy)pyridine 2,2,2-trifluoroacetate instead of (R)-3-hydroxypyrrolidine, was converted into the title compound (32 mg, 34%) which was obtained as an off-white solid. MS (ESI): 431.4 ([M+H]+).

Example 130

5-[3-[(5-chloro-2-pyridyl)oxy]azetidin-1-yl]-2-[[5-methyl-3-(6-methyl-3-pyridyl)isoxazol-4-yl]methyl]pyridazin-3-one

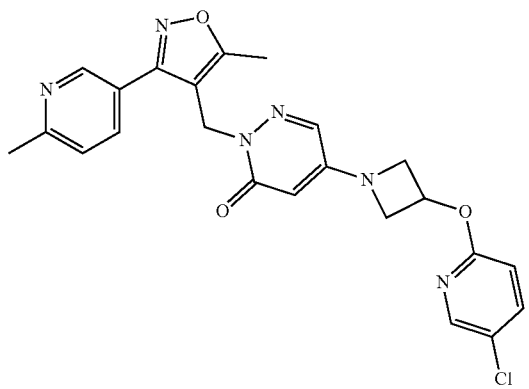 [SMILES: Cc1ccc(-c2noc(C)c2Cn2ncc(N3CC(Oc4ccc(Cl)cn4)C3)cc2=O)cn1]

In analogy to experiment of example 3, 5-chloro-2-[[5-methyl-3-(6-methyl-3-pyridyl)isoxazol-4-yl]methyl]pyridazin-3-one, using 2-(azetidin-3-yloxy)-5-chloropyridine 2,2,2-trifluoroacetate instead of (R)-3-hydroxypyrrolidine, was converted into the title compound (52 mg, 59%) which was obtained as a white solid. MS (ESI): 465.1 ([M+H]+).

Example 131

5-[(7S)-7-hydroxy-5-oxa-2-azaspiro[3.4]octan-2-yl]-2-[[5-methyl-3-(6-methyl-3-pyridyl)isoxazol-4-yl]methyl]pyridazin-3-one

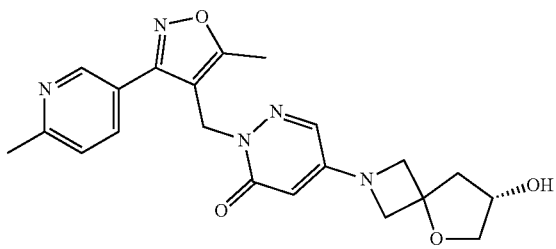 [SMILES: Cc1ccc(-c2noc(C)c2Cn2ncc(N3CC4(C[C@H](O)CO4)C3)cc2=O)cn1]

In analogy to experiment of example 3, 5-chloro-2-[[5-methyl-3-(6-methyl-3-pyridyl)isoxazol-4-yl]methyl]pyridazin-3-one, using (7SR)-5-oxa-2-azaspiro[3.4]octan-7-ol2,2,2-trifluoroacetate instead of (R)-3-hydroxypyrrolidine, was converted into the title compound (218 mg, 89%) which was obtained as a white solid. MS (ESI): 410.3 ([M+H]+).

Example 132

5-[(7R)-7-hydroxy-5-oxa-2-azaspiro[3.4]octan-2-yl]-2-[[5-methyl-3-(6-methyl-3-pyridyl)isoxazol-4-yl]methyl]pyridazin-3-one

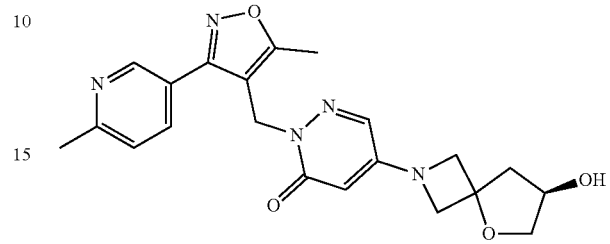

In analogy to experiment of example 3, 5-chloro-2-[[5-methyl-3-(6-methyl-3-pyridyl)isoxazol-4-yl]methyl]pyridazin-3-one, using (7R)-5-oxa-2-azaspiro[3.4]octan-7-ol2,2,2-trifluoroacetate instead of (R)-3-hydroxypyrrolidine, was converted into the title compound (240 mg, 91%) which was obtained as an off-white solid. MS (ESI): 410.3 ([M+H]+).

Example 133

5-[(7S)-7-methoxy-5-oxa-2-azaspiro[3.4]octan-2-yl]-2-[[5-methyl-3-(6-methyl-3-pyridyl)isoxazol-4-yl]methyl]pyridazin-3-one

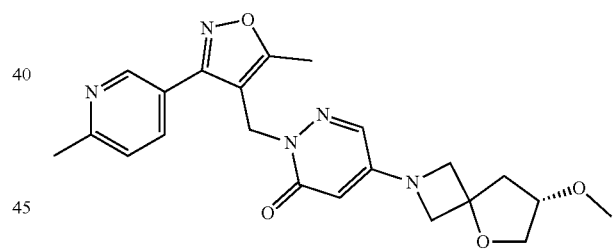

To a solution of 5-[(7S)-7-hydroxy-5-oxa-2-azaspiro[3.4]octan-2-yl]-2-[[5-methyl-3-(6-methyl-3-pyridyl)isoxazol-4-yl]methyl]pyridazin-3-one in DMF (1 mL) and THF (1 mL) was added sodium hydride (60% dispersion in mineral oil) (16 mg, 0.40 mmol). After stirring at room temperature for 30 min methyl iodide (31 µL, 0.50 mmol) was added and the reaction mixture was stirred at room temperature for 18 h. The reaction mixture was quenched with water and then extracted with EtOAc (40 mL) and water (5 mL). The aqueous layer was backextracted with EtOAc (40 mL). The organic layers were washed three times with water (5 mL) and with brine (5 mL). The organic layers were combined, dried over sodium sulfate, filtered and concentrated. Purification by flash chromatography (silica, gradient: 0% to 5% MeOH in CH2Cl2) afforded the title compound (67 mg, 64%) as an off-white foam. MS (ESI): 424.3 ([M+H]+).

Example 134

5-[(7R)-7-methoxy-5-oxa-2-azaspiro[3.4]octan-2-yl]-2-[[5-methyl-3-(6-methyl-3-pyridyl)isoxazol-4-yl]methyl]pyridazin-3-one

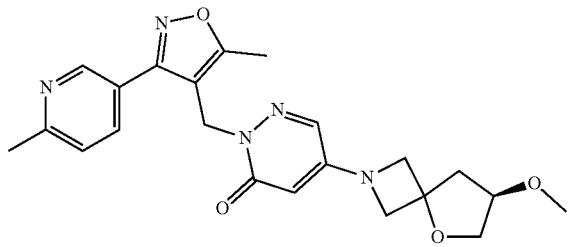

In analogy to experiment of example 133, using 5-[(7R)-7-hydroxy-5-oxa-2-azaspiro[3.4]octan-2-yl]-2-[[5-methyl-3-(6-methyl-3-pyridyl)isoxazol-4-yl]methyl]pyridazin-3-one instead of 5-[(7S)-7-hydroxy-5-oxa-2-azaspiro[3.4]octan-2-yl]-2-[[5-methyl-3-(6-methyl-3-pyridyl)isoxazol-4-yl]methyl]pyridazin-3-one was converted into the title compound (80 mg, 77%) which was obtained as an off-white foam. MS (ESI): 424.3 ([M+H]$^+$).

Example 135

5-[(7R)-7-ethoxy-5-oxa-2-azaspiro[3.4]octan-2-yl]-2-[[5-methyl-3-(6-methyl-3-pyridyl)isoxazol-4-yl]methyl]pyridazin-3-one

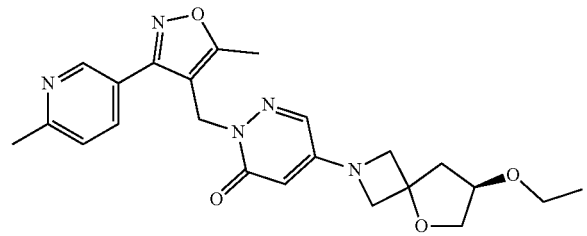 [SMILES: CCO[C@H]1COC2(C1)CN(c1cnn(Cc3c(-c4ccc(C)nc4)noc3C)c(=O)c1)C2]

In analogy to experiment of example 133, using 5-[(7R)-7-hydroxy-5-oxa-2-azaspiro[3.4]octan-2-yl]-2-[[5-methyl-3-(6-methyl-3-pyridyl)isoxazol-4-yl]methyl]pyridazin-3-one instead of 5-[(7S)-7-hydroxy-5-oxa-2-azaspiro[3.4]octan-2-yl]-2-[[5-methyl-3-(6-methyl-3-pyridyl)isoxazol-4-yl]methyl]pyridazin-3-one and using ethyl iodide instead of methyl iodide was converted into the title compound (82 mg, 77%) which was obtained as an off-white foam. MS (ESI): 438.3 ([M+H]$^+$).

Example 136

5-[3-(cyclopropoxy)azetidin-1-yl]-2-[[5-methyl-3-(6-methyl-3-pyridyl)isoxazol-4-yl]methyl]pyridazin-3-one

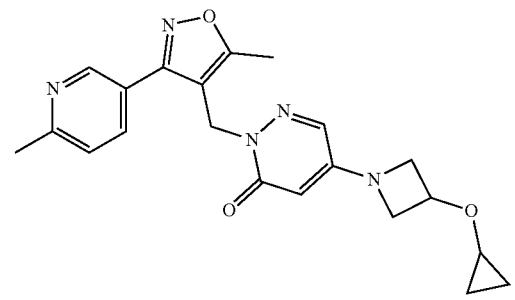 [SMILES: Cc1ccc(-c2noc(C)c2Cn2ncc(N3CC(OC4CC4)C3)cc2=O)cn1]

In analogy to experiment of example 3, 5-chloro-2-[[5-methyl-3-(6-methyl-3-pyridyl)isoxazol-4-yl]methyl]pyridazin-3-one, using 3-cyclopropoxyazetidine instead of (R)-3-hydroxypyrrolidine, was converted into the title compound (191 mg, 57%) which was obtained as an off-white solid. MS (ESI): 394.2 ([M+H]$^+$).

Example 137

5-((1-cyclopropylazetidin-3-yl)(methyl)amino)-2-((5-methyl-3-(6-methylpyridin-3-yl)isoxazol-4-yl)methyl)pyridazin-3(2H)-one

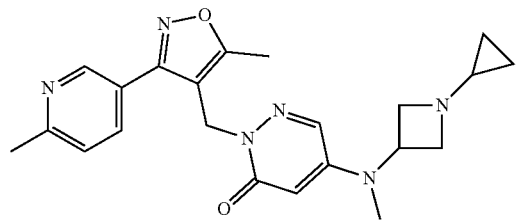 [SMILES: Cc1ccc(-c2noc(C)c2Cn2ncc(N(C)C3CN(C4CC4)C3)cc2=O)cn1]

a) tert-butyl 3-[methyl-[1-[[5-methyl-3-(6-methyl-3-pyridyl)isoxazol-4-yl]methyl]-6-oxo-pyridazin-4-yl]amino]azetidine-1-carboxylate In analogy to experiment of example 64, 5-chloro-2-[[5-methyl-3-(6-methyl-3-pyridyl)isoxazol-4-yl]methyl]pyridazin-3-one, using tert-butyl 3-(methylamino)azetidine-1-carboxylate instead of N-methylcyclopropanamine oxalate, was converted into the title compound (196 mg, 67%) which was obtained as a light brown foam. MS (ESI): 467.2 ([M+H]$^+$).

b) 5-[azetidin-3-yl(methyl)amino]-2-[[5-methyl-3-(6-methyl-3-pyridyl)isoxazol-4-yl]methyl]pyridazin-3-one In analogy to experiment of example 50 b, t tert-butyl 3-[methyl-[1-[[5-methyl-3-(6-methyl-3-pyridyl)isoxazol-4-yl]methyl]-6-oxo-pyridazin-4-yl]amino]azetidine-1-carboxylate instead of tert-butyl (2R)-2-methyl-4-[1-[[5-methyl-3-(6-methyl-3-pyridyl)isoxazol-4-yl]methyl]-6-oxopyridazin-4-yl]piperazine-1-carboxylate was converted into the title compound (80 mg, 68%) which was obtained as a white foam. MS (ESI): 367.1 ([M+H]+).

c) 5-((1-cyclopropylazetidin-3-yl)(methyl)amino)-2-((5-methyl-3-(6-methylpyridin-3-yl)isoxazol-4-yl)methyl)pyridazin-3(2H)-one In analogy to experiment of example 59, 5-[azetidin-3-yl(methyl)amino]-2-[[5-methyl-3-(6-methyl-3-pyridyl)isoxazol-4-yl]methyl]pyridazin-3-one instead of 2-[[5-methyl-3-(6-methyl-3-pyridyl)isoxazol-4-yl]methyl]-5-[(3R)-3-methylpiperazin-1-yl]pyridazin-3-one was converted into the title compound (10 mg, 30%) which was obtained as a white viscous oil. MS (ESI): 407.2 ([M+H]+).

Example 138

5-[3-[(6-chloro-3-pyridyl)oxy]azetidin-1-yl]-2-[[5-methyl-3-(6-methyl-3-pyridyl)isoxazol-4-yl]methyl]pyridazin-3-one

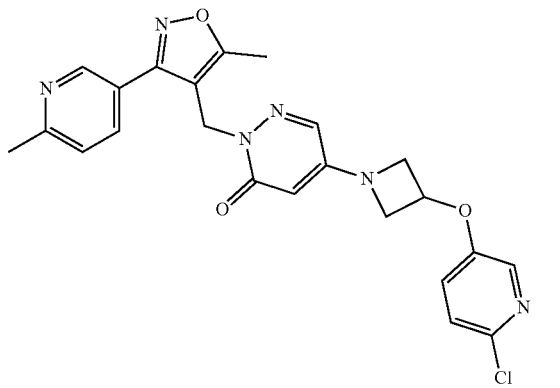 [SMILES: Cc1ccc(-c2noc(C)c2Cn2ncc(N3CC(Oc4ccc(Cl)nc4)C3)cc2=O)cn1]

To a suspension of 5-(3-hydroxyazetidin-1-yl)-2-[[5-methyl-3-(6-methyl-3-pyridyl)isoxazol-4-yl]methyl]pyridazin-3-one (100 mg, 0.283 mmol) in THF (2 mL) was added 2-chloro-5-hydroxypyridine (48 mg, 0.37 mmol) and triphenylphosphine (97 mg, 0.37 mmol). After cooling to 0° C. diisopropyl azodicarboxylate (72 µL, 0.37 mmol) dissolved in THF (0.5 mL) was added dropwise at 0° C. Then the reaction mixture was stirred at room temperature for 18 h and at 50° C. for 24 h. The reaction mixture was cooled to room temperature and then extracted with EtOAc (20 mL) and saturated solution of NaHCO₃ (5 mL). The aqueous layer was back extracted with EtOAc (20 mL). The organic layers were washed with water (5 mL) and brine (5 mL). The organic layers were combined, dried (Na₂SO₄), filtered and concentrated in vacuo. Purification by flash chromatography (silica, gradient: 0% to 10% MeOH in CH₂Cl₂) afforded the title compound (38 mg, 29%) as a white foam. MS (ESI): 465.3 ([M+H]+).

Example 139

5-(4-methoxy-1-piperidyl)-2-[[5-methyl-3-(6-methyl-3-pyridyl)isoxazol-4-yl]methyl]pyridazin-3-one

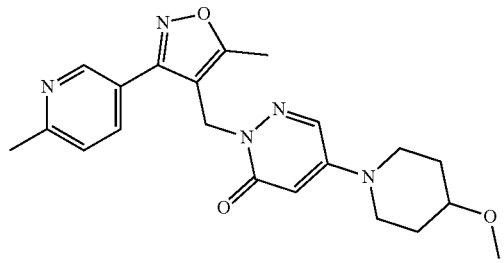

In analogy to experiment of example 3, 5-chloro-2-[[5-methyl-3-(6-methyl-3-pyridyl)isoxazol-4-yl]methyl]pyridazin-3-one, using 4-methoxypiperidine instead of (R)-3-hydroxypyrrolidine, was converted into the title compound (58 mg, 93%) which was obtained as an off-white foam. MS (ESI): 396.3 ([M+H]+).

Example 140

5-(3-methoxyazetidin-1-yl)-2-[[5-methyl-3-(5-methylisoxazol-3-yl)isoxazol-4-yl]methyl]pyridazin-3-one

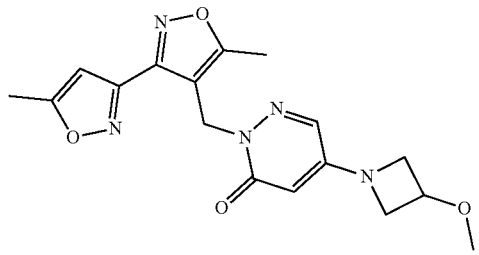

In analogy to experiment of example 3, 5-chloro-2-[[5-methyl-3-(5-methylisoxazol-3-yl)isoxazol-4-yl]methyl]pyridazin-3-one (building block O), using 3-methoxyazetidine hydrochloride instead of (R)-3-hydroxypyrrolidine, was converted into the title compound (57 mg, 98%) which was obtained as an off-white solid. MS (ESI): 358.2 ([M+H]+).

Example 141

5-[3-(cyclopropylmethoxy)azetidin-1-yl]-2-[[5-methyl-3-(5-methylisoxazol-3-yl)isoxazol-4-yl]methyl]pyridazin-3-one

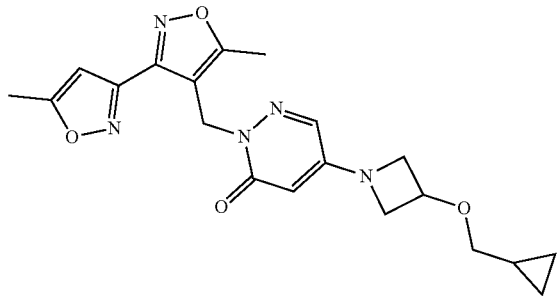 [SMILES: Cc1cc(-c2noc(C)c2Cn2ncc(N3CC(OCC4CC4)C3)cc2=O)no1]

In analogy to experiment of example 3, 5-chloro-2-[[5-methyl-3-(5-methylisoxazol-3-yl)isoxazol-4-yl]methyl]pyridazin-3-one (building block O), using 3-(cyclopropylmethoxy)azetidine 2,2,2-trifluoroacetic acid instead of (R)-3-hydroxypyrrolidine, was converted into the title compound (62 mg, 96%) which was obtained as an off-white solid. MS (ESI): 398.3 ([M+H]$^+$).

Example 142

2-[[5-methyl-3-(5-methylisoxazol-3-yl)isoxazol-4-yl]methyl]-5-(5-oxa-2-azaspiro[3.4]octan-2-yl)pyridazin-3-one

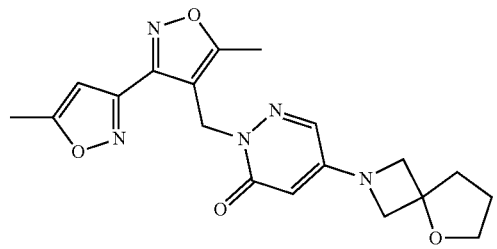 [SMILES: Cc1cc(-c2noc(C)c2Cn2ncc(N3CC4(CCCO4)C3)cc2=O)no1]

In analogy to experiment of example 3, 5-chloro-2-[[5-methyl-3-(5-methylisoxazol-3-yl)isoxazol-4-yl]methyl]pyridazin-3-one (building block O), using 5-oxa-2-azaspiro[3.4]octane hydrochloride instead of (R)-3-hydroxypyrrolidine, was converted into the title compound (59 mg, 94%) which was obtained as an off-white foam. MS (ESI): 384.2 ([M+H]$^+$).

Example 143

2-((3-(5-Chloropyridin-2-yl)-5-methylisoxazol-4-yl)methyl)-5-(3-(cyclopropylmethoxy)azetidin-1-yl)pyridazin-3(2H)-one

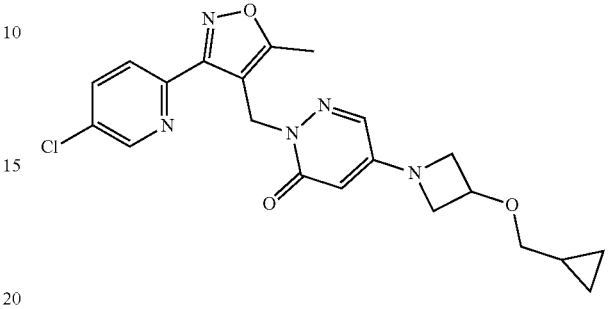

In analogy to experiment of example 3, 5-chloro-2-[[3-(5-chloro-2-pyridyl)-5-methyl-isoxazol-4-yl]methyl]pyridazin-3-one (building block M), using 3-(cyclopropylmethoxy)azetidine 2,2,2-trifluoroacetate instead of (R)-3-hydroxypyrrolidine, was converted into the title compound (74 mg, 81%) which was obtained as an off-white solid. MS (ESI): 428.3 ([M+H]$^+$).

Example 144

2-((3-(5-Chloropyridin-2-yl)-5-methylisoxazol-4-yl)methyl)-5-(5-oxa-2-azaspiro[3.4]octan-2-yl)pyridazin-3(2H)-one

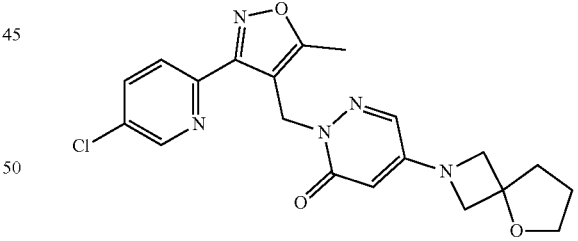

In analogy to experiment of example 3, 5-chloro-2-[[3-(5-chloro-2-pyridyl)-5-methyl-isoxazol-4-yl]methyl]pyridazin-3-one (building block M), using 5-oxa-2-azaspiro[3.4]octane hydrochloride instead of (R)-3-hydroxypyrrolidine, was converted into the title compound (58 mg, 94%) which was obtained as an off-white solid. MS (ESI): 414.2 ([M+H]$^+$).

Example 145

5-(6-methoxy-2-pyridyl)-2-((5-methyl-3-(6-methyl-3-pyridyl)isoxazol-4-yl)methyl)pyridazin-3-one

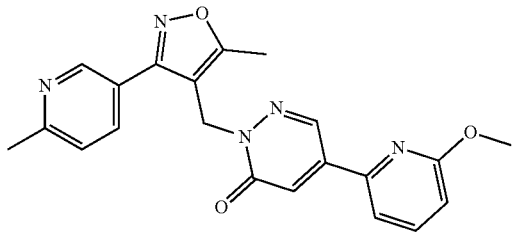

To a stirred solution of 5-chloro-2-[[5-methyl-3-(6-methyl-3-pyridyl)isoxazol-4-yl]methyl]pyridazin-3-one (100 mg, 0.31 mmol) in 1,4-dioxane (4 mL) and water (0.5 mL) at 25° C. under argon was added (6-methoxypyridin-2-yl)boronic acid (148 mg, 0.63 mmol) followed by $Na_2CO_3$ (100 mg, 1.94 mmol). This solution was purged with argon at 25° C. for 20 min. $Pd(PPh_3)_4$ (11 mg, 0.009 mmol) was added at 25° C. and again it was purged with argon at 25° C. for 5 min. The reaction was stirred at 100° C. for 16 h. After cooling to 25° C. the reaction mixture was filtered through a celite pad, washed with ethyl acetate (10 mL). The filtrate was concentrated under reduced pressure and the crude residue was purified by preparative HPLC (column: YMC Triart C-18, eluent: $CH_3CN$ and 10 mm $NH_4OAc$ in water) to afford the title compound (73 mg, 59%) as a white solid. MS (ESI): 390.1 ([M+H]$^+$).

Example 147

5-[3-[(2-chloro-4-pyridyl)oxy]azetidin-1-yl]-2-[[5-methyl-3-(6-methyl-3-pyridyl)isoxazol-4-yl]methyl]pyridazin-3-one

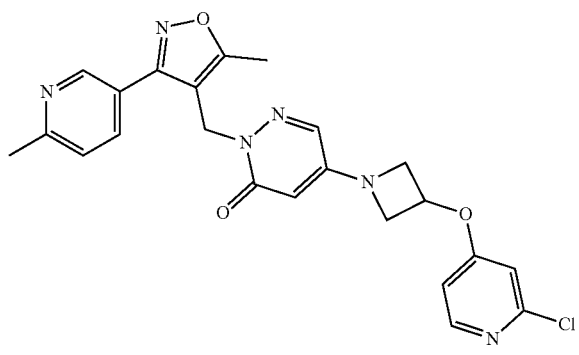 [SMILES: Cc1ccc(-c2noc(C)c2Cn2ncc(N3CC(Oc4ccnc(Cl)c4)C3)cc2=O)cn1]

In analogy to experiment of example 138, 5-(3-hydroxyazetidin-1-yl)-2-[[5-methyl-3-(6-methyl-3-pyridyl)isoxazol-4-yl]methyl]pyridazin-3-one, using 2-chloro-4-hydroxypyridine instead of 2-chloro-5-hydroxypyridine, was converted into the title compound (68 mg, 52%) which was obtained as an off-white solid. MS (ESI): 465.1 ([M+H]$^+$).

Example 148

5-(5-chloro-3-pyridyl)-2-((5-methyl-3-(6-methyl-3-pyridyl)isoxazol-4-yl)methyl)pyridazin-3-one

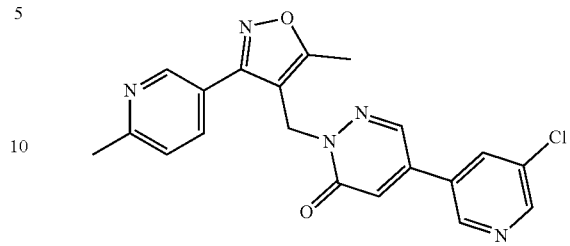

In analogy to experiment of example 145, 5-chloro-2-[[5-methyl-3-(6-methyl-3-pyridyl)isoxazol-4-yl]methyl]pyridazin-3-one, using (5-chloropyridin-3-yl)boronic acid instead of (6-methoxypyridin-2-yl)boronic acid, was converted into the title compound (52 mg, 42%) which was obtained as an off-white solid. MS (ESI): 394.1 ([M+H]$^+$).

Example 149

5-(6-(difluoromethoxy)pyridin-3-yl)-2-((5-methyl-3-(6-methylpyridin-3-yl)isoxazol-4-yl)methyl)pyridazin-3(2H)-one

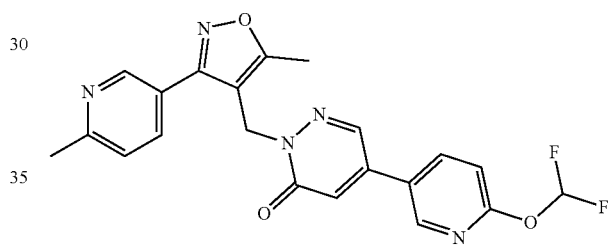

In analogy to experiment of example 67, 5-chloro-2-[[5-methyl-3-(6-methyl-3-pyridyl)isoxazol-4-yl]methyl]pyridazin-3-one, using 2-(difluoromethoxy)-5-(4,4,5,5-tetramethyl-1,3,2-dioxaborolan-2-yl)pyridine instead of phenylboronic acid, was converted into the title compound (76 mg, 71%) which was obtained as a light brown gum. MS (ESI): 426.2 ([M+H]$^+$).

Example 150

5-(3-tert-butoxyazetidin-1-yl)-2-[[5-methyl-3-(6-methyl-3-pyridyl)isoxazol-4-yl]methyl]pyridazin-3-one

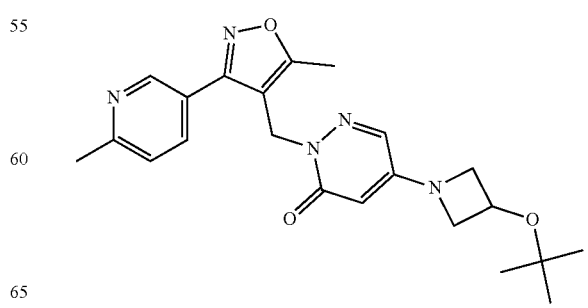

In analogy to experiment of example 3, 5-chloro-2-[[5-methyl-3-(6-methyl-3-pyridyl)isoxazol-4-yl]methyl]pyridazin-3-one, using 3-(tert-butoxy)azetidine hydrochloride instead of (R)-3-hydroxypyrrolidine, was converted into the title compound (378 mg, 82%) which was obtained as an off-white foam. MS (ESI): 410.3 ([M+H]$^+$).

Example 151

5-(6-ethoxypyridin-3-yl)-2-((5-methyl-3-(6-methylpyridin-3-yl)isoxazol-4-yl)methyl)pyridazin-3(2H)-one

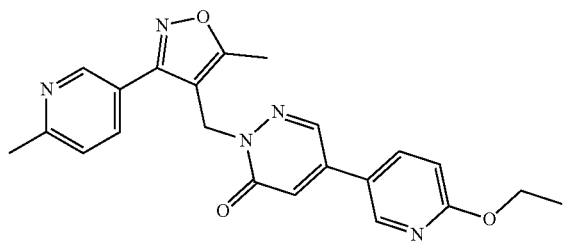 [SMILES: CCOc1ccc(-c2cnn(Cc3c(-c4ccc(C)nc4)noc3C)c(=O)c2)cn1]

In analogy to experiment of example 67, 5-chloro-2-[[5-methyl-3-(6-methyl-3-pyridyl)isoxazol-4-yl]methyl]pyridazin-3-one, using 2-ethoxy-5-(4,4,5,5-tetramethyl-1,3,2-dioxaborolan-2-yl)pyridine instead of phenylboronic acid, was converted into the title compound (95 mg, 75%) which was obtained as an off-white solid. MS (ESI): 404.3 ([M+H]$^+$).

Example 152

5-(1-cyclopropyl-1H-pyrazol-4-yl)-2-((5-methyl-3-(6-methylpyridin-3-yl)isoxazol-4-yl)methyl)pyridazin-3(2H)-one

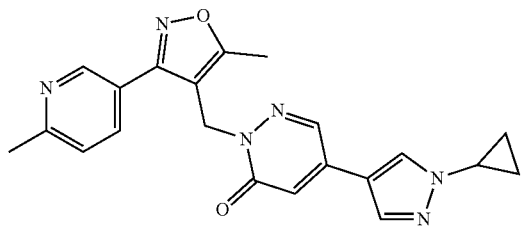 [SMILES: Cc1ccc(-c2noc(C)c2Cn2ncc(-c3cnn(C4CC4)c3)cc2=O)cn1]

In analogy to experiment of example 67, 5-chloro-2-[[5-methyl-3-(6-methyl-3-pyridyl)isoxazol-4-yl]methyl]pyridazin-3-one, using 1-cyclopropyl-4-(4,4,5,5-tetramethyl-1,3,2-dioxaborolan-2-yl)-1H-pyrazole instead of phenylboronic acid, was converted into the title compound (50 mg, 82%) which was obtained as a brown solid. MS (ESI): 389.4 ([M+H]$^+$).

Example 153

5-(1-(2,2-difluoroethyl)-1H-pyrazol-4-yl)-2-((5-methyl-3-(6-methylpyridin-3-yl)isoxazol-4-yl)methyl)pyridazin-3(2H)-one

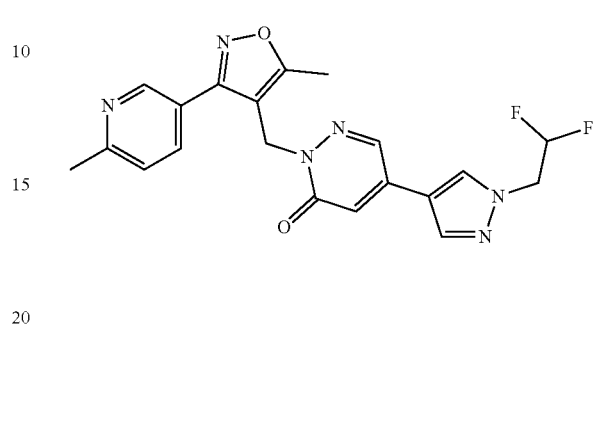

In analogy to experiment of example 67, 5-chloro-2-[[5-methyl-3-(6-methyl-3-pyridyl)isoxazol-4-yl]methyl]pyridazin-3-one, using 1-(2,2-difluoroethyl)-4-(4,4,5,5-tetramethyl-1,3,2-dioxaborolan-2-yl)-1H-pyrazole instead of phenylboronic acid, was converted into the title compound (55 mg, 85%) which was obtained as a white solid. MS (ESI): 413.2 ([M+H]$^+$).

Example 154

5-(1-(difluoromethyl)-1H-pyrazol-4-yl)-2-((5-methyl-3-(6-methylpyridin-3-yl)isoxazol-4-yl)methyl)pyridazin-3(2H)-one

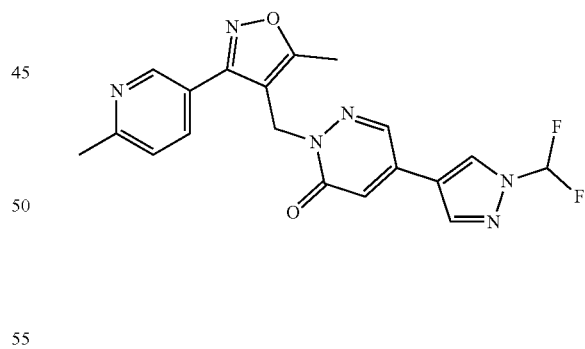

In analogy to experiment of example 67, 5-chloro-2-[[5-methyl-3-(6-methyl-3-pyridyl)isoxazol-4-yl]methyl]pyridazin-3-one, using 1-(difluoromethyl)-4-(4,4,5,5-tetramethyl-1,3,2-dioxaborolan-2-yl)-1H-pyrazole instead of phenylboronic acid, was converted into the title compound (52 mg, 83%) which was obtained as a white solid. MS (ESI): 399.2 ([M+H]$^+$).

Example 155

5-(1-ethyl-1H-pyrazol-4-yl)-2-((5-methyl-3-(6-methylpyridin-3-yl)isoxazol-4-yl)methyl)pyridazin-3(2H)-one

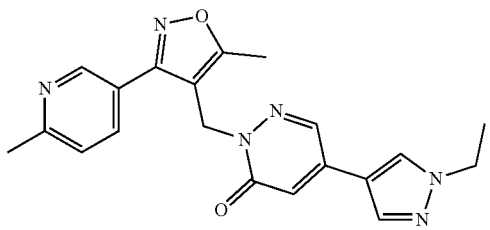 [SMILES: CCn1cc(-c2cnn(Cc3c(-c4ccc(C)nc4)noc3C)c(=O)c2)cn1]

In analogy to experiment of example 67, 5-chloro-2-[[5-methyl-3-(6-methyl-3-pyridyl)isoxazol-4-yl]methyl]pyridazin-3-one, using (1-ethyl-1H-pyrazol-4-yl)boronic acid instead of phenylboronic acid, was converted into the title compound (56 mg, 83%) which was obtained as a light brown solid. MS (ESI): 377.2 ([M+H]$^+$).

Example 156

5-(2-(dimethylamino)pyridin-4-yl)-2-((5-methyl-3-(6-methylpyridin-3-yl)isoxazol-4-yl)methyl)pyridazin-3(2H)-one

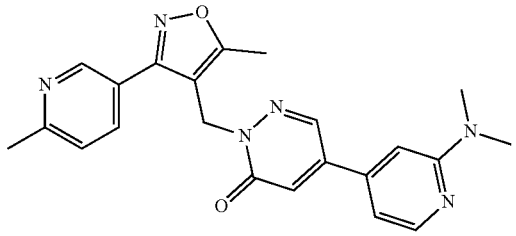

In analogy to experiment of example 67, 5-chloro-2-[[5-methyl-3-(6-methyl-3-pyridyl)isoxazol-4-yl]methyl]pyridazin-3-one, using (2-(dimethylamino)pyridin-4-yl)boronic acid instead of phenylboronic acid, was converted into the title compound (43 mg, 45%) which was obtained as a brown solid. MS (ESI): 403.2 ([M+H]$^+$).

Example 157

5-(1-(cyclopropylmethyl)-1H-pyrazol-4-yl)-2-((5-methyl-3-(6-methylpyridin-3-yl)isoxazol-4-yl)methyl)pyridazin-3(2H)-one

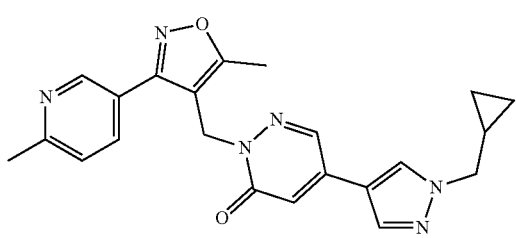 [SMILES: Cc1ccc(-c2noc(C)c2Cn2ncc(-c3cnn(CC4CC4)c3)cc2=O)cn1]

In analogy to experiment of example 67, 5-chloro-2-[[5-methyl-3-(6-methyl-3-pyridyl)isoxazol-4-yl]methyl]pyridazin-3-one, using 1-(cyclopropylmethyl)-4-(4,4,5,5-tetramethyl-1,3,2-dioxaborolan-2-yl)-1H-pyrazole instead of phenylboronic acid, was converted into the title compound (11.5 mg, 18%) which was obtained as an off-white solid. MS (ESI): 403.2 ([M+H]$^+$).

Example 158

2-[[5-methyl-3-(6-methyl-3-pyridyl)isoxazol-4-yl]methyl]-5-[3-(2,2,2-trifluoroethoxy)azetidin-1-yl]pyridazin-3-one

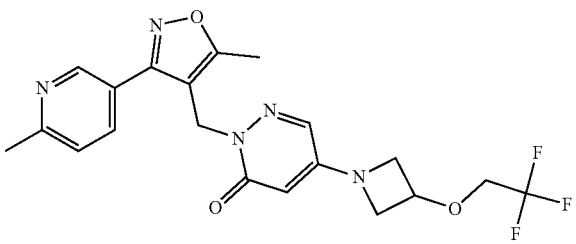 [SMILES: Cc1ccc(-c2noc(C)c2Cn2ncc(N3CC(OCC(F)(F)F)C3)cc2=O)cn1]

In analogy to experiment of example 146, 5-chloro-2-[[5-methyl-3-(6-methyl-3-pyridyl)isoxazol-4-yl]methyl]pyridazin-3-one, using tert-butyl 3-(2,2,2-trifluoroethoxy)azetidine-1-carboxylate instead of tert-butyl 7-methyl-5-oxa-2-azaspiro[3.4]octane-2-carboxylate, was converted into the title compound (78 mg, 95%) which was obtained as an off-white foam. MS (ESI): 436.3 ([M+H]$^+$).

Example 160

2-[[3-(4-chlorophenyl)-5-methyl-isoxazol-4-yl]methyl]-5-(3-methoxyazetidin-1-yl)pyridazin-3-one

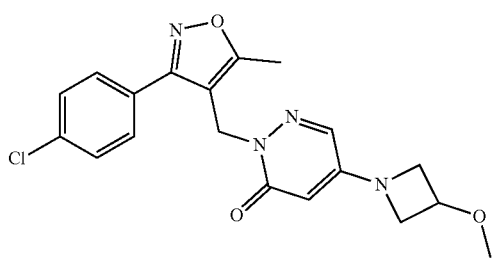 [SMILES: COC1CN(c2cnn(Cc3c(-c4ccc(Cl)cc4)noc3C)c(=O)c2)C1]

In analogy to experiment of example 5, 5-chloro-2-[[3-(4-chlorophenyl)-5-methyl-isoxazol-4-yl]methyl]pyridazin-3-one (building block Q), using 3-methoxyazetidine hydrochloride instead of piperidin-4-ol, was converted into the title compound (49 mg, 86%) which was obtained as a white solid. MS (ESI): 387.3 ([M+H]$^+$).

Example 161

2-[[3-(4-chlorophenyl)-5-methyl-isoxazol-4-yl]methyl]-5-(3-ethoxyazetidin-1-yl)pyridazin-3-one

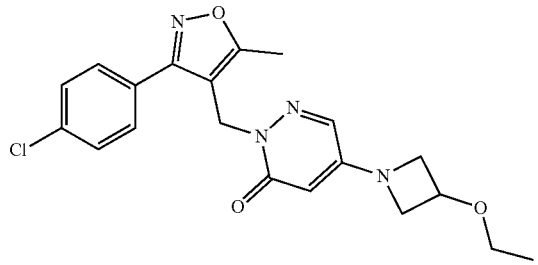 [SMILES: CCOC1CN(c2cnn(Cc3c(-c4ccc(Cl)cc4)noc3C)c(=O)c2)C1]

In analogy to experiment of example 5, 5-chloro-2-[[3-(4-chlorophenyl)-5-methyl-isoxazol-4-yl]methyl]pyridazin-3-one (building block Q), using 3-ethoxyazetidine hydrochloride instead of piperidin-4-ol, was converted into the title compound (51 mg, 86%) which was obtained as a white solid. MS (ESI): 401.2 ([M+H]$^+$).

Example 162

2-[[3-(4-chlorophenyl)-5-methyl-isoxazol-4-yl]methyl]-5-(5-oxa-2-azaspiro[3.4]octan-2-yl)pyridazin-3-one

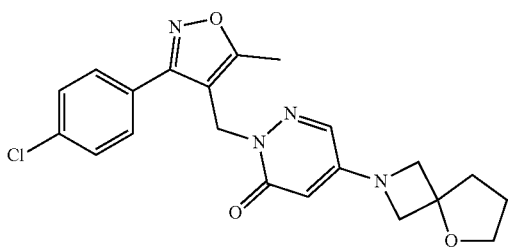 [SMILES: Cc1onc(-c2ccc(Cl)cc2)c1Cn1ncc(N2CC3(CCCO3)C2)cc1=O]

In analogy to experiment of example 5, 5-chloro-2-[[3-(4-chlorophenyl)-5-methyl-isoxazol-4-yl]methyl]pyridazin-3-one (building block Q), using 3-ethoxyazetidine hydrochloride instead of piperidin-4-ol, was converted into the title compound (57 mg, 93%) which was obtained as a colorless oil. MS (ESI): 413.2 ([M+H]$^+$).

Example 163

2-((5-methyl-3-(6-methylpyridin-3-yl)isoxazol-4-yl)methyl)-5-(2-(piperazin-1-yl)pyridin-4-yl)pyridazin-3(2H)-one

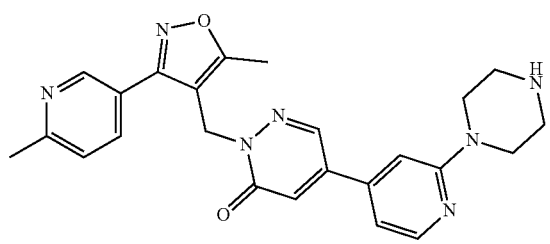 [SMILES: Cc1ccc(-c2noc(C)c2Cn2ncc(-c3ccnc(N4CCNCC4)c3)cc2=O)cn1]

a) tert-butyl 4-[4-[1-[[5-methyl-3-(6-methyl-3-pyridyl)isoxazol-4-yl]methyl]-6-oxo-pyridazin-4-yl]-2-pyridyl]piperazine-1-carboxylate In analogy to experiment of example 67, 5-chloro-2-[[5-methyl-3-(6-methyl-3-pyridyl)isoxazol-4-yl]methyl]pyridazin-3-one, using tert-butyl 4-(4-(4,4,5,5-tetramethyl-1,3,2-dioxaborolan-2-yl)pyridin-2-yl)piperazine-1-carboxylate instead of phenylboronic acid, was converted into the title compound (108 mg, 84%) which was obtained as a white foam. MS (ESI): 544.3 ([M+H]$^+$).

b) 2-((5-methyl-3-(6-methylpyridin-3-yl)isoxazol-4-yl)methyl)-5-(2-(piperazin-1-yl)pyridin-4-yl)pyridazin-3(2H)-one In analogy to experiment of example 50 b, tert-butyl 4-[4-[1-[[5-methyl-3-(6-methyl-3-pyridyl)isoxazol-4-yl]methyl]-6-oxo-pyridazin-4-yl]-2-pyridyl]piperazine-1-carboxylate instead of tert-butyl (2R)-2-methyl-4-[1-[[5-methyl-3-(6-methyl-3-pyridyl)isoxazol-4-yl]methyl]-6-oxo-pyridazin-4-yl]piperazine-1-carboxylate was converted into the title compound (61 mg, 75%) which was obtained as a yellow foam. MS (ESI): 444.3 ([M+H]$^+$).

Example 166

2-[[5-methyl-3-(6-methyl-3-pyridyl)isoxazol-4-yl]methyl]-5-[4-(2-methylpyrazol-3-yl)-1-piperidyl]pyridazin-3-one

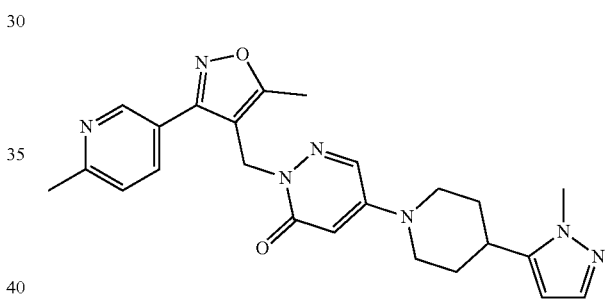

In analogy to experiment of example 5, 5-chloro-2-[[5-methyl-3-(6-methyl-3-pyridyl)isoxazol-4-yl]methyl]pyridazin-3-one, using 4-(1-methyl-1H-pyrazol-5-yl)piperidine instead of piperidin-4-ol, was converted into the title compound (68 mg, 97%) which was obtained as an off-white foam. MS (ESI): 446.3 ([M+H]$^+$).

Example 167

5-[4-(2-ethylpyrazol-3-yl)-1-piperidyl]-2-[[5-methyl-3-(6-methyl-3-pyridyl)isoxazol-4-yl]methyl]pyridazin-3-one

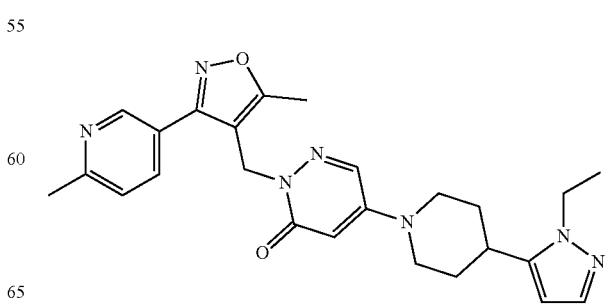

In analogy to experiment of example 5, 5-chloro-2-[[5-methyl-3-(6-methyl-3-pyridyl)isoxazol-4-yl]methyl]pyridazin-3-one, using 4-(1-ethyl-1H-pyrazol-5-yl)piperidine instead of piperidin-4-ol, was converted into the title compound (69 mg, 95%) which was obtained as an off-white foam. MS (ESI): 460.4 ([M+H]⁺).

Example 168

5-[3-(difluoromethoxy)azetidin-1-yl]-2-[[5-methyl-3-(6-methyl-3-pyridyl)isoxazol-4-yl]methyl]pyridazin-3-one

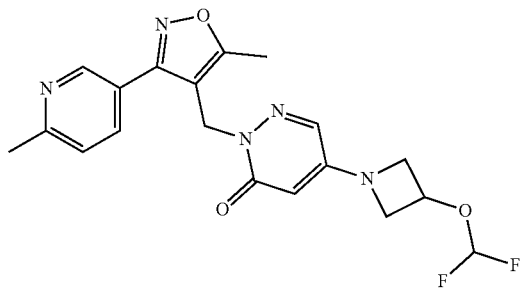 [SMILES: Cc1ccc(-c2noc(C)c2Cn2ncc(N3CC(OC(F)F)C3)cc2=O)cn1]

In analogy to experiment of example 146, 5-chloro-2-[[5-methyl-3-(6-methyl-3-pyridyl)isoxazol-4-yl]methyl]pyridazin-3-one, using tert-butyl 3-(difluoromethoxy)azetidine-1-carboxylate instead of tert-butyl 7-methyl-5-oxa-2-azaspiro[3.4]octane-2-carboxylate, was converted into the title compound (73 mg, 96%) which was obtained as an off-white foam. MS (ESI): 404.2 ([M+H]⁺).

Example 169

5-(3-methoxyazetidin-1-yl)-2-[[5-methyl-3-(6-methylpyridazin-3-yl)isoxazol-4-yl]methyl]pyridazin-3-one

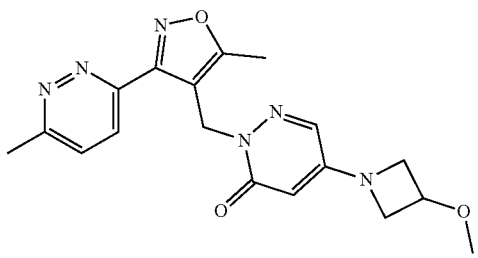

In analogy to experiment of example 5, 5-chloro-2-[[5-methyl-3-(6-methylpyridazin-3-yl)isoxazol-4-yl]methyl]pyridazin-3-one (building block F), using 3-methoxyazetidine hydrochloride instead of piperidin-4-ol, was converted into the title compound (30 mg, 51%) which was obtained as a white crystalline. MS (ESI): 369.2 ([M+H]⁺).

Example 170

5-(3-ethoxyazetidin-1-yl)-2-[[5-methyl-3-(6-methylpyridazin-3-yl)isoxazol-4-yl]methyl]pyridazin-3-one

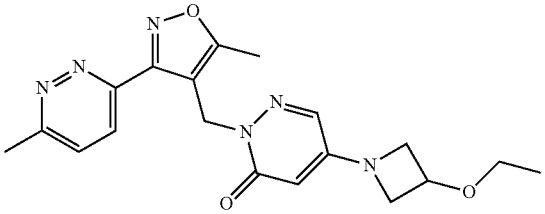 [SMILES: CCOC1CN(c2cnn(Cc3c(-c4ccc(C)nn4)noc3C)c(=O)c2)C1]

In analogy to experiment of example 5, 5-chloro-2-[[5-methyl-3-(6-methylpyridazin-3-yl)isoxazol-4-yl]methyl]pyridazin-3-one (building block F), using 3-ethoxyazetidine hydrochloride instead of piperidin-4-ol, was converted into the title compound (54 mg, 90%) which was obtained as a white crystalline. MS (ESI): 383.3 ([M+H]⁺).

Example 171

2-[[5-methyl-3-(6-methylpyridazin-3-yl)isoxazol-4-yl]methyl]-5-(5-oxa-2-azaspiro[3.4]octan-2-yl)pyridazin-3-one

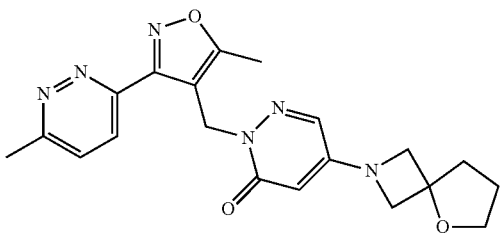 [SMILES: Cc1ccc(-c2noc(C)c2Cn2ncc(N3CC4(CCCO4)C3)cc2=O)nn1]

In analogy to experiment of example 5, 5-chloro-2-[[5-methyl-3-(6-methylpyridazin-3-yl)isoxazol-4-yl]methyl]pyridazin-3-one (building block F), using 5-oxa-2-azaspiro[3.4]octane hydrochloride instead of piperidin-4-ol, was converted into the title compound (46 mg, 74%) which was obtained as a white crystalline. MS (ESI): 395.3 ([M+H]⁺).

Example 172

5-(1-isobutylpyrazol-4-yl)-2-[[5-methyl-3-(6-methyl-3-pyridyl)isoxazol-4-yl]methyl]pyridazin-3-one

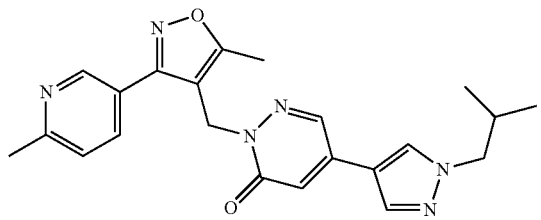 [SMILES: Cc1ccc(-c2noc(C)c2Cn2ncc(-c3cnn(CC(C)C)c3)cc2=O)cn1]

In analogy to experiment of example 145, 5-chloro-2-[[5-methyl-3-(6-methyl-3-pyridyl)isoxazol-4-yl]methyl]pyridazin-3-one, using 1-(2-methylpropyl)-4-(tetramethyl-1,3,2-dioxaborolan-2-yl)-1H-pyrazole instead of (6-methoxypyridin-2-yl)boronic acid, was converted into the title compound (83 mg, 65%) which was obtained as a white solid. MS (ESI): 405.1 ([M+H]$^+$).

Example 173

5-(6-cyclopropyl-3-pyridyl)-2-[[5-methyl-3-(6-methyl-3-pyridyl)isoxazol-4-yl]methyl]pyridazin-3-one

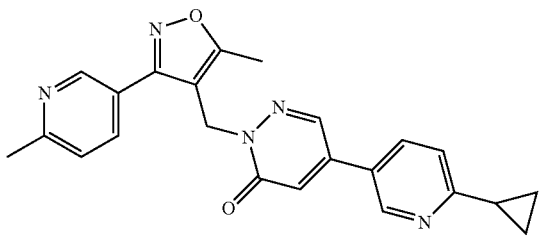 [SMILES: Cc1ccc(-c2noc(C)c2Cn2ncc(-c3ccc(C4CC4)nc3)cc2=O)cn1]

In analogy to experiment of example 145, 5-chloro-2-[[5-methyl-3-(6-methyl-3-pyridyl)isoxazol-4-yl]methyl]pyridazin-3-one, using (6-cyclopropylpyridin-3-yl)boronic acid instead of (6-methoxypyridin-2-yl)boronic acid, was converted into the title compound (87 mg, 68%) which was obtained as a white solid. MS (ESI): 400.1 ([M+H]$^+$).

Example 174

5-(6-(methylamino)-3-pyridyl)-2-((5-methyl-3-(6-methyl-3-pyridyl)isoxazol-4-yl)methyl)pyridazin-3-one

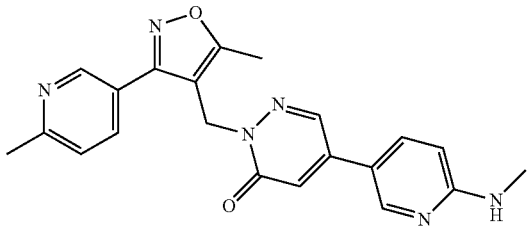

In analogy to experiment of example 145, 5-chloro-2-[[5-methyl-3-(6-methyl-3-pyridyl)isoxazol-4-yl]methyl]pyridazin-3-one, using N-methyl-5-(tetramethyl-1,3,2-dioxaborolan-2-yl)pyridin-2-amine instead of (6-methoxypyridin-2-yl)boronic acid, was converted into the title compound (41 mg, 33%) which was obtained as a white solid. MS (ESI): 389.1 ([M+H]$^+$).

Example 175

5-(2-(difluoromethoxy)pyridin-4-yl)-2-((5-methyl-3-(6-methylpyridin-3-yl)isoxazol-4-yl)methyl)pyridazin-3(2H)-one

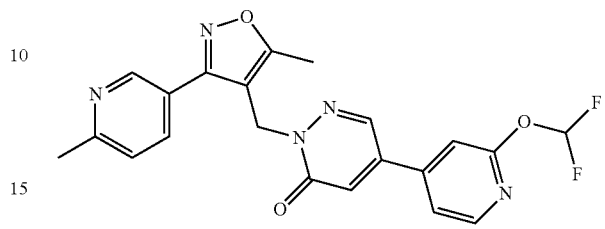

In analogy to experiment of example 67, [1-[[5-methyl-3-(6-methyl-3-pyridyl)isoxazol-4-yl]methyl]-6-oxo-pyridazin-4-yl]boronic acid (building block Z), using 4-bromo-2-(difluoromethoxy)pyridine instead of phenylboronic acid, was converted into the title compound (57 mg, 67%) which was obtained as an off-white solid. MS (ESI): 426.3 ([M+H]$^+$).

Example 176

2-((5-methyl-3-(6-methylpyridin-3-yl)isoxazol-4-yl)methyl)-5-(1-((3-methyloxetan-3-yl)methyl)-1H-pyrazol-4-yl)pyridazin-3(2H)-one

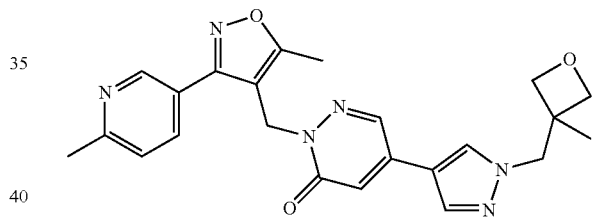

In analogy to experiment of example 67, [1-[[5-methyl-3-(6-methyl-3-pyridyl)isoxazol-4-yl]methyl]-6-oxo-pyridazin-4-yl]boronic acid (building block Z), using 4-bromo-1-((3-methyloxetan-3-yl)methyl)-1H-pyrazole instead of phenylboronic acid, was converted into the title compound (25 mg, 38%) which was obtained as a light brown solid. MS (ESI): 433.3 ([M+H]$^+$).

Example 177

2-((5-methyl-3-(6-methylpyridin-3-yl)isoxazol-4-yl)methyl)-5-(2-((tetrahydrofuran-3-yl)oxy)pyridin-4-yl)pyridazin-3(2H)-one

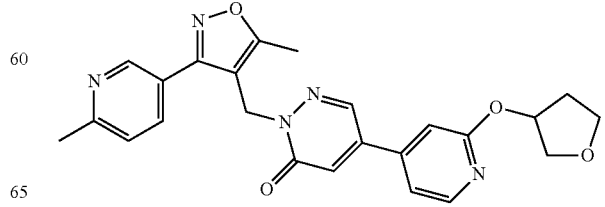

In analogy to experiment of example 67, 5-chloro-2-[[5-methyl-3-(6-methyl-3-pyridyl)isoxazol-4-yl]methyl]pyridazin-3-one, using 2-((tetrahydrofuran-3-yl)oxy)-4-(4,4,5,5-tetramethyl-1,3,2-dioxaborolan-2-yl)pyridine instead of phenylboronic acid, was converted into the title compound (85 mg, 81%) which was obtained as an off-white foam. MS (ESI): 446.3 ([M+H]+).

Example 178

2-[[5-methyl-3-(6-methyl-3-pyridyl)isoxazol-4-yl]methyl]-5-[(3R)-3-methylpyrrolidin-1-yl]pyridazin-3-one

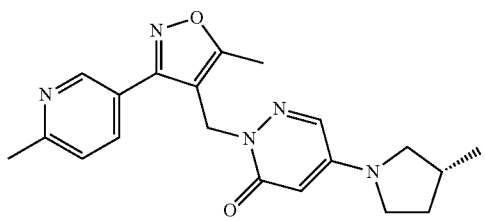

In analogy to experiment of example 5, 5-chloro-2-[[5-methyl-3-(6-methyl-3-pyridyl)isoxazol-4-yl]methyl]pyridazin-3-one, using (R)-3-methylpyrrolidine hydrochloride instead of piperidin-4-ol, was converted into the title compound (44.2 mg, 77%) which was obtained as a light yellow oil. MS (ESI): 366.3 ([M+H]+).

Example 179

5-(5,6-dimethoxypyridin-3-yl)-2-((5-methyl-3-(6-methylpyridin-3-yl)isoxazol-4-yl)methyl)pyridazin-3(2H)-one

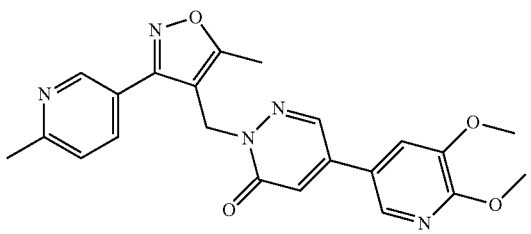

In analogy to experiment of example 67, 5-chloro-2-[[5-methyl-3-(6-methyl-3-pyridyl)isoxazol-4-yl]methyl]pyridazin-3-one, using (5,6-dimethoxypyridin-3-yl)boronic acid instead of phenylboronic acid, was converted into the title compound (59 mg, 59%) which was obtained as an off-white foam. MS (ESI): 420.2 ([M+H]+).

Example 180

5-(6-ethoxy-5-methylpyridin-3-yl)-2-((5-methyl-3-(6-methylpyridin-3-yl)isoxazol-4-yl)methyl)pyridazin-3(2H)-one

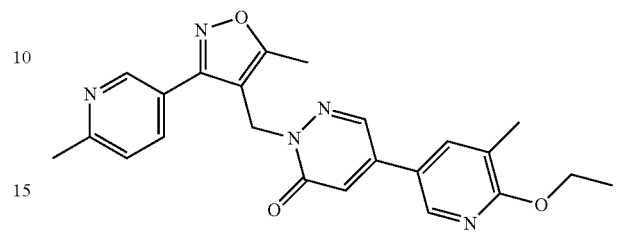

In analogy to experiment of example 67, [1-[[5-methyl-3-(6-methyl-3-pyridyl)isoxazol-4-yl]methyl]-6-oxo-pyridazin-4-yl]boronic acid (building block Z), using 5-bromo-2-ethoxy-3-methylpyridine instead of phenylboronic acid, was converted into the title compound (37 mg, 57%) which was obtained as a light brown solid. MS (ESI): 418.3 ([M+H]+).

Example 181

5-(3-fluoroazetidin-1-yl)-2-[[5-methyl-3-(6-methyl-3-pyridyl)isoxazol-4-yl]methyl]pyridazin-3-one

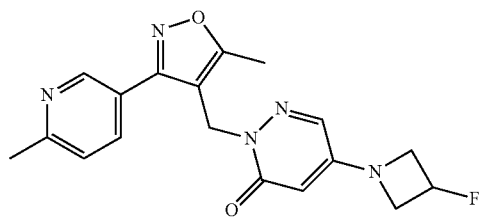 [SMILES: Cc1ccc(-c2noc(C)c2Cn2ncc(N3CC(F)C3)cc2=O)cn1]

In analogy to experiment of example 3, 5-chloro-2-[[5-methyl-3-(6-methyl-3-pyridyl)isoxazol-4-yl]methyl]pyridazin-3-one, using 3-fluoroazetidine hydrochloride instead of (R)-3-hydroxypyrrolidine, was converted into the title compound (65 mg, 96%) which was obtained as an off-white solid. MS (ESI): 356.2 ([M+H]+).

Example 182

2-((5-(Difluoromethyl)-3-(6-methylpyridin-3-yl)isoxazol-4-yl)methyl)-5-((2S,6R)-2,6-dimethylmorpholino)pyridazin-3(2H)-one

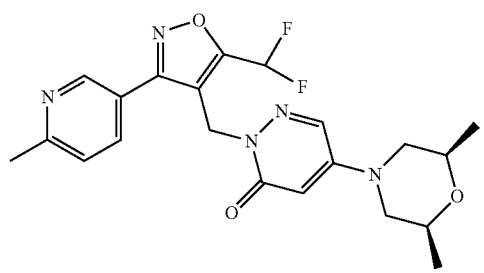

In analogy to experiment of example 3, 5-chloro-2-[[5-(difluoromethyl)-3-(6-methyl-3-pyridyl)isoxazol-4-yl]methyl]pyridazin-3-one (building block G), using cis-2,6-dimethylmorpholine instead of (R)-3-hydroxypyrrolidine, was converted into the title compound (76 mg, 86%) which was obtained as a light yellow foam. MS (ESI): 432.3 ([M+H]+).

Example 183

5-(5-fluoro-6-methoxypyridin-3-yl)-2-((5-methyl-3-(6-methylpyridin-3-yl)isoxazol-4-yl)methyl)pyridazin-3(2H)-one

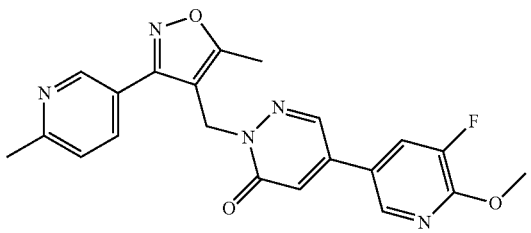

In analogy to experiment of example 67, 5-chloro-2-[[5-methyl-3-(6-methyl-3-pyridyl)isoxazol-4-yl]methyl]pyridazin-3-one, using (5-fluoro-6-methoxypyridin-3-yl)boronic acid instead of phenylboronic acid, was converted into the title compound (69 mg, 72%) which was obtained as an off-white solid. MS (ESI): 408.2 ([M+H]+).

Example 184

5-[(3S)-4-isopropyl-3-methyl-piperazin-1-yl]-2-[[5-methyl-3-(6-methyl-3-pyridyl)isoxazol-4-yl]methyl]pyridazin-3-one

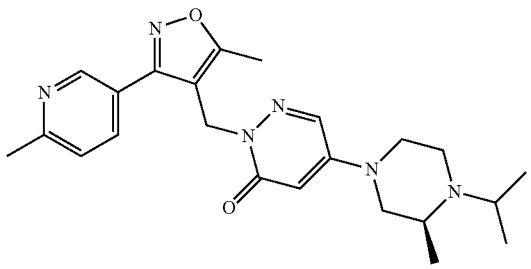 [SMILES: Cc1ccc(-c2noc(C)c2Cn2ncc(N3CCN(C(C)C)[C@@H](C)C3)cc2=O)cn1]

To a solution of 2-[[5-methyl-3-(6-methyl-3-pyridyl)isoxazol-4-yl]methyl]-5-[(3S)-3-methylpiperazin-1-yl]pyridazin-3-one in THF (1 mL) was added acetone (67 µL, 0.91 mmol), sodium triacetoxyborohydride (59 mg, 0.27 mmol) and acetic acid (10.4 µL, 0.18 mmol). The reaction mixture was stirred at room temperature for 22 h, before being concentrated and suspended in dichloroethane (15 mL). The organic layer was washed with aqueous Na2CO3 (20 mL) and with water/brine (1:1) (20 mL). The aqueous layers were back extracted with dichloroethane (15 mL). The organic layers were combined dried (MgSO4) and concentrated in vacuo. Purification by preparative HPLC afforded the title compound (51 mg, 66%) as a white powder. MS (ESI): 423.3 ([M+H]+).

Example 185

5-[3-(cyclopropylmethoxy)azetidin-1-yl]-2-[[5-methyl-3-(6-methylpyridazin-3-yl)isoxazol-4-yl]methyl]pyridazin-3-one

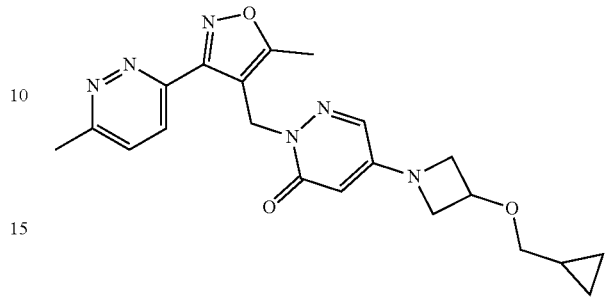

a) 5-(3-hydroxyazetidin-1-yl)-2-[[5-methyl-3-(6-methylpyridazin-3-yl)isoxazol-4-yl]methyl]pyridazin-3-one In analogy to experiment of example 5, 5-chloro-2-[[5-methyl-3-(6-methylpyridazin-3-yl)isoxazol-4-yl]methyl]pyridazin-3-one (building block F), using azetidin-3-ol hydrochloride instead of piperidin-4-ol, was converted into the title compound (101 mg, 62%) which was obtained as an off-white solid. MS (ESI): 355.2 ([M+H]+).

b) 5-[3-(cyclopropylmethoxy)azetidin-1-yl]-2-[[5-methyl-3-(6-methylpyridazin-3-yl)isoxazol-4-yl]methyl]pyridazin-3-one In analogy to experiment of example 133, 5-(3-hydroxyazetidin-1-yl)-2-[[5-methyl-3-(6-methylpyridazin-3-yl)isoxazol-4-yl]methyl]pyridazin-3-one instead of 5-[(7S)-7-hydroxy-5-oxa-2-azaspiro[3.4]octan-2-yl]-2-[[5-methyl-3-(6-methyl-3-pyridyl)isoxazol-4-yl]methyl]pyridazin-3-one, using (bromomethyl)cyclopropane instead of methyl iodide was converted into the title compound (38 mg, 72%) which was obtained as a white solid. MS (ESI): 409.3 ([M+H]+).

Example 186

2-[[5-methyl-3-(6-methyl-3-pyridyl)isoxazol-4-yl]methyl]-5-[3-(6-methylpyridazin-3-yl)oxyazetidin-1-yl]pyridazin-3-one

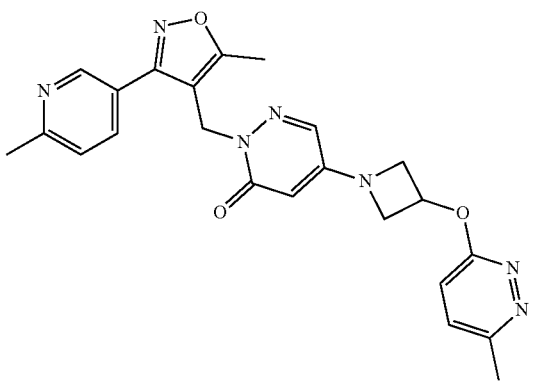 [SMILES: Cc1ccc(-c2noc(C)c2Cn2ncc(N3CC(Oc4ccc(C)nn4)C3)cc2=O)cn1]

In analogy to experiment of example 138, 5-chloro-2-[[5-methyl-3-(6-methyl-3-pyridyl)isoxazol-4-yl]methyl]pyridazin-3-one, using tert-butyl 3-((6-methylpyridazin-3-yl)oxy)azetidine-1-carboxylate instead of tert-butyl 7-methyl-5-oxa-2-azaspiro[3.4]octane-2-carboxylate, was converted into the title compound (75 mg, 89%) which was obtained as a white foam. MS (ESI): 446.3 ([M+H]$^+$).

Example 188

5-(5-chloro-6-methoxypyridin-3-yl)-2-((5-methyl-3-(6-methylpyridin-3-yl)isoxazol-4-yl)methyl)pyridazin-3(2H)-one

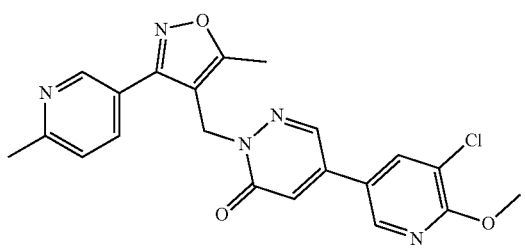

In analogy to experiment of example 67, 5-chloro-2-[[5-methyl-3-(6-methyl-3-pyridyl)isoxazol-4-yl]methyl]pyridazin-3-one, using (5-chloro-6-methoxypyridin-3-yl)boronic acid instead of phenylboronic acid, was converted into the title compound (72 mg, 72%) which was obtained as an off-white solid. MS (ESI): 424.2 ([M+H]$^+$).

Example 189

5-(2-chloro-5-fluoro-3-pyridyl)-2-((5-methyl-3-(6-methyl-3-pyridyl)isoxazol-4-yl)methyl)pyridazin-3-one

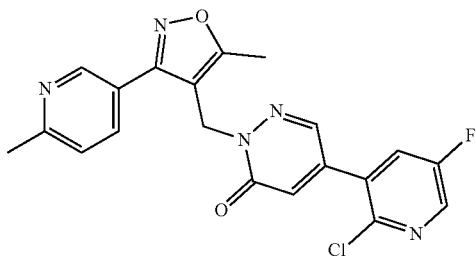 [SMILES: Cc1ccc(-c2noc(C)c2Cn2ncc(-c3cc(F)cnc3Cl)cc2=O)cn1]

In analogy to experiment of example 145, 5-chloro-2-[[5-methyl-3-(6-methyl-3-pyridyl)isoxazol-4-yl]methyl]pyridazin-3-one, using (2-chloro-5-fluoropyridin-3-yl)boronic acid instead of (6-methoxypyridin-2-yl)boronic acid, was converted into the title compound (78 mg, 46%) which was obtained as an off-white solid. MS (ESI): 412.0 ([M+H]$^+$).

Example 190

5-(6-isopropoxy-3-pyridyl)-2-((5-methyl-3-(6-methyl-3-pyridyl)isoxazol-4-yl)methyl)pyridazin-3-one

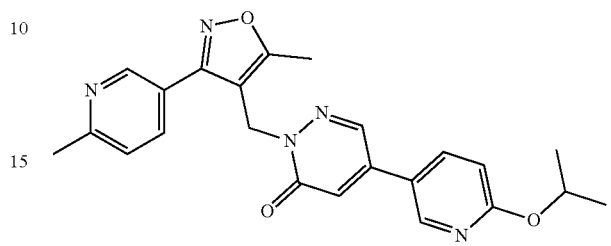

In analogy to experiment of example 145, 5-chloro-2-[[5-methyl-3-(6-methyl-3-pyridyl)isoxazol-4-yl]methyl]pyridazin-3-one, using [6-(propan-2-yloxy)pyridin-3-yl]boronic acid instead of (6-methoxypyridin-2-yl)boronic acid, was converted into the title compound (109 mg, 68%) which was obtained as a white solid. MS (ESI): 418.2 ([M+H]$^+$).

Example 191

5-(5-fluoro-2-methoxypyridin-4-yl)-2-((5-methyl-3-(6-methylpyridin-3-yl)isoxazol-4-yl)methyl)pyridazin-3(2H)-one

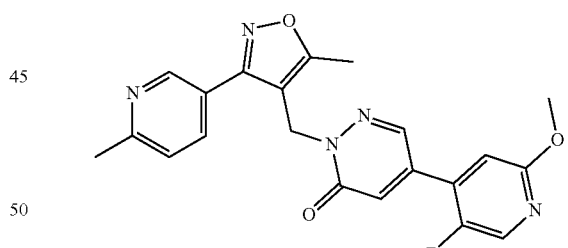

In analogy to experiment of example 67, 5-chloro-2-[[5-methyl-3-(6-methyl-3-pyridyl)isoxazol-4-yl]methyl]pyridazin-3-one, using (5-fluoro-2-methoxypyridin-4-yl)boronic acid instead of phenylboronic acid, was converted into the title compound (61 mg, 63%) which was obtained as an off-white foam. MS (ESI): 408.2 ([M+H]$^+$).

Example 192

5-(2,6-dimethylpyridin-4-yl)-2-((5-methyl-3-(6-methylpyridin-3-yl)isoxazol-4-yl)methyl)pyridazin-3(2H)-one

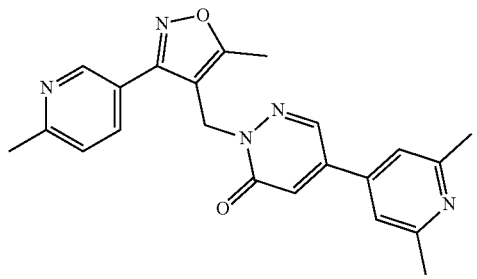

In analogy to experiment of example 67, 5-chloro-2-[[5-methyl-3-(6-methyl-3-pyridyl)isoxazol-4-yl]methyl]pyridazin-3-one, using (2,6-dimethylpyridin-4-yl)boronic acid instead of phenylboronic acid, was converted into the title compound (66 mg, 72%) which was obtained as an off-white solid. MS (ESI): 388.2 ([M+H]+).

Example 193

5-(7,7-difluoro-5-oxa-2-azaspiro[3.4]octan-2-yl)-2-[[5-methyl-3-(6-methyl-3-pyridyl)isoxazol-4-yl]methyl]pyridazin-3-one

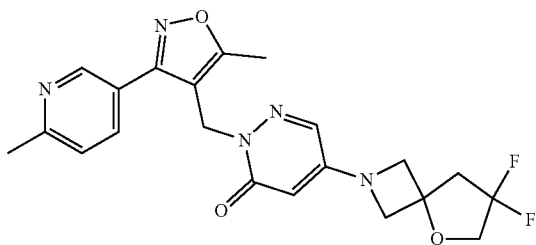 [SMILES: Cc1ccc(-c2noc(C)c2Cn2ncc(N3CC4(C3)CC(F)(F)CO4)cc2=O)cn1]

In analogy to experiment of example 3, 5-chloro-2-[[5-methyl-3-(6-methyl-3-pyridyl)isoxazol-4-yl]methyl]pyridazin-3-one, using 7,7-difluoro-5-oxa-2-azoniaspiro[3.4]octane 2,2,2-trifluoroacetate instead of (R)-3-hydroxypyrrolidine, was converted into the title compound (78 mg, 96%) which was obtained as a light yellow solid. MS (ESI): 430.7 ([M+H]+).

Example 194

5-[(2R,3R)-3-methoxy-2-methyl-azetidin-1-yl]-2-[[5-methyl-3-(6-methyl-3-pyridyl)isoxazol-4-yl]methyl]pyridazin-3-one

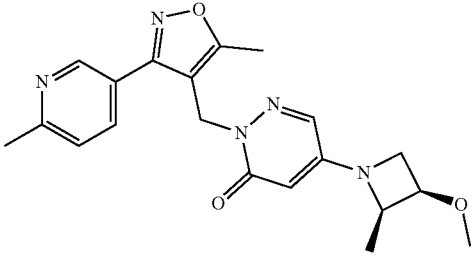

a) 5-[(2R,3R)-3-hydroxy-2-methyl-azetidin-1-yl]-2-[[5-methyl-3-(6-methyl-3-pyridyl)isoxazol-4-yl]methyl]pyridazin-3-one In analogy to experiment of example 5, 5-chloro-2-[[5-methyl-3-(6-methyl-3-pyridyl)isoxazol-4-yl]methyl]pyridazin-3-one, using (2R,3R)-2-methylazetidin-3-ol hydrochloride instead of piperidin-4-ol, was converted into the title compound (489 mg, 94%) which was obtained as an off-white foam. MS (ESI): 368.2 ([M+H]+).

b) 5-[(2R,3R)-3-methoxy-2-methyl-azetidin-1-yl]-2-[[5-methyl-3-(6-methyl-3-pyridyl)isoxazol-4-yl]methyl]pyridazin-3-one In analogy to experiment of example 133, using 5-[(2R,3R)-3-hydroxy-2-methyl-azetidin-1-yl]-2-[[5-methyl-3-(6-methyl-3-pyridyl)isoxazol-4-yl]methyl]pyridazin-3-one instead of 5-[(7S)-7-hydroxy-5-oxa-2-azaspiro[3.4]octan-2-yl]-2-[[5-methyl-3-(6-methyl-3-pyridyl)isoxazol-4-yl]methyl]pyridazin-3-one was converted into the title compound (63 mg, 87%) which was obtained as an off-white foam. MS (ESI): 382.2 ([M+H]+).

Example 195

2-((5-methyl-3-(6-methylpyridin-3-yl)isoxazol-4-yl)methyl)-5-(7-oxa-2-azaspiro[3.5]nonan-2-yl)pyridazin-3(2H)-one

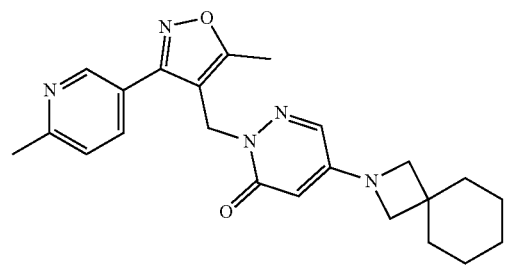 [SMILES: Cc1ccc(-c2noc(C)c2Cn2ncc(N3CC4(CCCCC4)C3)cc2=O)cn1]

In analogy to experiment of example 3, 5-chloro-2-[[5-methyl-3-(6-methyl-3-pyridyl)isoxazol-4-yl]methyl]pyridazin-3-one, using 2-azaspiro[3.5]nonane instead of (R)-3-hydroxypyrrolidine, was converted into the title compound (101 mg, 79%) which was obtained as a light yellow foam. MS (ESI): 406.2 ([M+H]+).

Example 196

5-(2-ethyl-4-pyridyl)-2-((5-methyl-3-(6-methyl-3-pyridyl)isoxazol-4-yl)methyl)pyridazin-3-one

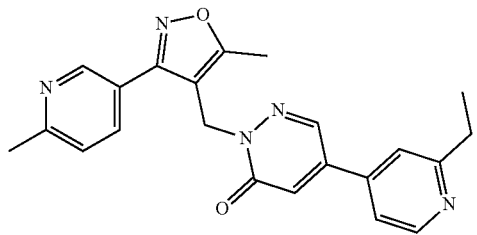 [SMILES: CCc1cc(-c2cnn(Cc3c(-c4ccc(C)nc4)noc3C)c(=O)c2)ccn1]

In analogy to experiment of example 145, 5-chloro-2-[[5-methyl-3-(6-methyl-3-pyridyl)isoxazol-4-yl]methyl]pyridazin-3-one, using (2-ethylpyridin-4-yl)boronic acid instead of (6-methoxypyridin-2-yl)boronic acid, was converted into the title compound (97 mg, 61%) which was obtained as a colorless viscous oil. MS (ESI): 388.1 ([M+H]+).

Example 197

5-[(2S,3S)-3-methoxy-2-methyl-azetidin-1-yl]-2-[[5-methyl-3-(6-methyl-3-pyridyl)isoxazol-4-yl]methyl]pyridazin-3-one

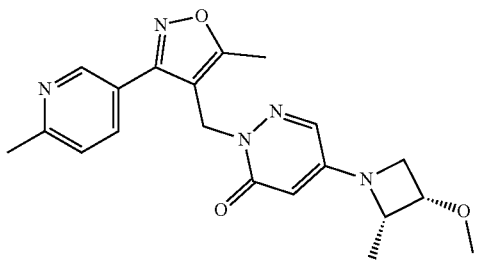

a) 5-[(2S,3S)-3-hydroxy-2-methyl-azetidin-1-yl]-2-[[5-methyl-3-(6-methyl-3-pyridyl)isoxazol-4-yl]methyl]pyridazin-3-one In analogy to experiment of example 5, 5-chloro-2-[[5-methyl-3-(6-methyl-3-pyridyl)isoxazol-4-yl]methyl]pyridazin-3-one, using (2S,3S)-2-methylazetidin-3-ol hydrochloride instead of piperidin-4-ol, was converted into the title compound (470 mg, 69%) which was obtained as an off-white foam. MS (ESI): 368.2 ([M+H]+).

b) 5-[(2S,3S)-3-methoxy-2-methyl-azetidin-1-yl]-2-[[5-methyl-3-(6-methyl-3-pyridyl)isoxazol-4-yl]methyl]pyridazin-3-one In analogy to experiment of example 133, using 5-[(2S,3S)-3-hydroxy-2-methyl-azetidin-1-yl]-2-[[5-methyl-3-(6-methyl-3-pyridyl)isoxazol-4-yl]methyl]pyridazin-3-one instead of 5-[(7S)-7-hydroxy-5-oxa-2-azaspiro[3.4]octan-2-yl]-2-[[5-methyl-3-(6-methyl-3-pyridyl)isoxazol-4-yl]methyl]pyridazin-3-one was converted into the title compound (50 mg, 80%) which was obtained as an off-white foam. MS (ESI): 382.2 ([M+H]+).

Example 198

5-[(2S,3S)-3-ethoxy-2-methyl-azetidin-1-yl]-2-[[5-methyl-3-(6-methyl-3-pyridyl)isoxazol-4-yl]methyl]pyridazin-3-one

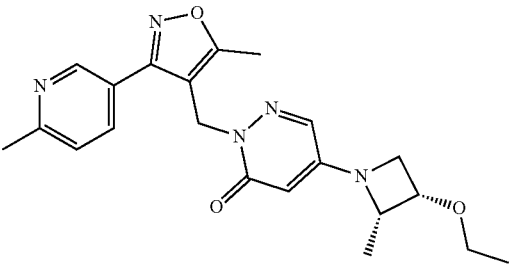 [SMILES: CCO[C@H]1CN(c2cnn(Cc3c(-c4ccc(C)nc4)noc3C)c(=O)c2)[C@H]1C]

In analogy to experiment of example 133, 5-[(2S,3S)-3-hydroxy-2-methyl-azetidin-1-yl]-2-[[5-methyl-3-(6-methyl-3-pyridyl)isoxazol-4-yl]methyl]pyridazin-3-one instead of 5-[(7S)-7-hydroxy-5-oxa-2-azaspiro[3.4]octan-2-yl]-2-[[5-methyl-3-(6-methyl-3-pyridyl)isoxazol-4-yl]methyl]pyridazin-3-one, using iodoethane instead of iodomethane was converted into the title compound (45 mg, 55%) which was obtained as a light brown oil MS (ESI): 396.3 ([M+H]+).

Example 199

2-((5-methyl-3-(6-methylpyridin-3-yl)isoxazol-4-yl)methyl)-5-(7-oxa-2-azaspiro[3.5]nonan-2-yl)pyridazin-3(2H)-one

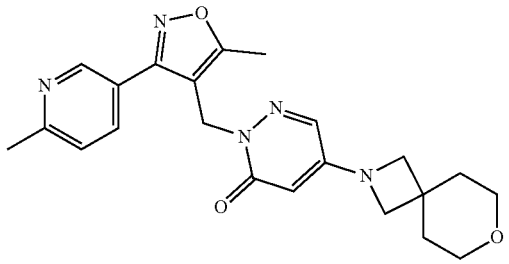 [SMILES: Cc1ccc(-c2noc(C)c2Cn2ncc(N3CC4(CCOCC4)C3)cc2=O)cn1]

In analogy to experiment of example 3, 5-chloro-2-[[5-methyl-3-(6-methyl-3-pyridyl)isoxazol-4-yl]methyl]pyridazin-3-one, using 7-oxa-2-azaspiro[3.5]nonane instead of (R)-3-hydroxypyrrolidine, was converted into the title compound (100 mg, 78%) which was obtained as alight yellow foam. MS (ESI): 408.2 ([M+H]+).

Example 200

5-[(7R)-7-fluoro-5-oxa-2-azaspiro[3.4]octan-2-yl]-2-[[5-methyl-3-(6-methyl-3-pyridyl)isoxazol-4-yl]methyl]pyridazin-3-one

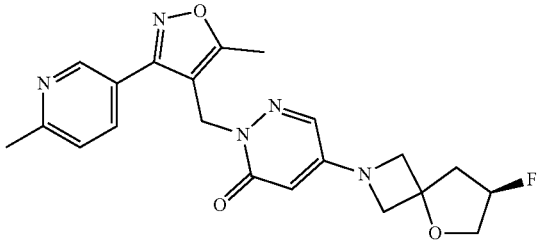 [SMILES: Cc1ccc(-c2noc(C)c2Cn2ncc(N3CC4(C[C@@H](F)CO4)C3)cc2=O)cn1]

In analogy to experiment of example 3, 5-chloro-2-[[5-methyl-3-(6-methyl-3-pyridyl)isoxazol-4-yl]methyl]pyridazin-3-one, using (7R)-7-fluoro-5-oxa-2-azoniaspiro[3.4]octane 2,2,2-trifluoroacetate instead of (R)-3-hydroxypyrrolidine, was converted into the title compound (78 mg, 100%) which was obtained as an off-white solid. MS (ESI): 412.2 ([M+H]$^+$).

Example 201

5-[(7S)-7-fluoro-5-oxa-2-azaspiro[3.4]octan-2-yl]-2-[[5-methyl-3-(6-methyl-3-pyridyl)isoxazol-4-yl]methyl]pyridazin-3-one

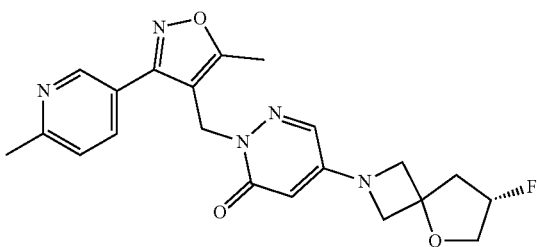 [SMILES: Cc1ccc(-c2noc(C)c2Cn2ncc(N3CC4(C[C@H](F)CO4)C3)cc2=O)cn1]

In analogy to experiment of example 3, 5-chloro-2-[[5-methyl-3-(6-methyl-3-pyridyl)isoxazol-4-yl]methyl]pyridazin-3-one, using (7S)-7-fluoro-5-oxa-2-azoniaspiro[3.4]octane 2,2,2-trifluoroacetate instead of (R)-3-hydroxypyrrolidine, was converted into the title compound (63 mg, 81%) which was obtained as an off-white solid. MS (ESI): 412.4 ([M+H]$^+$).

Example 202

2-((5-methyl-3-(6-methylpyridin-3-yl)isoxazol-4-yl)methyl)-5-(2-(methylamino)pyridin-4-yl)pyridazin-3(2H)-one

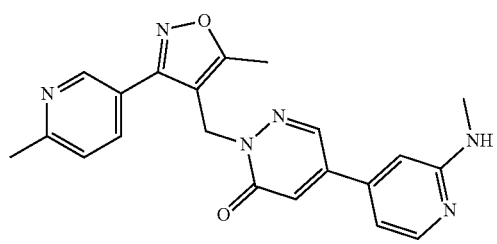 [SMILES: CNc1cc(-c2cnn(Cc3c(-c4ccc(C)nc4)noc3C)c(=O)c2)ccn1]

In analogy to experiment of example 67, 5-chloro-2-[[5-methyl-3-(6-methyl-3-pyridyl)isoxazol-4-yl]methyl]pyridazin-3-one, using N-methyl-4-(4,4,5,5-tetramethyl-1,3,2-dioxaborolan-2-yl)pyridin-2-amine instead of phenylboronic acid, was converted into the title compound (71 mg, 77%) which was obtained as a yellow foam. MS (ESI): 389.2 ([M+H]$^+$).

Example 203

5-[(7R)-7-(difluoromethoxy)-5-oxa-2-azaspiro[3.4]octan-2-yl]-2-[[5-methyl-3-(6-methyl-3-pyridyl)isoxazol-4-yl]methyl]pyridazin-3-one

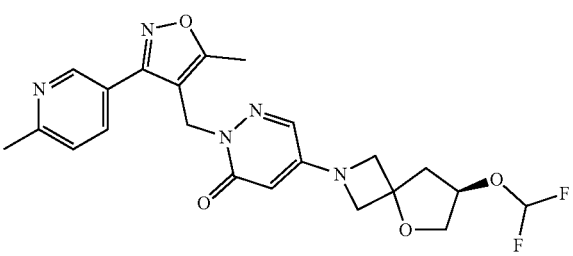 [SMILES: Cc1ccc(-c2noc(C)c2Cn2ncc(N3CC4(C[C@@H](OC(F)F)CO4)C3)cc2=O)cn1]

In analogy to experiment of example 3, 5-chloro-2-[[5-methyl-3-(6-methyl-3-pyridyl)isoxazol-4-yl]methyl]pyridazin-3-one, using (7R)-7-(difluoromethoxy)-5-oxa-2-azoniaspiro[3.4]octane 2,2,2-trifluoroacetate instead of (R)-3-hydroxypyrrolidine, was converted into the title compound (98 mg, 90%) which was obtained as a light yellow foam. MS (ESI): 460.2 ([M+H]$^+$).

Example 204

5-[(7S)-7-(difluoromethoxy)-5-oxa-2-azaspiro[3.4]octan-2-yl]-2-[[5-methyl-3-(6-methyl-3-pyridyl)isoxazol-4-yl]methyl]pyridazin-3-one

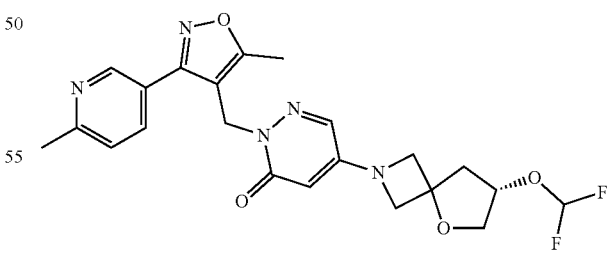

In analogy to experiment of example 3, 5-chloro-2-[[5-methyl-3-(6-methyl-3-pyridyl)isoxazol-4-yl]methyl]pyridazin-3-one, using (7S)-7-(difluoromethoxy)-5-oxa-2-azoniaspiro[3.4]octane 2,2,2-trifluoroacetate instead of (R)-3-hydroxypyrrolidine, was converted into the title compound (97 mg, 89%) which was obtained as a light yellow foam. MS (ESI): 460.3 ([M+H]$^+$).

Example 205

5-((2R,6S)-2,6-dimethylmorpholino)-2-((3-(5-fluoro-6-methylpyridin-3-yl)-5-methylisoxazol-4-yl)methyl)pyridazin-3(2H)-one

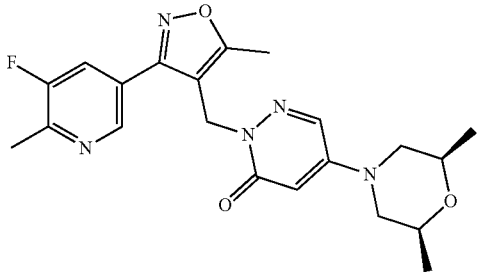

In analogy to experiment of example 64, 5-chloro-2-[[3-(5-fluoro-6-methyl-3-pyridyl)-5-methyl-isoxazol-4-yl]methyl]pyridazin-3-one (building block J), using cis-2,6-dimethylmorpholine instead of N-methylcyclopropanamine oxalate, was converted into the title compound (54 mg, 95%) which was obtained as a white solid. MS (ESI): 414.2 ([M+H]$^+$).

Example 206

5-[3-(2,2-difluoroethoxy)azetidin-1-yl]-2-[[5-methyl-3-(6-methyl-3-pyridyl)isoxazol-4-yl]methyl]pyridazin-3-one

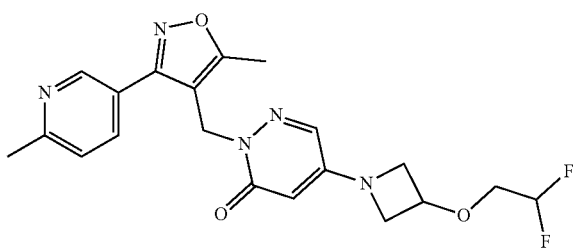 [SMILES: Cc1ccc(-c2noc(C)c2Cn2ncc(N3CC(OCC(F)F)C3)cc2=O)cn1]

In analogy to experiment of example 133, 5-(3-hydroxyazetidin-1-yl)-2-[[5-methyl-3-(6-methyl-3-pyridyl)isoxazol-4-yl]methyl]pyridazin-3-one, using 2,2-difluoroethyl trifluoromethanesulfonate instead of iodomethane was converted into the title compound (45 mg, 69%) which was obtained as an off-white solid. MS (ESI): 418.3 ([M+H]$^+$).

Example 207

2-((3-(5-fluoro-6-methylpyridin-3-yl)-5-methyl-isoxazol-4-yl)methyl)-5-(2-methoxypyridin-4-yl)pyridazin-3(2H)-one

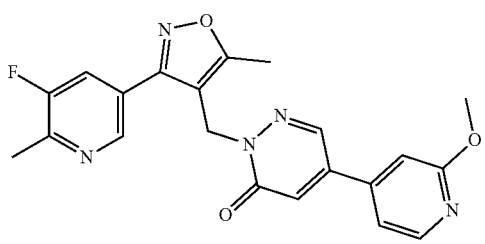 [SMILES: COc1cc(-c2cnn(Cc3c(-c4cnc(C)c(F)c4)noc3C)c(=O)c2)ccn1]

In analogy to experiment of example 67, 5-chloro-2-[[3-(5-fluoro-6-methyl-3-pyridyl)-5-methyl-isoxazol-4-yl]methyl]pyridazin-3-one (building block J), using (2-methoxypyridin-4-yl)boronic acid instead of phenylboronic acid, was converted into the title compound (42 mg, 69%) which was obtained as a white solid. MS (ESI): 408.2 ([M+H]$^+$).

Example 208

2-((3-(5-fluoro-6-methylpyridin-3-yl)-5-methyl-isoxazol-4-yl)methyl)-5-(5-oxa-2-azaspiro[3.4]octan-2-yl)pyridazin-3(2H)-one

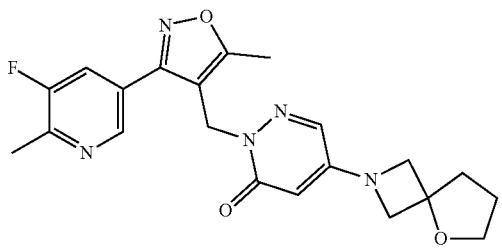 [SMILES: Cc1ncc(-c2noc(C)c2Cn2ncc(N3CC4(CCCO4)C3)cc2=O)cc1F]

In analogy to experiment of example 64, 5-chloro-2-[[3-(5-fluoro-6-methyl-3-pyridyl)-5-methyl-isoxazol-4-yl]methyl]pyridazin-3-one (building block J), using 5-oxa-2-azaspiro[3.4]octane oxalate instead of N-methylcyclopropanamine oxalate, was converted into the title compound (55 mg, 89%) which was obtained as a white solid. MS (ESI): 412.2 ([M+H]$^+$).

Example 209

2-((3-(6-chloropyridin-3-yl)-5-methylisoxazol-4-yl)methyl)-5-(5-oxa-2-azaspiro[3.4]octan-2-yl)pyridazin-3(2H)-one

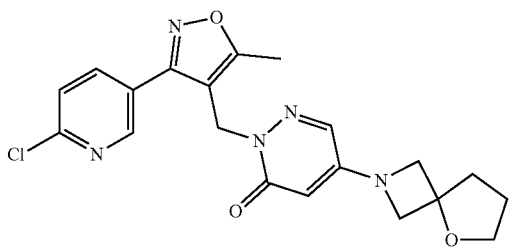 [SMILES: Cc1onc(-c2ccc(Cl)nc2)c1Cn1ncc(N2CC3(CCCO3)C2)cc1=O]

In analogy to experiment of example 3, 5-chloro-2-[[3-(6-chloro-3-pyridyl)-5-methyl-isoxazol-4-yl]methyl]pyridazin-3-one (building block D), using 5-oxa-2-azaspiro[3.4]octane oxalate instead of (R)-3-hydroxypyrrolidine, was converted into the title compound (21 mg, 62%) which was obtained as a white solid. MS (ESI): 414.2 ([M+H]$^+$).

Example 210

2-((5-methyl-3-(6-methyl-3-pyridyl)isoxazol-4-yl)methyl)-5-(1-propylpyrazol-4-yl)pyridazin-3-one

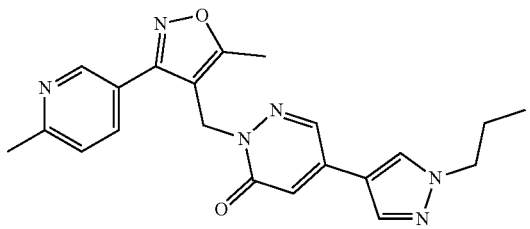 [SMILES: CCCn1cc(-c2cnn(Cc3c(-c4ccc(C)nc4)noc3C)c(=O)c2)cn1]

In analogy to experiment of example 145, 5-chloro-2-[[5-methyl-3-(6-methyl-3-pyridyl)isoxazol-4-yl]methyl]pyridazin-3-one, using 1-propyl-4-(tetramethyl-1,3,2-dioxaborolan-2-yl)-1H-pyrazole instead of (6-methoxypyridin-2-yl)boronic acid and Pd(amphos)Cl$_2$ instead of Pd(PPh$_3$)$_4$, was converted into the title compound (41 mg, 34%) which was obtained as a white solid. MS (ESI): 391.1 ([M+H]$^+$).

Example 211

6-(1-((5-methyl-3-(6-methyl-3-pyridyl)isoxazol-4-yl)methyl)-6-oxo-pyridazin-4-yl)pyridine-2-carbonitrile

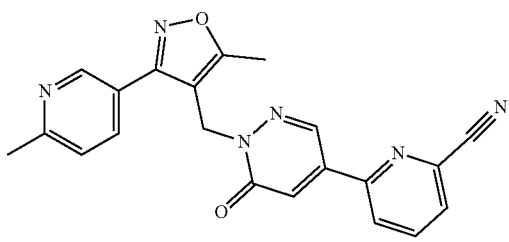 [SMILES: Cc1ccc(-c2noc(C)c2Cn2ncc(-c3cccc(C#N)n3)cc2=O)cn1]

In analogy to experiment of example 145, 5-chloro-2-[[5-methyl-3-(6-methyl-3-pyridyl)isoxazol-4-yl]methyl]pyridazin-3-one, using 6-(tetramethyl-1,3,2-dioxaborolan-2-yl)pyridine-2-carbonitrile instead of (6-methoxypyridin-2-yl)boronic acid and Pd(amphos)Cl$_2$ instead of Pd(PPh$_3$)$_4$, was converted into the title compound (18 mg, 18%) which was obtained as a white solid. MS (ESI): 385.1 ([M+H]$^+$).

Example 212

2-((3-(6-chloropyridin-3-yl)-5-methylisoxazol-4-yl)methyl)-5-(3-methoxyazetidin-1-yl)pyridazin-3(2H)-one

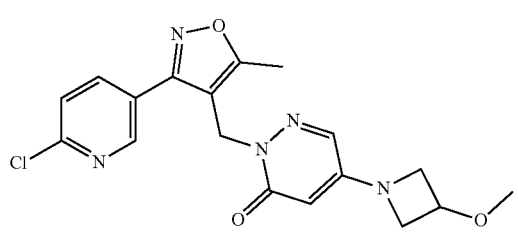 [SMILES: COC1CN(c2cnn(Cc3c(-c4ccc(Cl)nc4)noc3C)c(=O)c2)C1]

In analogy to experiment of example 3, 5-chloro-2-[[3-(6-chloro-3-pyridyl)-5-methyl-isoxazol-4-yl]methyl]pyridazin-3-one (building block D), using 3-methoxyazetidine hydrochloride instead of (R)-3-hydroxypyrrolidine, was converted into the title compound (23 mg, 65%) which was obtained as an off-white solid. MS (ESI): 388.1 ([M+H]$^+$).

Example 213

5-(3-ethoxyazetidin-1-yl)-2-((3-(5-fluoro-6-methylpyridin-3-yl)-5-methylisoxazol-4-yl)methyl)pyridazin-3(2H)-one

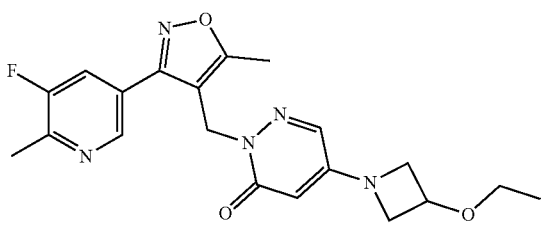 [SMILES: CCOC1CN(c2cnn(Cc3c(-c4cnc(C)c(F)c4)noc3C)c(=O)c2)C1]

In analogy to experiment of example 64, 5-chloro-2-[[3-(5-fluoro-6-methyl-3-pyridyl)-5-methyl-isoxazol-4-yl]methyl]pyridazin-3-one (building block J), using 3-ethoxyazetidine hydrochloride instead of N-methylcyclopropanamine oxalate, was converted into the title compound (32 mg, 38%) which was obtained as an off-white solid. MS (ESI): 400.2 ([M+H]$^+$).

Example 214

2-((3-(6-chloropyridin-3-yl)-5-methylisoxazol-4-yl)methyl)-5-(2-methoxypyridin-4-yl)pyridazin-3(2H)-one

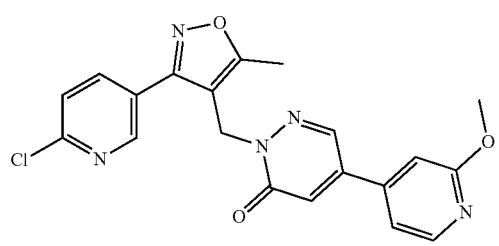 [SMILES: COc1cc(-c2cnn(Cc3c(-c4ccc(Cl)nc4)noc3C)c(=O)c2)ccn1]

a) 4-(2-methoxy-4-pyridyl)-1H-pyridazin-6-one

To a solution of 4-chloro-1H-pyridazin-6-one (125 mg, 0.958 mmol) in ethanol (2.5 mL) under nitrogen at room temperature, were added (2-methoxypyridin-4-yl)boronic acid (161 mg, 1.05 mmol), Pd(PPh$_3$)$_4$ (55.9 mg, 0.0479 mmol) and aqueous Na$_2$CO$_3$ (2.0 M, 1.44 mL, 2.87 mmol). The reaction mixture was heated in a microwave oven to 120° C. for 10 min, and then at to 150° C. for further 10 min. The reaction mixture was evaporated and purified directly by preparative HPLC to provide the title compound (75 mg, 39%) as an off-white solid. MS (ESI): 204.2 ([M+H]$^+$).

b) 2-((3-(6-chloropyridin-3-yl)-5-methylisoxazol-4-yl)methyl)-5-(2-methoxypyridin-4-yl)pyridazin-3(2H)-one To solution of 4-(chloromethyl)-3-(6-chloropyridin-3-yl)-5-methylisoxazole (30 mg, 0.123 mmol) in N,N-dimethylacetamide (0.60 mL), were added K$_2$CO$_3$ (22.2 mg, 0.160 mmol) and 4-(2-methoxy-4-pyridyl)-1H-pyridazin-6-one (27.6 mg, 0.136 mmol). The mixture was heated to 70° C. in an oil bath for 45 min, before being cooled to room temperature and diluted with water. The aqueous layer was extracted three times with ethyl acetate. The combined extracts were dried (Na$_2$SO$_4$), filtered and concentrated in vacuo. Purification by flash chromatography (silica, gradient: 0% to 100% EtOAc in heptane) afforded the title compound (37 mg, 73%) as a white solid. MS (ESI): 410.1 ([M+H]$^+$).

Example 215

2-((3-(6-chloropyridin-3-yl)-5-methylisoxazol-4-yl)methyl)-5-(1-methyl-1H-pyrazol-4-yl)pyridazin-3(2H)-one

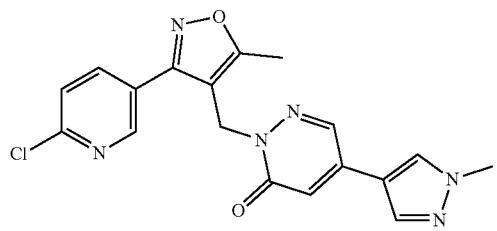 [SMILES: Cc1onc(-c2ccc(Cl)nc2)c1Cn1ncc(-c2cnn(C)c2)cc1=O]

a) 4-(1-methylpyrazol-4-yl)-1H-pyridazin-6-one

In analogy to experiment of example 214 a, 4-chloro-H-pyridazin-6-one, using 1-methyl-4-(4,4,5,5-tetramethyl-1,3,2-dioxaborolan-2-yl)-1H-pyrazole instead of (2-methoxypyridin-4-yl)boronic acid, was converted into the title compound (471 mg, 37%) which was obtained as an off-white solid. MS (ESI): 177.0 ([M+H]$^+$).

b) 2-((3-(6-chloropyridin-3-yl)-5-methylisoxazol-4-yl)methyl)-5-(1-methyl-1H-pyrazol-4-yl)pyridazin-3(2H)-one In analogy to experiment of example 214 b, 4-(chloromethyl)-3-(6-chloropyridin-3-yl)-5-methylisoxazole, using 4-(1-methylpyrazol-4-yl)-1H-pyridazin-6-one instead of 4-(2-methoxy-4-pyridyl)-1H-pyridazin-6-one, was converted into the title compound (37 mg, 78%) which was obtained as a white solid. MS (ESI): 383.1 ([M+H]$^+$).

Example 216

2-((5-methyl-3-(6-methylpyridin-3-yl)isoxazol-4-yl)methyl)-5-(5-oxa-2-azaspiro[3.5]nonan-2-yl)pyridazin-3(2H)-one

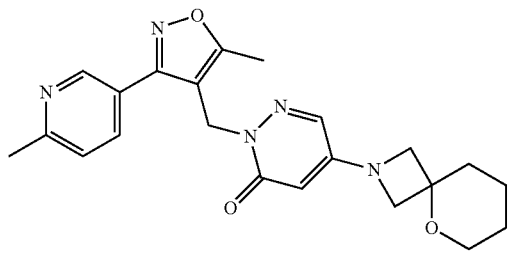 [SMILES: Cc1ccc(-c2noc(C)c2Cn2ncc(N3CC4(CCCCO4)C3)cc2=O)cn1]

In analogy to experiment of example 3, 5-chloro-2-[[5-methyl-3-(6-methyl-3-pyridyl)isoxazol-4-yl]methyl]pyridazin-3-one, using 5-oxa-2-azaspiro[3.5]nonane oxalate instead of (R)-3-hydroxypyrrolidine, was converted into the title compound (53 mg, 82%) which was obtained as an off-white solid. MS (ESI): 408.2 ([M+H]$^+$).

Example 217

2-((3-(6-chloropyridin-3-yl)-5-methylisoxazol-4-yl)methyl)-5-(7,7-difluoro-5-oxa-2-azaspiro[3.4]octan-2-yl)pyridazin-3(2H)-one

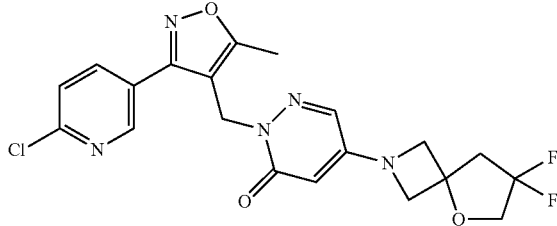 [SMILES: Cc1onc(-c2ccc(Cl)nc2)c1Cn1ncc(N2CC3(C2)CC(F)(F)CO3)cc1=O]

In analogy to experiment of example 3, 5-chloro-2-[[3-(6-chloro-3-pyridyl)-5-methyl-isoxazol-4-yl]methyl]pyridazin-3-one (building block D), using 7,7-difluoro-5-oxa-2-azaspiro[3.4]octane 2,2,2-trifluoroacetate instead of (R)-3-hydroxypyrrolidine and replacing the solvent with N,N-dimethylacetamide, was converted into the title compound (386 mg, 71%) which was obtained as a light grey solid. MS (ESI): 450.2 ([M+H]$^+$).

Example 218

2-((5-methyl-3-(6-methylpyridin-3-yl)isoxazol-4-yl)methyl)-5-(3-methylimidazo[1,2-a]pyridin-6-yl)pyridazin-3(2H)-one

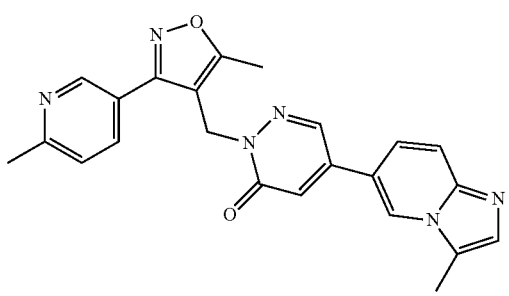 [SMILES: Cc1ccc(-c2noc(C)c2Cn2ncc(-c3ccc4ncc(C)n4c3)cc2=O)cn1]

In analogy to experiment of example 67, [1-[[5-methyl-3-(6-methyl-3-pyridyl)isoxazol-4-yl]methyl]-6-oxo-pyridazin-4-yl]boronic acid (building block Z), using 6-bromo-3-methylimidazo[1,2-a]pyridine instead of phenyl-boronic acid, was converted into the title compound (28 mg, 29%) which was obtained as a light yellow solid. MS (ESI): 413.2 ([M+H]+).

Example 219

2-((3-(6-chloropyridin-3-yl)-5-methylisoxazol-4-yl)methyl)-5-((2RS,6SR)-2,6-dimethylmorpholino)pyridazin-3(2H)-one

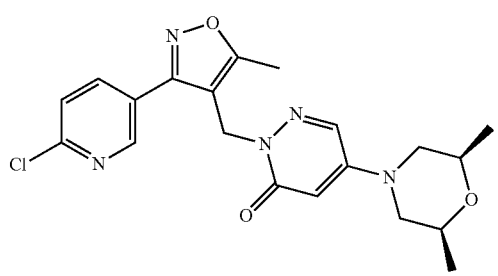 [SMILES: Cc1onc(-c2ccc(Cl)nc2)c1Cn1ncc(N2C[C@@H](C)O[C@@H](C)C2)cc1=O]

In analogy to experiment of example 3, 5-chloro-2-[[3-(6-chloro-3-pyridyl)-5-methyl-isoxazol-4-yl]methyl]pyridazin-3-one (building block D), using cis-2,6-dimethyl-morpholine instead of (R)-3-hydroxypyrrolidine and replacing the solvent with N,N-dimethylacetamide, was converted into the title compound (53 mg, 77%) which was obtained as a white foam. MS (ESI): 416.1 ([M+H]+).

Example 220

2-((3-(6-chloropyridin-3-yl)-5-methyl-1,2-oxazol-4-yl)methyl)-5-(3-ethoxyazetidin-1-yl)pyridazin-3-one

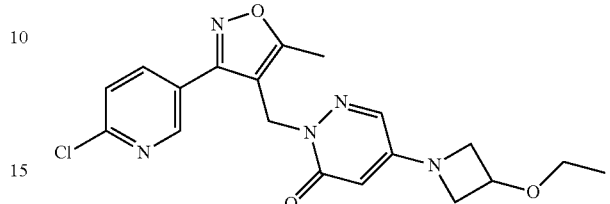

In analogy to experiment of example 3, 5-chloro-2-[[3-(6-chloro-3-pyridyl)-5-methyl-isoxazol-4-yl]methyl]pyridazin-3-one (building block D), using 3-ethoxyazetidine hydrochloride instead of (R)-3-hydroxypyrrolidine and replacing the solvent with N,N-dimethylacetamide, was converted into the title compound (27 mg, 82%) which was obtained as a yellow solid. MS (ESI): 402.1 ([M+H]+).

Example 221

2-((3-(6-chloropyridin-3-yl)-5-methylisoxazol-4-yl)methyl)-5-(1-ethyl-1H-pyrazol-4-yl)pyridazin-3(2H)-one

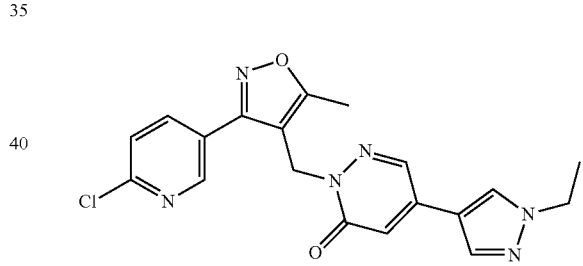

a) 4-(1-ethylpyrazol-4-yl)-1H-pyridazin-6-one

In analogy to experiment of example 214 a, 4-chloro-H-pyridazin-6-one, using (1-ethyl-1H-pyrazol-4-yl)boronic acid instead of (2-methoxypyridin-4-yl)boronic acid, was converted into the title compound (95 mg, 46%) which was obtained as a light yellow solid. MS (ESI): 191.1 ([M+H]+).

b) 2-((3-(6-chloropyridin-3-yl)-5-methylisoxazol-4-yl)methyl)-5-(1-ethyl-1H-pyrazol-4-yl)pyridazin-3(2H)-one In analogy to experiment of example 214 b, 4-(chloromethyl)-3-(6-chloropyridin-3-yl)-5-methylisoxazole, using 4-(1-ethylpyrazol-4-yl)-1H-pyridazin-6-one instead of 4-(2-methoxy-4-pyridyl)-1H-pyridazin-6-one, was converted into the title compound (20 mg, 56%) which was obtained as a white solid. MS (ESI): 397.1 ([M+H]+).

Example 222

2-((3-(6-chloropyridin-3-yl)-5-methylisoxazol-4-yl)methyl)-5-(1-cyclopropyl-1H-pyrazol-4-yl)pyridazin-3(2H)-one

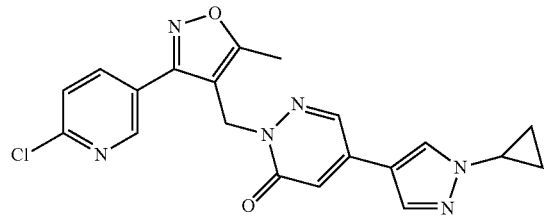 [SMILES: Cc1onc(-c2ccc(Cl)nc2)c1Cn1ncc(-c2cnn(C3CC3)c2)cc1=O]

a) 4-(1-cyclopropylpyrazol-4-yl)-1H-pyridazin-6-one

In analogy to experiment of example 214 a, 4-chloro-1H-pyridazin-6-one, using 1-cyclopropyl-4-(4,4,5,5-tetramethyl-1,3,2-dioxaborolan-2-yl)-1H-pyrazole instead of (2-methoxypyridin-4-yl)boronic acid, was converted into the title compound (159 mg, 68%) which was obtained as an off-white solid. MS (ESI): 203.1 ([M+H]$^+$).

b) 2-((3-(6-chloropyridin-3-yl)-5-methylisoxazol-4-yl)methyl)-5-(1-cyclopropyl-1H-pyrazol-4-yl)pyridazin-3(2H)-one In analogy to experiment of example 214 b, 4-(chloromethyl)-3-(6-chloropyridin-3-yl)-5-methylisoxazole, using 4-(1-cyclopropylpyrazol-4-yl)-1H-pyridazin-6-one instead of 4-(2-methoxy-4-pyridyl)-1H-pyridazin-6-one, was converted into the title compound (28 mg, 83%) which was obtained as a white solid. MS (ESI): 409.1 ([M+H]$^+$).

Example 223

2-(1-((3-(6-chloropyridin-3-yl)-5-methylisoxazol-4-yl)methyl)-6-oxo-1,6-dihydropyridazin-4-yl)hexahydropyrrolo[1,2-a]pyrazin-6(2H)-one

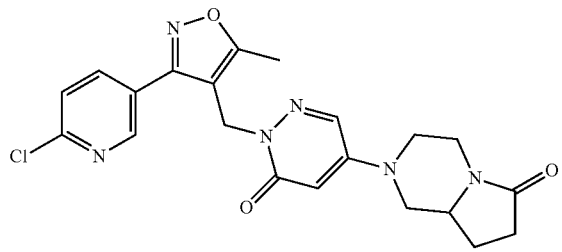 [SMILES: Cc1onc(-c2ccc(Cl)nc2)c1Cn1ncc(N2CCN3C(=O)CCC3C2)cc1=O]

In analogy to experiment of example 3, 5-chloro-2-[[3-(6-chloro-3-pyridyl)-5-methyl-isoxazol-4-yl]methyl]pyridazin-3-one (building block D), using hexahydropyrrolo[1,2-a]pyrazin-6(2H)-one instead of (R)-3-hydroxypyrrolidine and replacing the solvent with N,N-dimethylacetamide, was converted into the title compound (8.6 mg, 28%) which was obtained as an orange oil. MS (ESI): 441.2 ([M+H]$^+$).

Example 224

2-((3-(6-chloropyridin-3-yl)-5-methylisoxazol-4-yl)methyl)-5-(3-cyclopropoxyazetidin-1-yl)pyridazin-3(2H)-one

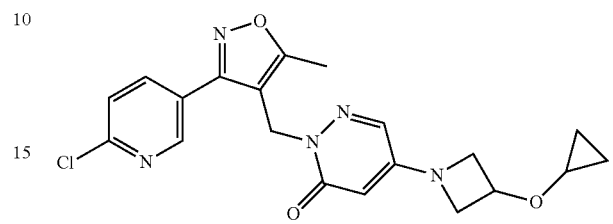

In analogy to experiment of example 3, 5-chloro-2-[[3-(6-chloro-3-pyridyl)-5-methyl-isoxazol-4-yl]methyl]pyridazin-3-one (building block D), using 3-cyclopropoxyazetidine instead of (R)-3-hydroxypyrrolidine and replacing the solvent with N,N-dimethylacetamide, was converted into the title compound (39 mg, 46%) which was obtained as a white solid. MS (ESI): 414.1 ([M+H]$^+$).

Example 226

2-((5-methyl-3-(6-methylpyridin-3-yl)isoxazol-4-yl)methyl)-5-(3-oxa-9-azaspiro[5.5]undecan-9-yl)pyridazin-3(2H)-one

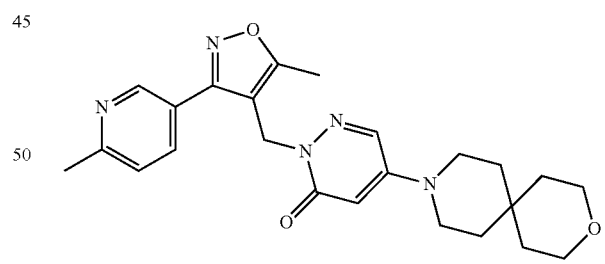

In analogy to experiment of example 3, 5-chloro-2-[[5-methyl-3-(6-methyl-3-pyridyl)isoxazol-4-yl]methyl]pyridazin-3-one, using 3-oxa-9-azaspiro[5.5]undecane instead of (R)-3-hydroxypyrrolidine, was converted into the title compound (107 mg, 78%) which was obtained as a yellow powder. MS (ESI): 436.3 ([M+H]$^+$).

Example 227

(S)-2-((3-(6-chloropyridin-3-yl)-5-methylisoxazol-4-yl)methyl)-5-(2-methylmorpholino)pyridazin-3(2H)-one

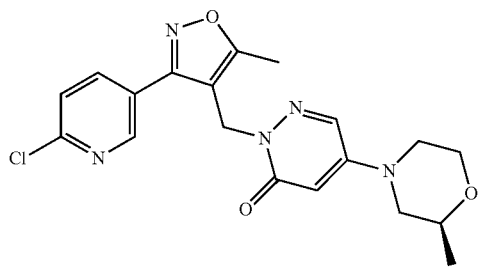 [SMILES: Cc1onc(-c2ccc(Cl)nc2)c1Cn1ncc(N2CCO[C@@H](C)C2)cc1=O]

In analogy to experiment of example 3, 5-chloro-2-[[3-(6-chloro-3-pyridyl)-5-methyl-isoxazol-4-yl]methyl]pyridazin-3-one (building block D), using (S)-2-methylmorpholine hydrochloride instead of (R)-3-hydroxypyrrolidine and replacing the solvent with N,N-dimethylacetamide, was converted into the title compound (16 mg, 47%) which was obtained as alight yellow foam. MS (ESI): 402.2 ([M+H]$^+$).

Example 228

5-(2-methoxypyridin-4-yl)-2-((5-methyl-3-(5-(trifluoromethyl)pyrimidin-2-yl)isoxazol-4-yl)methyl)pyridazin-3(2H)-one

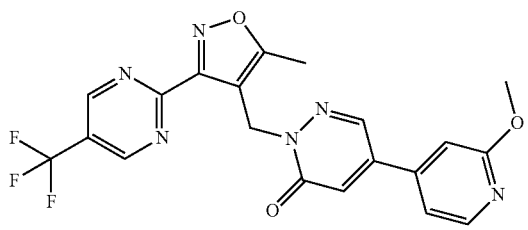 [SMILES: COc1cc(-c2cnn(Cc3c(-c4ncc(C(F)(F)F)cn4)noc3C)c(=O)c2)ccn1]

In analogy to experiment of example 214 b, 4-(chloromethyl)-5-methyl-3-[5-(trifluoromethyl)pyrimidin-2-yl]isoxazole was converted into the title compound (17 mg, 59%) which was obtained as a white solid. MS (ESI): 445.2 ([M+H]$^+$).

Example 229

5-(3-methoxyazetidin-1-yl)-2-((5-methyl-3-(5-(trifluoromethyl)pyrimidin-2-yl)isoxazol-4-yl)methyl)pyridazin-3(2H)-one

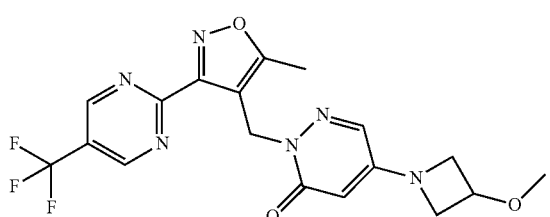

In analogy to experiment of example 3, 5-chloro-2-[[5-methyl-3-[5-(trifluoromethyl)pyrimidin-2-yl]isoxazol-4-yl]methyl]pyridazin-3-one (building block R), using 3-methoxyazetidine hydrochloride instead of (R)-3-hydroxypyrrolidine and replacing the solvent with N,N-dimethylacetamide, was converted into the title compound (10.8 mg, 39%) which was obtained as a light yellow solid. MS (ESI): 423.1 ([M+H]$^+$).

Example 230

(R)-2-((3-(6-chloropyridin-3-yl)-5-methylisoxazol-4-yl)methyl)-5-(7-fluoro-5-oxa-2-azaspiro[3.4]octan-2-yl)pyridazin-3(2H)-one

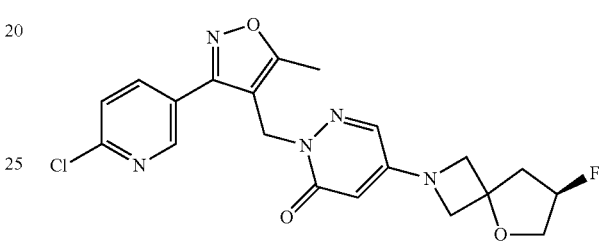

In analogy to experiment of example 3, 5-chloro-2-[[3-(6-chloro-3-pyridyl)-5-methyl-isoxazol-4-yl]methyl]pyridazin-3-one (building block D), using (R)-7-fluoro-5-oxa-2-azaspiro[3.4]octane 2,2,2-trifluoroacetate instead of (R)-3-hydroxypyrrolidine and replacing the solvent with N,N-dimethylacetamide, was converted into the title compound (5 mg, 20%) which was obtained as a white foam. MS (ESI): 432.1 ([M+H]$^+$).

Example 232

(S)-2-((3-(6-chloropyridin-3-yl)-5-methylisoxazol-4-yl)methyl)-5-(7-fluoro-5-oxa-2-azaspiro[3.4]octan-2-yl)pyridazin-3(2H)-one

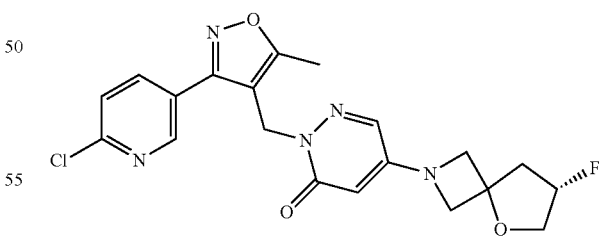

In analogy to experiment of example 3, 5-chloro-2-[[3-(6-chloro-3-pyridyl)-5-methyl-isoxazol-4-yl]methyl]pyridazin-3-one (building block D), using (S)-7-fluoro-5-oxa-2-azaspiro[3.4]octane hydrochloride instead of (R)-3-hydroxypyrrolidine and replacing the solvent with N,N-dimethylacetamide, was converted into the title compound (8 mg, 31%) which was obtained as a white solid. MS (ESI): 432.1 ([M+H]$^+$).

Example 233

2-((3-(6-chloropyridin-3-yl)-5-methylisoxazol-4-yl)methyl)-5-(5-oxa-2-azaspiro[3.5]nonan-2-yl)pyridazin-3(2H)-one

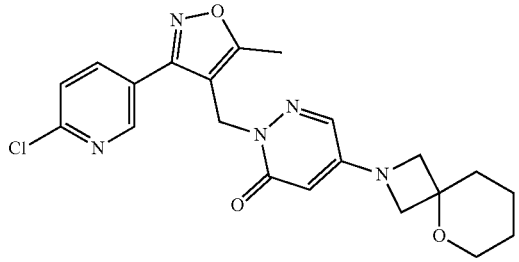 [SMILES: Cc1onc(-c2ccc(Cl)nc2)c1Cn1ncc(N2CC3(CCCCO3)C2)cc1=O]

In analogy to experiment of example 3, 5-chloro-2-[[3-(6-chloro-3-pyridyl)-5-methyl-isoxazol-4-yl]methyl]pyridazin-3-one (building block D), using 5-oxa-2-azaspiro[3.5]nonane oxalate instead of (R)-3-hydroxypyrrolidine and replacing the solvent with N,N-dimethylacetamide, was converted into the title compound (31 mg, 88%) which was obtained as a light yellow solid. MS (ESI): 428.2 ([M+H]$^+$).

Example 234

5-(3-(tert-butoxy)azetidin-1-yl)-2-((5-methyl-3-(6-methylpyridazin-3-yl)isoxazol-4-yl)methyl)pyridazin-3(2H)-one

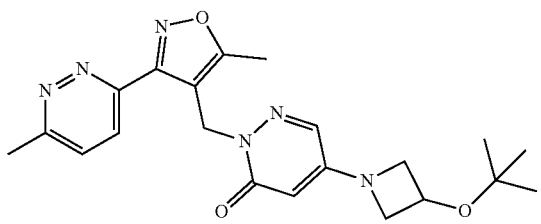 [SMILES: Cc1ccc(-c2noc(C)c2Cn2ncc(N3CC(OC(C)(C)C)C3)cc2=O)nn1]

In analogy to experiment of example 5, 5-chloro-2-[[5-methyl-3-(6-methylpyridazin-3-yl)isoxazol-4-yl]methyl]pyridazin-3-one (building block F), using 3-(tert-butoxy)azetidine hydrochloride instead of piperidin-4-ol, was converted into the title compound (53 mg, 92%) which was obtained as an off-white solid. MS (ESI): 411.3 ([M+H]$^+$).

Example 235

2-((5-methyl-3-(6-methylpyridazin-3-yl)isoxazol-4-yl)methyl)-5-(5-oxa-2-azaspiro[3.5]nonan-2-yl)pyridazin-3(2H)-one

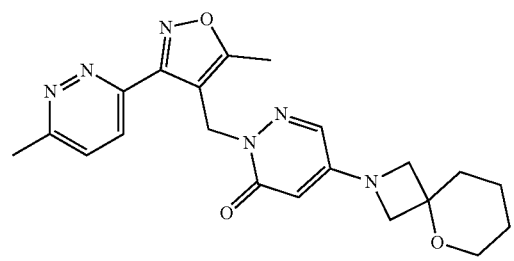 [SMILES: Cc1ccc(-c2noc(C)c2Cn2ncc(N3CC4(CCCCO4)C3)cc2=O)nn1]

In analogy to experiment of example 5, 5-chloro-2-[[5-methyl-3-(6-methylpyridazin-3-yl)isoxazol-4-yl]methyl]pyridazin-3-one (building block F), using 5-oxa-2-azaspiro[3.5]nonane oxalate instead of piperidin-4-ol, was converted into the title compound (295 mg, 92%) which was obtained as a white solid. MS (ESI): 409.2 ([M+H]$^+$).

Example 236

5-[3-[(2-chloro-4-pyridyl)oxy]azetidin-1-yl]-2-[[5-methyl-3-(6-methylpyridazin-3-yl)isoxazol-4-yl]methyl]pyridazin-3-one

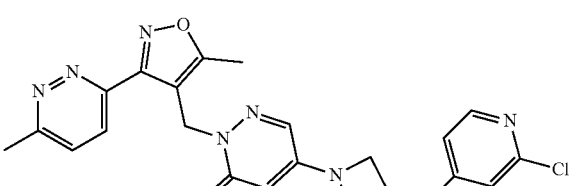

In analogy to experiment of example 5, 5-chloro-2-[[5-methyl-3-(6-methylpyridazin-3-yl)isoxazol-4-yl]methyl]pyridazin-3-one (building block F), using 4-(azetidin-3-yloxy)-2-chloropyridine 2,2,2-trifluoroacetic acid instead of piperidin-4-ol, was converted into the title compound (57 mg, 88%) which was obtained as an off-white solid. MS (ESI): 466.2 ([M+H]$^+$).

Example 237

5-[(7R)-7-methoxy-5-oxa-2-azaspiro[3.4]octan-2-yl]-2-[[5-methyl-3-[6-(trifluoromethyl)-3-pyridyl]isoxazol-4-yl]methyl]pyridazin-3-one

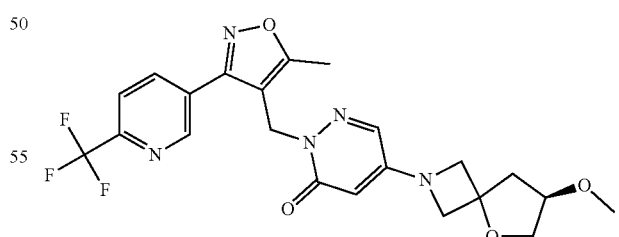

In analogy to experiment of example 5, 5-chloro-2-[[5-methyl-3-[6-(trifluoromethyl)-3-pyridyl]isoxazol-4-yl]methyl]pyridazin-3-one (building block C), using (7R)-7-methoxy-5-oxa-2-azaspiro[3.4]octane hydrochloride instead of piperidin-4-ol, was converted into the title compound (31 mg, 47%) which was obtained as an off-white foam. MS (ESI): 478.3 ([M+H]$^+$).

Example 238

5-[3-(cyclobutoxy)azetidin-1-yl]-2-[[5-methyl-3-(6-methylpyridazin-3-yl)isoxazol-4-yl]methyl]pyridazin-3-one

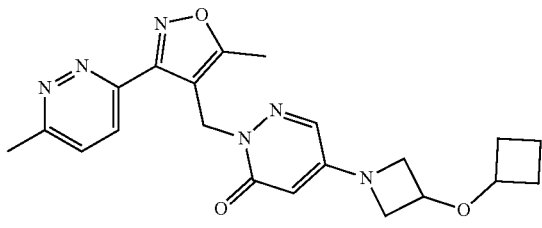 [SMILES: Cc1ccc(-c2noc(C)c2Cn2ncc(N3CC(OC4CCC4)C3)cc2=O)nn1]

In analogy to experiment of example 5, 5-chloro-2-[[5-methyl-3-(6-methylpyridazin-3-yl)isoxazol-4-yl]methyl]pyridazin-3-one (building block F), using 3-cyclobutoxyazetidine hydrochloride instead of piperidin-4-ol, was converted into the title compound (16 mg, 33%) which was obtained as an off-white solid. MS (ESI): 409.3 ([M+H]+).

Example 239

5-[3-(cyclopropoxy)azetidin-1-yl]-2-[[5-methyl-3-(6-methylpyridazin-3-yl)isoxazol-4-yl]methyl]pyridazin-3-one

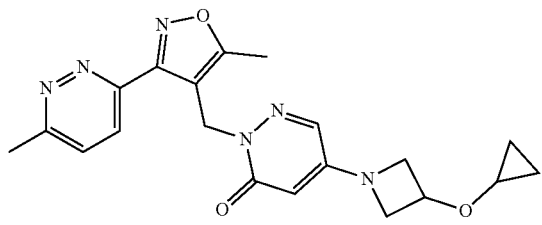 [SMILES: Cc1ccc(-c2noc(C)c2Cn2ncc(N3CC(OC4CC4)C3)cc2=O)nn1]

In analogy to experiment of example 5, 5-chloro-2-[[5-methyl-3-(6-methylpyridazin-3-yl)isoxazol-4-yl]methyl]pyridazin-3-one (building block F), using 3-cyclopropoxyazetidine instead of piperidin-4-ol, was converted into the title compound (2.5 mg, 5%) which was obtained a colorless oil. MS (ESI): 395.2 ([M+H]+).

Example 240

2-[[5-methyl-3-(6-methylpyridazin-3-yl)isoxazol-4-yl]methyl]-5-[(7R)-7-methyl-5-oxa-2-azaspiro[3.4]octan-2-yl]pyridazin-3-one or enantiomer

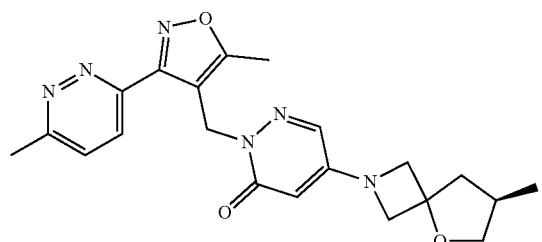

In analogy to experiment of example 5, 5-chloro-2-[[5-methyl-3-(6-methylpyridazin-3-yl)isoxazol-4-yl]methyl]pyridazin-3-one (building block F), using racemic 7-methyl-5-oxa-2-azaspiro[3.4]octane 2,2,2-trifluoroacetic acid instead of piperidin-4-ol, was converted into the racemic title compound (82 mg, 91%) which was obtained as an off-white foam. MS (ESI): 409.3 ([M+H]+). Separation of the enantiomers by chiral HPLC (column: Chiralcel OD) afforded the (−)-title compound (29 mg) which was obtained as an off white foam. MS (ESI): 409.2 ([M+H]+).

Example 241

2-[[5-methyl-3-(6-methylpyridazin-3-yl)isoxazol-4-yl]methyl]-5-[(7S)-7-methyl-5-oxa-2-azaspiro[3.4]octan-2-yl]pyridazin-3-one or enantiomer

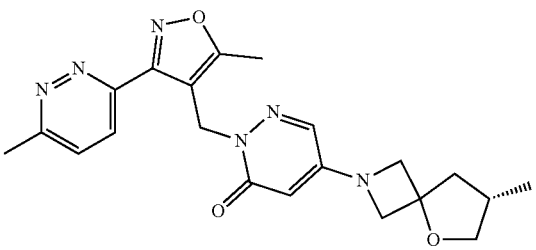

In analogy to experiment of example 240, separation of the enantiomers by chiral HPLC (column: Chiralcel OD) afforded the (+)-title compound (31 mg) which was obtained as an off white foam. MS (ESI): 409.2 ([M+H]+).

Example 242

5-[(7R)-7-(difluoromethoxy)-5-oxa-2-azaspiro[3.4]octan-2-yl]-2-[[5-methyl-3-(6-methylpyridazin-3-yl)isoxazol-4-yl]methyl]pyridazin-3-one

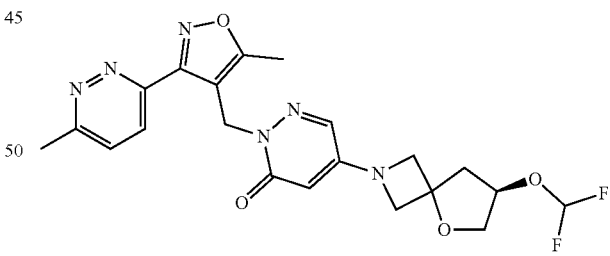

In analogy to experiment of example 3, 5-chloro-2-[[5-methyl-3-(6-methylpyridazin-3-yl)isoxazol-4-yl]methyl]pyridazin-3-one (building block F), using (R)-7-(difluoromethoxy)-5-oxa-2-azaspiro[3.4]octane hydrochloride instead of (R)-3-hydroxypyrrolidine, was converted into the (+)-title compound (38 mg, 89%) which was obtained as a white solid. MS (ESI): 461.2 ([M+H]+).

Example 243

5-((2S,6R)-2,6-dimethylmorpholin-4-yl)-2-((5-(fluoromethyl)-3-(6-methylpyridin-3-yl)-1,2-oxazol-4-yl)methyl)pyridazin-3-one

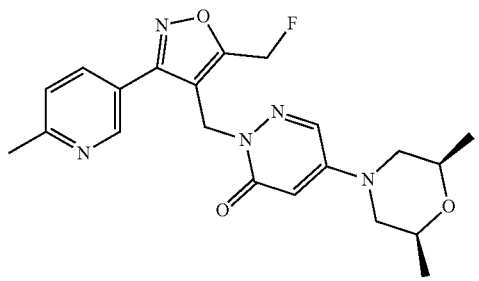

In analogy to experiment of example 3, 5-chloro-2-[[5-(fluoromethyl)-3-(6-methyl-3-pyridyl)isoxazol-4-yl]methyl]pyridazin-3-one (building block B), using cis-2,6-dimethylmorpholine instead of (R)-3-hydroxypyrrolidine, was converted into the title compound (20 mg, 56%) which was obtained as a yellow foam. MS (ESI): 414.2 ([M+H]$^+$).

Example 244

5-[3-(2,2-difluoroethoxy)azetidin-1-yl]-2-[[5-methyl-3-[6-(trifluoromethyl)-3-pyridyl]isoxazol-4-yl]methyl]pyridazin-3-one

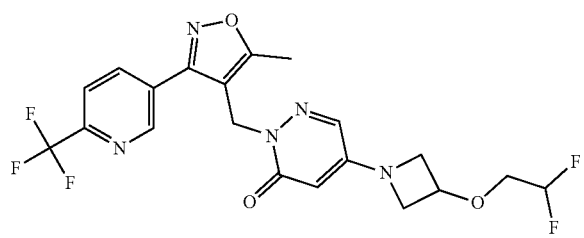 [SMILES: Cc1onc(-c2ccc(C(F)(F)F)nc2)c1Cn1ncc(N2CC(OCC(F)F)C2)cc1=O]

a) 5-(3-hydroxyazetidin-1-yl)-2-[[5-methyl-3-[6-(trifluoromethyl)-3-pyridyl]isoxazol-4-yl]methyl]pyridazin-3-one In analogy to experiment of example 5, 5-chloro-2-[[5-methyl-3-[6-(trifluoromethyl)-3-pyridyl]isoxazol-4-yl]methyl]pyridazin-3-one instead of 5-chloro-2-[[5-methyl-3-(6-methyl-3-pyridyl)isoxazol-4-yl]methyl]pyridazin-3-one, using azetidin-3-ol hydrochloride instead of piperidin-4-ol, was converted into the title compound (199 mg, 88%) which was obtained as a white foam. MS (ESI): 408.2 ([M+H]$^+$).

b) 5-[3-(2,2-difluoroethoxy)azetidin-1-yl]-2-[[5-methyl-3-[6-(trifluoromethyl)-3-pyridyl]isoxazol-4-yl]methyl]pyridazin-3-one In analogy to experiment of example 133, 5-(3-hydroxyazetidin-1-yl)-2-[[5-methyl-3-[6-(trifluoromethyl)-3-pyridyl]isoxazol-4-yl]methyl]pyridazin-3-one instead of 5-[(7S)-7-hydroxy-5-oxa-2-azaspiro[3.4]octan-2-yl]-2-[[5-methyl-3-(6-methyl-3-pyridyl)isoxazol-4-yl]methyl]pyridazin-3-one, using 2,2-difluoroethyl trifluoromethanesulfonate instead of methyl iodide was converted into the title compound (38 mg, 66%) which was obtained as a colorless amorphous. MS (ESI): 472.2 ([M+H]$^+$).

Example 245

2-((3-(6-chloropyridin-3-yl)-5-methylisoxazol-4-yl)methyl)-5-(3-(2,2-difluoroethoxy)azetidin-1-yl)pyridazin-3(2H)-one In analogy to experiment of example 3, 5-chloro-2-[[3-(6-chloro-3-pyridyl)-5-methyl-isoxazol-4-yl]methyl]pyridazin-3-one (building block D), using 3-(2,2-difluoroethoxy)azetidine hydrochloride instead of (R)-3-hydroxypyrrolidine and replacing the solvent with N,N-dimethylacetamide, was converted into the title compound (253 mg, 65%) which was obtained as a white solid. MS (ESI): 438.3 ([M+H]$^+$).

Example 246

5-[(7S)-7-(difluoromethoxy)-5-oxa-2-azaspiro[3.4]octan-2-yl]-2-[[5-methyl-3-(6-methylpyridazin-3-yl)isoxazol-4-yl]methyl]pyridazin-3-one In analogy to experiment of example 3, 5-chloro-2-[[5-methyl-3-(6-methylpyridazin-3-yl)isoxazol-4-yl]methyl]pyridazin-3-one (building block F), using (S)-7-(difluoromethoxy)-5-oxa-2-azaspiro[3.4]octane 2,2,2-trifluoroacetate instead of (R)-3-hydroxypyrrolidine, was converted into the (−)-title compound (35 mg, 81%) which was obtained as a white solid. MS (ESI): 461.2 ([M+H]$^+$).

Example 247

2-[[5-methyl-3-(6-methylpyridazin-3-yl)isoxazol-4-yl]methyl]-5-(3-oxa-9-azaspiro[5.5]undecan-9-yl)pyridazin-3-one

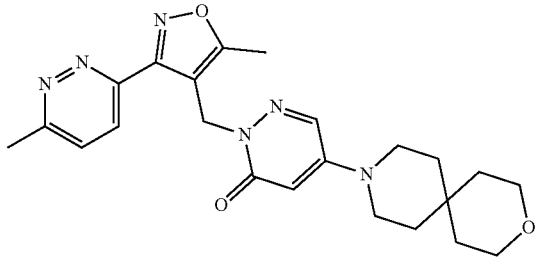 [SMILES: Cc1ccc(-c2noc(C)c2Cn2ncc(N3CCC4(CCOCC4)CC3)cc2=O)nn1]

In analogy to experiment of example 3, 5-chloro-2-[[5-methyl-3-(6-methylpyridazin-3-yl)isoxazol-4-yl]methyl]pyridazin-3-one (building block F), using 3-oxa-9-azaspiro[5.5]undecane instead of (R)-3-hydroxypyrrolidine, was converted into the title compound (31 mg, 73%) which was obtained as a white solid. MS (ESI): 437.1 ([M+H]$^+$).

Example 248

2-((3-(6-chloropyridin-3-yl)-5-methylisoxazol-4-yl)methyl)-5-(3-oxa-9-azaspiro[5.5]undecan-9-yl)pyridazin-3(2H)-one

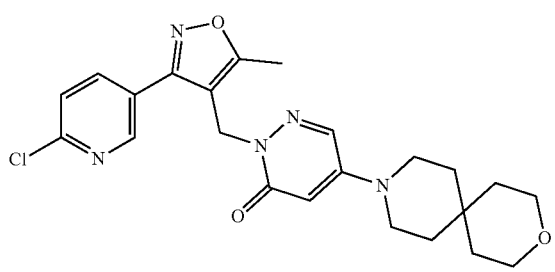 [SMILES: Cc1onc(-c2ccc(Cl)nc2)c1Cn1ncc(N2CCC3(CCOCC3)CC2)cc1=O]

In analogy to experiment of example 3, 5-chloro-2-[[3-(6-chloro-3-pyridyl)-5-methyl-isoxazol-4-yl]methyl]pyridazin-3-one (building block D), using 3-oxa-9-azaspiro[5.5]undecane instead of (R)-3-hydroxypyrrolidine and replacing the solvent with N,N-dimethylacetamide, was converted into the title compound (17 mg, 46%) which was obtained as a green oil. MS (ESI): 456.3 ([M+H]$^+$).

Example 249

5-(3-cyclopropoxyazetidin-1-yl)-2-((5-methyl-3-(5-(trifluoromethyl)pyrimidin-2-yl)isoxazol-4-yl)methyl)pyridazin-3(2H)-one

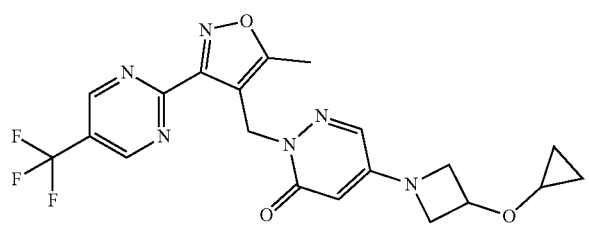 [SMILES: Cc1onc(-c2ncc(C(F)(F)F)cn2)c1Cn1ncc(N2CC(OC3CC3)C2)cc1=O]

In analogy to experiment of example 3, 5-chloro-2-[[5-methyl-3-[5-(trifluoromethyl)pyrimidin-2-yl]isoxazol-4-yl]methyl]pyridazin-3-one (building block R), using 3-cyclopropoxyazetidine instead of (R)-3-hydroxypyrrolidine and replacing the solvent with N,N-dimethylacetamide, was converted into the title compound (11 mg, 34%) which was obtained as a white solid. MS (ESI): 449.2 ([M+H]$^+$).

Example 250

5-(7,7-difluoro-5-oxa-2-azaspiro[3.4]octan-2-yl)-2-((5-methyl-3-(5-(trifluoromethyl)pyrimidin-2-yl)isoxazol-4-yl)methyl)pyridazin-3(2H)-one

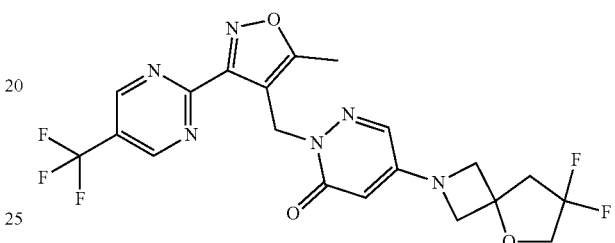

In analogy to experiment of example 3, 5-chloro-2-[[5-methyl-3-[5-(trifluoromethyl)pyrimidin-2-yl]isoxazol-4-yl]methyl]pyridazin-3-one (building block R), using 7,7-difluoro-5-oxa-2-azaspiro[3.4]octane 2,2,2-trifluoroacetate instead of (R)-3-hydroxypyrrolidine and replacing the solvent with N,N-dimethylacetamide, was converted into the title compound (23 mg, 57%) which was obtained as a white solid. MS (ESI): 485.2 ([M+H]$^+$).

Example 251

2-((3-(6-chloropyridin-3-yl)-5-methylisoxazol-4-yl)methyl)-5-(3-(trifluoromethoxy)azetidin-1-yl)pyridazin-3(2H)-one

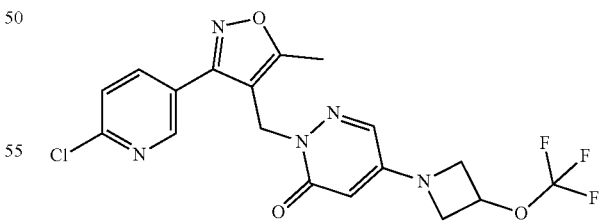

In analogy to experiment of example 3, 5-chloro-2-[[3-(6-chloro-3-pyridyl)-5-methyl-isoxazol-4-yl]methyl]pyridazin-3-one (building block D), using 3-(trifluoromethoxy)azetidine hydrochloride instead of (R)-3-hydroxypyrrolidine and replacing the solvent with N,N-dimethylacetamide, was converted into the title compound (23 mg, 64%) which was obtained as a white solid. MS (ESI): 442.1 ([M+H]$^+$).

Example 252

2-((3-(6-chloropyridazin-3-yl)-5-methylisoxazol-4-yl)methyl)-5-(3-methoxyazetidin-1-yl)pyridazin-3(2H)-one

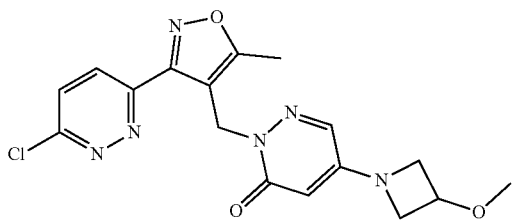 [SMILES: COC1CN(c2cnn(Cc3c(-c4ccc(Cl)nn4)noc3C)c(=O)c2)C1]

In analogy to experiment of example 3, 5-chloro-2-[[3-(6-chloropyridazin-3-yl)-5-methyl-isoxazol-4-yl]methyl]pyridazin-3-one (building block S), using 3-methoxyazetidine hydrochloride instead of (R)-3-hydroxypyrrolidine and replacing the solvent with N,N-dimethylacetamide, was converted into the title compound (18 mg, 50%) which was obtained as alight yellow solid. MS (ESI): 389.1 ([M+H]+).

Example 253

2-((3-(6-chloropyridin-3-yl)-5-methylisoxazol-4-yl)methyl)-5-(3-cyclobutoxyazetidin-1-yl)pyridazin-3(2H)-one

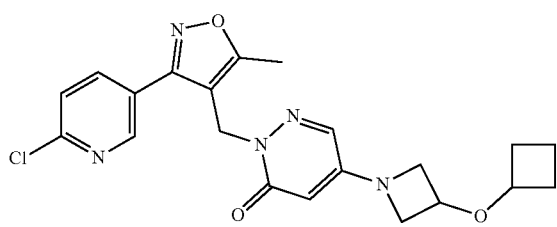 [SMILES: Cc1onc(-c2ccc(Cl)nc2)c1Cn1ncc(N2CC(OC3CCC3)C2)cc1=O]

In analogy to experiment of example 3, 5-chloro-2-[[3-(6-chloro-3-pyridyl)-5-methyl-isoxazol-4-yl]methyl]pyridazin-3-one (building block D), using 3-cyclobutoxyazetidine hydrochloride instead of (R)-3-hydroxypyrrolidine and replacing the solvent with N,N-dimethylacetamide, was converted into the title compound (13.5 mg, 53%) which was obtained as a white solid. MS (ESI): 428.1 ([M+H]+).

Example 254

2-((3-(6-chloropyridin-3-yl)-5-methylisoxazol-4-yl)methyl)-5-(3-(2,2,2-trifluoroethoxy)azetidin-1-yl)pyridazin-3(2H)-one

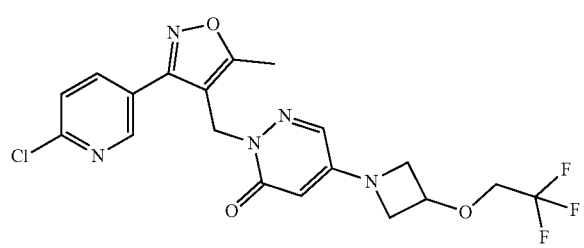 [SMILES: Cc1onc(-c2ccc(Cl)nc2)c1Cn1ncc(N2CC(OCC(F)(F)F)C2)cc1=O]

In analogy to experiment of example 3, 5-chloro-2-[[3-(6-chloro-3-pyridyl)-5-methyl-isoxazol-4-yl]methyl]pyridazin-3-one (building block D), using 3-(2,2,2-trifluoroethoxy)azetidine bis(2,2,2-trifluoroacetate) instead of (R)-3-hydroxypyrrolidine and replacing the solvent with N,N-dimethylacetamide, was converted into the title compound (14 mg, 37%) which was obtained as an off-white solid. MS (ESI): 456.1 ([M+H]+).

Example 255

2-((3-(6-chloropyridin-3-yl)-5-methylisoxazol-4-yl)methyl)-5-(3-(difluoromethoxy)azetidin-1-yl)pyridazin-3(2H)-one

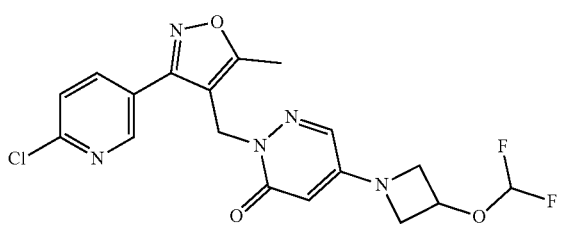 [SMILES: Cc1onc(-c2ccc(Cl)nc2)c1Cn1ncc(N2CC(OC(F)F)C2)cc1=O]

In analogy to experiment of example 3, 5-chloro-2-[[3-(6-chloro-3-pyridyl)-5-methyl-isoxazol-4-yl]methyl]pyridazin-3-one (building block D), using 3-(difluoromethoxy)azetidine instead of (R)-3-hydroxypyrrolidine and replacing the solvent with N,N-dimethylacetamide, was converted into the title compound (7 mg, 22%) which was obtained as a light brown foam. MS (ESI): 424.1 ([M+H]+).

Example 256

2-((3-(6-chloropyridin-3-yl)-5-methylisoxazol-4-yl)methyl)-5-(1-oxa-8-azaspiro[4.5]decan-8-yl)pyridazin-3(2H)-one

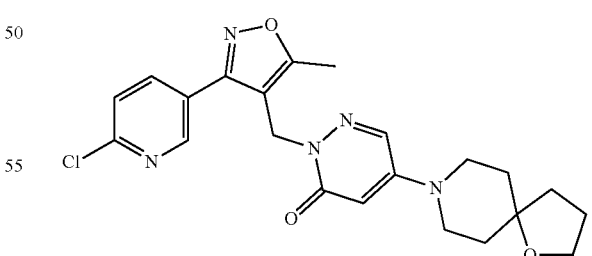

In analogy to experiment of example 3, 5-chloro-2-[[3-(6-chloro-3-pyridyl)-5-methyl-isoxazol-4-yl]methyl]pyridazin-3-one (building block D), using 1-oxa-8-azaspiro[4.5]decane instead of (R)-3-hydroxypyrrolidine and replacing the solvent with N,N-dimethylacetamide, was converted into the title compound (13 mg, 40%) which was obtained as a white foam. MS (ESI): 442.1 ([M+H]+).

Example 257

2-((3-(6-chloropyridin-3-yl)-5-methylisoxazol-4-yl)methyl)-5-(7-oxa-2-azaspiro[3.5]nonan-2-yl)pyridazin-3(2H)-one

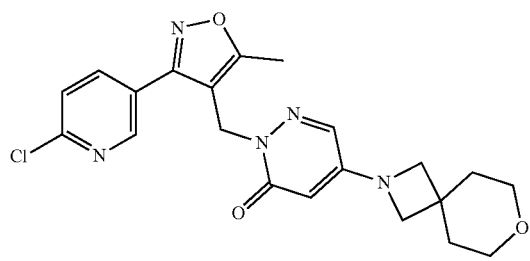 [SMILES: Cc1onc(-c2ccc(Cl)nc2)c1Cn1ncc(N2CC3(CCOCC3)C2)cc1=O]

In analogy to experiment of example 3, 5-chloro-2-[[3-(6-chloro-3-pyridyl)-5-methyl-isoxazol-4-yl]methyl]pyridazin-3-one (building block D), using 7-oxa-2-azaspiro[3.5]nonane hemioxalate instead of (R)-3-hydroxypyrrolidine and replacing the solvent with N,N-dimethylacetamide, was converted into the title compound (16 mg, 50%) which was obtained as a white foam. MS (ESI): 428.1 ([M+H]$^+$).

Example 258

2-((3-(6-chloropyridin-3-yl)-5-methylisoxazol-4-yl)methyl)-5-(2-oxa-7-azaspiro[3.5]nonan-7-yl)pyridazin-3(2H)-one

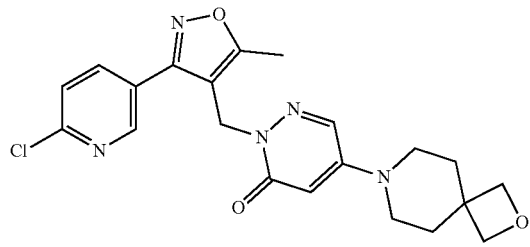 [SMILES: Cc1onc(-c2ccc(Cl)nc2)c1Cn1ncc(N2CCC3(CC2)COC3)cc1=O]

In analogy to experiment of example 3, 5-chloro-2-[[3-(6-chloro-3-pyridyl)-5-methyl-isoxazol-4-yl]methyl]pyridazin-3-one (building block D), using 2-oxa-7-azaspiro[3.5]nonane oxalate instead of (R)-3-hydroxypyrrolidine and replacing the solvent with N,N-dimethylacetamide, was converted into the title compound (21 mg, 66%) which was obtained as a white foam. MS (ESI): 428.1 ([M+H]$^+$).

Example 259

2-[[5-cyclopropyl-3-(6-methylpyridazin-3-yl)isoxazol-4-yl]methyl]-5-(5-oxa-2-azaspiro[3.5]nonan-2-yl)pyridazin-3-one

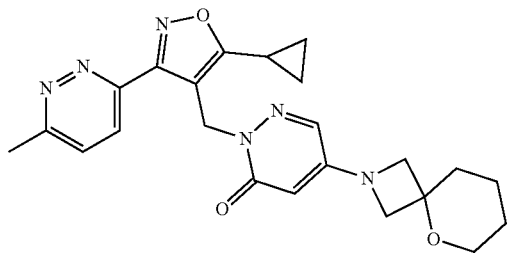 [SMILES: Cc1ccc(-c2noc(C3CC3)c2Cn2ncc(N3CC4(CCCCO4)C3)cc2=O)nn1]

In analogy to experiment of example 3, 5-chloro-2-[[5-cyclopropyl-3-(6-methylpyridazin-3-yl)isoxazol-4-yl]methyl]pyridazin-3-one (building block I), using 5-oxa-2-azaspiro[3.5]nonane hydrochloride instead of (R)-3-hydroxypyrrolidine, was converted into the title compound (7.6 mg, 19%) which was obtained as an off-white solid. MS (ESI): 435.3 ([M+H]$^+$).

Example 260

2-((3-(6-cyclopropylpyridin-3-yl)-5-methylisoxazol-4-yl)methyl)-5-(7,7-difluoro-5-oxa-2-azaspiro[3.4]octan-2-yl)pyridazin-3(2H)-one

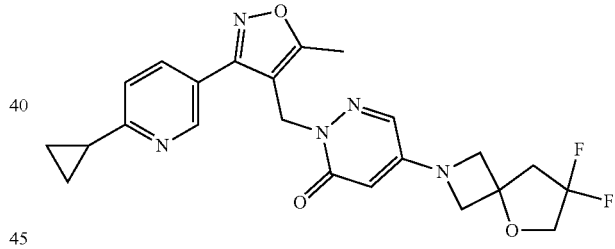

To a solution of 2-((3-(6-chloropyridin-3-yl)-5-methylisoxazol-4-yl)methyl)-5-(7,7-difluoro-5-oxa-2-azaspiro[3.4]octan-2-yl)pyridazin-3(2H)-one (Example 217, 20 mg, 0.0445 mmol) in anhydrous tetrahydrofuran (0.50 mL) under argon were added a solution of cyclopropylzinc(II) bromide in tetrahydrofuran (0.5 M, 0.107 mL, 53.4 mmol) and Pd(Ph$_3$)$_4$ (5.14 mg, 4.45 µmol). The mixture was heated to 70° C. for 4 h before being cooled to room temperature. A further portion of cyclopropylzinc(II) bromide in THF (0.5 M, 88.9 µL, 44.5 µmol) and Pd(Ph$_3$)$_4$ (5.14 mg, 4.45 µmol) were added to the reaction mixture which was then heated to 70° C. for 18 h. The reaction was cooled to room temperature before being quenched by addition of aqueous NH$_4$Cl 20 wt. %. The aqueous layer was extracted three times with ethyl acetate. The combined organic layers were dried (Na$_2$SO$_4$), filtered and concentrated in vacuo. The crude residue was purified by flash chromatography (silica, gradient: 0% to 100% EtOAc in heptane) to afford the title compound (3 mg, 15%) as an off-white solid. MS (ESI): 456.3 ([M+H]$^+$).

Example 261

5-[(3R)-3-tert-butoxypyrrolidin-1-yl]-2-[[5-methyl-3-(6-methylpyridazin-3-yl)isoxazol-4-yl]methyl]pyridazin-3-one

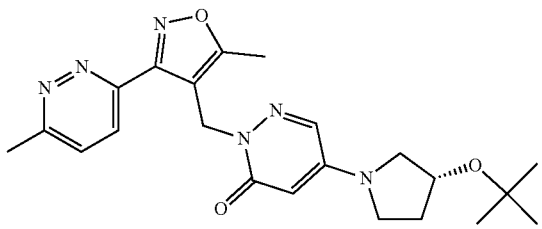 [SMILES: Cc1ccc(-c2noc(C)c2Cn2ncc(N3CC[C@@H](OC(C)(C)C)C3)cc2=O)nn1]

To a mixture of 5-chloro-2-[[5-methyl-3-(6-methylpyridazin-3-yl)isoxazol-4-yl]methyl]pyridazin-3-one (building block F, 33 mg, 0.10 mmol), (3R)-3-tert-butoxypyrrolidine oxalate (49 mg, 0.21 mmol) and potassium carbonate (72 mg, 0.52 mmol) was added acetonitrile (1 mL). The reaction mixture was stirred at 40° C. for 18 h. Then the reaction mixture was diluted with EtOAc (20 mL) and water (10 mL). The aqueous layer was back extracted with EtOAc (20 mL). The organic layers were washed with brine (20 mL). The organic layers were combined, dried (MgSO₄), filtered and concentrated in vacuo. Purification by flash chromatography (silica, gradient: 0% to 10% MeOH in EtOAc) afforded the title compound (43 mg, 97%) as an off-white foam. MS (ESI): 425.2 ([M+H]⁺).

Example 262

2-((3-(6-chloropyridin-3-yl)-5-methylisoxazol-4-yl)methyl)-5-(4-methoxy-4-methylpiperidin-1-yl)pyridazin-3(2H)-one

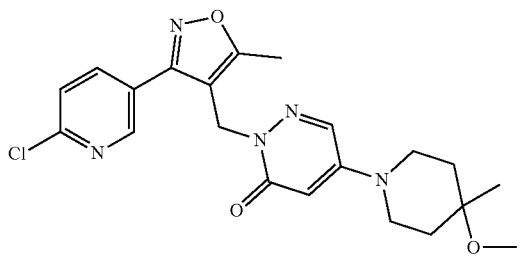 [SMILES: COC1(C)CCN(c2cnn(Cc3c(-c4ccc(Cl)nc4)noc3C)c(=O)c2)CC1]

In analogy to experiment of example 3, 5-chloro-2-[[3-(6-chloro-3-pyridyl)-5-methyl-isoxazol-4-yl]methyl]pyridazin-3-one (building block D), using 4-methoxy-4-methylpiperidine hydrochloride instead of (R)-3-hydroxypyrrolidine and replacing the solvent with N,N-dimethylacetamide, was converted into the title compound (13 mg, 41%) which was obtained as a white foam. MS (ESI): 430.2 ([M+H]⁺).

Example 263

2-((3-(6-chloropyridin-3-yl)-5-methylisoxazol-4-yl)methyl)-5-(4-(pyridazin-4-yl)piperazin-1-yl)pyridazin-3(2H)-one

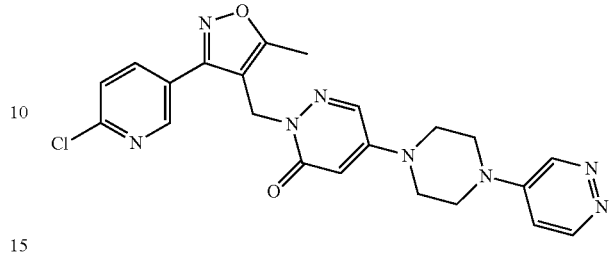

In analogy to experiment of example 3, 5-chloro-2-[[3-(6-chloro-3-pyridyl)-5-methyl-isoxazol-4-yl]methyl]pyridazin-3-one (building block D), using 4-(piperazin-1-yl)pyridazine hydrochloride instead of (R)-3-hydroxypyrrolidine and replacing the solvent with N,N-dimethylacetamide, was converted into the title compound (6 mg, 17%) which was obtained as a light yellow foam. MS (ESI): 465.2 ([M+H]⁺).

Example 264

2-[[5-methyl-3-(6-methylpyridazin-3-yl)isoxazol-4-yl]methyl]-5-[3-(2,2,2-trifluoro-1,1-dimethyl-ethoxy)azetidin-1-yl]pyridazin-3-one

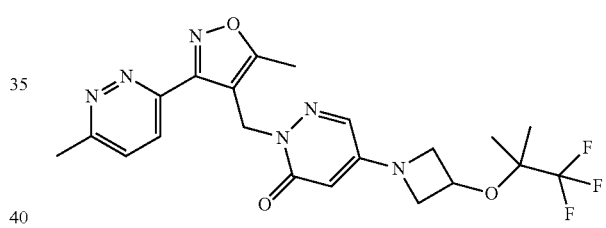

In analogy to experiment of example 261, 5-chloro-2-[[5-methyl-3-(6-methylpyridazin-3-yl)isoxazol-4-yl]methyl]pyridazin-3-one (building block F), using 3-(2,2,2-trifluoro-1,1-dimethyl-ethoxy)azetidine hydrochloride instead of (3R)-3-tert-butoxypyrrolidine oxalate, was converted into the title compound (45 mg, 93%) which was obtained as a white solid. MS (ESI): 465.2 ([M+H]⁺).

Example 265

(S)-2-((3-(6-chloropyridin-3-yl)-5-methylisoxazol-4-yl)methyl)-5-(3-((1,1,1-trifluoropropan-2-yl)oxy)azetidin-1-yl)pyridazin-3(2H)-one or enantiomer

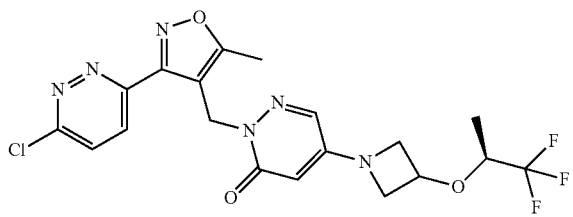 [SMILES: Cc1onc(-c2ccc(Cl)nn2)c1Cn1ncc(N2CC(O[C@@H](C)C(F)(F)F)C2)cc1=O]

In analogy to experiment of example 3, 5-chloro-2-[[3-(6-chloro-3-pyridyl)-5-methyl-isoxazol-4-yl]methyl]pyridazin-3-one (building block D), using 3-((1,1,1-trifluoropropan-2-yl)oxy)azetidine 2,2,2-trifluoroacetate instead of (R)-3-hydroxypyrrolidine and replacing the solvent with N,N-dimethylacetamide, was converted into the racemic title compound (307 mg, 88%) which was obtained as a white solid. MS (ESI): 470.1 ([M+H]$^+$). Separation of the enantiomers by chiral HPLC (column: Chiralpack AD) afforded the enantiomerically pure title compound (130 mg, % e.e.>99%) which was obtained as a white solid. MS (ESI): 470.0 ([M+H]$^+$).

Example 266

(R)-2-((3-(6-chloropyridin-3-yl)-5-methylisoxazol-4-yl)methyl)-5-(3-((1,1,1-trifluoropropan-2-yl)oxy)azetidin-1-yl)pyridazin-3(2H)-one or enantiomer

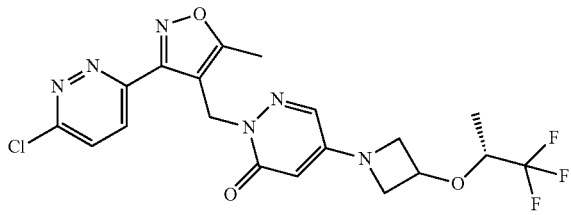 [SMILES: Cc1onc(-c2ccc(Cl)nn2)c1Cn1ncc(N2CC(O[C@H](C)C(F)(F)F)C2)cc1=O]

In analogy to experiment of example 265, separation of the enantiomers by chiral HPLC (column: Chiralpack AD) afforded the enantiomerically pure title compound (101 mg, % e.e.>99%) which was obtained as a white solid. MS (ESI): 470.0 ([M+H]$^+$).

Example 268

4-chloro-5-(3-ethoxyazetidin-1-yl)-2-((5-methyl-3-(6-methylpyridin-3-yl)isoxazol-4-yl)methyl)pyridazin-3(2H)-one

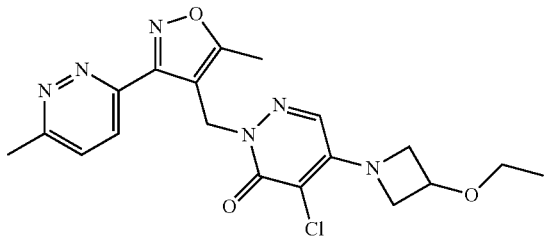 [SMILES: CCOC1CN(c2cnn(Cc3c(-c4ccc(C)nn4)noc3C)c(=O)c2Cl)C1]

a) 4,5-dichloro-2-[[5-methyl-3-(6-methyl-3-pyridyl)isoxazol-4-yl]methyl]pyridazin-3-one A mixture of 4-(chloromethyl)-5-methyl-3-(6-methylpyridin-3-yl)isoxazole (100 mg, 0.449 mmol), 4,5-dichloropyridazin-3(2H)-one (81.5 mg, 0.494 mmol) and potassium carbonate (93.1 mg, 0.674 mmol) in N,N-dimethylacetamide (1.0 mL) was heated to 70° C. for 30 min. The mixture was diluted with water and extracted three times with ethyl acetate. The combined extracts were dried (Na$_2$SO$_4$), filtered and concentrated in vacuo. Purification by flash chromatography (silica, gradient: 0% to 100% EtOAc in heptane) afforded the title compound (110 mg, 70%) as a white solid. MS (ESI): 351.0; 353.0 ([M+H]$^+$).

b) 4-chloro-5-(3-ethoxyazetidin-1-yl)-2-((5-methyl-3-(6-methylpyridin-3-yl)isoxazol-4-yl)methyl)pyridazin-3(2H)-one A mixture of 4,5-dichloro-2-[[5-methyl-3-(6-methyl-3-pyridyl)isoxazol-4-yl]methyl]pyridazin-3-one (50 mg, 0.142 mmol), 3-ethoxyazetidine hydrochloride (21.6 mg, 0.157 mmol) and potassium carbonate (59 mg, 0.427 mmol) in N,N-dimethylacetamide (1 mL) was heated to 70° C. for 4 h. The mixture was cooled to room temperature, diluted with water and extracted 3 times with ethyl acetate. The combined organic extracts were dried (Na$_2$SO$_4$), filtered and concentrated in vacuo. Purification by flash chromatography (silica, gradient: 0% to 100% EtOAc in heptane) afforded the title compound (23 mg, 39%) as a colorless gum. MS (ESI): 416.1 ([M+H]$^+$).

Example 269

2-((3-(6-chloropyridazin-3-yl)-5-methylisoxazol-4-yl)methyl)-5-(7,7-difluoro-5-oxa-2-azaspiro[3.4]octan-2-yl)pyridazin-3(2H)-one

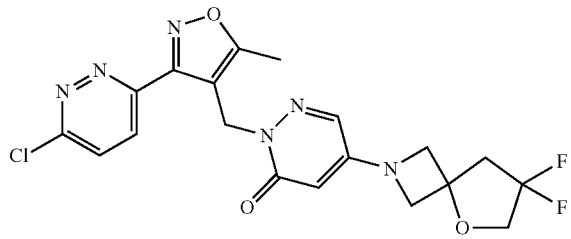 [SMILES: Cc1onc(-c2ccc(Cl)nn2)c1Cn1ncc(N2CC3(C2)CC(F)(F)CO3)cc1=O]

In analogy to experiment of example 268 b, 5-chloro-2-[[3-(6-chloropyridazin-3-yl)-5-methyl-isoxazol-4-yl]methyl]pyridazin-3-one (building block S), using 7,7-difluoro-5-oxa-2-azaspiro[3.4]octane hydrochloride instead of 3-ethoxyazetidine hydrochloride, was converted into the title compound (3.5 mg, 19%) which was obtained as a white solid. MS (ESI): 451.2 ([M+H]$^+$).

Example 270

2-((3-(6-chloropyridin-3-yl)-5-methylisoxazol-4-yl)methyl)-5-(1-oxa-7-azaspiro[3.5]nonan-7-yl)pyridazin-3(2H)-one

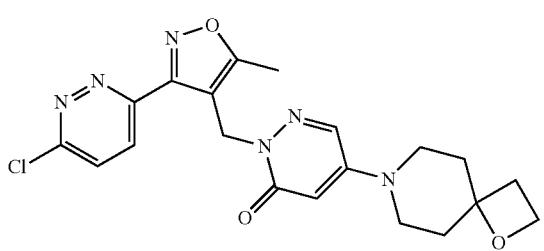 [SMILES: Cc1onc(-c2ccc(Cl)nn2)c1Cn1ncc(N2CCC3(CCO3)CC2)cc1=O]

In analogy to experiment of example 3, 5-chloro-2-[[3-(6-chloro-3-pyridyl)-5-methyl-isoxazol-4-yl]methyl]pyridazin-3-one (building block D), using 1-oxa-7-azaspiro[3.5]nonane oxalate instead of (R)-3-hydroxypyrrolidine and replacing the solvent with N,N-dimethylacetamide, was converted into the title compound (13 mg, 51%) which was obtained as a colorless oil. MS (ESI): 428.2 ([M+H]+).

Example 271

5-(3-(tert-butoxy)azetidin-1-yl)-2-((3-(6-chloro-pyridazin-3-yl)-5-methylisoxazol-4-yl)methyl)pyridazin-3(2H)-one

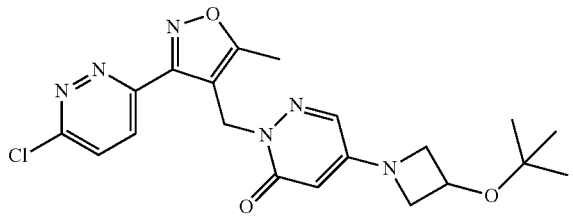 [SMILES: Cc1onc(-c2ccc(Cl)nn2)c1Cn1ncc(N2CC(OC(C)(C)C)C2)cc1=O]

In analogy to experiment of example 268 b, 5-chloro-2-[[3-(6-chloropyridazin-3-yl)-5-methyl-isoxazol-4-yl]methyl]pyridazin-3-one (building block S), using 3-(tert-butoxy)azetidine hydrochloride instead of 3-ethoxyazetidine hydrochloride, was converted into the title compound (7.3 mg, 28%) which was obtained as a white solid. MS (ESI): 431.1 ([M+H]+).

Example 272

4-chloro-2-((3-(6-chloropyridin-3-yl)-5-methylisoxazol-4-yl)methyl)-5-(3-ethoxyazetidin-1-yl)pyridazin-3(2H)-one

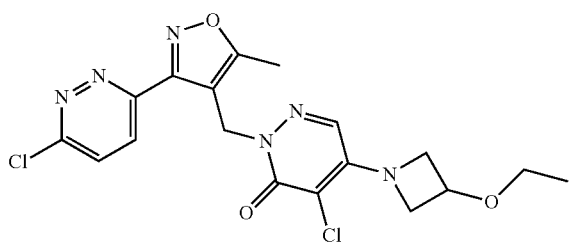 [SMILES: CCOC1CN(c2cnn(Cc3c(-c4ccc(Cl)nn4)noc3C)c(=O)c2Cl)C1]

a) 4,5-dichloro-2-[[3-(6-chloro-3-pyridyl)-5-methyl-isoxazol-4-yl]methyl]pyridazin-3-one In analogy to experiment of example 268 a, 4-(chloromethyl)-3-(6-chloro-3-pyridyl)-5-methyl-isoxazole instead of 4-(chloromethyl)-5-methyl-3-(6-methylpyridin-3-yl)isoxazole, was converted into the title compound (71 mg, 57%) as a white solid. MS (ESI): 436.1; 438.0 ([M+H]+).

b) 4-chloro-2-((3-(6-chloropyridin-3-yl)-5-methyl-isoxazol-4-yl)methyl)-5-(3-ethoxyazetidin-1-yl)pyridazin-3(2H)-one In analogy to experiment of example 268 b, 4,5-dichloro-2-[[3-(6-chloro-3-pyridyl)-5-methyl-isoxazol-4-yl]methyl]pyridazin-3-one instead of 4,5-dichloro-2-[[5-methyl-3-(6-methyl-3-pyridyl)isoxazol-4-yl]methyl]pyridazin-3-one, was converted into the title compound (16 mg, 69%) as a white solid. MS (ESI): 436.2; 438.2 ([M+H]+).

Example 273

(S)-5-(8-fluoro-5-oxa-2-azaspiro[3.5]nonan-2-yl)-2-((5-methyl-3-(6-methylpyridin-3-yl)isoxazol-4-yl)methyl)pyridazin-3(2H)-one or enantiomer

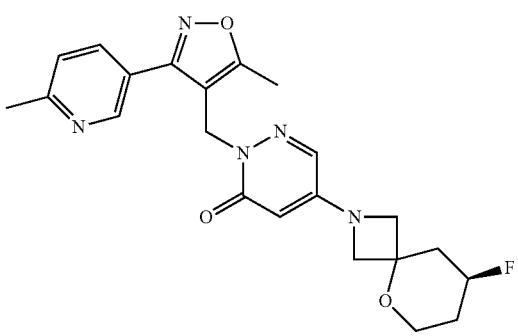 [SMILES: Cc1ccc(-c2noc(C)c2Cn2ncc(N3CC4(C[C@@H](F)CCO4)C3)cc2=O)cn1]

In analogy to experiment of example 261, 5-chloro-2-[[5-methyl-3-(6-methyl-3-pyridyl)isoxazol-4-yl]methyl]pyridazin-3-one (building block A), using and a regioisomeric mixture of 7-fluoro-5-oxa-2-azaspiro[3.5]nonane 2,2,2-trifluoroacetic acid and 8-fluoro-5-oxa-2-azaspiro[3.5]nonane 2,2,2-trifluoroacetic acid instead of (3R)-3-tert-butoxypyrrolidine oxalate, was converted into the title compound as racemic mixture of regioisomers. Separation by chiral SFC afforded the title compound (66.5 mg, 43%) which was obtained as a brown semisolid. MS (ESI): 426.2 ([M+H]+).

Example 274

(R)-5-(8-fluoro-5-oxa-2-azaspiro[3.5]nonan-2-yl)-2-((5-methyl-3-(6-methylpyridin-3-yl)isoxazol-4-yl)methyl)pyridazin-3(2H)-one or enantiomer

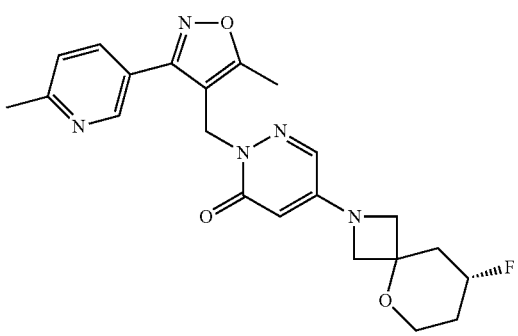 [SMILES: Cc1ccc(-c2noc(C)c2Cn2ncc(N3CC4(C[C@H](F)CCO4)C3)cc2=O)cn1]

In analogy to experiment of example 273, separation by chiral SFC afforded the title compound (54.1 mg, 35%) which was obtained as a brown semisolid. MS (ESI): 426.2 ([M+H]+).

Example 275

(R)-5-(7-fluoro-5-oxa-2-azaspiro[3.5]nonan-2-yl)-2-((5-methyl-3-(6-methylpyridin-3-yl)isoxazol-4-yl)methyl)pyridazin-3(2H)-one or enantiomer

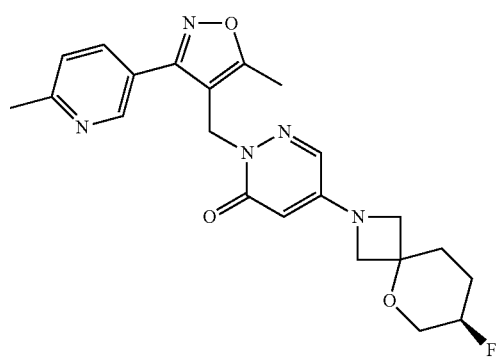 [SMILES: Cc1ccc(-c2noc(C)c2Cn2ncc(N3CC4(CC[C@@H](F)CO4)C3)cc2=O)cn1]

To a solution of 5-chloro-2-((5-methyl-3-(6-methylpyridin-3-yl)isoxazol-4-yl)methyl)pyridazin-3(2H)-one (250 mg, 0.789 mmol) in acetonitrile (2.63 mL) at room temperature, was added (R)-7-fluoro-5-oxa-2-azaspiro[3.5]nonane hydrochloride or enantiomer (186 mg, 1.03 mmol) and potassium carbonate (545 mg, 3.95 mmol). The mixture was stirred at 82° C. for 4 h, then partitioned between water and EtOAc. The aqueous layer was extracted three times with EtOAc. The combined organic layers were dried (Na₂SO₄), filtered and concentrated in vacuo. Purification by flash chromatography (silica, gradient: 50% to 80% EtOAc in heptane), followed by crystallization in AcOEt/heptane afforded the title compound (250 mg, 74%) as a white solid. MS (ESI) m/z: 426.3 ([M+H]⁺).

Example 276

(S)-5-(7-fluoro-5-oxa-2-azaspiro[3.5]nonan-2-yl)-2-((5-methyl-3-(6-methylpyridin-3-yl)isoxazol-4-yl)methyl)pyridazin-3(2H)-one or enantiomer

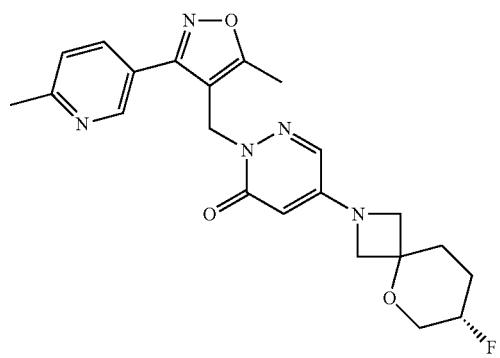 [SMILES: Cc1ccc(-c2noc(C)c2Cn2ncc(N3CC4(CC[C@H](F)CO4)C3)cc2=O)cn1]

In analogy to experiment of example 275, 5-chloro-2-((5-methyl-3-(6-methylpyridin-3-yl)isoxazol-4-yl)methyl)pyridazin-3(2H)-one (building block A), using (S)-7-fluoro-5-oxa-2-azaspiro[3.5]nonane hydrochloride or enantiomer instead of (R)-7-fluoro-5-oxa-2-azaspiro[3.5]nonane hydrochloride or enantiomer, was converted into the title compound (3.4 mg, 18%) which was obtained as a colorless semisolid. MS (ESI): 426.2 ([M+H]⁺).

Example 277

2-((3-(6-chloropyridin-3-yl)-5-methylisoxazol-4-yl)methyl)-5-(4-(pyrimidin-5-yl)piperazin-1-yl)pyridazin-3(2H)-one

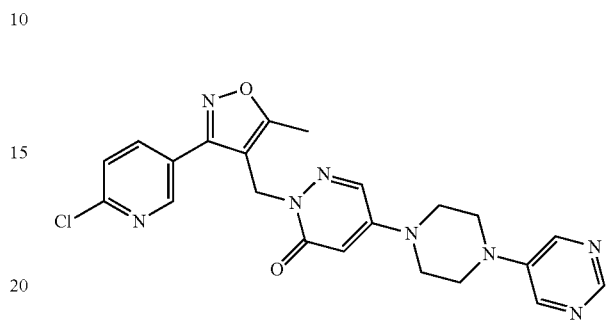

In analogy to experiment of example 3, 5-chloro-2-[[3-(6-chloro-3-pyridyl)-5-methyl-isoxazol-4-yl]methyl]pyridazin-3-one (building block D), using 5-(piperazin-1-yl)pyrimidine hydrochloride instead of (R)-3-hydroxypyrrolidine and replacing the solvent with N,N-dimethylacetamide, was converted into the title compound (5.3 mg, 15%) which was obtained as a white solid. MS (ESI): 465.3 ([M+H]⁺).

Example 278

2-((3-(6-chloropyridin-3-yl)-5-methylisoxazol-4-yl)methyl)-5-(4-(pyridin-3-yl)piperazin-1-yl)pyridazin-3(2H)-one

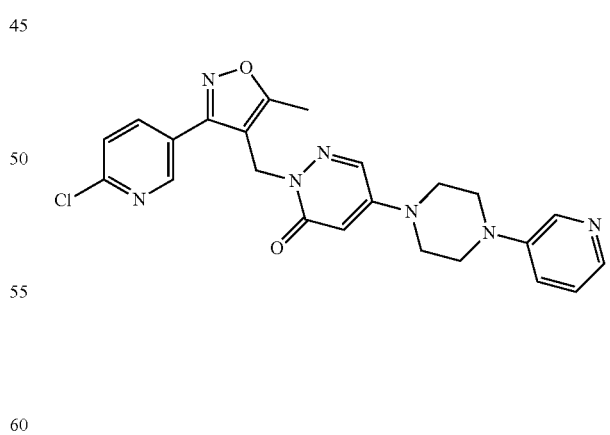

In analogy to experiment of example 3, 5-chloro-2-[[3-(6-chloro-3-pyridyl)-5-methyl-isoxazol-4-yl]methyl]pyridazin-3-one (building block D), using 1-(pyridin-3-yl)piperazine instead of (R)-3-hydroxypyrrolidine and replacing the solvent with N,N-dimethylacetamide, was converted into the title compound (14 mg, 41%) which was obtained as a white solid. MS (ESI): 464.3 ([M+H]⁺).

Example 279

5-(3-ethoxyazetidin-1-yl)-2-((5-(fluoromethyl)-3-(6-methylpyridazin-3-yl)isoxazol-4-yl)methyl)pyridazin-3(2H)-one

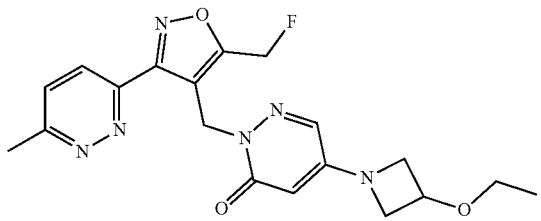 [SMILES: CCOC1CN(c2cnn(Cc3c(-c4ccc(C)nn4)noc3CF)c(=O)c2)C1]

a) 4-(3-ethoxyazetidin-1-yl)-1H-pyridazin-6-one

To a solution of 5-chloropyridazin-3(2H)-one (130 mg, 0.946 mmol) in N,N-dimethylacetamide (2.5 mL) were added potassium carbonate (654 mg, 4.73 mmol) and 3-ethoxyazetidine hydrochloride (174 mg, 1.23 mmol). The mixture was heated to 60° C. for 2 h before being cooled to room temperature. The reaction mixture was purified directly by preparative HPLC to provide the title compound (66 mg, 36%) as a light brown solid. MS (ESI): 196.1 ([M+H]$^+$).

b) 5-(3-ethoxyazetidin-1-yl)-2-((5-(fluoromethyl)-3-(6-methylpyridazin-3-yl)isoxazol-4-yl)methyl)pyridazin-3(2H)-one To solution of 4-(chloromethyl)-5-(fluoromethyl)-3-(6-methylpyridazin-3-yl)isoxazole (25 mg, 0.103 mmol) in N,N-dimethylacetamide (0.50 mL) were added potassium carbonate (15.7 mg, 0.114 mmol) and 4-(3-ethoxyazetidin-1-yl)-1H-pyridazin-6-one (30.3 mg, 0.155 mmol). The mixture was heated to 60° C. for 16 h before being allowed to cool to room temperature. The reaction mixture was filtered on a sintered funnel and rinsed with the minimal amount of N,N-dimethylacetamide. The filtrate was purified directly by preparative HPLC to provide the title compound (18 mg, 55%) as a white powder. MS (ESI): 401.1 ([M+H]$^+$).

Example 280

2-((3-(6-chloropyridin-3-yl)-5-methylisoxazol-4-yl)methyl)-5-(4-(4-methyl-1,2,5-oxadiazol-3-yl)piperazin-1-yl)pyridazin-3(2H)-one

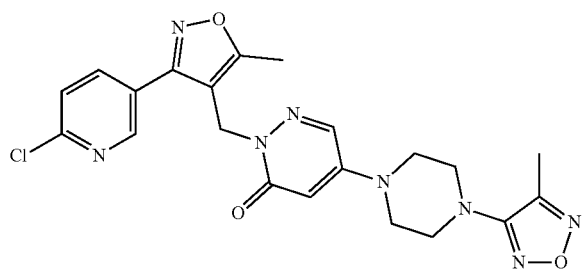 [SMILES: Cc1nonc1N1CCN(c2cnn(Cc3c(-c4ccc(Cl)nc4)noc3C)c(=O)c2)CC1]

In analogy to experiment of example 3, 5-chloro-2-[[3-(6-chloro-3-pyridyl)-5-methyl-isoxazol-4-yl]methyl]pyridazin-3-one (building block D), using 3-methyl-4-(piperazin-1-yl)-1,2,5-oxadiazole hydrochloride instead of (R)-3-hydroxypyrrolidine and replacing the solvent with N,N-dimethylacetamide, was converted into the title compound (5 mg, 14%) which was obtained as a white solid. MS (ESI): 469.3 ([M+H]$^+$).

Example 281

5-(3-methoxyazetidin-1-yl)-2-((5-methyl-3-(6-(trifluoromethyl)pyridazin-3-yl)isoxazol-4-yl)methyl)pyridazin-3(2H)-one

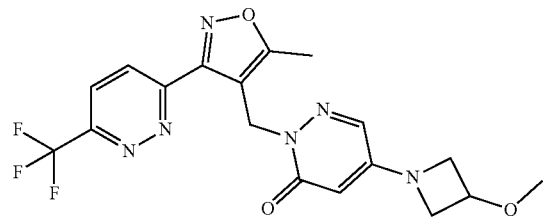 [SMILES: COC1CN(c2cnn(Cc3c(-c4ccc(C(F)(F)F)nn4)noc3C)c(=O)c2)C1]

In analogy to experiment of example 268 b, 5-chloro-2-[[5-methyl-3-[6-(trifluoromethyl)pyridazin-3-yl]isoxazol-4-yl]methyl]pyridazin-3-one (building block T), using 3-methoxyazetidine hydrochloride instead of 3-ethoxyazetidine hydrochloride, was converted into the title compound (4.7 mg, 39%) which was obtained as a white solid. MS (ESI): 423.3 ([M+H]$^+$).

Example 282

5-(5-chloro-6-methoxypyridin-3-yl)-2-((3-(6-chloropyridazin-3-yl)-5-methylisoxazol-4-yl)methyl)pyridazin-3(2H)-one

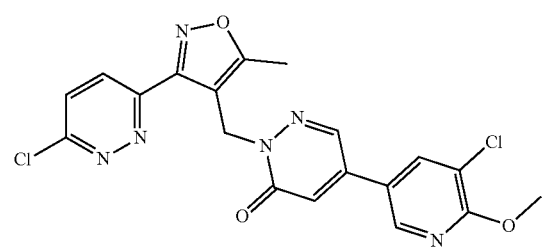 [SMILES: COc1ncc(-c2cnn(Cc3c(-c4ccc(Cl)nn4)noc3C)c(=O)c2)cc1Cl]

a) 4-(5-chloro-6-methoxy-3-pyridyl)-1H-pyridazin-6-one

In analogy to experiment of example 67, 4-chloro-H-pyridazin-6-one instead of 5-chloro-2-[[5-methyl-3-(6-methyl-3-pyridyl)isoxazol-4-yl]methyl]pyridazin-3-one, using (5-chloro-6-methoxypyridin-3-yl)boronic acid instead of phenylboronic acid, was converted into the title compound (396 mg, 44%) which was obtained as a white solid. MS (ESI): 238.1 ([M+H]$^+$).

b) 5-(5-chloro-6-methoxypyridin-3-yl)-2-((3-(6-chloropyridazin-3-yl)-5-methylisoxazol-4-yl)methyl)pyridazin-3(2H)-one In analogy to experiment of example 214 b, 4-(chloromethyl)-3-(6-chloropyridazin-3-yl)-5-methyl-isoxazole, using 4-(5-chloro-6-methoxy-3-pyridyl)-1H-pyridazin-6-one instead of 4-(2-methoxy-4-pyridyl)-1H-pyridazin-6-one, was converted into the title compound (19.5 mg, 67%) which was obtained as a white solid. MS (ESI): 445.3; 447.2 ([M+H]$^+$).

Example 285

2-((3-(6-chloropyridin-3-yl)-5-methylisoxazol-4-yl)methyl)-5-(4-(2-methylpyridin-3-yl)piperazin-1-yl)pyridazin-3(2H)-one

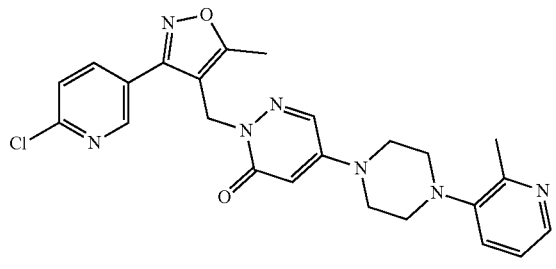 [SMILES: Cc1ncccc1N1CCN(c2cnn(Cc3c(-c4ccc(Cl)nc4)noc3C)c(=O)c2)CC1]

In analogy to experiment of example 3, 5-chloro-2-[[3-(6-chloro-3-pyridyl)-5-methyl-isoxazol-4-yl]methyl]pyridazin-3-one (building block D), using 1-(2-methylpyridin-3-yl)piperazine dihydrochloride instead of (R)-3-hydroxypyrrolidine and replacing the solvent with N,N-dimethylacetamide, was converted into the title compound (18 mg, 42%) which was obtained as a white foam. MS (ESI): 478.3 ([M+H]$^+$).

Example 286

2-((3-(6-chloropyridin-3-yl)-5-methylisoxazol-4-yl)methyl)-5-((2S,3S)-3-methoxy-2-methylazetidin-1-yl)pyridazin-3(2H)-one

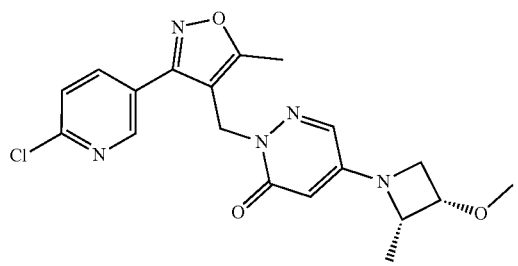 [SMILES: CO[C@H]1CN(c2cnn(Cc3c(-c4ccc(Cl)nc4)noc3C)c(=O)c2)[C@H]1C]

a) 2-[[3-(6-chloro-3-pyridyl)-5-methyl-isoxazol-4-yl]methyl]-5-[(2S,3S)-3-hydroxy-2-methyl-azetidin-1-yl]pyridazin-3-one In analogy to experiment of example 3, 5-chloro-2-[[3-(6-chloro-3-pyridyl)-5-methyl-isoxazol-4-yl]methyl]pyridazin-3-one (building block D), using (2S,3S)-2-methylazetidin-3-ol hydrochloride instead of (R)-3-hydroxypyrrolidine and replacing the solvent with N,N-dimethylacetamide, was converted into the title compound (310 mg, 69%) which was obtained as a white foam. MS (ESI): 388.5 ([M+H]$^+$).

b) 2-((3-(6-chloropyridin-3-yl)-5-methylisoxazol-4-yl)methyl)-5-((2S,3S)-3-methoxy-2-methylazetidin-1-yl)pyridazin-3(2H)-one In analogy to experiment of example 133, 2-[[3-(6-chloro-3-pyridyl)-5-methyl-isoxazol-4-yl]methyl]-5-[(2S, 3S)-3-hydroxy-2-methyl-azetidin-1-yl]pyridazin-3-one instead of 5-[(7S)-7-hydroxy-5-oxa-2-azaspiro[3.4]octan-2-yl]-2-[[5-methyl-3-(6-methyl-3-pyridyl)isoxazol-4-yl]methyl]pyridazin-3-one was converted into the title compound (8 mg, 26%) which was obtained as alight yellow foam. MS (ESI): 402.2 ([M+H]$^+$).

Example 287

5-[(8S)-8-fluoro-5-oxa-2-azaspiro[3.5]nonan-2-yl]-2-[[5-methyl-3-(6-methylpyridazin-3-yl)isoxazol-4-yl]methyl]pyridazin-3-one or enantiomer

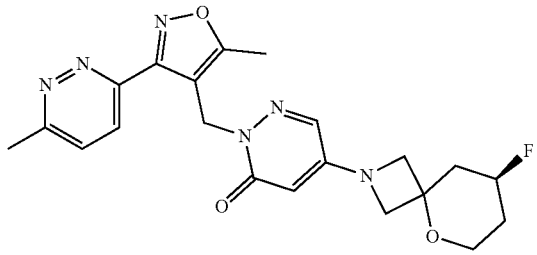 [SMILES: Cc1ccc(-c2noc(C)c2Cn2ncc(N3CC4(C[C@@H](F)CCO4)C3)cc2=O)nn1]

In analogy to experiment of example 261, 5-chloro-2-[[5-methyl-3-(6-methylpyridazin-3-yl)isoxazol-4-yl]methyl]pyridazin-3-one (building block F), using a regioisomeric mixture of 7-fluoro-5-oxa-2-azaspiro[3.5]nonane 2,2,2-trifluoroacetic acid and 8-fluoro-5-oxa-2-azaspiro[3.5]nonane 2,2,2-trifluoroacetic acid instead of (3R)-3-tert-butoxypyrrolidine oxalate, was converted into the racemic title compound as a mixture of two isomers (114 mg, 100%) as a brown oil. MS (ESI): 427.3 ([M+H]$^+$). Separation of the enantiomers by chiral SFC (column: Chiralpak IB 20×250 mm 5 Um Daicel) afforded the title compound (19 mg) which was obtained as an off-white foam. MS (ESI): 427.2 ([M+H]$^+$).

Example 288

(S)-5-(7-fluoro-5-oxa-2-azaspiro[3.5]nonan-2-yl)-2-((5-methyl-3-(6-methylpyridazin-3-yl)isoxazol-4-yl)methyl)pyridazin-3(2H)-one or enantiomer

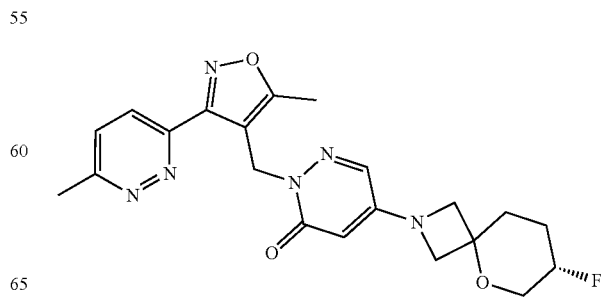

221

In analogy to experiment of example 275, 5-chloro-2-[[5-methyl-3-(6-methylpyridazin-3-yl)isoxazol-4-yl]methyl]pyridazin-3-one (building block F), using (S)-7-fluoro-5-oxa-2-azaspiro[3.5]nonane hydrochloride or enantiomer instead of (R)-7-fluoro-5-oxa-2-azaspiro[3.5]nonane hydrochloride or enantiomer, was converted into the (+)-title compound (32 mg, 16%) as a yellow solid. MS (ESI) m/z: 427.6 ([M+H]$^+$).

Example 289

2-((3-(6-chloropyridin-3-yl)-5-methylisoxazol-4-yl)methyl)-5-((2R,3R)-3-hydroxy-2-methylazetidin-1-yl)pyridazin-3(2H)-one

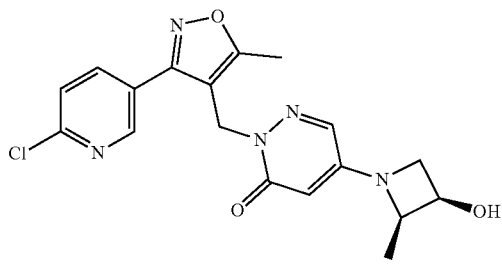 [SMILES: Cc1onc(-c2ccc(Cl)nc2)c1Cn1ncc(N2C[C@@H](O)[C@H]2C)cc1=O]

In analogy to experiment of example 3, 5-chloro-2-[[3-(6-chloro-3-pyridyl)-5-methyl-isoxazol-4-yl]methyl]pyridazin-3-one (building block D), using (2R,3R)-2-methylazetidin-3-ol hydrochloride instead of (R)-3-hydroxypyrrolidine and replacing the solvent with N,N-dimethylacetamide, was converted into the title compound (195 mg, 34%) which was obtained as a white foam. MS (ESI): 388.5 ([M+H]$^+$).

Example 291

2-((3-(6-chloropyridin-3-yl)-5-methylisoxazol-4-yl)methyl)-5-((2S,3S)-3-ethoxy-2-methylazetidin-1-yl)pyridazin-3(2H)-one

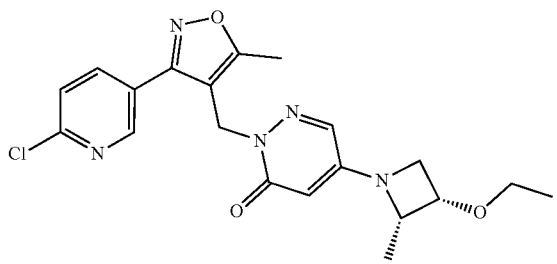 [SMILES: CCO[C@H]1CN(c2cnn(Cc3c(-c4ccc(Cl)nc4)noc3C)c(=O)c2)[C@H]1C]

In analogy to experiment of example 133, 2-[[3-(6-chloro-3-pyridyl)-5-methyl-isoxazol-4-yl]methyl]-5-[(2S,3S)-3-hydroxy-2-methyl-azetidin-1-yl]pyridazin-3-one instead of 5-[(7S)-7-hydroxy-5-oxa-2-azaspiro[3.4]octan-2-yl]-2-[[5-methyl-3-(6-methyl-3-pyridyl)isoxazol-4-yl]methyl]pyridazin-3-one, using iodoethane instead of iodomethane, was converted into the title compound (1.0 mg, 3%) which was obtained as a light yellow foam. MS (ESI): 416.6 ([M+H]$^+$).

Example 294

2-((3-(6-chloropyridin-3-yl)-5-methylisoxazol-4-yl)methyl)-5-((2R,3R)-3-ethoxy-2-methylazetidin-1-yl)pyridazin-3(2H)-one

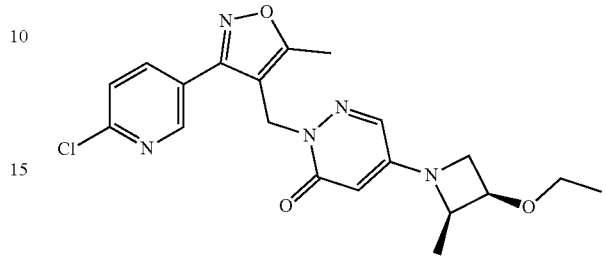

In analogy to experiment of example 133, 2-[[3-(6-chloro-3-pyridyl)-5-methyl-isoxazol-4-yl]methyl]-5-[(2R,3R)-3-hydroxy-2-methyl-azetidin-1-yl]pyridazin-3-one instead of 5-[(7S)-7-hydroxy-5-oxa-2-azaspiro[3.4]octan-2-yl]-2-[[5-methyl-3-(6-methyl-3-pyridyl)isoxazol-4-yl]methyl]pyridazin-3-one, using iodoethane instead of iodomethane, was converted into the title compound (21 mg, 39%) which was obtained as a light white foam. MS (ESI): 416.6 ([M+H]$^+$).

Example 295

2-((5-(fluoromethyl)-3-(6-methylpyridazin-3-yl)isoxazol-4-yl)methyl)-5-(5-oxa-2-azaspiro[3.4]octan-2-yl)pyridazin-3(2H)-one

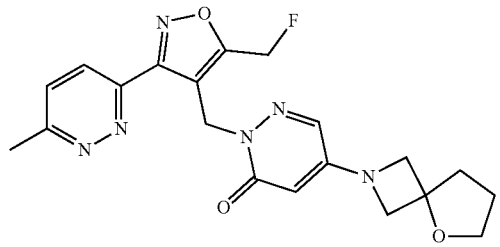 [SMILES: Cc1ccc(-c2noc(CF)c2Cn2ncc(N3CC4(CCCO4)C3)cc2=O)nn1]

a) 4-(5-oxa-2-azaspiro[3.4]octan-2-yl)-1H-pyridazin-6-one

In analogy to experiment of example 279 a, 5-chloropyridazin-3(2H)-one, using 5-oxa-2-azaspiro[3.4]octane hemioxalate instead of 3-ethoxyazetidine hydrochloride, was converted into the title compound (226 mg, 75%) which was obtained as a white solid. MS (ESI): 208.1 ([M+H]$^+$).

b) 2-((5-(fluoromethyl)-3-(6-methylpyridazin-3-yl)isoxazol-4-yl)methyl)-5-(5-oxa-2-azaspiro[3.4]octan-2-yl)pyridazin-3(2H)-one In analogy to experiment of example 279 b, 4-(chloromethyl)-5-(fluoromethyl)-3-(6-methylpyridazin-3-yl)isoxazole, using 4-(5-oxa-2-azaspiro[3.4]octan-2-yl)-1H-pyridazin-6-one instead of 4-(3-ethoxyazetidin-1-yl)-1H-

Example 296

(R or S)-2-((3-(6-chloropyridin-3-yl)-5-methylisoxazol-4-yl)methyl)-5-(8-fluoro-5-oxa-2-azaspiro[3.5]nonan-2-yl)pyridazin-3(2H)-one

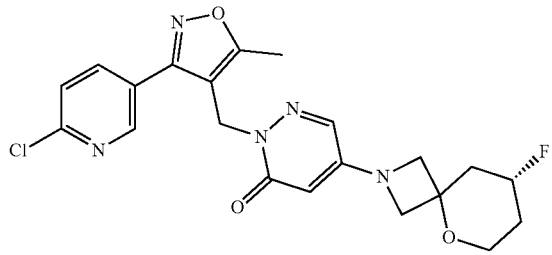 [SMILES: Cc1onc(-c2ccc(Cl)nc2)c1Cn1ncc(N2CC3(C[C@H](F)CCO3)C2)cc1=O]

In analogy to experiment of example 3, 5-chloro-2-[[3-(6-chloro-3-pyridyl)-5-methyl-isoxazol-4-yl]methyl]pyridazin-3-one (building block D), using using a regioisomeric mixture of 7-fluoro-5-oxa-2-azaspiro[3.5]nonane 2,2,2-trifluoroacetic acid and 8-fluoro-5-oxa-2-azaspiro[3.5]nonane 2,2,2-trifluoroacetic acid instead of (R)-3-hydroxypyrrolidine, was reacted. Separation of the enantiomers by chiral SFC (column: Chiralpak IB 20×250 mm 5 Um Daicel) afforded the title compound (20 mg, 23%) which was obtained as a white solid. MS (ESI): 446.2 ([M+H]⁺).

Example 297

(R)-2-((3-(6-chloropyridin-3-yl)-5-methylisoxazol-4-yl)methyl)-5-(7-fluoro-5-oxa-2-azaspiro[3.5]nonan-2-yl)pyridazin-3(2H)-one or enantiomer

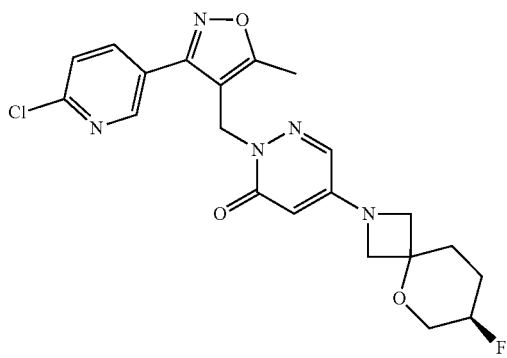 [SMILES: Cc1onc(-c2ccc(Cl)nc2)c1Cn1ncc(N2CC3(CC[C@@H](F)CO3)C2)cc1=O]

In analogy to experiment of example 275, 5-chloro-2-[[3-(6-chloro-3-pyridyl)-5-methyl-isoxazol-4-yl]methyl]pyridazin-3-one (building block D) was converted into the (−)-title compound (5.31 g, 53%) as an off-white solid. MS (ESI) m/z: 446.0 ([M+H]⁺).

Example 298

(S)-2-((3-(6-chloropyridin-3-yl)-5-methylisoxazol-4-yl)methyl)-5-(7-fluoro-5-oxa-2-azaspiro[3.5]nonan-2-yl)pyridazin-3(2H)-one or enantiomer

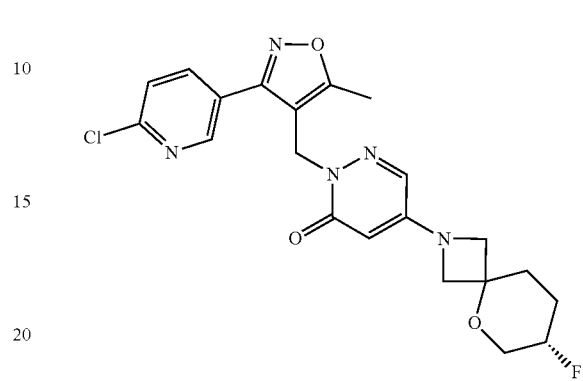

In analogy to experiment of example 275, 5-chloro-2-[[3-(6-chloro-3-pyridyl)-5-methyl-isoxazol-4-yl]methyl]pyridazin-3-one (building block D), using (S)-7-fluoro-5-oxa-2-azaspiro[3.5]nonane hydrochloride instead of (R)-7-fluoro-5-oxa-2-azaspiro[3.5]nonane hydrochloride was converted into the (+)-title compound (353 mg, 36%) as an off-white foam. MS (ESI) m/z: 446.1 ([M+H]⁺).

Example 302

2-[[5-methyl-3-(6-methylpyridazin-3-yl)isoxazol-4-yl]methyl]-5-(1-oxa-9-azaspiro[5.5]undecan-9-yl)pyridazin-3-one

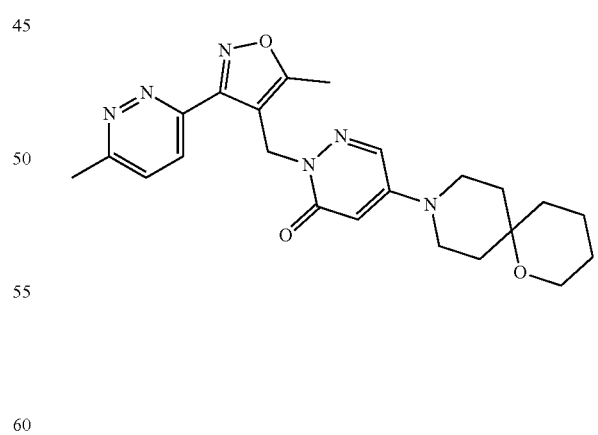

In analogy to experiment of example 5, 5-chloro-2-[[5-methyl-3-(6-methylpyridazin-3-yl)isoxazol-4-yl]methyl]pyridazin-3-one (building block F), using 1-oxa-9-azaspiro[5.5]undecane hydrochloride instead of piperidin-4-ol, was converted into the title compound (38 mg, 92%) which was obtained as an off-white solid. MS (ESI): 437.4 ([M+H]⁺).

Example 303

2-((5-methyl-3-(6-methylpyridazin-3-yl)isoxazol-4-yl)methyl)-5-(1-oxa-9-azaspiro[5.5]undecan-9-yl)pyridazin-3(2H)-one

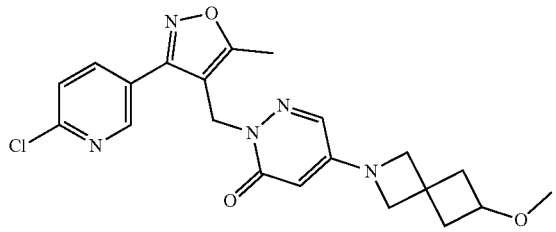 [SMILES: COC1CC2(C1)CN(c1cnn(Cc3c(-c4ccc(Cl)nc4)noc3C)c(=O)c1)C2]

a) 2-[[3-(6-chloro-3-pyridyl)-5-methyl-isoxazol-4-yl]methyl]-5-(6-hydroxy-2-azaspiro[3.3]heptan-2-yl)pyridazin-3-one In analogy to experiment of example 3, 5-chloro-2-[[3-(6-chloro-3-pyridyl)-5-methyl-isoxazol-4-yl]methyl]pyridazin-3-one (building block D), using 2-azaspiro[3.3]heptan-6-ol hydrochloride instead of (R)-3-hydroxypyrrolidine and replacing the solvent with N,N-dimethylacetamide, was converted into the title compound (255 mg, 80%) which was obtained as an off-white solid. MS (ESI): 414.1 ([M+H]+).

b) 2-((5-methyl-3-(6-methylpyridazin-3-yl)isoxazol-4-yl)methyl)-5-(1-oxa-9-azaspiro[5.5]undecan-9-yl)pyridazin-3(2H)-one In analogy to experiment of example 133, 2-[[3-(6-chloro-3-pyridyl)-5-methyl-isoxazol-4-yl]methyl]-5-(6-hydroxy-2-azaspiro[3.3]heptan-2-yl)pyridazin-3-one instead of 5-[(7S)-7-hydroxy-5-oxa-2-azaspiro[3.4]octan-2-yl]-2-[[5-methyl-3-(6-methyl-3-pyridyl)isoxazol-4-yl]methyl]pyridazin-3-one, replacing the solvent with tetrahydrofuran, was converted into the title compound (25 mg, 81%) which was obtained as a white solid. MS (ESI): 428.2 ([M+H]+).

Example 305

5-[3-(1-methylcyclopropoxy)azetidin-1-yl]-2-[[5-methyl-3-(6-methylpyridazin-3-yl)isoxazol-4-yl]methyl]pyridazin-3-one

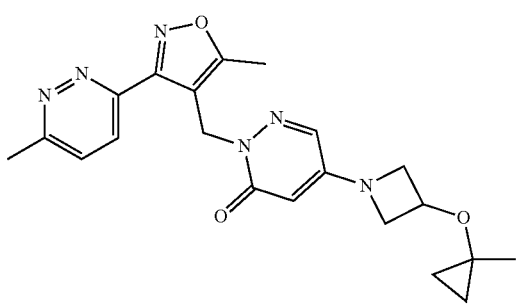

In analogy to experiment of example 5, 5-chloro-2-[[5-methyl-3-(6-methylpyridazin-3-yl)isoxazol-4-yl]methyl]pyridazin-3-one (building block F), using 3-(1-methylcyclopropoxy)azetidine hydrochloride instead of piperidin-4-ol, was converted into the title compound (3.5 mg, 18%) which was obtained as an off-white solid. MS (ESI): 409.3 ([M+H]+).

Example 306

5-(3-(2,2-difluoroethoxy)azetidin-1-yl)-2-((5-methyl-3-(6-methylpyridazin-3-yl)isoxazol-4-yl)methyl)pyridazin-3(2H)-one

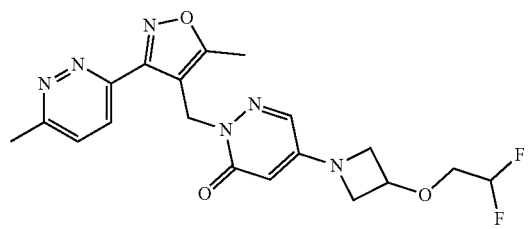 [SMILES: Cc1ccc(-c2noc(C)c2Cn2ncc(N3CC(OCC(F)F)C3)cc2=O)nn1]

In analogy to experiment of example 3, 5-chloro-2-[[5-methyl-3-(6-methylpyridazin-3-yl)isoxazol-4-yl]methyl]pyridazin-3-one (building block F), using 3-(2,2-difluoroethoxy)azetidine hydrochloride instead of (R)-3-hydroxypyrrolidine and replacing the solvent with N,N-dimethylacetamide, was converted into the title compound (11 mg, 28%) which was obtained as a white solid. MS (ESI): 419.3 ([M+H]+).

Example 310

5-(6,6-dimethyl-5-oxa-2-azaspiro[3.4]octan-2-yl)-2-[[5-methyl-3-(6-methylpyridazin-3-yl)isoxazol-4-yl]methyl]pyridazin-3-one

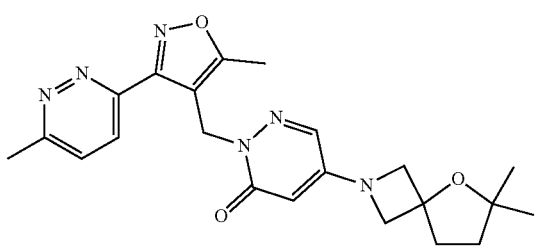

In analogy to experiment of example 5, 5-chloro-2-[[5-methyl-3-(6-methylpyridazin-3-yl)isoxazol-4-yl]methyl]pyridazin-3-one (building block F), using 6,6-dimethyl-5-oxa-2-azaspiro[3.4]octane hydrochloride instead of piperidin-4-ol, was converted into the title compound (20 mg, 90%) which was obtained as an off-white solid. MS (ESI): 423.4 ([M+H]+).

Example 311

(S)-2-((5-methyl-3-(6-methylpyridazin-3-yl)isoxazol-4-yl)methyl)-5-(8-(trifluoromethyl)-5-oxa-2-azaspiro[3.5]nonan-2-yl)pyridazin-3(2H)-one or enantiomer

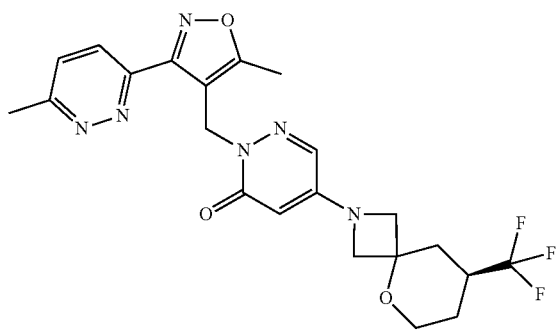 [SMILES: Cc1ccc(-c2noc(C)c2Cn2ncc(N3CC4(C[C@@H](C(F)(F)F)CCO4)C3)cc2=O)nn1]

In analogy to experiment of example 275, 5-chloro-2-[[5-methyl-3-(6-methylpyridazin-3-yl)isoxazol-4-yl]methyl]pyridazin-3-one (building block F), using 8-(trifluoromethyl)-5-oxa-2-azaspiro[3.5]nonane hydrochloride instead of (R)-7-fluoro-5-oxa-2-azaspiro[3.5]nonane hydrochloride, was converted into the racemic title compound (81 mg, 85%) as a yellow oil. Separation of the enantiomers by chiral HPLC (column: Chiralpak AD) afforded the (−)-title compound (1.9 mg, 2%) which was obtained as a colorless gum. MS (ESI) m/z: 477.7 ([M+H]$^+$).

Example 312

(R)-2-((5-methyl-3-(6-methylpyridazin-3-yl)isoxazol-4-yl)methyl)-5-(8-(trifluoromethyl)-5-oxa-2-azaspiro[3.5]nonan-2-yl)pyridazin-3(2H)-one or enantiomer

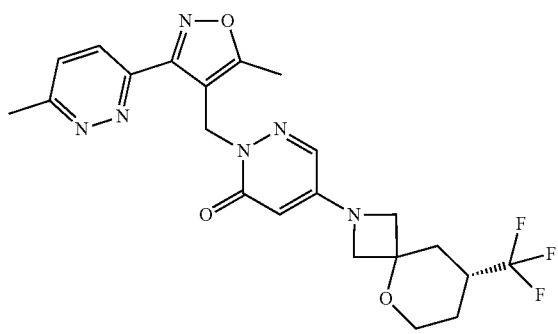 [SMILES: Cc1ccc(-c2noc(C)c2Cn2ncc(N3CC4(C[C@H](C(F)(F)F)CCO4)C3)cc2=O)nn1]

In analogy to experiment of example 311, separation of the enantiomers by chiral HPLC (column: Chiralpak AD) afforded the (+)-title compound (3.3 mg, 3%) which was obtained as a colorless gum. MS (ESI) m/z: 477.7 ([M+H]$^+$).

Example 313

(R)-2-((5-methyl-3-(6-methylpyridazin-3-yl)isoxazol-4-yl)methyl)-5-(7-methyl-5-oxa-2-azaspiro[3.5]nonan-2-yl)pyridazin-3(2H)-one or enantiomer

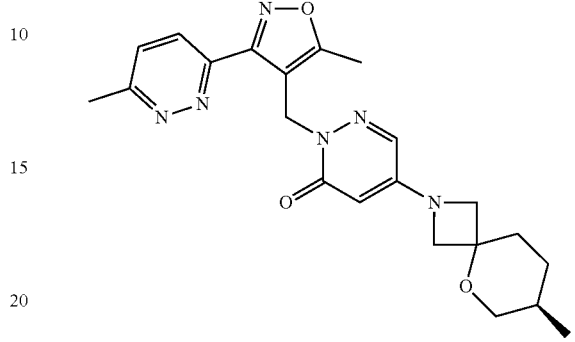

In analogy to experiment of example 275, 5-chloro-2-[[5-methyl-3-(6-methylpyridazin-3-yl)isoxazol-4-yl]methyl]pyridazin-3-one (building block F), using (R)-7-methyl-5-oxa-2-azaspiro[3.5]nonane hydrochloride instead of (R)-7-fluoro-5-oxa-2-azaspiro[3.5]nonane hydrochloride, was converted into the (−)-title compound (255 mg, 77%) as an orange foam. MS (ESI) m/z: 423.4 ([M+H]$^+$).

Example 315

5-[6-(difluoromethoxy)-2-azaspiro[3.3]heptan-2-yl]-2-[[5-methyl-3-(6-methylpyridazin-3-yl)isoxazol-4-yl]methyl]pyridazin-3-one

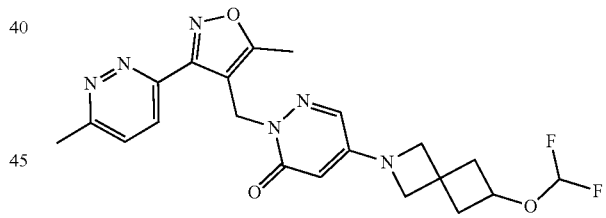

a) 5-(6-hydroxy-2-azaspiro[3.3]heptan-2-yl)-2-[[5-methyl-3-(6-methylpyridazin-3-yl)isoxazol-4-yl]methyl]pyridazin-3-one In analogy to experiment of example 5, 5-chloro-2-[[5-methyl-3-(6-methylpyridazin-3-yl)isoxazol-4-yl]methyl]pyridazin-3-one (building block F), using 2-azaspiro[3.3]heptan-6-ol hydrochloride instead of piperidin-4-ol, was converted into the title compound (177 mg, 95%) which was obtained as an off-white solid. MS (ESI): 395.3 ([M+H]$^+$).

b) 5-[6-(difluoromethoxy)-2-azaspiro[3.3]heptan-2-yl]-2-[[5-methyl-3-(6-methylpyridazin-3-yl)isoxazol-4-yl]methyl]pyridazin-3-one A suspension of 5-(6-hydroxy-2-azaspiro[3.3]heptan-2-yl)-2-[[5-methyl-3-(6-methylpyridazin-3-yl)isoxazol-4-yl]methyl]pyridazin-3-one (30 mg, 0.076 mmol) in acetonitrile (0.75 mL) was evacuated and back filled with argon for three times. Then copper (I) iodide (2.9 mg, 0.015 mmol) was added followed by the addition of 2,2-difluoro-2-(fluorosulfonyl)acetic acid (27 mg, 0.153 mmol). The clear solution was stirred in a closed tube at room temperature for 18 h. The reaction mixture was diluted with EtOAc (15 mL) and washed twice with aqueous sodium carbonate (1.0 M, 15 mL). The aqueous layers were extracted with EtOAc (15 mL). The combined organic layers were dried (MgSO$_4$), filtered and evaporated in vacuo. Purification by flash chromatography (silica, gradient: 0% to 10% MeOH in EtOAc) afforded the title compound (3.1 mg, 9.3%) as a colorless oil. MS (ESI): 445.3 ([M+H]$^+$).

Example 316

2-[[5-methyl-3-(6-methylpyridazin-3-yl)isoxazol-4-yl]methyl]-5-(5-oxa-2-azaspiro[3.6]decan-2-yl)pyridazin-3-one

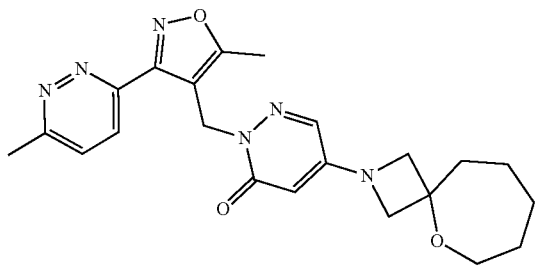 [SMILES: Cc1ccc(-c2noc(C)c2Cn2ncc(N3CC4(CCCCCO4)C3)cc2=O)nn1]

In analogy to experiment of example 5, 5-chloro-2-[[5-methyl-3-(6-methylpyridazin-3-yl)isoxazol-4-yl]methyl]pyridazin-3-one (building block F), using 5-oxa-2-azaspiro[3.6]decane hydrochloride instead of piperidin-4-ol, was converted into the title compound (67 mg, 81%) which was obtained as an off-white solid. MS (ESI): 423.3 ([M+H]$^+$).

Example 317

(S)-2-((5-methyl-3-(6-methylpyridazin-3-yl)isoxazol-4-yl)methyl)-5-(8-methyl-5-oxa-2-azaspiro[3.5]nonan-2-yl)pyridazin-3(2H)-one or enantiomer

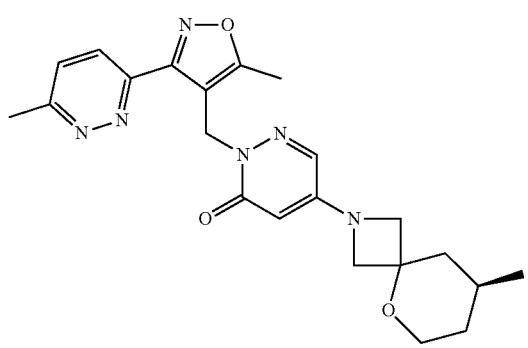

In analogy to experiment of example 275, 5-chloro-2-[[5-methyl-3-(6-methylpyridazin-3-yl)isoxazol-4-yl]methyl]pyridazin-3-one (building block F), using 8-methyl-5-oxa-2-azaspiro[3.5]nonane hydrochloride instead of (R)-7-fluoro-5-oxa-2-azaspiro[3.5]nonane hydrochloride was converted into the racemic title compound (268 mg, 99%) as an orange solid. Separation of the enantiomers by chiral HPLC (column: Chiralpak AD) afforded the (−)-title compound (61 mg, 23%) which was obtained as an off-white solid. MS (ESI) m/z: 423.3 ([M+H]$^+$).

Example 318

(R)-2-((5-methyl-3-(6-methylpyridazin-3-yl)isoxazol-4-yl)methyl)-5-(8-methyl-5-oxa-2-azaspiro[3.5]nonan-2-yl)pyridazin-3(2H)-one or enantiomer

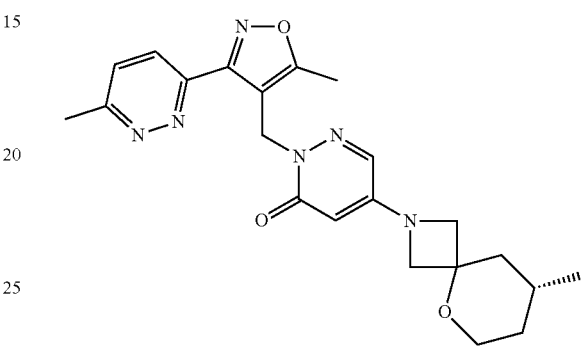

In analogy to experiment of example 317, separation of the enantiomers by chiral HPLC (column: Chiralpak AD) afforded the (+)-title compound (65 mg, 24%) which was obtained as an off-white solid. MS (ESI) m/z: 423.3 ([M+H]$^+$).

Example 319

(R)-5-(7-fluoro-5-oxa-2-azaspiro[3.5]nonan-2-yl)-2-((5-methyl-3-(6-methylpyridazin-3-yl)isoxazol-4-yl)methyl)pyridazin-3(2H)-one or enantiomer

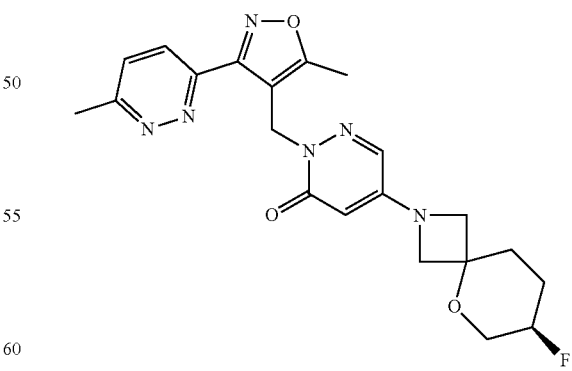

In analogy to experiment of example 275, 5-chloro-2-[[5-methyl-3-(6-methylpyridazin-3-yl)isoxazol-4-yl]methyl]pyridazin-3-one (building block F) was converted into the (−)-title compound (660 mg, 84%) as an orange foam. MS (ESI) m/z: 427.3 ([M+H]$^+$).

Example 320

(S)-2-((5-methyl-3-(6-methylpyridazin-3-yl)isoxazol-4-yl)methyl)-5-(7-(trifluoromethyl)-5-oxa-2-azaspiro[3.5]nonan-2-yl)pyridazin-3(2H)-one or enantiomer

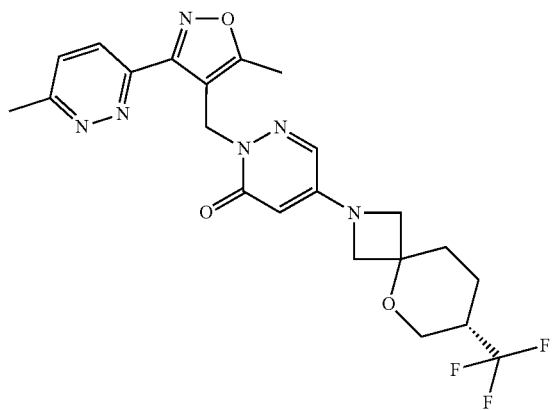 [SMILES: Cc1ccc(-c2noc(C)c2Cn2ncc(N3CC4(CC[C@H](C(F)(F)F)CO4)C3)cc2=O)nn1]

In analogy to experiment of example 275, 5-chloro-2-[[5-methyl-3-(6-methylpyridazin-3-yl)isoxazol-4-yl]methyl]pyridazin-3-one (building block F), using 7-(trifluoromethyl)-5-oxa-2-azaspiro[3.5]nonane hydrochloride instead of (R)-7-fluoro-5-oxa-2-azaspiro[3.5]nonane hydrochloride was converted into the racemic title compound (850 mg, 99%) as an orange oil. Separation of the enantiomers by chiral HPLC (column: Chiralpak OD) afforded the (+)-title compound (14.5 mg, 15%) which was obtained as a white solid. MS (ESI) m/z: 477.6 ([M+H]$^+$).

Example 321

(R)-2-((5-methyl-3-(6-methylpyridazin-3-yl)isoxazol-4-yl)methyl)-5-(7-(trifluoromethyl)-5-oxa-2-azaspiro[3.5]nonan-2-yl)pyridazin-3(2H)-one or enantiomer

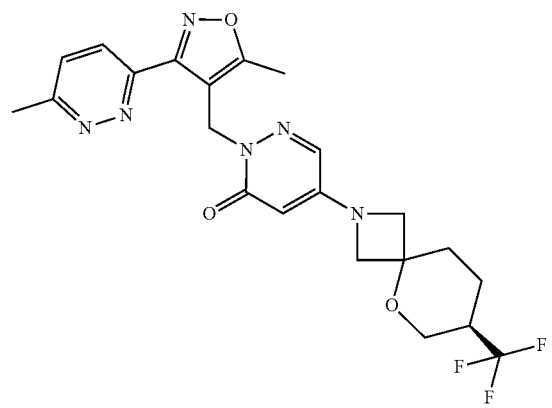 [SMILES: Cc1ccc(-c2noc(C)c2Cn2ncc(N3CC4(CC[C@@H](C(F)(F)F)CO4)C3)cc2=O)nn1]

In analogy to experiment of example 320, separation of the enantiomers by chiral HPLC (column: Chiralpak OD) afforded the (−)-title compound (13.6 mg, 14%) which was obtained as a white solid. MS (ESI) m/z: 477.6 ([M+H]$^+$).

Example 322

(R)-2-((3-(6-chloropyridin-3-yl)-5-methylisoxazol-4-yl)methyl)-5-(8-methyl-5-oxa-2-azaspiro[3.5]nonan-2-yl)pyridazin-3(2H)-one

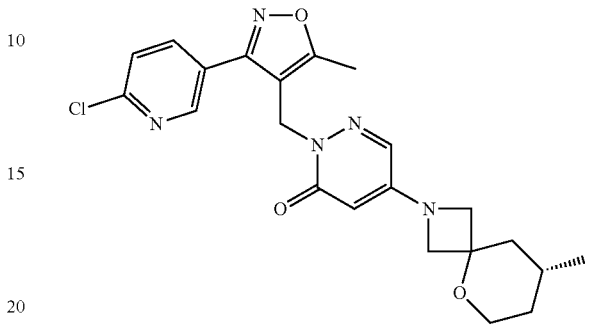

In analogy to experiment of example 275, 5-chloro-2-[[3-(6-chloro-3-pyridyl)-5-methyl-isoxazol-4-yl]methyl]pyridazin-3-one (building block D), using 8-methyl-5-oxa-2-azaspiro[3.5]nonane hydrochloride instead of (R)-7-fluoro-5-oxa-2-azaspiro[3.5]nonane hydrochloride was converted into the racemic title compound (86 mg, 99%) as an orange oil. Separation of the enantiomers by chiral HPLC (column: Chiralpak OD) afforded the (−)-title compound (40 mg, 45%) which was obtained as a colorless gum. MS (ESI) m/z: 442.6 ([M+H]$^+$).

Example 323

(R)-2-((3-(6-chloropyridin-3-yl)-5-methylisoxazol-4-yl)methyl)-5-(7-(trifluoromethyl)-5-oxa-2-azaspiro[3.5]nonan-2-yl)pyridazin-3(2H)-one or enantiomer

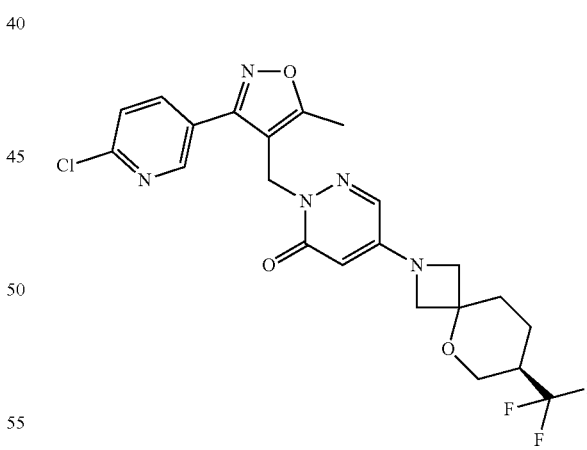

In analogy to experiment of example 275, 5-chloro-2-[[3-(6-chloro-3-pyridyl)-5-methyl-isoxazol-4-yl]methyl]pyridazin-3-one (building block D), using 7-(trifluoromethyl)-5-oxa-2-azaspiro[3.5]nonane hydrochloride instead of (R)-7-fluoro-5-oxa-2-azaspiro[3.5]nonane hydrochloride was converted into the racemic title compound (60 mg, 99%) as a yellow oil. Separation of the enantiomers by chiral HPLC (column: Chiralpak OD) afforded the (−)-title compound (23 mg, 37%) which was obtained as a colorless gum. MS (ESI) m/z: 496.6 ([M+H]$^+$).

Example 324

2-((5-ethyl-3-(6-methylpyridazin-3-yl)isoxazol-4-yl)methyl)-5-(5-oxa-2-azaspiro[3.5]nonan-2-yl)pyridazin-3(2H)-one

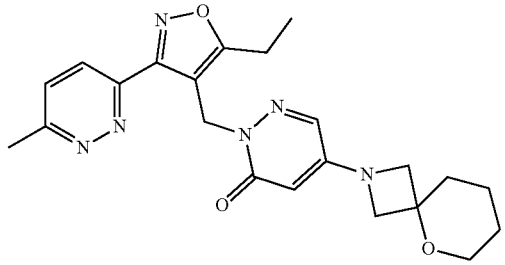 [SMILES: CCc1onc(-c2ccc(C)nn2)c1Cn1ncc(N2CC3(CCCCO3)C2)cc1=O]

In analogy to experiment of example 3, 5-chloro-2-[[5-ethyl-3-(6-methylpyridazin-3-yl)isoxazol-4-yl]methyl]pyridazin-3-one (building block U), using 5-oxa-2-azaspiro[3.5]nonane hydrochloride instead of (R)-3-hydroxypyrrolidine, was converted into the title compound (19 mg, 97%) which was obtained as a colorless oil. MS (ESI): 423.6 ([M+H]+).

Example 325

(R)-2-((5-ethyl-3-(6-methylpyridazin-3-yl)isoxazol-4-yl)methyl)-5-(7-fluoro-5-oxa-2-azaspiro[3.5]nonan-2-yl)pyridazin-3(2H)-one or enantiomer

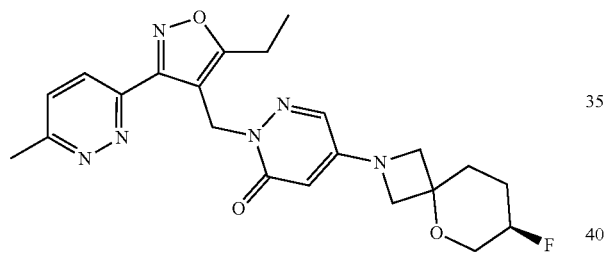

In analogy to experiment of example 275, 5-chloro-2-[[5-ethyl-3-(6-methylpyridazin-3-yl)isoxazol-4-yl]methyl]pyridazin-3-one (building block U) was converted into the title compound (250 mg, 94%) as a white powder. MS (ESI) m/z: 441.5 ([M+H]+).

Example 326

5-[(4S)-4-fluoro-1-oxa-9-azaspiro[5.5]undecan-9-yl]-2-[[5-methyl-3-(6-methylpyridazin-3-yl)isoxazol-4-yl]methyl]pyridazin-3-one or enantiomer

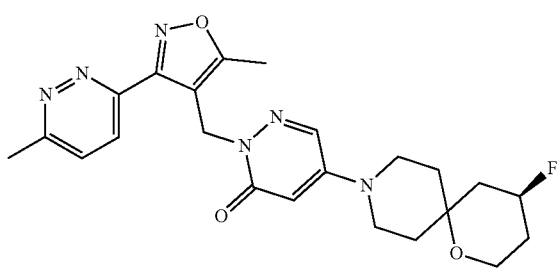 [SMILES: Cc1ccc(-c2noc(C)c2Cn2ncc(N3CCC4(CC3)C[C@@H](F)CCO4)cc2=O)nn1]

In analogy to experiment of example 275, 5-chloro-2-[[5-methyl-3-(6-methylpyridazin-3-yl)isoxazol-4-yl]methyl]pyridazin-3-one (building block F), using 4-fluoro-1-oxa-9-azaspiro[5.5]undecane instead of (R)-7-fluoro-5-oxa-2-azaspiro[3.5]nonane hydrochloride was converted into the racemic title compound (210 mg, 28%) as a white solid. Separation of the enantiomers by chiral SFC (Chiralpak IA) afforded the title compound (53.1 mg, 7%) as a light brown solid. MS (ESI) m/z: 455 ([M+H]+).

Example 327

5-[(4R)-4-fluoro-1-oxa-9-azaspiro[5.5]undecan-9-yl]-2-[[5-methyl-3-(6-methylpyridazin-3-yl)isoxazol-4-yl]methyl]pyridazin-3-one or enantiomer

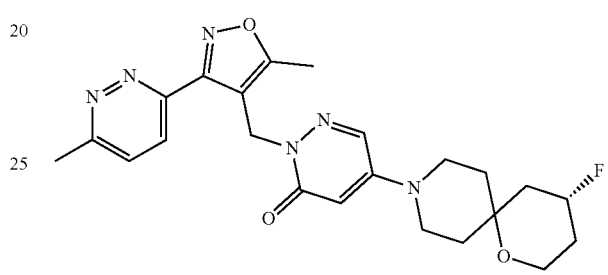

In analogy to experiment of example 326. Separation of the enantiomers by chiral SFC (Chiralpak IA) afforded the title compound (63.8 mg, 9%) as a light brown solid. MS (ESI) m/z: 455 ([M+H]+).

Example 328

2-((5-(fluoromethyl)-3-(6-methylpyridazin-3-yl)isoxazol-4-yl)methyl)-5-(5-oxa-2-azaspiro[3.5]nonan-2-yl)pyridazin-3(2H)-one

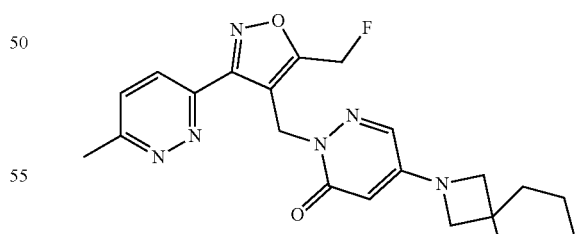

In analogy to experiment of example 5, 5-chloro-2-[[5-(fluoromethyl)-3-(6-methylpyridazin-3-yl)isoxazol-4-yl]methyl]pyridazin-3-one (building block K), using 5-oxa-2-azaspiro[3.5]nonane hydrochloride instead of piperidin-4-ol, was converted into the title compound (23 mg, 58%) which was obtained as a white powder. MS (ESI): 427.5 ([M+H]+).

Example 329

(R)-5-(7-fluoro-5-oxa-2-azaspiro[3.5]nonan-2-yl)-2-((5-(fluoromethyl)-3-(6-methylpyridazin-3-yl)isoxazol-4-yl)methyl)pyridazin-3(2H)-one or enantiomer

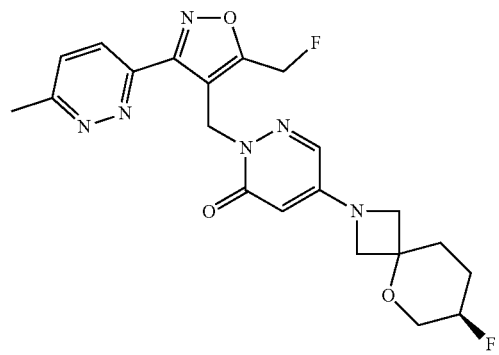 [SMILES: Cc1ccc(-c2noc(CF)c2Cn2ncc(N3CC4(CC[C@@H](F)CO4)C3)cc2=O)nn1]

In analogy to experiment of example 275, 5-chloro-2-[[5-(fluoromethyl)-3-(6-methylpyridazin-3-yl)isoxazol-4-yl]methyl]pyridazin-3-one (building block K) was converted into the title compound (19 mg, 55%) which was obtained as a colorless oil. MS (ESI): 445.3 ([M+H]$^+$).

Example 330

2-[[3-(6-chloro-3-pyridyl)-5-methyl-isoxazol-4-yl]methyl]-5-[(4R)-4-fluoro-1-oxa-9-azaspiro[5.5]undecan-9-yl]pyridazin-3-one or enantiomer

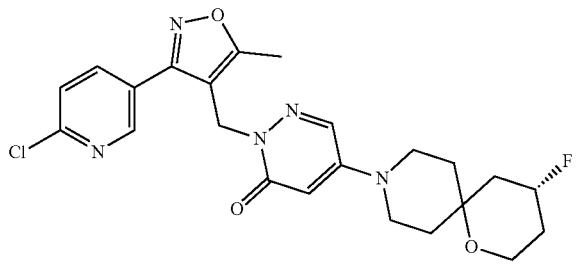 [SMILES: Cc1onc(-c2ccc(Cl)nc2)c1Cn1ncc(N2CCC3(CC2)C[C@H](F)CCO3)cc1=O]

In analogy to experiment of example 5, 5-chloro-2-[[3-(6-chloro-3-pyridyl)-5-methyl-isoxazol-4-yl]methyl]pyridazin-3-one (building block D), using 4-fluoro-1-oxa-9-azaspiro[5.5]undecane instead of piperidin-4-ol, was converted into the racemic title compound (42 mg, 59%) which was obtained as a yellow oil. MS (ESI): 474.2 ([M+H]$^+$). Separation of the enantiomers by chiral HPLC (column: Chiracel OD) afforded the title compound (12 mg) which was obtained as a grey oil. MS (ESI): 474.2 ([M+H]$^+$).

Example 331

2-[[3-(6-chloro-3-pyridyl)-5-methyl-isoxazol-4-yl]methyl]-5-[(4S)-4-fluoro-1-oxa-9-azaspiro[5.5]undecan-9-yl]pyridazin-3-one or enantiomer

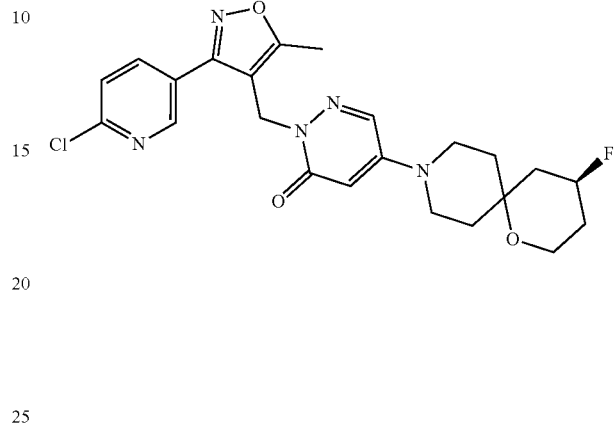

In analogy to experiment of example 330, separation of the enantiomers by chiral HPLC (column: Chiracel OD) afforded the title compound (12 mg) which was obtained as an off-white solid. MS (ESI): 474.2 ([M+H]$^+$).

Example 332

(R)-5-(7-fluoro-5-oxa-2-azaspiro[3.5]nonan-2-yl)-2-((5-methyl-3-(5-(trifluoromethyl)pyrimidin-2-yl)isoxazol-4-yl)methyl)pyridazin-3(2H)-one or enantiomer

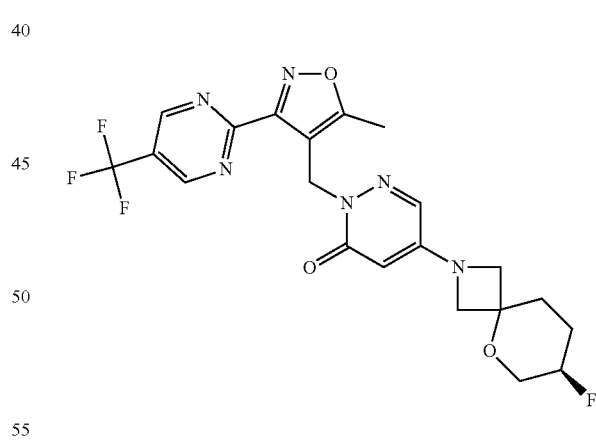

In analogy to experiment of example 275, 5-chloro-2-[[5-methyl-3-[5-(trifluoromethyl)pyrimidin-2-yl]isoxazol-4-yl]methyl]pyridazin-3-one (building block R) was converted into the title compound (205 mg, 68%) which was obtained as a white solid. MS (ESI): 481.6 ([M+H]$^+$).

Example 333

2-[[3-(6-chloro-3-pyridyl)-5-methyl-isoxazol-4-yl]methyl]-5-(1-oxa-9-azaspiro[5.5]undecan-9-yl)pyridazin-3-one

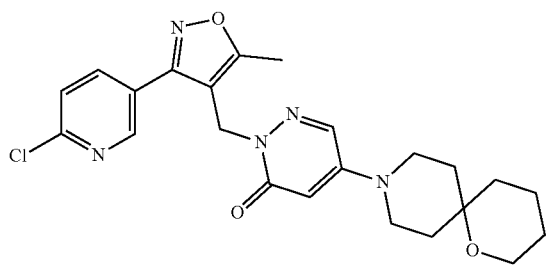 [SMILES: Cc1onc(-c2ccc(Cl)nc2)c1Cn1ncc(N2CCC3(CCCCO3)CC2)cc1=O]

In analogy to experiment of example 5, 5-chloro-2-[[3-(6-chloro-3-pyridyl)-5-methyl-isoxazol-4-yl]methyl]pyridazin-3-one (building block D), using 1-oxa-9-azaspiro[5.5]undecane hydrochloride instead of piperidin-4-ol, was converted into the title compound (68 mg, 90%) which was obtained as a colorless oil. MS (ESI): 456.2 ([M+H]$^+$).

Example 334

(R)-5-(7-fluoro-5-oxa-2-azaspiro[3.5]nonan-2-yl)-2-((5-methyl-3-(6-(trifluoromethyl)pyridazin-3-yl)isoxazol-4-yl)methyl)pyridazin-3(2H)-one

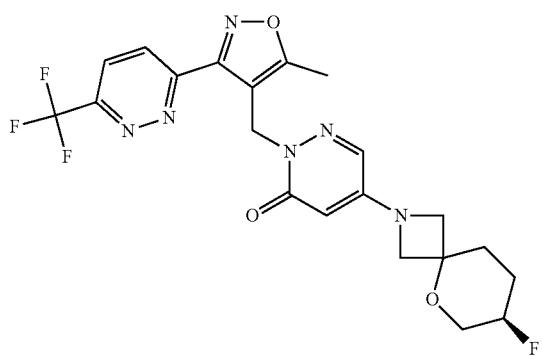 [SMILES: Cc1onc(-c2ccc(C(F)(F)F)nn2)c1Cn1ncc(N2CC3(CC[C@@H](F)CO3)C2)cc1=O]

In analogy to experiment of example 275, 5-chloro-2-[[5-methyl-3-[6-(trifluoromethyl)pyridazin-3-yl]isoxazol-4-yl]methyl]pyridazin-3-one (building block T) was converted into the title compound (30 mg, 99%) which was obtained as a colorless oil. MS (ESI): 481.6 ([M+H]$^+$).

Example 335

2-((5-methyl-3-(6-(trifluoromethyl)pyridazin-3-yl)isoxazol-4-yl)methyl)-5-(5-oxa-2-azaspiro[3.5]nonan-2-yl)pyridazin-3(2H)-one

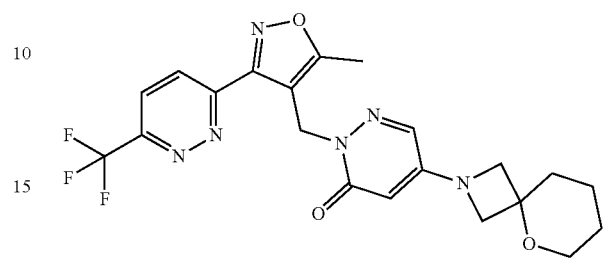

In analogy to experiment of example 5, 5-chloro-2-[[5-methyl-3-[6-(trifluoromethyl)pyridazin-3-yl]isoxazol-4-yl]methyl]pyridazin-3-one (building block T), using 5-oxa-2-azaspiro[3.5]nonane hydrochloride instead of piperidin-4-ol, was converted into the title compound (26 mg, 89%) which was obtained as a colorless oil. MS (ESI): 463.2 ([M+H]$^+$).

What is claimed is:
1. A compound of formula (I) or (II)

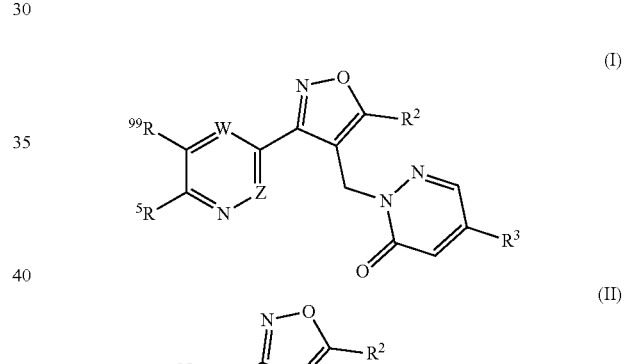

or a pharmaceutically acceptable salt thereof,
wherein
W is selected from N and CR$^4$;
Y is selected from N and CH;
Z is selected from N and CH;
R$^{99}$ is selected from C$_{1-6}$-alkyl, C$_{1-6}$-alkoxy, halo-C$_{1-6}$-alkoxy, hydroxy-C$_{1-6}$-alkyl, C$_{3-8}$-cycloalkyl, H, and halogen;
R$^2$ is selected from H, halogen, C$_{1-6}$-alkyl, C$_{3-8}$-cycloalkyl, and halo-C$_{1-6}$-alkyl;
R$^3$ is selected from heterocycloalkyl substituted with R$^6$, R$^7$ and R$^8$, amino substituted on the nitrogen atom by one or two substituents independently selected from R$^9$ and R$^{10}$, aryl substituted with R$^{11}$, R$^{12}$ and R$^{13}$, and heteroaryl substituted with R$^{11}$, R$^{12}$ and R$^{13}$;
R$^4$ is selected from H, C$_{1-6}$-alkyl, C$_{1-6}$-alkoxy, C$_{3-8}$-cycloalkyl, and halogen;

239

R⁵ is selected from H, C₁₋₆-alkyl, C₃₋₈-cycloalkyl, halo-C₁₋₆-alkyl, and halogen;

R⁶, R⁷ and R⁸ are each independently selected from H, C₁₋₆-alkyl, C₁₋₆-alkoxy, C₁₋₆-alkoxy-C₁₋₆-alkyl, C₁₋₆-alkoxycarbonyl, cyano, amino substituted on the nitrogen atom by one or two substituents each independently selected from R²² and R²³, C₃₋₈-cycloalkyl, wherein the C₃₋₈-cycloalkyl is substituted with R²⁴, R²⁵ and R²⁶, C₃₋₈-cycloalkoxy, wherein the C₃₋₈-cycloalkoxy is substituted with R²⁴, R²⁵ and R²⁶, C₃₋₈-cycloalkyl-C₁₋₆-alkoxy, wherein the C₃₋₈-cycloalkyl-C₁₋₆-alkoxy is substituted with R²⁴, R²⁵ and R²⁶, C₃₋₈-cycloalkylaminocarbonyl, wherein the C₃₋₈-cycloalkylaminocarbonyl is substituted with R²⁴, R²⁵ and R²⁶, C₃₋₈-cycloalkylcarbonyl, wherein the C₃₋₈-cycloalkylcarbonyl is substituted with R²⁴, R²⁵ and R²⁶, C₃₋₈-cycloalkyl-C₁₋₆-alkoxycarbonyl, wherein the C₃₋₈-cycloalkyl-C₁₋₆-alkoxycarbonyl is substituted with R²⁴, R²⁵ and aryloxy substituted with R²⁷, R²⁸ and R²⁹, aryl substituted with R²⁷, R²⁸ and R²⁹, heteroaryl substituted with R²⁷, R²⁸ and R²⁹, heteroaryloxy substituted with R²⁷, R²⁸ and R²⁹, halo-C₁₋₆-alkoxy, halo-C₁₋₆-alkyl, halogen, hydroxy, hydroxy-C₁₋₆-alkyl, and oxo;

R⁹ and R¹⁰ are each independently selected from H, halo-C₁₋₆-alkyl, C₁₋₆-alkyl, heterocycloalkyl substituted with R³⁰, R³¹ and R³², heterocycloalkyl-C₁₋₆-alkyl substituted with R³⁰, R³¹ and R³², hydroxy-C₁₋₆-alkyl, C₁₋₆-alkoxy, C₃₋₈-cycloalkyl, and halogen;

R¹¹, R¹² and R¹³ are each independently selected from H, hydroxy, hydroxy-C₁₋₆-alkyl, C₁₋₆-alkoxy, C₁₋₆-alkyl, cyano, aryl, C₃₋₈-cycloalkyl, halo-C₁₋₆-alkyl, halo-C₁₋₆-alkoxy, heteroaryl, amino substituted on the nitrogen atom by one or two substituents each independently selected from R¹⁴ and R¹⁵, C₃₋₈-cycloalkyl-C₁₋₆-alkyl, heterocycloalkyl substituted with R¹⁶, R¹⁷ and R¹⁸, heterocycloalkoxy substituted with R¹⁶, R¹⁷ and R¹⁸, heterocycloalkyl-C₁₋₆-alkyl substituted with R¹⁶, R¹⁷ and R¹⁸, and halogen;

R¹⁴ and R¹⁵ are each independently selected from H, and C₁₋₆-alkyl;

R¹⁶, R¹⁷ and R¹⁸ are each independently selected from H, halogen, C₁₋₆-alkoxy, C₃₋₈-cycloalkyl, C₁₋₆-alkyl;

R²² and R²³ are each independently selected from H, C₁₋₆-alkyl, and C₁₋₆-alkylcarbonyl;

R²⁴, R²⁵ and R²⁶ are each independently selected from C₁₋₆-alkyl, H, C₁₋₆-alkoxy, C³⁻⁸-cycloalkyl, halo-C₁₋₆-alkyl, halo-C₁₋₆-alkoxy, halogen, hydroxy, and oxo;

R²⁷, R²⁸ and R²⁹ are each independently selected from H, C₁₋₆-alkoxy, C₁₋₆-alkyl, C₃₋₈-cycloalkyl, and halogen; and R³⁰, R³¹ and R³² are each independently selected from H, halogen, C₁₋₆-alkoxy, C₃₋₈-cycloalkyl, C₁₋₆-alkyl.

2. The compound of formula (I) according to claim 1, or a pharmaceutically acceptable salt thereof, wherein
W is CR⁴; Y is N;
Z is selected from N, and CH;
R⁹⁹ is H;
R² is methyl;
R³ is selected from azetidinyl substituted with R⁶, R⁷ and R⁸, and 5-oxa-2-azaspiro[3.5]nonanyl substituted with R⁶, R⁷ and R⁸;
R⁴ is H,
R⁵ is selected from methyl and fluoro; and
R⁶, R⁷ and R⁸ are independently selected from tert-butoxy, H, fluoro.

240

3. The compound of claim 1, or a pharmaceutically acceptable salt thereof, wherein R² is selected from H, C₁₋₆-alkyl, C₃₋₈-cycloalkyl, and halo-C₁₋₆-alkyl.

4. The compound of claim 1, or a pharmaceutically acceptable salt thereof, wherein R³ is selected from heterocycloalkyl substituted with R⁶, R⁷ and R⁸, and heteroaryl substituted with R¹¹, R¹² and R¹³.

5. The compound of claim 1, or a pharmaceutically acceptable salt thereof, wherein R³ is selected from
heterocycloalkyl substituted with R⁶, R⁷ and R⁸, wherein heterocycloalkyl is selected from pyrrolidinyl, piperidinyl, morpholinyl, piperazinyl, 2-oxa-6-azaspiro[3.3]heptanyl, 1,2,3,4,6,7,8,8a-octahydropyrrolo[1,2-a]pyrazinyl, 3,5,6,7,8,8a-hexahydro-1H-oxazolo[3,4-a]pyrazinyl, 2-oxa-7-azaspiro[3.5]nonanyl, 1-oxa-7-azaspiro[3.5]nonanyl, 3,3a,4,5,6,6a-hexahydro-1H-furo[3,4-c]pyrrolyl, 2,6-diazaspiro[3.3]heptanyl, 5-oxa-2-azaspiro[3.4]octanyl, 7-oxa-2-azaspiro[3.5]nonanyl, 3-oxa-9-azaspiro[5.5]undecanyl, 5-oxa-2-azaspiro[3.5]nonanyl, 1-oxa-9-azaspiro[5.5]undecanyl, 5-oxa-2-azaspiro[3.6]decanyl, 2-azaspiro[3.3]heptanyl, 4,7-diazaspiro[2.5]octanyl, 2-azaspiro[3.5]nonanyl, 6-oxa-3-azabicyclo[3.1.1]heptanyl, 1-oxa-8-azaspiro[4.5]decanyl, 8-oxa-3-azabicyclo[3.2.1]octanyl, 3-oxa-6-azabicyclo[3.1.1]heptanyl, 3-oxa-8-azabicyclo[3.2.1]octanyl, and azetidinyl; and heteroaryl substituted with R⁶, R⁷ and R⁸, wherein heteroaryl is selected from pyridinyl, imidazo[1,2-a]pyridinyl, and pyrazolyl.

6. The compound of claim 1, or a pharmaceutically acceptable salt thereof, wherein R⁵ is selected from C₁₋₆-alkyl, C₃₋₈-cycloalkyl, halo-C₁₋₆-alkyl, and halogen.

7. The compound according to claim 1, or a pharmaceutically acceptable salt thereof, wherein
R⁶, R⁷ and R⁸ are each independently selected from H; C₁₋₆-alkyl; C₁₋₆-alkoxy; C₁₋₆-alkoxycarbonyl; cyano; amino substituted on the nitrogen atom by one or two substituents each independently selected from R²² and R²³; C₃₋₈-cycloalkyl-C₁₋₆-alkoxy, wherein the C₃₋₈-cycloalkyl is substituted with R²⁴, R²⁵, and R²⁶ wherein R²⁴, R²⁵ and R²⁶ are each independently selected from H and C₁₋₆-alkyl; C₃₋₈-cycloalkylaminocarbonyl, wherein the C₃₋₈-cycloalkyl is, substituted with R²⁴, R²⁵ and R²⁶, wherein R²⁴, R²⁵ and R²⁶ are H; C₃₋₈-cycloalkylcarbonyl, wherein the C₃₋₈-cycloalkyl is substituted with R²⁴, R²⁵ and R²⁶, wherein R²⁴, R²⁵ and R²⁶ are each independently selected from H and C₁₋₆-alkyl; C₃₋₈-cycloalkyl substituted with R²⁴, R²⁵ and R²⁶, wherein R²⁴, R²⁵, and R²⁶ are each independently selected from H and C₁₋₆-alkyl; C₃₋₈-cycloalkoxy substituted with R²⁴, R²⁵ and R²⁶, wherein R²⁴, R²⁵ and R²⁶ are each H; aryloxy, wherein the aryl is substituted with R²⁷, R²⁸ and R²⁹, wherein R²⁷, R²⁸ and R²⁹ are each independently selected from H and halogen, and wherein the aryl is phenyl; aryl substituted with R²⁷, R²⁸ and R²⁹, wherein R²⁷, R²⁸ and R²⁹ are each independently selected from H and alkoxy; and wherein the aryl is phenyl; heteroaryl substituted with R²⁷, R²⁸ and R²⁹, wherein R²⁷, R²⁸ and R²⁹ are each independently selected from H and C₁₋₆-alkyl, and wherein the heteroaryl is selected from imidazolyl, triazolyl, pyrimidinyl, pyridazinyl, pyrazolyl, pyridinyl and oxadiazolyl; heteroaryloxy, wherein the heteroaryl is substituted with R²⁷, R²⁸ and R²⁹, wherein R²⁷, R²⁸ and R²⁹ are each independently selected from H, C₁₋₆-alkyl, and halogen, and wherein the heteroaryl is selected from pyridinyl, and pyridazinyl; halo-$C_{1-6}$-alkoxy; halo-$C_{1-6}$-alkyl; halogen; oxo; hydroxy; and hydroxy-$C_{1-6}$-alkyl.

8. The compound according to claim 1, or a pharmaceutically acceptable salt thereof, wherein $R^6$ is selected from H, $C_{1-6}$-alkyl, $C_{1-6}$-alkoxy, $C_{3-8}$-cycloalkyl, $C_{3-8}$-cycloalkoxy, and halogen.

9. The compound of claim 1, or a pharmaceutically acceptable salt thereof, wherein $R^7$ is selected from H, $C_{1-6}$-alkyl, and halogen.

10. The compound of claim 1, or a pharmaceutically acceptable salt thereof, wherein $R^8$ is H.

11. The compound of claim 1, wherein the compound is selected from:

N-methyl-N-((3S)-1-(1-((5-methyl-3-(6-methylpyridin-3-yl)-1,2-oxazol-4-yl)methyl)-6-oxopyridazin-4-yl)pyrrolidin-3-yl)acetamide;

N-methyl-N-((3R)-1-(1-((5-methyl-3-(6-methylpyridin-3-yl)-1,2-oxazol-4-yl)methyl)-6-oxopyridazin-4-yl)pyrrolidin-3-yl)acetamide;

5-((3R)-3-hydroxypyrrolidin-1-yl)-2-((5-methyl-3-(6-methylpyridin-3-yl)-1,2-oxazol-4-yl)methy)pyridazin-3-one;

5-((3S)-3-hydroxypyrrolidin-1-yl)-2-((5-methyl-3-(6-methylpyridin-3-yl)-1,2-oxazol-4-yl)methyl)pyridazin-3-one;

5-(4-hydroxypiperidin-1-yl)-2-((5-methyl-3-(6-methylpyridin-3-yl)-1,2-oxazol-4-yl)methyl)pyridazin-3-one;

5-(2,2-dimethylmorpholin-4-yl)-2-((5-methyl-3-(6-methylpyridin-3-yl)-1,2-oxazol-4-yl)methyl)pyridazin-3-one;

5-((2S,6R)-2,6-dimethylmorpholin-4-yl)-2-((5-methyl-3-(6-methylpyridin-3-yl)-1,2-oxazol-4-yl)methyl)pyridazin-3-one;

ethyl 1-(1-((5-methyl-3-(6-methylpyridin-3-yl)-1,2-oxazol-4-yl)methyl)-6-oxopyridazin-4-yl)piperidine-4-carboxylate;

5-(4-(cyclopropanecarbonyl)piperazin-1-yl)-2-((5-methyl-3-(6-methylpyridin-3-yl)isoxazol-4-yl)methyl)pyridazin-3(2H)-one;

2-((5-methyl-3-(6-methylpyridin-3-yl)isoxazol-4-y)methyl)-5-(4-(1-methylcyclopropanecarbonyl)piperazin-1-yl)pyridazin-3(2H)-one;

2-((3-(4-Fluorophenyl)-5-methylisoxazol-4-y)methyl)-5-morpholinopyridazin-3(2H)-one;

5-cis-2,6-Dimethylmorpholino)-2-((3-(4-fluorophenyl)-5-methylisoxazol-4-yl)methyl)pyridazin-3(2H)-one;

2-((3-(5-Chloropyridin-2-yl)-5-methylisoxazol-4-yl)methyl)-5-(cis-2,6-dimethylmorpholino)pyridazin-3(2H)-one;

2-((3-(5-Chloropyridin-2-yl)-5-cyclopropylisoxazol-4-yl)methyl)-5-(cis-2,6-dimethylmorpholino)pyridazin-3(2H)-one;

2-((3-(4-Fluorophenyl)-5-methylisoxazol-4-yl)methyl)-5-(4-(1-methylcyclopropanecarbonyl)piperazin-1-yl)pyridazin-3(2H)-one;

2-((3-(5-Chloropyridin-2-yl)-5-methylisoxazol-4-yl)methyl)-5-(4-(1-methylcyclopropanecarbonyl)piperazin-1-yl)pyridazin-3(2H)-one;

2-((5-methyl-3-(6-methylpyridin-3-yl)isoxazol-4-y)methyl)-5-(trifluoromethyl)pyridazin-3(2H)-one;

5-(tert-butyl)-2-((5-methyl-3-(6-methylpyridin-3-yl)isoxazol-4-yl)methyl)pyridazin-3(2H)-one;

5-isopropyl-2-((5-methyl-3-(6-methylpyridin-3-yl)isoxazol-4-yl)methyl)pyridazin-3(2H)-one;

5-ethyl-2-((5-methyl-3-(6-methylpyridin-3-yl)isoxazol-4-yl)methyl)pyridazin-3(2H)-one;

tert-Butyl 4-(1-((5-methyl-3-(6-methylpyridin-3-yl)isoxazol-4-yl)methyl)-6-oxo-1,6-dihydropyridazin-4-yl)-5,6-dihydropyridine-1(2H)-carboxylate;

2-((5-Methyl-3-(6-methylpyridin-3-yl)isoxazol-4-yl)methyl)-5-morpholinopyridazin-3(2H)-one;

5-(3,6-Dihydro-2H-pyran-4-yl)-2-((5-methyl-3-(6-methylpyridin-3-yl)isoxazol-4-yl)methyl)pyridazin-3(2H)-one;

2-((5-Methyl-3-(6-methylpyridin-3-yl)isoxazol-4-yl)methyl)-5-(4-(trifluoromethyl)piperidin-1-yl)pyridazin-3(2H)-one;

2-((3-(5-Chloropyridin-2-yl)-5-cyclopropylisoxazol-4-yl)methyl)-5-(4-(cyclopropanecarbonyl)piperazin-1-yl)pyridazin-3(2H)-one;

2-((3-(5-Chloropyridin-2-yl)-5-cyclopropylisoxazol-4-yl)methyl)-5-(4-(1-methylcyclopropanecarbonyl)piperazin-1-yl)pyridazin-3(2H)-one;

N-Cyclopropyl-1-(1-((5-methyl-3-(6-methylpyridin-3-yl)isoxazol-4-yl)methyl)-6-oxo-1,6-dihydropyridazin-4-yl)piperidine-4-carboxamide;

5-((1R,5 S)-8-Oxa-3-azabicyclo[3.2.1]octan-3-yl)-2-((5-methyl-3-(6-methylpyridin-3-yl)isoxazol-4-yl)methy)pyridazin-3(2H)-one;

5-((2S,6S)-2,6-Dimethylmorpholino)-2-((5-methyl-3-(6-methylpyridin-3-yl)isoxazol-4-yl)methyl)pyridazin-3(2H)-one;

5-((2R,6R)-2,6-Dimethylmorpholino)-2-((5-methyl-3-(6-methylpyridin-3-yl)isoxazol-4-yl)methyl)pyridazin-3(2H)-one;

2-((5-Methyl-3-(6-methylpyridin-3-yl)isoxazol-4-yl)methyl)-5-(4-(2,2,2-trifluoroethyl)piperazin-1-yl)pyridazin-3(2H)-one;

5-(cis-2,6-Dimethylmorpholino)-2-((3-(6-methylpyridin-3-yl)isoxazol-4-yl)methyl)pyridazin-3(2H)-one;

5-(3-Oxa-6-azabicyclo [3.2.1]heptan-6-yl)-2-((5-methyl-3-(6-methylpyridin-3-yl)isoxazol-4-y)methyl)pyridazin-3(2H)-one;

1-(1-((5-Methyl-3-(6-methylpyridin-3-y)isoxazol-4-y)methyl)-6-oxo-1,6-dihydropyridazin-4-yl)piperidine-4-carbonitrile;

5-(3-Oxa-8-azabicyclo [3.2.1]octan-8-yl)-2-((5-methyl-3-(6-methylpyridin-3-yl)isoxazol-4-y)methyl)pyridazin-3(2H)-one;

5-(4-Cyclopropylpiperazin-1-yl)-2-45-methyl-3-(6-methylpyridin-3-yl)isoxazol-4-yl)methyl)pyridazin-3(2H)-one;

5-Cyclopropyl-2-((5-methyl-3-(6-methylpyridin-3-yl)isoxazol-4-yl)methyl)pyridazin-3 (2H)-one;

2-((5-Methyl-3-(6-methylpyridin-3-yl)isoxazol-4-yl)methyl)-5-(2-oxa-6-azaspiro[3.3]heptan-6-yl)pyridazin-3(2H)-one;

5-(cis-2,6-Dimethylmorpholino)-2-((5-methyl-3-(6-(trifluoromethyl)pyridin-3-yl)isoxazol-4-yl)methyl)pyridazin-3(2H)-one;

2-((5-Methyl-3-(6-(trifluoromethyl)pyridin-3-yl)isoxazol-4-yl)methyl)-5-(4-(1-4-1 methylcyclopropanecarbonyl)piperazin-1-yl)pyridazin-3 (2H)-one;

5-(cis-2,6-Dimethylmorpholino)-2-((3-(3-fluoropyridin-4-yl)-5-methylisoxazol-4-yl)methyl)pyridazin-3(2H)-one;

2-((3-(3-Fluoropyridin-4-yl)-5-methylisoxazol-4-yl)methyl)-5-(4-(1-methylcyclopropanecarbonyl)piperazin-1-yl)pyridazin-3(2H)-one;

2-(1-((5-methyl-3-(6-methylpyridin-3-yl)isoxazol-4-yl)
methyl)-6-oxo-1,6-dihydropyridazin-4-yl)hexahydro-
pyrrolo[1,2-a]pyrazin-6(2H)-one;

7-(1-((5-methyl-3-(6-methylpyridin-3-yl)isoxazol-4-yl)
methyl)-6-oxo-1,6-dihydropyridazin-4-yl)tetrahydro-
1H-oxazolo[3,4-a]pyrazin-3(5H)-one;

5-(dimethylamino)-2-((5-methyl-3-(6-methylpyridin-3-
yl)isoxazol-4-yl)methyl)pyridazin-3(2H)-one;

2-((5-Methyl-3-(6-methylpyridin-3-yl)isoxazol-4-yl)
methyl)-5-(2-oxa-7-azaspiro[3.5]nonan-7-yl)
pyridazin-3(2H)-one;

(R)-7-(1-((5-methyl-3-(6-methylpyridin-3-yl)isoxazol-4-
yl)methyl)-6-oxo-1,6-dihydropyridazin-4-yl)hexahy-
droimidazo[1,5-a]pyrazin-3(2H)-one;

(S)-7-(1-((5-methyl-3-(6-methylpyridin-3-yl)isoxazol-4-
y)methyl)-6-oxo-1,6-dihydropyridazin-4-yl)hexahy-
droimidazo[1,5-a]pyrazin-3(2H)-one;

2-((5-Methyl-3-(6-methylpyridin-3-yl)isoxazol-4-yl)
methyl)-5-((3aR,6aS)-tetrahydro-1H-furo[3,4-c]pyr-
rol-5(3H)-yl)pyridazin-3(2H)-one;

(R)-2-((5-Methyl-3-(6-methylpyridin-3-yl)isoxazol-4-yl)
methyl)-5-(3-methylpiperazin-1-yl)pyridazin-3(2H)-
one;

(S)-2-((5-Methyl-3-(6-methylpyridin-3-yl)isoxazol-4-yl)
methyl)-5-(3-methylpiperazin-1-yl)pyridazin-3(2H)-
one;

2-((3-(5-Chloro-3-fluoropyridin-2-yl)-5-methylisoxazol-
4-yl)methyl)-5-(cis-2,6-dimethylmorpholino)
pyridazin-3(2H)-one;

2-((3-(5-Chloro-3-fluoropyridin-2-yl)-5-methylisoxazol-
4-yl)methyl)-5-(4-(1-methylcyclopropanecarbonyl)
piperazin-1-yl)pyridazin-3(2H)-one;

5-(4-(3,5-Dimethyl-4H-1,2,4-triazol-4-yl)piperidin-1-yl)-
2-((5-methyl-3-(6-methylpyridin-3-yl)isoxazol-4-yl)
methyl)pyridazin-3(2H)-one;

5-(4-(3,5-Dimethyl-4H-1,2,4-triazol-4-yl)piperidin-1-yl)-
2-((3-(4-fluorophenyl)-5-methylisoxazol-4-yl)methyl)
pyridazin-3 (2H)-one;

(R)—N-Cyclopropyl-1-(1-((5-methyl-3-(6-methylpyri-
din-3-yl)isoxazol-4-yl)methyl)-6-oxo-1,6-dihydro-
pyridazin-4-yl)pyrrolidine-3-carboxamide;

(S)—N-Cyclopropyl-1-(1-((5-methyl-3-(6-methylpyri-
din-3-yl)isoxazol-4-yl)methyl)-6-oxo-1,6-dihydro-
pyridazin-4-yl)pyrrolidine-3-carboxamide;

5-(6-Cyclopropyl-2,6-diazaspiro[3.3]heptan-2-yl)-2-45-
methyl-3-(6-methylpyridin-3-yl)isoxazol-4-yl)methyl)
pyridazin-3(2H)-one;

(R)-5-(4-Cyclopropyl-3-methylpiperazin-1-yl)-2-((5-
methyl-3-(6-methylpyridin-3-yl)isoxazol-4-yl)methyl)
pyridazin-3 (2H)-one;

(S)-5-(4-Cyclopropyl-3-methyl piperazin-1-yl)-2-((5-
methyl-3-(6-methylpyridin-3-yl)isoxazol-4-yl)methyl)
pyridazin-3 (2H)-one;

5-(4-(2-methoxyphenyl)piperidin-1-yl)-2-((5-methyl-3-
(6-methylpyridin-3-yl)isoxazol-4-yl)methyl)
pyridazin-3 (2H)-one;

2-((5,5'-Dimethyl-13,3'-biisoxazoll-4-yl)methyl)-5-(cis-
2,6-dimethylmorpholino)pyridazin-3(2H)-one;

5-(4-Cyclopropylpiperazin-1-yl)-2-((5,5'-dimethyl[3,3'-
biisoxazo]1-4-yl)methyl)pyridazin-3(2H)-one;

5-(cyclopropyl(methyl)amino)-2-((5-methyl-3-(6-meth-
ylpyridin-3-yl)isoxazol-4-yl)methyl)pyridazin-3(2H)-
one;

5-(methyl(oxetan-3-yl)amino)-2-((5-methyl-3-(6-meth-
ylpyridin-3-yl)isoxazol-4-yl)methyl)pyridazin-3(2H)-
one;

5-(4-Cyclopropylpiperazin-1-yl)-2-45-methyl-3-(6-(trif-
luoromethyl)pyridin-3-yl)isoxazol-4-yl)methyl)
pyridazin-3 (2H)-one;

2-((5-methyl-3-(6-methylpyridin-3-yl)isoxazol-4-yl)
methyl)-5-phenylpyridazin-3 (2H)-one;

5-(4-fluorophenyl)-2- [[5-methyl-3-(6-methylpyridin-3-
yl)-1,2-oxazol-4-yl]methyl]pyridazin-3-one;

2-((5-Methyl-3-(6-methylpyridin-3-yl)isoxazol-4-yl)
methyl)-5-(2-azaspiro[3.3]heptan-2-yl)pyridazin-3
(2H)-one;

5-((2-hydroxy-2-methylpropyl)(methyl)amino)-2-((5-
methyl-3-(6-methylpyridin-3-yl)isoxazol-4-yl)methyl)
pyridazin-3 (2H)-one;

5-(2-fluorophenyl)-2- [[5-methyl-3-(6-methylpyridin-3-
yl)-1,2-oxazol-4-yl]methyl]pyridazin-3-one;

5-(cis-2,6-Dimethylmorpholino)-2-((3-(6-(trifluorom-
ethyl)pyridin-3-yl)isoxazol-4-yl)methyl)pyridazin-3
(2H)-one;

5-(2-methoxyphenyl)-2-((5-methyl-3-(6-methylpyridin-
3-yl)-1,2-oxazol-4-yl)methyl)pyridazin-3-one;

2-((5-Methyl-3-(6-methylpyridin-3-yl)isoxazol-4-yl)
methyl)-5-(4,7-di azaspiro[2.5]octan-7-yl)pyridazin-3
(2H)-one;

2-((5-Methyl-3-(6-methylpyridin-3-yl)isoxazol-4-yl)
methyl)-5-(piperazin-1-yl)pyridazin-3 (2H)-one;

5-(4-methoxyphenyl)-2- [[5-methyl-3-(6-methylpyridin-
3-yl)-1,2-oxazol-4-yl]methyl]pyridazin-3-one;

2-((5-Methyl-3-(6-methylpyridin-3-yl)isoxazol-4-yl)
methyl)-5-(2,6-diazaspiro[3.3]heptan-2-yl)pyridazin-3
(2H)-one;

2-((5-methyl-3-(6-methylpyridin-3-yl)isoxazol-4-yl)
methyl)-5-(methylamino)pyridazin-3 (2H)-one;

5-(4-ethoxyphenyl)-2-((5-methyl-3-(6-methylpyridin-3-
yl)isoxazol-4-yl)methyl)pyridazin-3 (2H)-one;

5-(3-fluoro-4-methoxyphenyl)-2-((5-methyl-3-(6-meth-
ylpyridin-3-yl)isoxazol-4-yl)methyl)pyridazin-3(2H)-
one;

5-(6-methoxypyridin-3-yl)-2-45-methyl-3-(6-methylpyri-
din-3-yl)isoxazol-4-yl)methyl)pyridazin-3 (2H)-one;

2-((5-Methyl-3-(6-methylpyridin-3-yl)isoxazol-4-yl)
methyl)-5-(6-methyl-2,6-diazaspiro[3.3]heptan-2-yl)
pyridazin-3 (2H)-one;

2-((5-methyl-3-(6-methylpyridin-3-yl)isoxazol-4-yl)
methyl)-5-(4-(trifluoromethyl)phenyl)pyridazin-3
(2H)-one;

5-(5-methoxypyridin-2-yl)-2-((5-methyl-3-(6-meth-
ylpyridin-3-yl)isoxazol-4-yl)methyl)pyridazin-3(2H)-
one;

1-(1-((5-Methyl-3-(6-methylpyridin-3-yl)isoxazol-4-yl)
methyl)-6-oxo-1,6-dihydropyridazin-4-yl)azetidine-3-
carbonitrile;

2-((3-(5-Chloropyridin-2-yl)-5-methylisoxazol-4-yl)
methyl)-5-(6-cyclopropyl-2,6-diazaspiro[3.3]heptan-2-
yl)pyridazin-3(2H)-one;

5-(6-Cyclopropyl-2,6-diazaspiro[3.3]heptan-2-yl)-2-45,
5'-dimethyl((3,3'-biisoxazoll-4-yl)methyl)pyridazin-3
(2H)-one;

2-((5-methyl-3-(6-methylpyridin-3-yl)isoxazol-4-yl)
methyl)-5-(((tetrahydro-2H-pyran-4-yl)methyl)amino)
pyridazin-3(2H)-one;

(S)-2-((5-Methyl-3-(6-methylpyridin-3-yl)isoxazol-4-yl)
methyl)-5-(2-methylmorpholino)pyridazin-3(2H)-one;

(R)-5-(3-(tert-Butoxy)pyrrolidin-1-yl)-2-((5-methyl-3-(6-
methylpyridin-3-yl)isoxazol-4-yl)methyl)pyridazin-3
(2H)-one;

(S)-5-(2-Methylmorpholino)-2-((3-(6-methylpyridin-3-
yl)isoxazol-4-yl)methyl)pyridazin-3(2H)-one;

(R)-5-(2-Methylmorpholino)-2-((3-(6-methylpyridin-3-yl)isoxazol-4-yl)methyl)pyridazin-3(2H)-one;

5-((3S,5R)-3,5-dimethylpiperazin-1-yl)-2-((5-methyl-3-(6-methylpyridin-3-yl)isoxazol-4-yl)methyl)pyridazin-3(2H)-one;

2-((5-Methyl-3-(6-methylpyridin-3-yl)isoxazol-4-yl)methyl)-5-(3-phenoxyazetidin-1-yl)pyridazin-3(2H)-one;

2-((5-Methyl-3-(6-methylpyridin-3-yl)isoxazol-4-yl)methyl)-5-(5-oxa-2-azaspiro[3.4]octan-2-yl)pyridazin-3(2H)-one;

5-((1-cyclopropylazetidin-3-yl)amino)-2-((5-methyl-3-(6-methylpyridin-3-yl)isoxazol-4-yl)methyl)pyridazin-3(2H)-one;

5-(azetidin-1-yl)-2-((5-methyl-3-(6-methylpyridin-3-yl)isoxazol-4-yl)methyl)pyridazin-3 (2H)-one;

5-(3-Hydroxy-3-methylazetidin-1-yl)-2-((5-methyl-3-(6-methylpyridin-3-yl)isoxazol-4-yl)methyl)pyridazin-3 (2H)-one;

5-(3-ethoxyazetidin-1-yl)-2-((5-methyl-3-(6-methylpyridin-3-yl)isoxazol-4-yl)methyl)pyridazin-3 (2H)-one;

5-(6-oxa-3-azabicyclo[3.1.1]heptan-3-yl)-2-((5-methyl-3-(6-methylpyridin-3-yl)isoxazol-4-yl)methyl)pyridazin-3(2H)-one;

5-(4-(2-Methoxypyridin-3-yl)piperazin-1-yl)-2-((5-methyl-3-(6-methylpyridin-3-yl)isoxazol-4-yl)methyl)pyridazin-3 (2H)-one;

5-(dimethylamino)-2-[ [3-(5-fluoro-6-methyl-3-pyridyl)-5-methyl-isoxazol-4-yl]methyl]pyridazin-3-one;

2-((5-methyl-3-(6-methyl-3-pyridyl)isoxazol-4-yl)methyl)-5-(1-methylpyrazol-4-yl)pyridazin-3-one;

5-(3-methoxyazetidin-1-yl)-2-((5-methyl-3-(6-methylpyridin-3-yl)isoxazol-4-yl)methyl)pyridazin-3(2H)-one;

5-(3-hydroxyazetidin-1-yl)-2-45-methyl-3-(6-methylpyridin-3-yl)isoxazol-4-yl)methyl)pyridazin-3 (2H)-one;

2-((5-methyl-3-(6-methylpyridin-3-yl)isoxazol-4-yl)methyl)-5-(2-methylpyridin-4-yl)pyridazin-3 (2H)-one;

5-(2-methoxypyridin-4-yl)-2-((5-methyl-3-(6-methylpyridin-3-yl)isoxazol-4-yl)methyl)pyridazin-3 (2H)-one;

2-((5-methyl-3-(6-methylpyridin-3-yl)isoxazol-4-yl)methyl)-5-(2-(trifluoromethyl)pyridin-4-yl)pyridazin-3(2H)-one;

5-(4-(2-Ethyl-1H-imidazol-1-yl)piperidin-1-yl)-2-((5-methyl-3-(6-methylpyridin-3-yl)isoxazol-4-yl)methyl)pyridazin-3 (2H)-one;

5-(4-(2-Methyl-1H-imidazol-1-yl)piperidin-1-yl)-2-((5-methyl-3-(6-methylpyridin-3-yl)isoxazol-4-yl)methyl)pyridazin-3 (2H)-one;

5-(3-(Cyclopropylmethoxy)azetidin-1-yl)-2-((5-methyl-3-(6-methylpyridin-3-yl)isoxazol-4-yl)methyl)pyridazin-3 (2H)-one;

5-(3-Isopropoxyazetidin-1-yl)-2-((5-methyl-3-(6-methylpyridin-3-yl)isoxazol-4-yl)methyl)pyridazin-3(2H)-one;

5-(3,4-dimethoxyphenyl)-2-((5-methyl-3-(6-methyl-3-pyridyl)isoxazol-4-yl)methyl)pyridazin-3-one;

2-((5-methyl-3-(6-methyl-3-pyridyl)isoxazol-4-yl)methyl)-5-(4-(trifluoromethoxy)phenyl)pyridazin-3-one;

5-(4-isopropoxyphenyl)-2-((5-methyl-3-(6-methyl-3-pyridyl)isoxazol-4-yl)methyl)pyridazin-3-one;

5-[6-(dimethylamino)-3-pyridyl]-2-((5-methyl-3-(6-methyl-3-pyridyl)isoxazol-4-yl)methyl)pyridazin-3-one;

5-(3-hydroxy-3-(trifluoromethyl)azetidin-1-yl)-2-((5-methyl-3-(6-methylpyridin-3-yl)isoxazol-4-yl)methyl)pyridazin-3 (2H)-one;

5-(3-hydroxy-3-methylpyrrolidin-1-yl)-2-((5-methyl-3-(6-methylpyridin-3-yl)isoxazol-4-yl)methyl)pyridazin-3 (2H)-one;

5-(4-hydroxy-4-methylpiperidin-1-yl)-2-((5-methyl-3-(6-methylpyridin-3-yl)isoxazol-4-yl)methyl)pyridazin-3 (2H)-one;

5-((3S)-3-(2-hydroxypropan-2-yl)pyrrolidin-1-yl)-2-((5-methyl-3-(6-methylpyridin-3-yl)-1,2-oxazol-4-yl)methyl)pyridazin-3-one;

2-ethyl-7-(1-((5-methyl-3-(6-methylpyridin-3-yl)isoxazol-4-yl)methyl)-6-oxo-1,6-dihydropyridazin-4-yl)hexahydroimidazo[1,5-a]pyrazin-3(2H)-one;

2-((5-methyl-3-(6-methylpyridin-3-yl)isoxazol-4-yl)methyl)-5 aS,6aS)-tetrahydro-2H-furo [3,2-b]pyrrol-4 (5H)-yl)pyridazin-3(2H)-one;

5-(3-(4-Fluorophenoxy)azetidin-1-yl)-2-((5-methyl-3-(6-methylpyridin-3-yl)isoxazol-4-yl)methyl)pyridazin-3 (2H)-one;

2-((5-Methyl-3-(6-methylpyridin-3-yl)isoxazol-4-yl)methyl)-5-(3-(pyridin-2-yloxy)azetidin-1-yl)pyridazin-3 (2H)-one;

5-((3 aR,6aS)-hexahydro-1H-furo[3,4-b]pyrrol-1-yl)-2-((5-methyl-3-(6-methylpyridin-3-yl)isoxazol-4-yl)methyl)pyridazin-3(2H)-one;

2-((5-Methyl-3-(6-methylpyridin-3-yl)isoxazol-4-yl)methyl)-5-(3-(pyridin-3-yloxy)azetidin-1-yl)pyridazin-3 (2H)-one;

5-(3-(3-Fluorophenoxy)azetidin-1-yl)-2-((5-methyl-3-(6-methylpyridin-3-yl)isoxazol-4-yl)methyl)pyridazin-3 (2H)-one;

5-(3-(2-Fluorophenoxy)azetidin-1-yl)-2-((5-methyl-3-(6-methylpyridin-3-yl)isoxazol-4-yl)methyl)pyridazin-3 (2H)-one;

2-((5-Methyl-3-(6-methylpyridin-3-yl)isoxazol-4-yl)methyl)-5-(3-(pyridin-4-yloxy)azetidin-1-yl)pyridazin-3 (2H)-one;

5-(3-((5-Chloropyridin-2-yl)oxy)azetidin-1-yl)-2-((5-methyl-3-(6-methylpyridin-3-yl)isoxazol-4-yl)methyl)pyridazin-3(2H)-one;

(S)-5-(7-Hydroxy-5-oxa-2-azaspiro[3 0.4]octan-2-yl)-2-((5-methyl-3-(6-methylpyridin-3-yl)isoxazol-4-yl)methyl)pyridazin-3(2H)-one;

(R)-5-(7-Hydroxy-5-oxa-2-azaspiro[3.4]octan-2-yl)-2-((5-methyl-3-(6-methylpyridin-3-yl)isoxazol-4-yl)methyl)pyridazin-3(2H)-one;

(S)-5-(7-Methoxy-5-oxa-2-azaspiro[3 0.4]octan-2-yl)-2-((5-methyl-3-(6-methylpyridin-3-yl)isoxazol-4-yl)methyl)pyridazin-3(2H)-one;

(R)-5-(7-Methoxy-5-oxa-2-azaspiro[3 0.4]octan-2-yl)-2-((5-methyl-3-(6-methylpyridin-3-yl)isoxazol-4-yl)methyl)pyridazin-3(2H)-one;

(R)-5-(7-Ethoxy-5-oxa-2-azaspiro[3.4]octan-2-yl)-2-((5-methyl-3-(6-methylpyridin-3-yl)isoxazol-4-yl)methyl)pyridazin-3(2H)-one;

5-(3-Cyclopropoxyazetidin-1-yl)-2-((5-methyl-3-(6-methylpyridin-3-yl)isoxazol-4-yl)methyl)pyridazin-3 (2H)-one;

5-((1-cyclopropylazetidin-3-yl)(methyl)amino)-2-((5-methyl-3-(6-methylpyridin-3-yl)isoxazol-4-yl)methyl)pyridazin-3(2H)-one;

5-(3-((6-Chloropyridin-3-yl)oxy)azetidin-1-yl)-2-((5-methyl-3-(6-methylpyridin-3-yl)isoxazol-4-yl)methyl)pyridazin-3(2H)-one;

5-(4-Methoxypiperidin-1-yl)-2-((5-methyl-3-(6-methylpyridin-3-yl)isoxazol-4-yl)methyl)pyridazin-3 (2H)-one;

2-((5,5'-Dimethyl((3,3'-biisoxazoll-4-yl)methyl)-5-(3-methoxyazetidin-1-yl)pyridazin-3 (2H)-one;

5-(3-(Cyclopropylmethoxy)azetidin-1-yl)-2-((5,5'-dimethyl-[3,3'-biisoxazol]-4-yl)methyl)pyridazin-3 (2H)-one;

2-((5,5'-Dimethyl((3,3'-biisoxazo11-4-yl)methyl)-5-(5-oxa-2-azaspiro[3.4]octan-2-yl)pyridazin-3 (2H)-one;

2-((3-(5-Chloropyridin-2-yl)-5-methylisoxazol-4-yl)methyl)-5-(3-(cyclopropylmethoxy)azetidin-1-yl)pyridazin-3(2H)-one;

2-((3-(5-Chloropyridin-2-yl)-5-methylisoxazol-4-yl)methyl)-5-(5-oxa-2-azaspiro[3 0.4]octan-2-yl)pyridazin-3(2H)-one;

5-(6-methoxy-2-pyridyl)-2-((5-methyl-3-(6-methyl-3-pyridyl)isoxazol-4-yl)methyl)pyridazin-3-one;

2-((5-Methyl-3-(6-methylpyridin-3-yl)isoxazol-4-yl)methyl)-5-(7-methyl-5-oxa-2-azaspiro[3 0.4]octan-2-yl)pyridazin-3(2H)-one;

5-(3-((2-Chloropyridin-4-yl)oxy)azetidin-1-yl)-2-((5-methyl-3-(6-methylpyridin-3-yl)isoxazol-4-yl)methyl)pyridazin-3 (2H)-one;

5-(5-chloro-3-pyridyl)-2-((5-methyl-3-(6-methyl-3-pyridyl)isoxazol-4-yl)methyl)pyridazin-3-one;

5-(6-(difluoromethoxy)pyridin-3-yl)-2-((5-methyl-3-(6-methylpyridin-3-yl)isoxazol-4-yl)methyl)pyridazin-3(2H)-one;

5-(3-(tert-Butoxy)azetidin-1-yl)-2-45-methyl-3-(6-methylpyridin-3-yl)isoxazol-4-yl)methyl)pyridazin-3 (2H)-one;

5-(6-ethoxypyridin-3-yl)-2-((5-methyl-3-(6-methylpyridin-3-yl)isoxazol-4-yl)methyl)pyridazin-3 (2H)-one;

5-(1-cyclopropyl-1H-pyrazol-4-yl)-2-((5-methyl-3-(6-methylpyridin-3-yl)isoxazol-4-yl)methyl)pyridazin-3(2H)-one;

5-(1-(2,2-difluoroethyl)-1H-pyrazol-4-yl)-2-((5-methyl-3-(6-methylpyridin-3-yl)isoxazol-4-yl)methyl)pyridazin-3(2H)-one;

5-(1-(difluoromethyl)-1H-pyrazol-4-yl)-2-((5-methyl-3-(6-methylpyridin-3-yl)isoxazol-4-yl)methyl)pyridazin-3(2H)-one;

5-(1-ethyl-1H-pyrazol-4-yl)-2-((5-methyl-3-(6-methylpyridin-3-yl)isoxazol-4-yl)methyl)pyridazin-3(2H)-one;

5-(2-(dimethylamino)pyridin-4-yl)-2-((5-methyl-3-(6-methylpyridin-3-yl)isoxazol-4-yl)methyl)pyridazin-3(2H)-one;

5-(1-(cyclopropylmethyl)-1H-pyrazol-4-yl)-2-((5-methyl-3-(6-methylpyridin-3-yl)isoxazol-4-yl)methyl)pyridazin-3(2H)-one;

2-((5-Methyl-3-(6-methylpyridin-3-yl)isoxazol-4-yl)methyl)-5-(3-(2,2,2-trifluoroethoxy)azetidin-1-yl)pyridazin-3(2H)-one;

5-(4-(4-Methoxypyrimidin-5-yl)piperazin-1-yl)-2-((5-methyl-3-(6-methylpyridin-3-yl)isoxazol-4-yl)methyl)pyridazin-3(2H)-one;

2-((3-(4-chlorophenyl)-5-methylisoxazol-4-yl)methyl)-5-(3-methoxyazetidin-1-yl)pyridazin-3(2H)-one;

2-((3-(4-chlorophenyl)-5-methylisoxazol-4-yl)methyl)-5-(3-ethoxyazetidin-1-yl)pyridazin-3(2H)-one;

2-((3-(4-chlorophenyl)-5-methylisoxazol-4-yl)methyl)-5-(5-oxa-2-azaspiro[3.4]octan-2-yl)pyridazin-3(2H)-one;

2-((5-methyl-3-(6-methylpyridin-3-yl)isoxazol-4-yl)methyl)-5-(2-(piperazin-1-yl)pyridin-4-yl)pyridazin-3(2H)-one;

2-((5-methyl-3-(6-methylpyridin-3-yl)isoxazol-4-yl)methyl)-5-(1-phenyl-1H-pyrazol-4-yl)pyridazin-3(2H)-one;

5-(4-(3-Methoxypyridazin-4-yl)piperazin-1-yl)-2-((5-methyl-3-(6-methylpyridin-3-yl)isoxazol-4-yl)methyl)pyridazin-3(2H)-one;

5-(4-(1-methyl-1H-pyrazol-5-yl)piperidin-1-yl)-2-((5-methyl-3-(6-methylpyridin-3-yl)isoxazol-4-yl)methyl)pyridazin-3(2H)-one;

5-(4-(1-ethyl-1H-pyrazol-5-yl)piperidin-1-yl)-2-((5-methyl-3-(6-methylpyridin-3-yl)isoxazol-4-yl)methyl)pyridazin-3(2H)-one;

5-(3-(Difluoromethoxy)azetidin-1-yl)-2-((5-methyl-3-(6-methylpyridin-3-yl)isoxazol-4-yl)methyl)pyridazin-3 (2H)-one;

5-(3-methoxyazetidin-1-yl)-2-((5-methyl-3-(6-methylpyridazin-3-yl)isoxazol-4-yl)methyl)pyridazin-3(2H)-one;

5-(3-ethoxyazetidin-1-yl)-2-((5-methyl-3-(6-methylpyridin-3-yl)i s oxazol-4-yl)methyl)pyridazin-3(2H)-one;

2-((5-methyl-3-(6-methylpyridazin-3-yl)isoxazol-4-yl)methyl)-5-(5-oxa-2-azaspiro[3 0.4]octan-2-yl)pyridazin-3(2H)-one;

5-(1-isobutylpyrazol-4-yl)-24 [5-methyl-3-(6-methyl-3-pyridyl)isoxazol-4-yl]methyl]pyridazin-3-one;

5-(6-cyclopropyl-3-pyridyl)-2- [[5-methyl-3-(6-methyl-3-pyridyl)isoxazol-4-yl]methyl]pyridazin-3-one;

5-(6-(methylamino)-3-pyridyl)-2-((5-methyl-3-(6-methyl-3-pyridyl)isoxazol-4-yl)methyl)pyridazin-3-one;

5-(2-(difluoromethoxy)pyridin-4-yl)-2-((5-methyl-3-(6-methylpyridin-3-yl)isoxazol-4-yl)methyl)pyridazin-3(2H)-one;

2-((5-methyl-3-(6-methylpyridin-3-yl)isoxazol-4-yl)methyl)-5-methyloxetan-3-yl)methyl)-1H-pyrazol-4-yl)pyridazin-3(2H)-one;

2-((5-methyl-3-(6-methylpyridin-3-yl)isoxazol-4-yl)methyl)-5-(2-((tetrahydrofuran-3-yl)oxy)pyridin-4-yl)pyridazin-3(2H)-one;

(R)-2-((5-methyl-3-(6-methylpyridin-3-yl)isoxazol-4-yl)methyl)-5-(3-methylpyrrolidin-1-yl)pyridazin-3 (2H)-one;

5-(5,6-dimethoxypyridin-3-yl)-2-((5-methyl-3-(6-methylpyridin-3-yl)isoxazol-4-yl)methyl)pyridazin-3(2H)-one;

5-(6-ethoxy-5-methylpyridin-3-yl)-2-((5-methyl-3-(6-methylpyridin-3-yl)isoxazol-4-yl)methyl)pyridazin-3(2H)-one;

5-(3-Fluoroazetidin-1-yl)-2-((5-methyl-3-(6-methylpyridin-3-yl)isoxazol-4-yl)methyl)pyridazin-3(2H)-one;

2-((5-(Difluoromethyl)-3-(6-methylpyridin-3-yl)isoxazol-4-yl)methyl)-5-((2S,6R)-2,6-dimethylmorpholino)pyridazin-3(2H)-one;

5-(5-fluoro-6-methoxypyridin-3-yl)-2-((5-methyl-3-(6-methylpyridin-3-yl)isoxazol-4-yl)methyl)pyridazin-3(2H)-one;

(S)-5-(4-isopropyl-3-methylpiperazin-1-yl)-2-((5-methyl-3-(6-methylpyridin-3-yl)isoxazol-4-yl)methyl)pyridazin-3 (2H)-one;

5-(3-(cyclopropylmethoxy)azetidin-1-yl)-2-((5-methyl-3-(6-methylpyridazin-3-yl)isoxazol-4-yl)methyl)pyridazin-3 (2H)-one;

2-((5-Methyl-3-(6-methylpyridin-3-yl)isoxazol-4-yl)methyl)-5-(3-((6-methylpyridazin-3-yl)oxy)azetidin-1-yl)pyridazin-3(2H)-one;

5-(2-(azetidin-1-yl)pyridin-4-yl)-2-((5-methyl-3-(6-methylpyridin-3-yl)isoxazol-4-yl)methyl)pyridazin-3 (2H)-one;

5-(5-chloro-6-methoxypyridin-3-yl)-2-((5-methyl-3-(6-methylpyridin-3-yl)isoxazol-4-yl)methyl)pyridazin-3 (2H)-one;

5-(2-chloro-5-fluoro-3-pyridyl)-2-((5-methyl-3-(6-methyl-3-pyridyl)isoxazol-4-yl)methyl)pyridazin-3-one;

5-(6-isopropoxy-3-pyridyl)-2-((5-methyl-3-(6-methyl-3-pyridyl)isoxazol-4-yl)methyl)pyridazin-3-one;

5-(5-fluoro-2-methoxypyridin-4-yl)-2-((5-methyl-3-(6-methylpyridin-3-yl)isoxazol-4-yl)methyl)pyridazin-3 (2H)-one;

5-(2,6-dimethylpyridin-4-yl)-2-((5-methyl-3-(6-methylpyridin-3-yl)isoxazol-4-yl)methyl)pyridazin-3(2H)-one;

5-(7,7-Difluoro-5-oxa-2-azaspiro[3.4]octan-2-yl)-2-(5-methyl-3-(6-methylpyridin-3-yl)isoxazol-4-yl)methyl)pyridazin-3 (2H)-one;

5-((2R,3R)-3-methoxy-2-methylazetidin-1-yl)-2-((5-methyl-3-(6-methylpyridin-3-yl)isoxazol-4-yl)methyl)pyridazin-3 (2H)-one;

2-((5-methyl-3-(6-methylpyridin-3-yl)isoxazol-4-yl)methyl)-5-(2-azaspiro[3.5]nonan-2-yl)pyridazin-3 (2H)-one;

5-(2-ethyl-4-pyridyl)-2-((5-methyl-3-(6-methyl-3-pyridyl)isoxazol-4-yl)methyl)pyridazin-3-one;

5-((2S,3 S)-3-methoxy-2-methylazetidin-1-yl)-2-((5-methyl-3-(6-methylpyridin-3-yl)isoxazol-4-yl)methyl)pyridazin-3(2H)-one;

5-((2S,3S)-3-ethoxy-2-methylazetidin-1-yl)-2-((5-methyl-3-(6-methylpyridin-3-yl)isoxazol-4-yl)methyl)pyridazin-3(2H)-one;

2-((5-methyl-3-(6-methylpyridin-3-yl)isoxazol-4-yl)methyl)-5-(7-oxa-2-azaspiro[3.5]nonan-2-yl)pyridazin-3(2H)-one;

(R)-5-(7-Fluoro-5-oxa-2-azaspiro[3 0.4]octan-2-yl)-2-((5-methyl-3-(6-methylpyridin-3-yl)isoxazol-4-yl)methyl)pyridazin-3(2H)-one;

(S)-5-(7-Fluoro-5-oxa-2-azaspiro[3 0.4]octan-2-yl)-2-((5-methyl-3-(6-methylpyridin-3-yl)isoxazol-4-yl)methyl)pyridazin-3(2H)-one;

2-((5-methyl-3-(6-methylpyridin-3-yl)isoxazol-4-yl)methyl)-5-(2-(methyl amino)pyridin-4-yl)pyridazin-3 (2H)-one;

(R)-5-(7-(Difluoromethoxy)-5-oxa-2-azaspiro[3 0.4]octan-2-yl)-2-((5-methyl-3-(6-methylpyridin-3-yl)isoxazol-4-yl)methyl)pyridazin-3 (2H)-one;

(S)-5-(7-(Difluoromethoxy)-5-oxa-2-azaspiro[3.4]octan-2-yl)-2-((5-methyl-3-(6-methylpyridin-3-yl)isoxazol-4-yl)methyl)pyridazin-3 (2H)-one;

5-((2R,6S)-2,6-dimethylmorpholino)-2-((3-(5-fluoro-6-methylpyridin-3-yl)-5-methylisoxazol-4-yl)methyl)pyridazin-3 (2H)-one;

5-(3-(2,2-difluoroethoxy)azetidin-1-yl)-2-((5-methyl-3-(6-methylpyridin-3-yl)isoxazol-4-yl)methyl)pyridazin-3(2H)-one;

2-((3-(5-fluoro-6-methylpyridin-3-yl)-5-methylisoxazol-4-yl)methyl)-5-(2-methoxypyridin-4-yl)pyridazin-3 (2H)-one;

2-((3-(5-fluoro-6-methylpyridin-3-yl)-5-methylisoxazol-4-yl)methyl)-5-(5-oxa-2-azaspiro[3 0.4]octan-2-yl)pyridazin-3(2H)-one;

2-((3-(6-chloropyridin-3-yl)-5-methylisoxazol-4-yl)methyl)-5-(5-oxa-2-azaspiro[3.4]octan-2-yl)pyridazin-3(2H)-one;

2-((5-methyl-3-(6-methyl-3-pyridyl)isoxazol-4-yl)methyl)-5-(1-propylpyrazol-4-yl)pyridazin-3-one;

6-(1-methyl-3-(6-methyl-3-pyridyl)isoxazol-4-yl)methyl)-6-oxo-pyridazin-4-yl)pyridine-2-carbonitrile;

2-((3-(6-chloropyridin-3-yl)-5-methylisoxazol-4-yl)methyl)-5-(3-methoxyazetidin-1-yl)pyridazin-3 (2H)-one;

5-(3-ethoxyazetidin-1-yl)-2-((3-(5-fluoro-6-methyl pyridin-3-yl)-5-methylisoxazol-4-yl)methyl)pyridazin-3 (2H)-one;

2-((3-(6-chloropyridin-3-yl)-5-methylisoxazol-4-yl)methyl)-5-(2-methoxypyridin-4-yl)pyridazin-3 (2H)-one;

2-((3-(6-chloropyridin-3-yl)-5-methylisoxazol-4-yl)methyl)-5-(1-methyl-1H-pyrazol-4-yl)pyridazin-3 (2H)-one;

2-((5-methyl-3-(6-methylpyridin-3-yl)isoxazol-4-yl)methyl)-5-(5-oxa-2-azaspiro[3.5]nonan-2-yl)pyridazin-3(2H)-one;

2-((3-(6-chloropyridin-3-yl)-5-methylisoxazol-4-yl)methyl)-5-(7,7-difluoro-5-oxa-2-azaspiro[3.4]octan-2-yl)pyridazin-3(2H)-one;

2-((5-methyl-3-(6-methylpyridin-3-yl)isoxazol-4-yl)methyl)-5-(3-methylimidazo [1,2-a]pyridin-6-yl)pyridazin-3(2H)-one;

2-((3-(6-chloropyridin-3-yl)-5-methylisoxazol-4-yl)methyl)-5-((2RS,6SR)-2,6-dimethylmorpholino)pyridazin-3(2H)-one;

2-43-(6-chloropyridin-3-yl)-5-methyl-1,2-oxazol-4-yl)methyl)-5-(3-ethoxyazetidin-1-yl)pyridazin-3-one;

2-((3-(6-chloropyridin-3-yl)-5-methylisoxazol-4-yl)methyl)-5-(1-ethyl-1H-pyrazol-4-yl)pyridazin-3 (2H)-one;

2-((3-(6-chloropyridin-3-yl)-5-methylisoxazol-4-yl)methyl)-5-(1-cyclopropyl-1H-pyrazol-4-yl)pyridazin-3 (2H)-one;

2-(1-(6-chloropyridin-3-yl)-5-methylisoxazol-4-yl)methyl)-6-oxo-1,6-dihydropyridazin-4-yl)hexahydropyrrolo [1,2-a]pyrazin-6(2H)-one;

2-((3-(6-chloropyridin-3-yl)-5-methylisoxazol-4-yl)methyl)-5-(3-cyclopropoxyazetidin-1-yl)pyridazin-3 (2H)-one;

(S)-7-(1-((3-(6-chloropyridin-3-yl)-5-methylisoxazol-4-yl)methyl)-6-oxo-1,6-dihydropyridazin-4-yl)hexahydroimidazo[1,5-a]pyrazin-3(2H)-one;

2-((5-methyl-3-(6-methylpyridin-3-yl)isoxazol-4-yl)methyl)-5-(3-oxa-9-azaspiro[5.5]undecan-9-yl)pyridazin-3 (2H)-one;

(S)-2-((3-(6-chloropyridin-3-yl)-5-methylisoxazol-4-yl)methyl)-5-(2-methylmorpholino)pyridazin-3 (2H)-one;

5-(2-methoxypyridin-4-yl)-2-((5-methyl-3-(5-(trifluoromethyl)pyrimidin-2-yl)isoxazol-4-yl)methyl)pyridazin-3(2H)-one;

5-(3-methoxyazetidin-1-yl)-2-45-methyl-3-(5-(trifluoromethyl)pyrimidin-2-yl)isoxazol-4-yl)methyl)pyridazin-3(2H)-one;

(R)-2-((3-(6-chloropyridin-3-yl)-5-methylisoxazol-4-yl)methyl)-5-(7-fluoro-5-oxa-2-azaspiro[30.4]octan-2-yl)pyridazin-3(2H)-one;

(R)-7-(1-(((3-(6-chloropyridin-3-yl)-5-methylisoxazol-4-yl)methyl)-6-oxo-1,6-dihydropyridazin-4-yl)hexahydroimidazo [1,5-a]pyrazin-3(2H)-one;
(S)-2-((3-(6-chloropyridin-3-yl)-5-methylisoxazol-4-yl)methyl)-5-(7-fluoro-5-oxa-2-azaspiro[3 0.4]octan-2-yl)pyridazin-3(2H)-one;
2-43-(6-chloropyridin-3-yl)-5-methylisoxazol-4-yl)methyl)-5-(5-oxa-2-azaspiro[3.5]nonan-2-yl)pyridazin-3(2H)-one;
5-(3-(tert-butoxy)azetidin-1-yl)-2-((5-methyl-3-(6-methylpyridazin-3-yl)isoxazol-4-yl)methyl)pyridazin-3(2H)-one;
2-((5-methyl-3-(6-methylpyridazin-3-yl)isoxazol-4-yl)methyl)-5-(5-oxa-2-azaspiro[3.5]nonan-2-yl)pyridazin-3(2H)-one;
5-(3-((2-chloropyridin-4-yl)oxy)azetidin-1-yl)-2-((5-methyl-3-(6-methylpyridazin-3-yl)isoxazol-4-yl)methyl)pyridazin-3(2H)-one;
(R)-5-(7-methoxy-5-oxa-2-azaspiro[3 0.4]octan-2-yl)-2-((5-methyl-3-(6-(trifluoromethyl)pyridin-3-yl)isoxazol-4-yl)methyl)pyridazin-3 (2H)-one;
5-(3-cyclobutoxyazetidin-1-yl)-2-((5-methyl-3-(6-methylpyridazin-3-yl)isoxazol-4-yl)methyl)pyridazin-3(2H)-one;
5-(3-cyclopropoxyazetidin-1-yl)-2-((5-methyl-3-(6-methylpyridazin-3-yl)isoxazol-4-yl)methyl)pyridazin-3(2H)-one;
(R)-2-((5-methyl-3-(6-methylpyridazin-3-yl)isoxazol-4-yl)methyl)-5-(7-methyl-5-oxa-2-azaspiro[3 0.4]octan-2-yl)pyridazin-3(2H)-one;
(S)-2-((5-methyl-3-(6-methylpyridazin-3-yl)isoxazol-4-yl)methyl)-5-(7-methyl-5-oxa-2-azaspiro[3 0.4]octan-2-yl)pyridazin-3(2H)-one;
(R)-5-(7-(difluoromethoxy)-5-oxa-2-azaspiro[3.4]octan-2-yl)-2-((5-methyl-3-(6-methylpyridazin-3-yl)isoxazol-4-yl)methyl)pyridazin-3(2H)-one;
5-((2S,6R)-2,6-dimethylmorpholin-4-yl)-2-((5-(fluoromethyl)-3-(6-methylpyridin-3-yl)-1,2-oxazol-4-yl)methyl)pyridazin-3-one;
5-(3-(2,2-difluoroethoxy)azetidin-1-yl)-2-((5-methyl-3-(6-(trifluoromethyl)pyridin-3-yl)isoxazol-4-yl)methyl)pyridazin-3(2H)-one;
2-((3-(6-chloropyridin-3-yl)-5-methylisoxazol-4-yl)methyl)-5-(3-(2,2-difluoroethoxy)azetidin-1-yl)pyridazin-3 (2H)-one;
(S)-5-(7-(difluoromethoxy)-5-oxa-2-azaspiro[3.4]octan-2-yl)-2-((5-methyl-3-(6-methylpyridazin-3-yl)isoxazol-4-yl)methyl)pyridazin-3 (2H)-one;
2-((5-methyl-3-(6-methylpyridazin-3-yl)isoxazol-4-yl)methyl)-5-(3-oxa-9-azaspiro[5.5]undecan-9-yl)pyridazin-3 (2H)-one;
2-((3-(6-chloropyridin-3-yl)-5-methylisoxazol-4-yl)methyl)-5-(3-oxa-9-azaspiro[5.5]undecan-9-yl)pyridazin-3 (2H)-one;
5-(3-cyclopropoxyazetidin-1-yl)-2-((5-methyl-3-(5-(trifluoromethyl)pyrimidin-2-yl)isoxazol-4-yl)methyl)pyridazin-3 (2H)-one;
5-(7,7-difluoro-5-oxa-2-azaspiro[3 0.4]octan-2-yl)-2-((5-methyl-3-(5-(trifluoromethyl)pyrimidin-2-yl)isoxazol-4-yl)methyl)pyridazin-3 (2H)-one;
2-((3-(6-chloropyridin-3-yl)-5-methylisoxazol-4-yl)methyl)-5-(3-(trifluoromethoxy)azetidin-1-yl)pyridazin-3 (2H)-one;
2-((3-(6-chloropyridazin-3-yl)-5-methylisoxazol-4-yl)methyl)-5-(3-methoxyazetidin-1-yl)pyridazin-3 (2H)-one;
2-((3-(6-chloropyridin-3-yl)-5-methylisoxazol-4-yl)methyl)-5-(3-cyclobutoxyazetidin-1-yl)pyridazin-3 (2H)-one;
2-((3-(6-chloropyridin-3-yl)-5-methylisoxazol-4-yl)methyl)-5-(3-(2,2,2-trifluoroethoxy)azetidin-1-yl)pyridazin-3(2H)-one;
2-((3-(6-chloropyridin-3-yl)-5-methylisoxazol-4-yl)methyl)-5-(3-(difluoromethoxy)azetidin-1-yl)pyridazin-3 (2H)-one;
2-((3-(6-chloropyridin-3-yl)-5-methylisoxazol-4-yl)methyl)-5-(1-oxa-8-azaspiro[4.5]decan-8-yl)pyridazin-3(2H)-one;
2-((3-(6-chloropyridin-3-yl)-5-methylisoxazol-4-yl)methyl)-5-(7-oxa-2-azaspiro[3.5]nonan-2-yl)pyridazin-3(2H)-one;
2-((3-(6-chloropyridin-3-yl)-5-methylisoxazol-4-yl)methyl)-5-(2-oxa-7-azaspiro[3.5]nonan-7-yl)pyridazin-3(2H)-one;
2-((5-cyclopropyl-3-(6-methylpyridazin-3-yl)isoxazol-4-yl)methyl)-5-(5-oxa-2-azaspiro[3.5]nonan-2-yl)pyridazin-3(2H)-one;
2-((3-(6-cyclopropylpyridin-3-yl)-5-methylisoxazol-4-yl)methyl)-5-(7,7-difluoro-5-oxa-2-azaspiro[3.4]octan-2-yl)pyridazin-3 (2H)-one;
(R)-5-(3-(tert-butoxy)pyrrolidin-1-yl)-2-((5-methyl-3-(6-methylpyridazin-3-yl)isoxazol-4-yl)methyl)pyridazin-3(2H)-one;
2-((3-(6-chloropyridin-3-yl)-5-methylisoxazol-4-yl)methyl)-5-(4-methoxy-4-methylpiperidin-1-yl)pyridazin-3 (2H)-one;
2-((3-(6-chloropyridin-3-yl)-5-methylisoxazol-4-yl)methyl)-5-(4-(pyridazin-4-yl)piperazin-1-yl)pyridazin-3 (2H)-one;
2-((5-methyl-3-(6-methylpyridazin-3-yl)isoxazol-4-yl)methyl)-5-(3-trifluoro-2-methylpropan-2-yl)oxy)azetidin-1-yl)pyridazin-3(2H)-one;
(S or R)-2-((3-(6-chloropyridin-3-yl)-5-methylisoxazol-4-yl)methyl)-5-(3-((1,1,1-trifluoropropan-2-yl)oxy)azetidin-1-yl)pyridazin-3(2H)-one;
(R or S)-2-((3-(6-chloropyridin-3-yl)-5-methylisoxazol-4-yl)methyl)-5-(3-((1,1,1-trifluoropropan-2-yl)oxy)azetidin-1-yl)pyridazin-3(2H)-one;
2-((3-(6-chloropyridin-3-yl)-5-methylisoxazol-4-yl)methyl)-5-4-6-methoxy-3-azabicyclo[3.1.0]hexan-3-yl)pyridazin-3(2H)-one;
4-chloro-5-(3-ethoxyazetidin-1-yl)-2-((5-methyl-3-(6-methylpyridin-3-yl)isoxazol-4-yl)methyl)pyridazin-3 (2H)-one;
2-((3-(6-chloropyridazin-3-yl)-5-methylisoxazol-4-yl)methyl)-5-(7,7-difluoro-5-oxa-2-azaspiro[3.4]octan-2-yl)pyridazin-3(2H)-one;
2-((3-(6-chloropyridin-3-yl)-5-methylisoxazol-4-yl)methyl)-5-(1-oxa-7-azaspiro[3.5]nonan-7-yl)pyridazin-3(2H)-one;
5-(3-(tert-butoxy)azetidin-1-yl)-2- ((3-(6-chloropyridazin-3-yl)-5-methylisoxazol-4-yl)methyl)pyridazin-3(2H)-one;
4-chloro-2-((3-(6-chloropyridin-3-yl)-5-methylisoxazol-4-yl)methyl)-5-(3-ethoxyazetidin-1-yl)pyridazin-3(2H)-one;
(S)-5-(8-fluoro-5-oxa-2-azaspiro[3.5]nonan-2-yl)-2-((5-methyl-3-(6-methylpyridazin-3-yl)isoxazol-4-yl)methyl)pyridazin-3(2H)-one;
(R)-5-(8-fluoro-5-oxa-2-azaspiro[3.5]nonan-2-yl)-2-((5-methyl-3-(6-methylpyridazin-3-yl)isoxazol-4-yl)methyl)pyridazin-3(2H)-one;

(R)-5-(7-fluoro-5-oxa-2-azaspiro[3.5]nonan-2-yl)-2-((5-methyl-3-(6-methylpyridin-3-yl)isoxazol-4-yl)methyl)pyridazin-3(2H)-one;
(S)-5-(7-fluoro-5-oxa-2-azaspiro[3.5]nonan-2-yl)-2-((5-methyl-3-(6-methylpyridin-3-yl)isoxazol-4-yl)methyl)pyridazin-3(2H)-one;
2-((3-(6-chloropyridin-3-yl)-5-methylisoxazol-4-yl)methyl)-5-(4-(pyrimidin-5-yl)piperazin-1-yl)pyridazin-3(2H)-one;
2-((3-(6-chloropyridin-3-yl)-5-methylisoxazol-4-yl)methyl)-5-(4-(pyridin-3-yl)piperazin-1-yl)pyridazin-3(2H)-one;
5-(3-ethoxyazetidin-1-yl)-2-((5-(fluoromethyl)-3-(6-methylpyridazin-3-yl)isoxazol-4-yl)methyl)pyridazin-3(2H)-one;
2-((3-(6-chloropyridin-3-yl)-5-methylisoxazol-4-yl)methyl)-5-(4-(4-methyl-1,2,5-oxadiazol-3-yl)piperazin-1-yl)pyridazin-3(2H)-one;
5-(3-methoxyazetidin-1-yl)-2-((5-methyl-3-(6-(trifluoromethyl)pyridazin-3-yl)isoxazol-4-yl)methyl)pyridazin-3(2H)-one;
5-(5-chloro-6-methoxypyridin-3-yl)-2-((3-(6-chloropyridin-3-yl)-5-methylisoxazol-4-yl)methyl)pyridazin-3(2H)-one;
2-((3-(6-chloropyridin-3-yl)-5-methylisoxazol-4-yl)methyl)-5-(4-(4-methylpyrimidin-5-yl)piperazin-1-yl)pyridazin-3(2H)-one;
5-(4-(3-chloropyridazin-4-yl)piperazin-1-yl)-2-((3-(6-chloropyridin-3-yl)-5-methylisoxazol-4-yl)methyl)pyridazin-3(2H)-one;
2-((3-(6-chloropyridin-3-yl)-5-methylisoxazol-4-yl)methyl)-5-(4-(2-methylpyridin-3-yl)piperazin-1-yl)pyridazin-3(2H)-one;
2-((3-(6-chloropyridin-3-yl)-5-methylisoxazol-4-yl)methyl)-5-((2S,3S) or (2R,3R)-3-methoxy-2-methylazetidin-1-yl)pyridazin-3(2H)-one;
(S)-5-(8-fluoro-5-oxa-2-azaspiro[3.5]nonan-2-yl)-2-((5-methyl-3-(6-methylpyridazin-3-yl)isoxazol-4-yl)methyl)pyridazin-3(2H)-one;
(S)-5-(7-fluoro-5-oxa-2-azaspiro[3.5]nonan-2-yl)-2-((5-methyl-3-(6-methylpyridazin-3-yl)isoxazol-4-yl)methyl)pyridazin-3(2H)-one;
2-((3-(6-chloropyridin-3-yl)-5-methylisoxazol-4-yl)methyl)-5-((2R,3R) or (2S,3S)-3-hydroxy-2-methylazetidin-1-yl)pyridazin-3(2H)-one;
2-((3-(6-chloropyridin-3-yl)-5-methyl-1,2-oxazol-4-yl)methyl)-5-(4-(4-methoxypyrimidin-5-yl)piperazin-1-yl)pyridazin-3-one;
2-((3-(6-chloropyridin-3-yl)-5-methylisoxazol-4-yl)methyl)-5-((2S,3S) or (2R,3R)-3-ethoxy-2-methylazetidin-1-yl)pyridazin-3(2H)-one;
2-((3-(6-chloropyridin-3-yl)-5-methylisoxazol-4-yl)methyl)-5-(4-(4-cyclopropylpyrimidin-5-yl)piperazin-1-yl)pyridazin-3(2H)-one;
5-(4-(5-chloropyridazin-4-yl)piperazin-1-yl)-2-((3-(6-chloropyridin-3-yl)-5-methylisoxazol-4-yl)methyl)pyridazin-3(2H)-one;
2-((3-(6-chloropyridin-3-yl)-5-methylisoxazol-4-yl)methyl)-5-((2R,3R) or (2S,3S)-3-ethoxy-2-methylazetidin-1-yl)pyridazin-3(2H)-one;
2-((5-(fluoromethyl)-3-(6-methylpyridazin-3-yl)isoxazol-4-yl)methyl)-5-(5-oxa-2-azaspiro[3.4]octan-2-yl)pyridazin-3(2H)-one;
(R or S)-2-((3-(6-chloropyridin-3-yl)-5-methylisoxazol-4-yl)methyl)-5-(8-fluoro-5-oxa-2-azaspiro[3.5]nonan-2-yl)pyridazin-3(2H)-one;
(R or S)-2-((3-(6-chloropyridin-3-yl)-5-methylisoxazol-4-yl)methyl)-5-(7-fluoro-5-oxa-2-azaspiro[3.5]nonan-2-yl)pyridazin-3(2H)-one;
(S or R)-2-((3-(6-chloropyridin-3-yl)-5-methylisoxazol-4-yl)methyl)-5-(7-fluoro-5-oxa-2-azaspiro[3.5]nonan-2-yl)pyridazin-3(2H)-one;
2-((3-(6-chloropyridin-3-yl)-5-methylisoxazol-4-yl)methyl)-5-(4-(3-methylpyridazin-4-yl)piperazin-1-yl)pyridazin-3(2H)-one;
2-((3-(6-chloropyridin-3-yl)-5-methylisoxazol-4-yl)methyl)-5-(4-(4-chloropyrimidin-5-yl)piperazin-1-yl)pyridazin-3(2H)-one;
2-((3-(6-chloropyridin-3-yl)-5-methylisoxazol-4-yl)methyl)-5-(4-(5-methylpyridazin-4-yl)piperazin-1-yl)pyridazin-3(2H)-one;
2-((5-methyl-3-(6-methylpyridazin-3-yl)isoxazol-4-yl)methyl)-5-(1-oxa-9-azaspiro[5.5]undecan-9-yl)pyridazin-3(2H)-one;
2-((3-(6-chloropyridin-3-yl)-5-methylisoxazol-4-yl)methyl)-5-(6-methoxy-2-azaspiro[3.3]heptan-2-yl)pyridazin-3(2H)-one;
2-((3-(6-chloropyridin-3-yl)-5-methylisoxazol-4-yl)methyl)-5-(4-(3-methoxypyridazin-4-yl)piperazin-1-yl)pyridazin-3(2H)-one;
2-((5-methyl-3-(6-methylpyridazin-3-yl)isoxazol-4-yl)methyl)-5-(3-(1-methylcyclopropoxy)azetidin-1-yl)pyridazin-3(2H)-one;
5-(3-(2,2-difluoroethoxy)azetidin-1-yl)-2-((5-methyl-3-(6-methylpyridazin-3-yl)isoxazol-4-yl)methyl)pyridazin-3(2H)-one;
(R)-2-((3-(6-chloropyridin-3-yl)-5-methylisoxazol-4-yl)methyl)-5-(7-methyl-5-oxa-2-azaspiro[3.5]nonan-2-yl)pyridazin-3(2H)-one;
(S)-2-((3-(6-chloropyridin-3-yl)-5-methylisoxazol-4-yl)methyl)-5-(7-methyl-5-oxa-2-azaspiro[3.5]nonan-2-yl)pyridazin-3(2H)-one;
(S)-5-(7-ethyl-5-oxa-2-azaspiro[3.4]octan-2-yl)-2-((5-methyl-3-(6-methylpyridazin-3-yl)isoxazol-4-yl)methyl)pyridazin-3(2H)-one;
5-(6,6-dimethyl-5-oxa-2-azaspiro[3.4]octan-2-yl)-2-((5-methyl-3-(6-methylpyridazin-3-yl)isoxazol-4-yl)methyl)pyridazin-3(2H)-one;
(S)-2-((5-methyl-3-(6-methylpyridazin-3-yl)isoxazol-4-yl)methyl)-5-(8-(trifluoromethyl)-5-oxa-2-azaspiro[3.5]nonan-2-yl)pyridazin-3(2H)-one;
(R)-2-((5-methyl-3-(6-methylpyridazin-3-yl)isoxazol-4-yl)methyl)-5-(8-(trifluoromethyl)-5-oxa-2-azaspiro[3.5]nonan-2-yl)pyridazin-3(2H)-one;
(R)-2-((5-methyl-3-(6-methylpyridazin-3-yl)isoxazol-4-yl)methyl)-5-(7-methyl-5-oxa-2-azaspiro[3.5]nonan-2-yl)pyridazin-3(2H)-one;
(S)-2-((5-methyl-3-(6-methylpyridazin-3-yl)isoxazol-4-yl)methyl)-5-(7-methyl-5-oxa-2-azaspiro[3.5]nonan-2-yl)pyridazin-3(2H)-one;
5-(6-(difluoromethoxy)-2-azaspiro[3.3]heptan-2-yl)-2-((5-methyl-3-(6-methylpyridazin-3-yl)isoxazol-4-yl)methyl)pyridazin-3(2H)-one;
2-((5-methyl-3-(6-methylpyridazin-3-yl)isoxazol-4-yl)methyl)-5-(5-oxa-2-azaspiro[3.6]decan-2-yl)pyridazin-3(2H)-one;
(S)-2-((5-methyl-3-(6-methylpyridazin-3-yl)isoxazol-4-yl)methyl)-5-(8-methyl-5-oxa-2-azaspiro[3.5]nonan-2-yl)pyridazin-3(2H)-one;
(R)-2-((5-methyl-3-(6-methylpyridazin-3-yl)isoxazol-4-yl)methyl)-5-(8-methyl-5-oxa-2-azaspiro[3.5]nonan-2-yl)pyridazin-3(2H)-one;

(R)-5-(7-fluoro-5-oxa-2-azaspiro[3.5]nonan-2-yl)-2-((5-methyl-3-(6-methylpyridazin-3-yl)isoxazol-4-yl)methyl)pyridazin-3(2H)-one;

(S)-2-((5-methyl-3-(6-methylpyridazin-3-yl)isoxazol-4-yl)methyl)-5-(7-(trifluoromethyl)-5-oxa-2-azaspiro[3.5]nonan-2-yl)pyridazin-3(2H)-one;

(R)-2-((5-methyl-3-(6-methylpyridazin-3-yl)isoxazol-4-yl)methyl)-5-(7-(trifluoromethyl)-5-oxa-2-azaspiro[3.5]nonan-2-yl)pyridazin-3(2H)-one;

(S)-2-((3-(6-chloropyridin-3-yl)-5-methylisoxazol-4-yl)methyl)-5-(8-methyl-5-oxa-2-azaspiro[3.5]nonan-2-yl)pyridazin-3(2H)-one;

(R)-2-((3-(6-chloropyridin-3-yl)-5-methylisoxazol-4-yl)methyl)-5-(7-(trifluoromethyl)-5-oxa-2-azaspiro[3.5]nonan-2-yl)pyridazin-3(2H)-one;

2-((5-ethyl-3-(6-methylpyridazin-3-yl)isoxazol-4-yl)methyl)-5-(5-oxa-2-azaspiro[3.5]nonan-2-yl)pyridazin-3(2H)-one;

(R)-2-((5-ethyl-3-(6-methylpyridazin-3-yl)isoxazol-4-yl)methyl)-5-(7-fluoro-5-oxa-2-azaspiro[3.5]nonan-2-yl)pyridazin-3(2H)-one;

5-((4S)-4-fluoro-1-oxa-9-azaspiro[5.5]undecan-9-yl)-2-((5-methyl-3-(6-methylpyridazin-3-yl)isoxazol-4-yl)methyl)pyridazin-3-one;

5-((4R)-4-fluoro-1-oxa-9-azaspiro[5.5]undecan-9-yl)-2-((5-methyl-3-(6-methylpyridazin-3-yl)isoxazol-4-yl)methyl)pyridazin-3-one;

2-((5-(fluoromethyl)-3-(6-methylpyridazin-3-yl)isoxazol-4-yl)methyl)-5-(5-oxa-2-azaspiro[3.5]nonan-2-yl)pyridazin-3(2H)-one;

(R)-5-(7-fluoro-5-oxa-2-azaspiro[3.5]nonan-2-yl)-2-((5-(fluoromethyl)-3-(6-methylpyridazin-3-yl)isoxazol-4-yl)methyl)pyridazin-3(2H)-one;

(R)-2-((3-(6-chloropyridin-3-yl)-5-methylisoxazol-4-yl)methyl)-5-(4-fluoro-1-oxa-9-azaspiro[5.5]undecan-9-yl)pyridazin-3(2H)-one;

(S)-2-((3-(6-chloropyridin-3-yl)-5-methylisoxazol-4-yl)methyl)-5-(4-fluoro-1-oxa-9-azaspiro[5.5]undecan-9-yl)pyridazin-3(2H)-one;

(R)-5-(7-fluoro-5-oxa-2-azaspiro[3.5]nonan-2-yl)-2-((5-methyl-3-(5-(trifluoromethyl)pyrimidin-2-yl)isoxazol-4-yl)methyl)pyridazin-3(2H)-one;

2-((3-(6-chloropyridin-3-yl)-5-methylisoxazol-4-yl)methyl)-5-(1-oxa-9-azaspiro[5.5]undecan-9-yl)pyridazin-3(2H)-one;

(R)-5-(7-fluoro-5-oxa-2-azaspiro[3.5]nonan-2-yl)-2-((5-methyl-3-(6-(trifluoromethyl)pyridazin-3-yl)isoxazol-4-yl)methyl)pyridazin-3(2H)-one; and 2-((5-methyl-3-(6-(trifluoromethyl)pyridazin-3-yl)isoxazol-4-yl)methyl)-5-(5-oxa-2-azaspiro[3.5]nonan-2-yl)pyridazin-3(2H)-one, or a pharmaceutically acceptable salts thereof.

12. The compound of claim 1, wherein the compound is selected from (R or S)-2-((3-(6-chloropyridin-3-yl)-5-methylisoxazol-4-yl)methyl)-5-(7-fluoro-5-oxa-2-azaspiro[3.5]nonan-2-yl)pyridazin-3(2H)-one; and 5-(3-(tert-butoxy)azetidin-1-yl)-2-((5-methyl-3-(6-methylpyridazin-3-yl)isoxazol-4-yl)methyl)pyridazin-3(2H)-one or a pharmaceutically acceptable salts thereof.

13. A pharmaceutical composition comprising a compound of claim 1, or a pharmaceutically acceptable salt thereof, and a therapeutically inert carrier.

14. A method of treating a $GABA_A$ $\alpha 5$ receptor-related disease or condition in a subject in need thereof comprising administering to said subject a therapeutically effective amount of a compound of claim 1, or a pharmaceutically acceptable salt thereof, wherein the $GABA_A$ $\alpha 5$ receptor-related disease or condition is selected from the group consisting of Alzheimer's disease, mild cognitive impairment, age-related cognitive decline, negative and/or cognitive symptoms associated with schizophrenia, bipolar disorders, autism spectrum disorder, Angelman syndrome, Rett syndrome, Prader-Willi syndrome, epilepsy, post-traumatic stress disorder, amyotrophic lateral sclerosis, and fragile-X disorder.

15. The method of claim 14, wherein the $GABA_A$ $\alpha 5$ receptor-related disease or condition is autism spectrum disorder.

* * * * *